United States Patent
Suh et al.

(10) Patent No.: US 11,987,592 B2
(45) Date of Patent: May 21, 2024

(54) COMPOUND AND ORGANIC LIGHT EMITTING DEVICE COMPRISING THE SAME

(71) Applicant: LG CHEM, LTD., Seoul (KR)

(72) Inventors: Sang Duk Suh, Daejeon (KR); Dong Hoon Lee, Daejeon (KR); Boon Jae Jang, Daejeon (KR); Min Woo Jung, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 611 days.

(21) Appl. No.: 17/279,192

(22) PCT Filed: Nov. 8, 2019

(86) PCT No.: PCT/KR2019/015195
§ 371 (c)(1),
(2) Date: Mar. 24, 2021

(87) PCT Pub. No.: WO2020/116800
PCT Pub. Date: Jun. 11, 2020

(65) Prior Publication Data
US 2022/0056048 A1 Feb. 24, 2022

(30) Foreign Application Priority Data

Dec. 5, 2018 (KR) .................. 10-2018-0155293
Nov. 4, 2019 (KR) .................. 10-2019-0139629

(51) Int. Cl.
*C07D 493/04* (2006.01)
*C07D 519/00* (2006.01)
(Continued)

(52) U.S. Cl.
CPC ......... *C07D 519/00* (2013.01); *H10K 85/615* (2023.02); *H10K 85/654* (2023.02);
(Continued)

(58) Field of Classification Search
None
See application file for complete search history.

(56) References Cited

U.S. PATENT DOCUMENTS

2004/0251816 A1 12/2004 Leo et al.
2009/0302743 A1* 12/2009 Kato .................. H05B 33/14
  313/504
(Continued)

FOREIGN PATENT DOCUMENTS

EP  2298774 A1  3/2011
EP  2301921 A1  3/2011
(Continued)

OTHER PUBLICATIONS

International Search Report and the Written Opinion of PCT/KR2019/015195, mailed Mar. 4, 2020.

*Primary Examiner* — Robert S Loewe
(74) *Attorney, Agent, or Firm* — BRYAN CAVE LEIGHTON PAISNER LLP

(57) ABSTRACT

Provided is a compound of Chemical Formula 1:

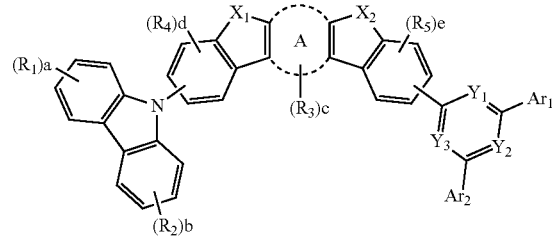

wherein:
  A is a benzene ring;
  $X_1$ and $X_2$ are each independently O or S;
  $Y_1$ to $Y_3$ are each independently N or CH, provided that at least one of $Y_1$ to $Y_3$ is N;
  $Ar_1$ and $Ar_2$ are each independently a substituted or unsubstituted: C6-αaryl or C2- 60 heteroaryl containing at least one of N, O, and S;
  $R_1$ to $R_3$ are each independently hydrogen, deuterium, halogen, cyano, nitro, amino, or a substituted or unsubstituted: C1-60 alkyl, C3-60 cycloalkyl, C2-60 alkenyl, C6-60 aryl, or C2-60 heteroaryl containing at least one of N, O, and S; and (Continued)

R$\alpha$ and R5 are each independently hydrogen, deuterium, halogen, cyano, nitro, amino, or a substituted or unsubstituted: C1-60 alkyl, C3-$\alpha$cycloalkyl, C2-60 alkenyl, C6-60 aryl, or C2-60 heteroaryl containing at least one of N, O, and S, and an organic light emitting device including the same.

13 Claims, 1 Drawing Sheet

(51) Int. Cl.
 *H10K 85/60* (2023.01)
 *H10K 50/11* (2023.01)
 *H10K 71/00* (2023.01)
 *H10K 101/30* (2023.01)
 *H10K 101/40* (2023.01)

(52) U.S. Cl.
 CPC ..... *H10K 85/6572* (2023.02); *H10K 85/6574* (2023.02); *H10K 85/6576* (2023.02); *H10K 50/11* (2023.02); *H10K 71/00* (2023.02); *H10K 2101/30* (2023.02); *H10K 2101/40* (2023.02)

(56) References Cited

U.S. PATENT DOCUMENTS

| | | | |
|---|---|---|---|
| 2009/0309488 A1* | 12/2009 | Kato | C09K 11/06 313/504 |
| 2011/0062862 A1 | 3/2011 | Yamamoto et al. | |
| 2012/0138915 A1 | 6/2012 | Nishimura et al. | |
| 2014/0158992 A1 | 6/2014 | Xia et al. | |
| 2018/0037546 A1 | 2/2018 | Sugino et al. | |
| 2022/0109115 A1* | 4/2022 | Mizuki | C07D 493/04 |

FOREIGN PATENT DOCUMENTS

| | | | |
|---|---|---|---|
| EP | 2301926 A1 | 3/2011 | |
| JP | 2010-045281 | 2/2010 | |
| JP | 2012-028548 | 2/2012 | |
| JP | 5238025 | 7/2013 | |
| JP | 5357150 | 12/2013 | |
| JP | 5666907 | 2/2015 | |
| JP | 5831654 | 12/2015 | |
| KR | 10-2000-0051826 | 8/2000 | |
| KR | 10-2012-0120886 | 11/2012 | |
| KR | 10-2017-0086243 | 7/2017 | |
| KR | 10-2018-0096444 | 8/2018 | |
| WO | 2003-012890 | 2/2003 | |
| WO | 2009-136596 | 11/2009 | |
| WO | WO-2018116152 A1 * | 6/2018 | C07D 493/04 |

* cited by examiner

[FIG. 1]
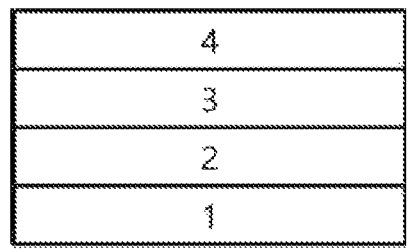
[FIG. 2]
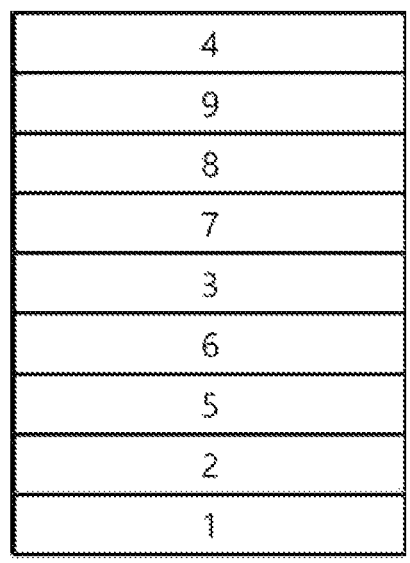

COMPOUND AND ORGANIC LIGHT EMITTING DEVICE COMPRISING THE SAME

CROSS-REFERENCE TO RELATED APPLICATIONS

This application is a National Stage Application of International Application No. PCT/KR2019/015195 filed on Nov. 8, 2019, which claims priority to or the benefit of Korean Patent Application No. 10-2018-0155293 filed with the Korean Intellectual Property Office on Dec. 5, 2018, and Korean Patent Application No. 10-2019-0139629 filed with the Korean Intellectual Property Office on Nov. 4, 2019, the disclosures of which are incorporated herein by reference in their entirety.

TECHNICAL FIELD

The present invention relates to a novel compound and to an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, an electron blocking layer, a light emitting layer, a hole blocking layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 1) Korean Unexamined Patent Publication No. 10-2000-0051826

BRIEF DESCRIPTION OF THE INVENTION

Technical Problem

It is an object of the present invention to provide a novel organic light emitting material and an organic light emitting device including the same.

Technical Solution

In one aspect of the invention, provided is a compound of Chemical Formula 1:

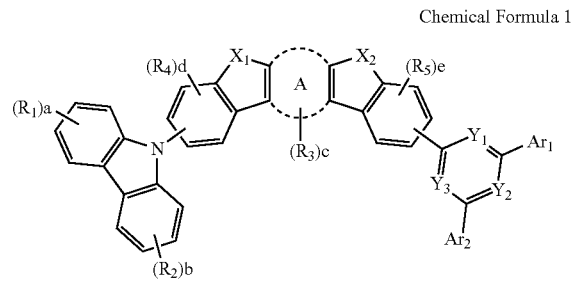

Chemical Formula 1 wherein, in Chemical Formula 1;
A is a benzene ring;
$X_1$ and $X_2$ are each independently O or S;
$Y_1$ to $Y_3$ are each independently N or CH, with the proviso that at least one of $Y_1$ to $Y_3$ is N;
$Ar_1$ and $Ar_2$ are each independently a substituted or unsubstituted $C_{6-60}$ aryl or a substituted or unsubstituted $C_{2-60}$ heteroaryl containing at least one heteroatom selected from the group consisting of N, O, and S;
$R_1$ to $R_3$ are each independently hydrogen, deuterium, halogen, cyano, nitro, amino, a substituted or unsubstituted $C_{1-60}$ alkyl, a substituted or unsubstituted $C_{3-60}$ cycloalkyl, a substituted or unsubstituted $C_{2-60}$ alkenyl, a substituted or unsubstituted $C_{6-60}$ aryl or a substituted or unsubstituted $C_{2-60}$ heteroaryl containing at least one heteroatom selected from the group consisting of N, O, and S;
$R_4$ and $R_5$ are each independently hydrogen, deuterium, halogen, cyano; nitro, amino, a substituted or unsubstituted $C_{1-60}$ alkyl, a substituted or unsubstituted $C_{3-60}$ cycloalkyl, a substituted or unsubstituted $C_{2-60}$ alkenyl, a substituted or unsubstituted $C_{6-60}$ aryl, or a substituted or unsubstituted $C_{2-60}$ heteroaryl containing at least one heteroatom selected from the group consisting of N, O, and S;
a and b are each independently an integer of 0 to 4;
c is an integer of 0 to 2; and
d and e are each independently an integer of 0 to 3.

In another aspect of the invention, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

Advantageous Effects

The compound of Chemical Formula 1 described above can be used as a material of an organic material layer of an organic light emitting device and can improve the efficiency, achieve low driving voltage and/or improve lifetime characteristics in the organic light emitting device. In particular, the compound of Chemical Formula 1 can be used as a hole injection material, hole transport material, hole injection and transport material, electron blocking material, light emitting material, hole blocking material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole transport layer 5, an electron blocking layer 6, a light emitting layer 3, a hole blocking layer 7, an electron transport layer 8, an electron injection layer 9, and a cathode 4.

DETAILED DESCRIPTION

Hereinafter, embodiments of the present invention will be described in more detail to facilitate understanding of the invention.

One embodiment of the invention provides a compound of Chemical Formula 1.

As used herein, the notation  mean a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae but is not limited thereto;

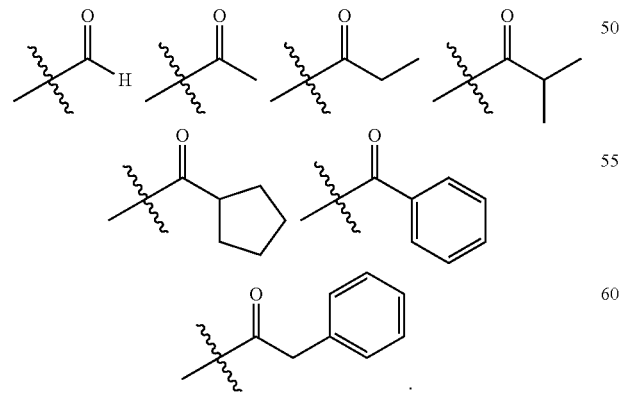

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto;

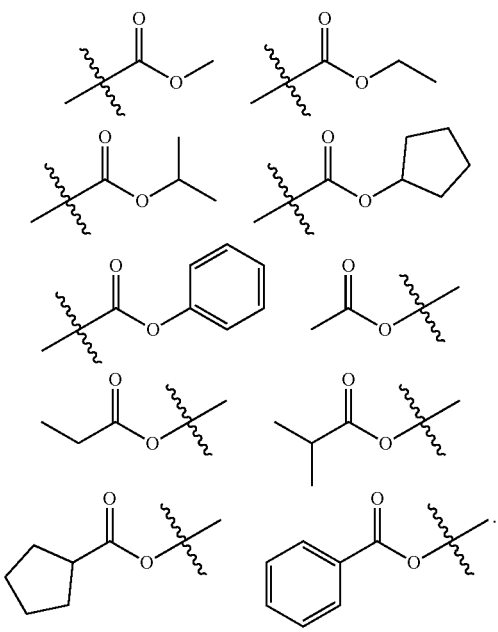

In the present specification, the number of carbon atoms of an imide group is not particularly limited, but is preferably 1 to 25. Specifically, the imide group can be a compound having the following structural formulae, but is not limited thereto;

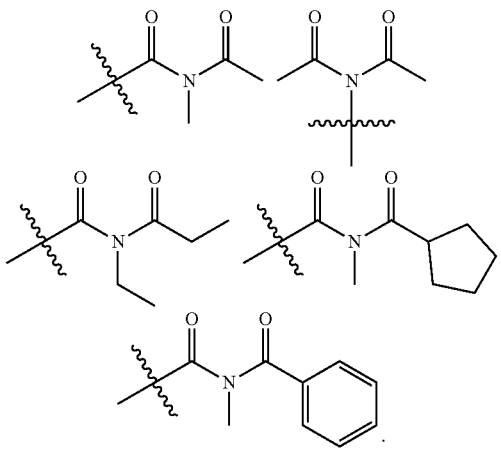

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be connected with each other to form a spiro structure. In the case where the fluorenyl group is substituted,

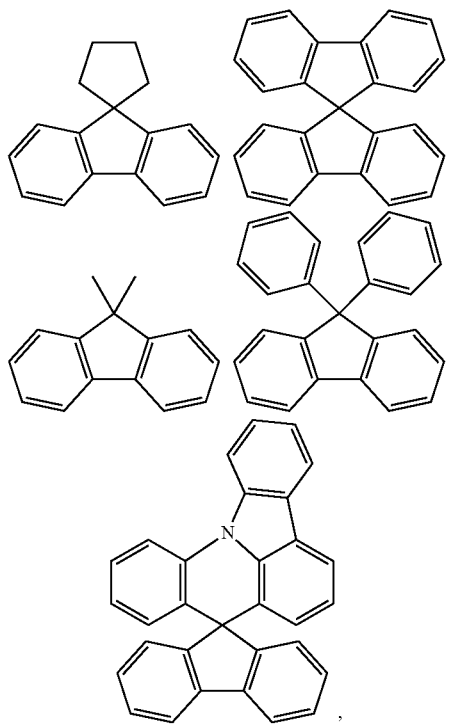

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, an thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine group can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

In Chemical Formula 1, Chemical Formula 1 can be any one of the following Chemical Formulas 1-1 to 1-6, depending on the fusion position of the benzene ring A:

[Chemical Formula 1-1]

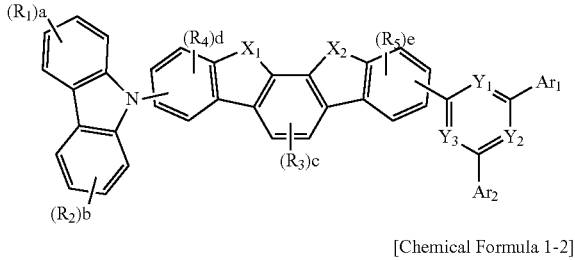

[Chemical Formula 1-2]

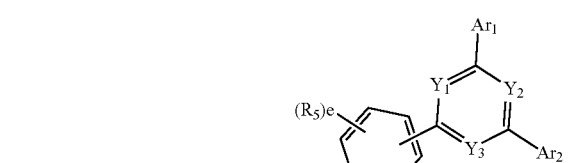

[Chemical Formula 1-3]

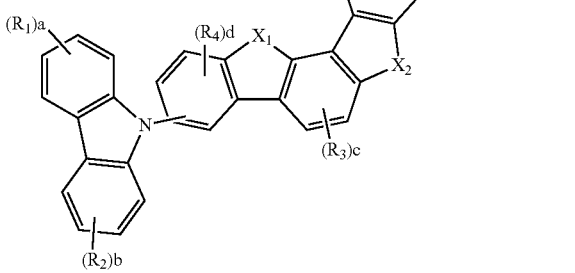

[Chemical Formula 1-4]

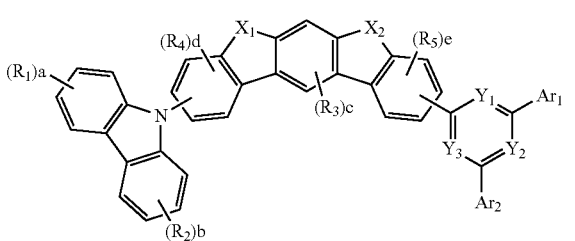

[Chemical Formula 1-5]

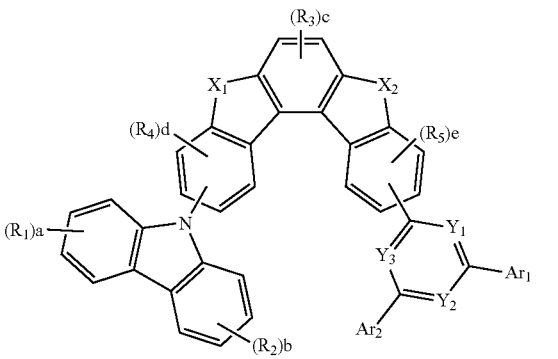

[Chemical Formula 1-6]

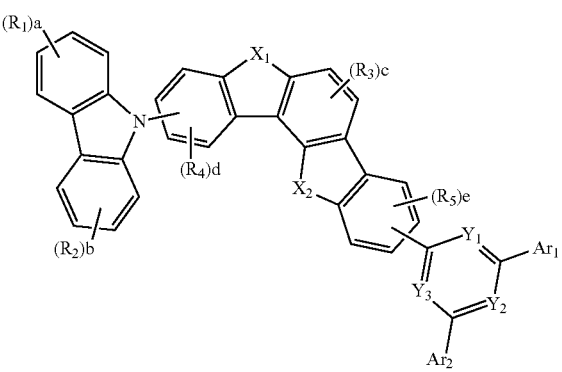

wherein, in Chemical Formulas 1-1 to 1-6;

$X_1$, $X_2$, $Y_1$ to $Y_3$, $Ar_1$, $Ar_2$, $R_1$ to $R_5$ and a to e are as the same as defined in Chemical Formula 1.

In the formulae, a represents the number of $R_1$, and when a is 2 or more, two or more $R_1$ can be the same as or different from each other. The description of b to e can be understood with reference to the description of a and the structure of Chemical Formula 1.

Preferably, $Y_1$ to $Y_3$ all are N.

Preferably, $Ar_1$ and $Ar_2$ can be each independently a substituted or unsubstituted $C_{6-20}$ aryl or a substituted or unsubstituted $C_{6-20}$ heteroaryl containing any one or more heteroatoms selected from the group consisting of N, O, and S.

More preferably, $Ar_1$ and $Ar_2$ can be each independently a phenyl, biphenylyl, terphenylyl, naphthyl, anthracenyl, phenanthrenyl, triphenylenyl, fluorenyl, dibenzofuranyl, dibenzothiophenyl, or phenyl substituted with five deuteriums.

Preferably, at least one of $Ar_1$ and $Ar_2$ can be a substituted or unsubstituted $C_{6-60}$ aryl.

More preferably at least one of $Ar_1$ and $Ar_2$ can be a substituted or unsubstituted $C_{6-20}$ aryl.

Most preferably at least one of $Ar_1$ and $Ar_2$ can be phenyl or phenyl substituted with five deuteriums.

The $R_3$ is a substituent on the benzene ring A.

Preferably, $R_1$ to $R_3$ can be each independently hydrogen, deuterium, a substituted or unsubstituted $C_{1-20}$ alkyl, a substituted or unsubstituted $C_{6-20}$ aryl, or a substituted or unsubstituted $C_{6-20}$ heteroaryl containing any one or more heteroatoms selected from the group consisting of N, O, and S.

More preferably, $R_1$ to $R_3$ can be each independently hydrogen, deuterium, or phenyl.

Preferably, $R_4$ and $R_5$ can be each independently hydrogen, a substituted or unsubstituted $C_{1-20}$ alkyl, a substituted or unsubstituted $C_{6-20}$ aryl, or a substituted or unsubstituted $C_{6-20}$ heteroaryl containing any one or more heteroatoms selected from the group consisting of N, O, and S.

More preferably, $R_4$ and $Rr$ can each independently be hydrogen or deuterium.

Representative examples of the compound of Chemical Formula 1 are as follows:

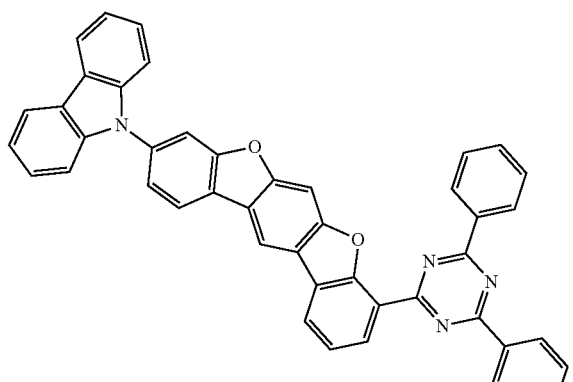

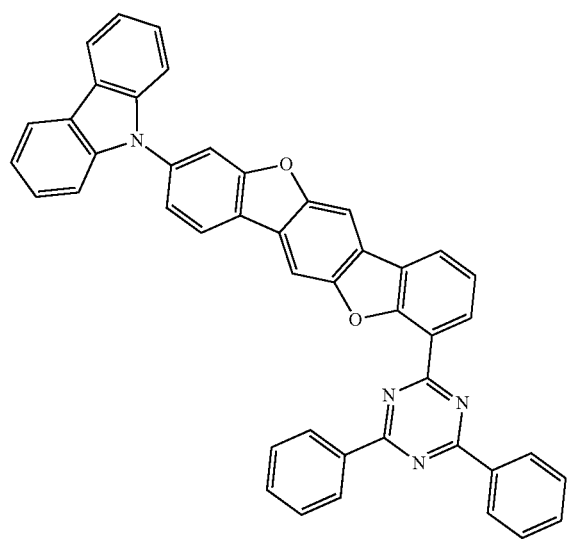

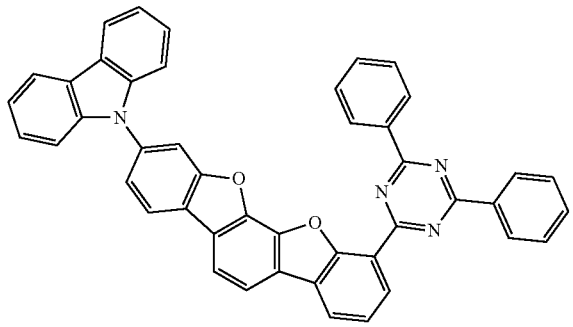

-continued

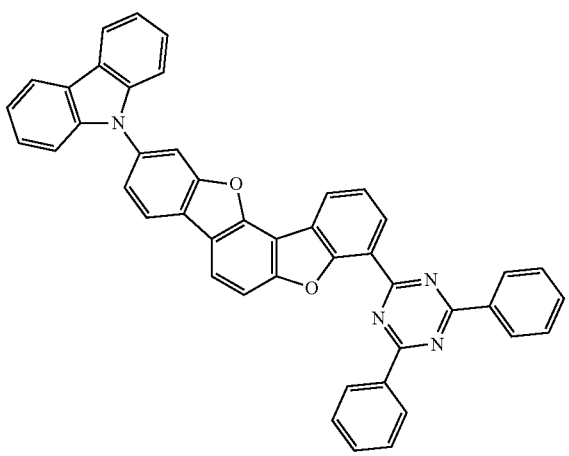

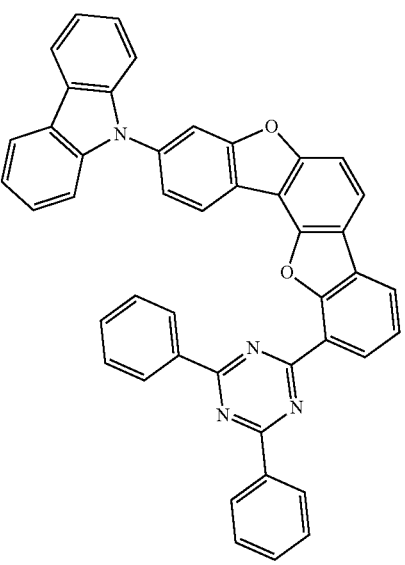

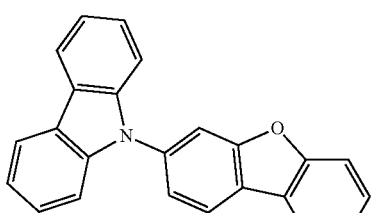

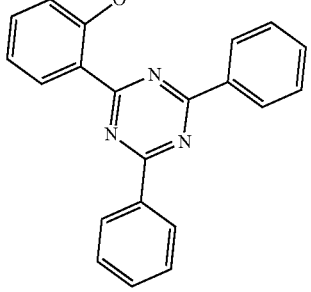

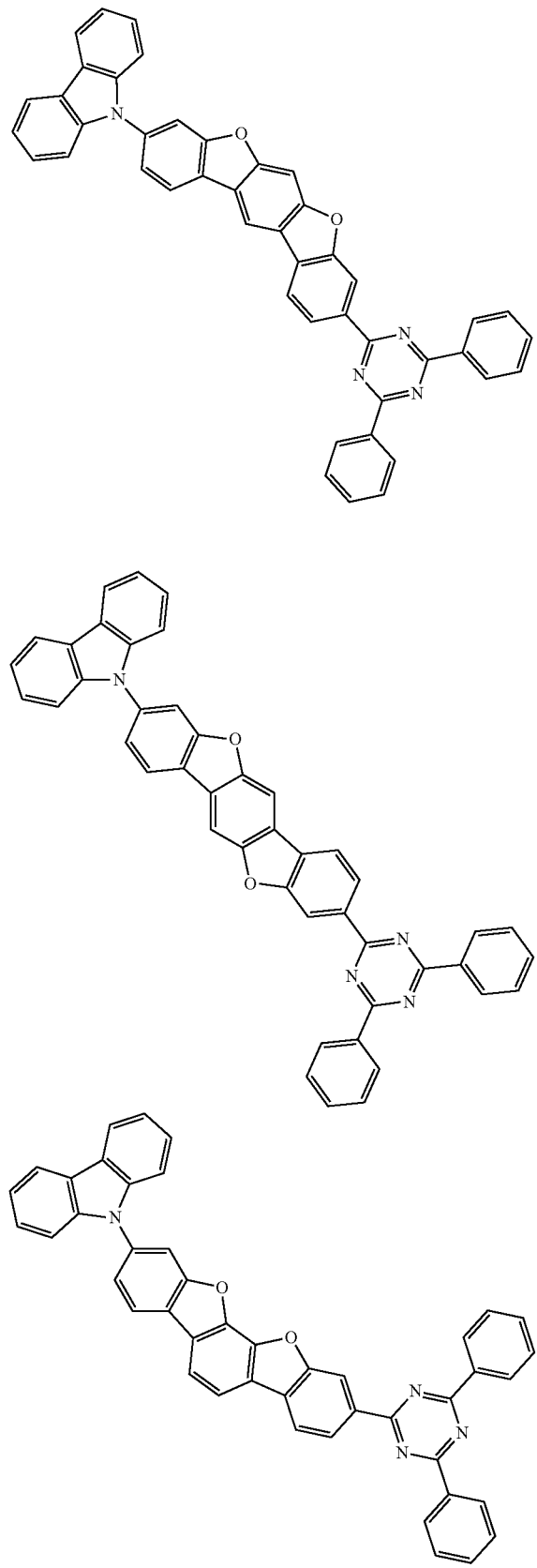
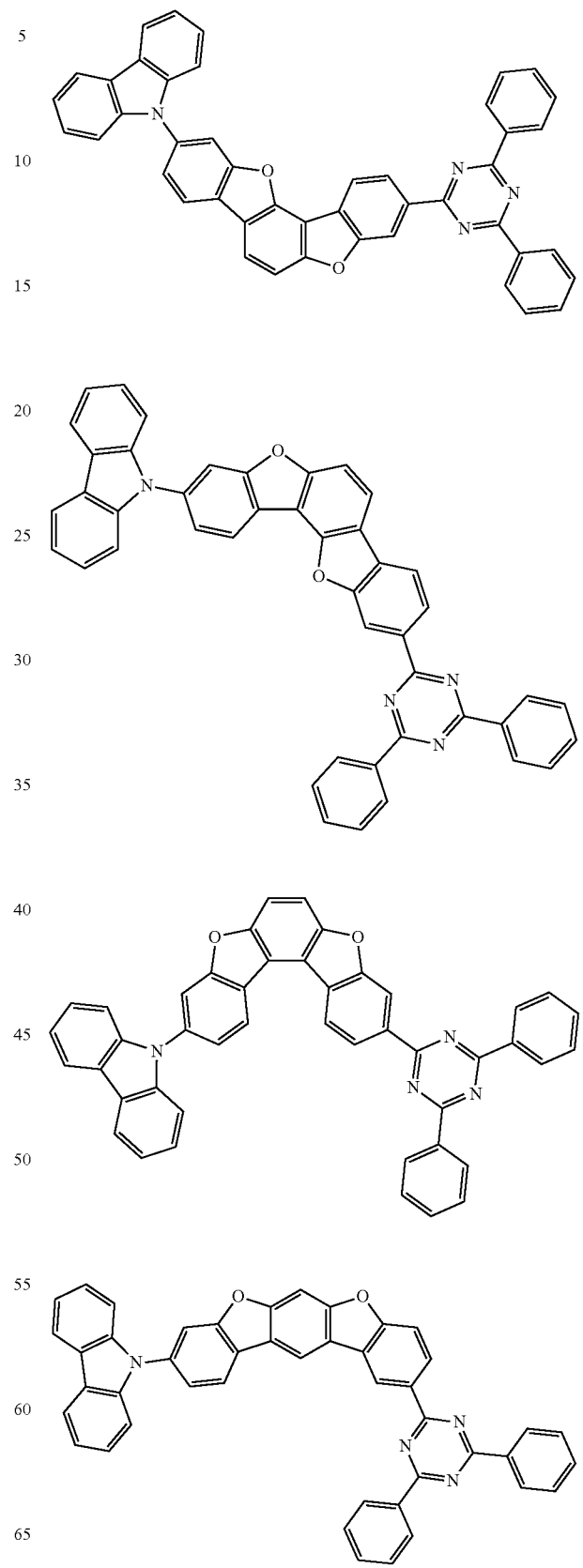

-continued
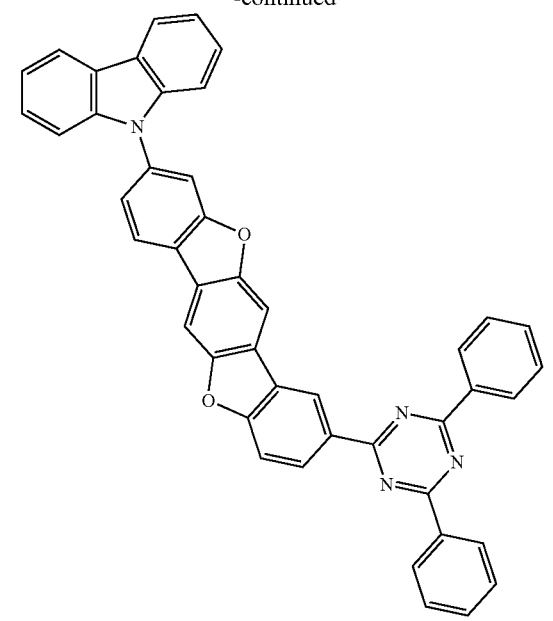
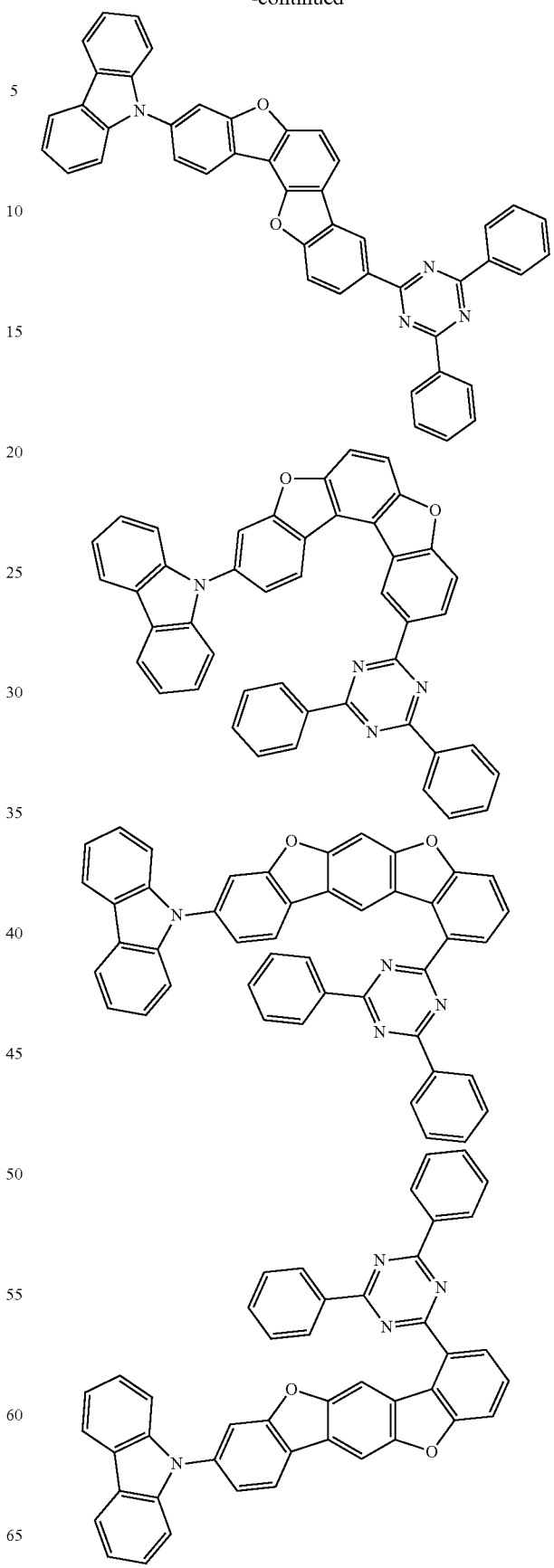

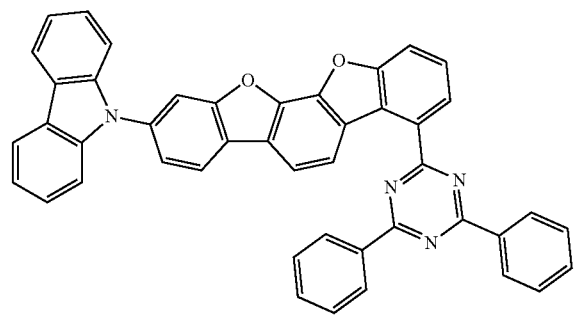
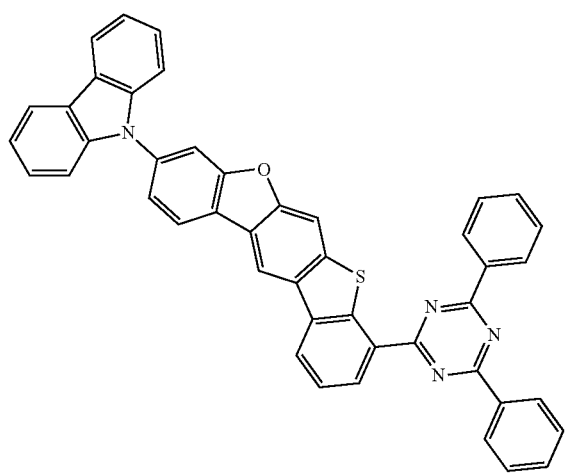
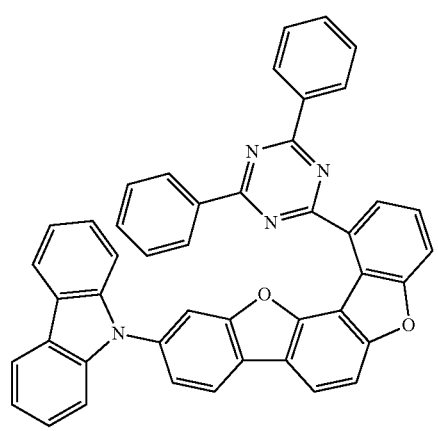
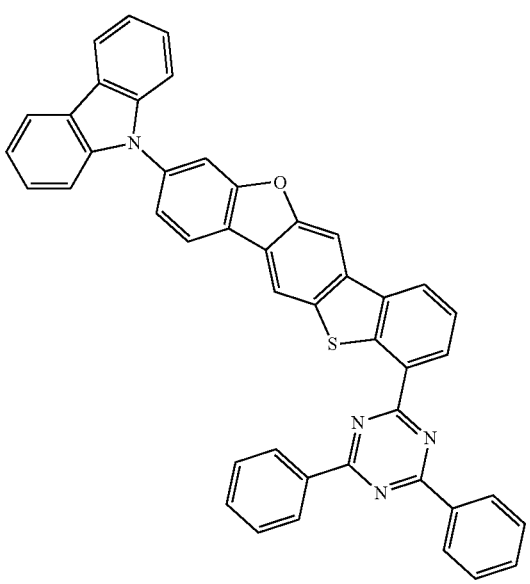
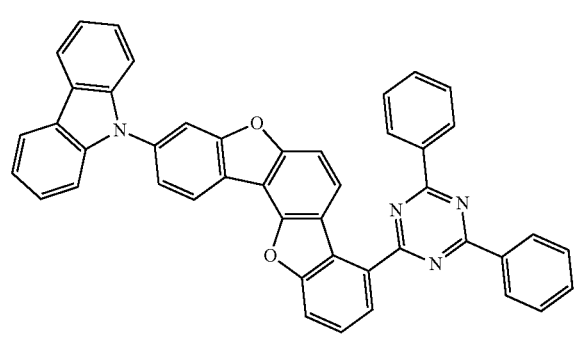
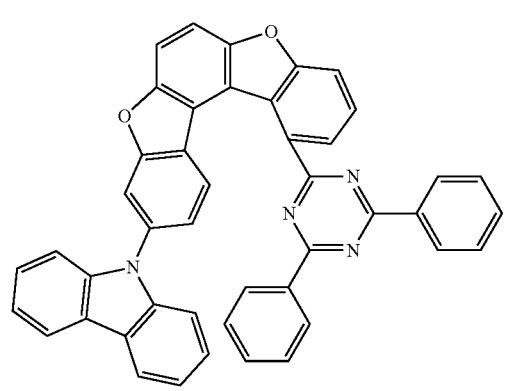
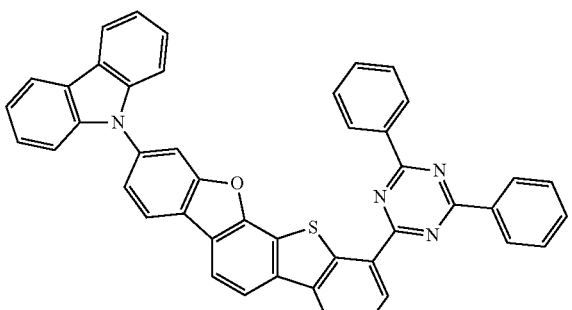

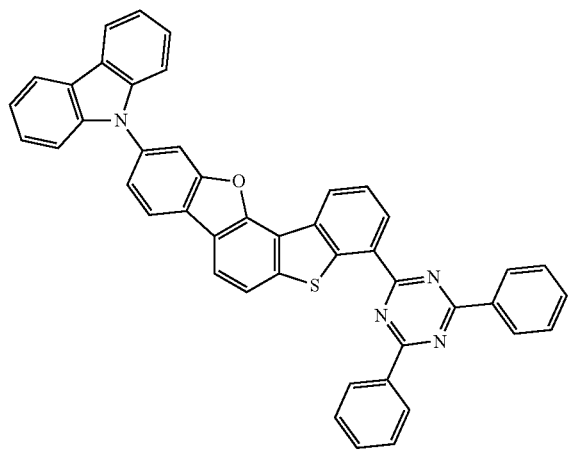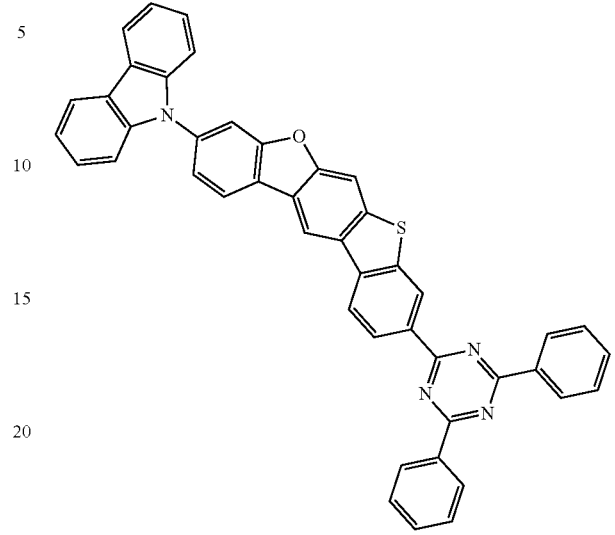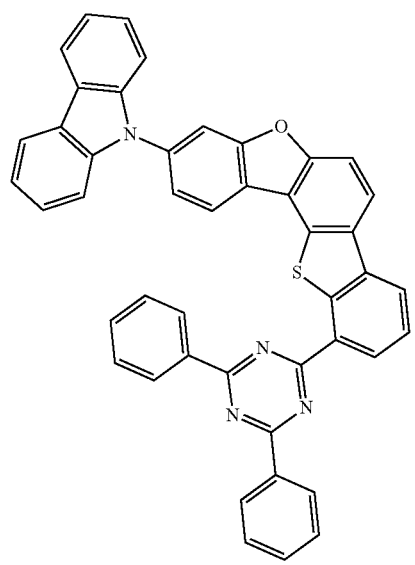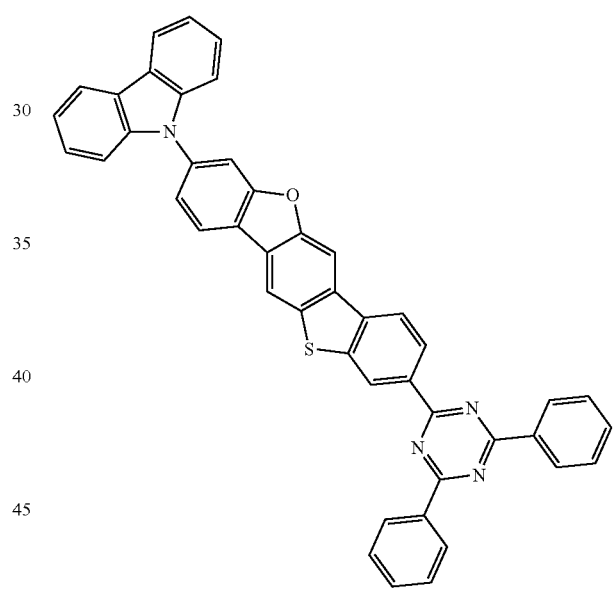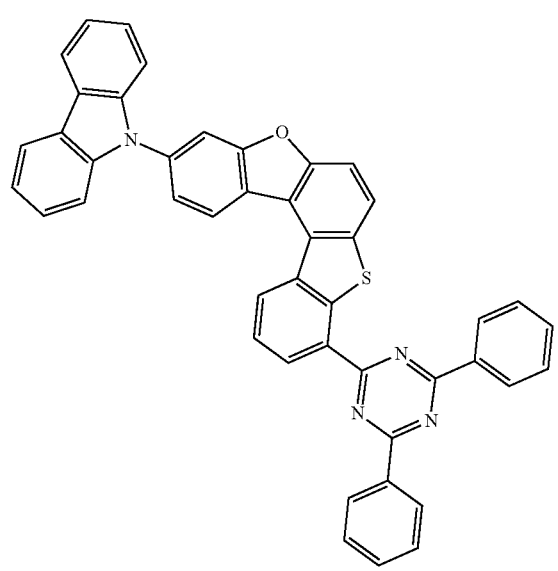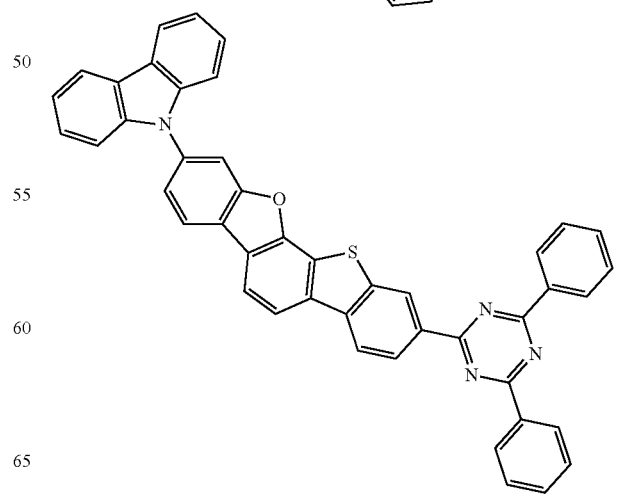

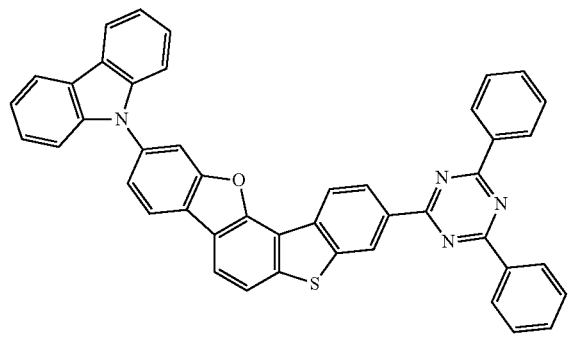
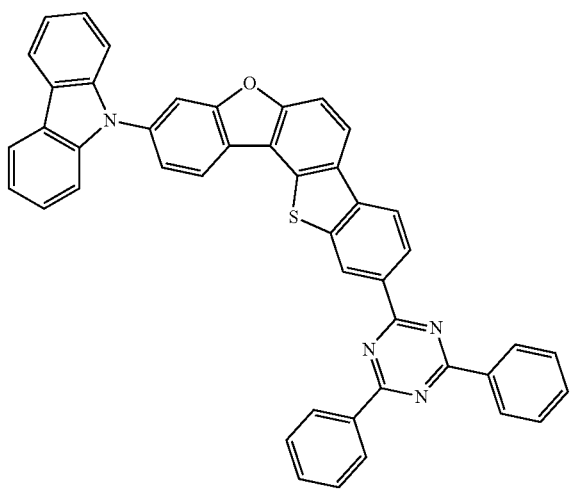
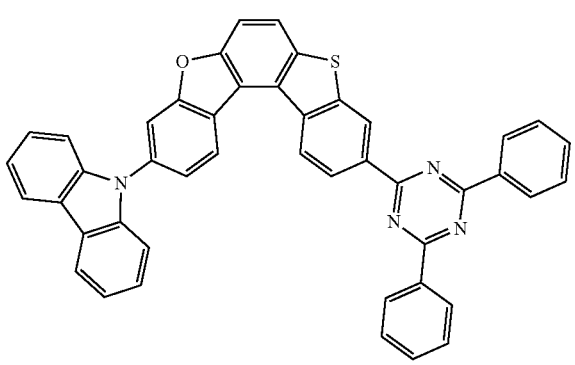
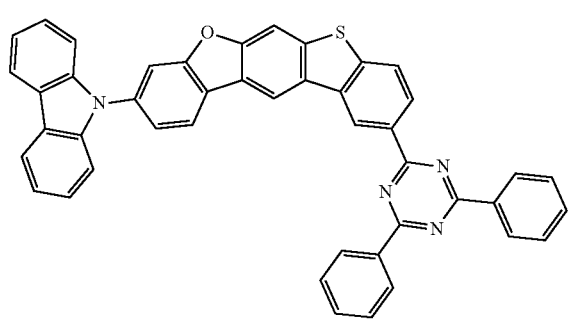
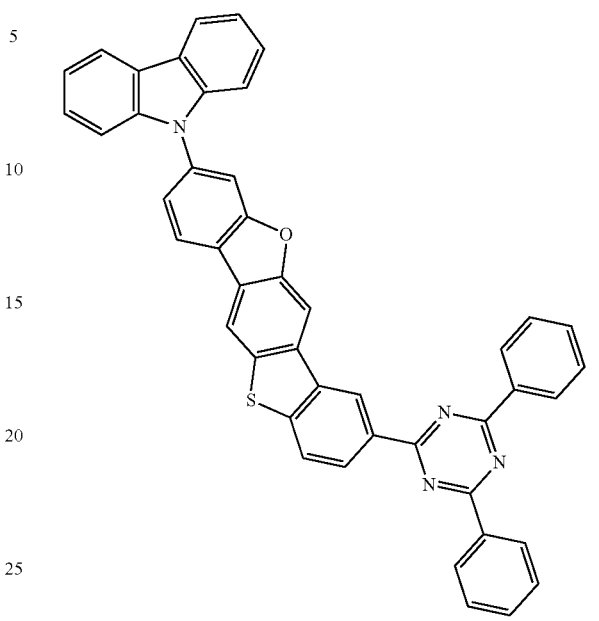
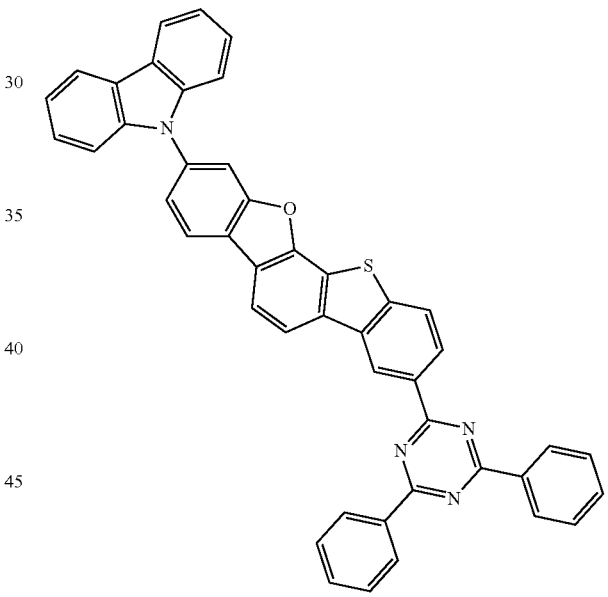
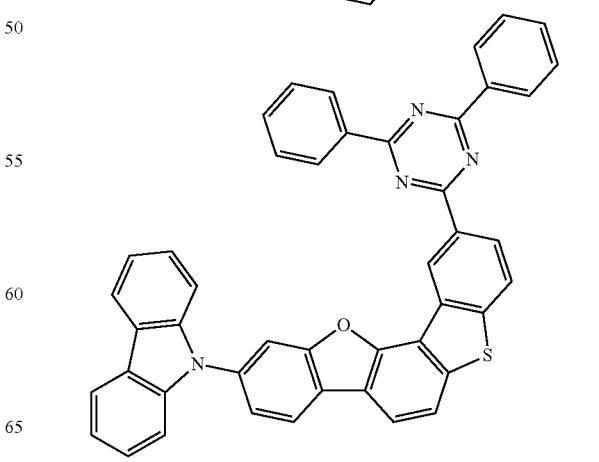

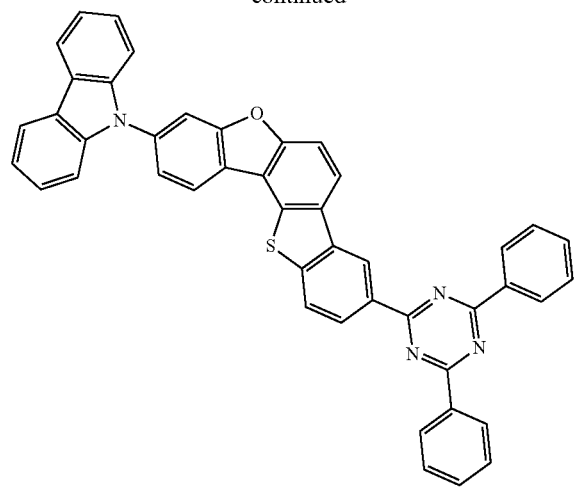
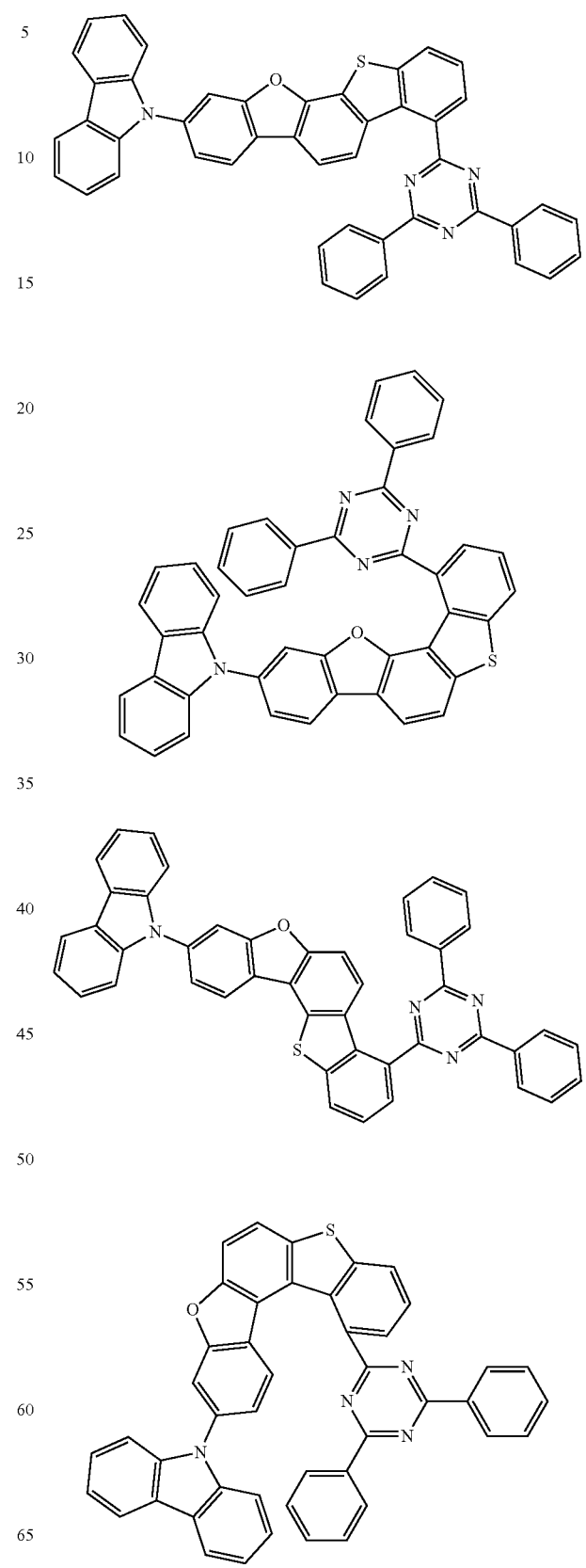

-continued
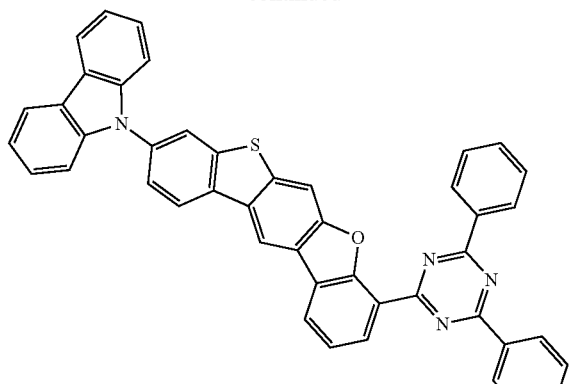
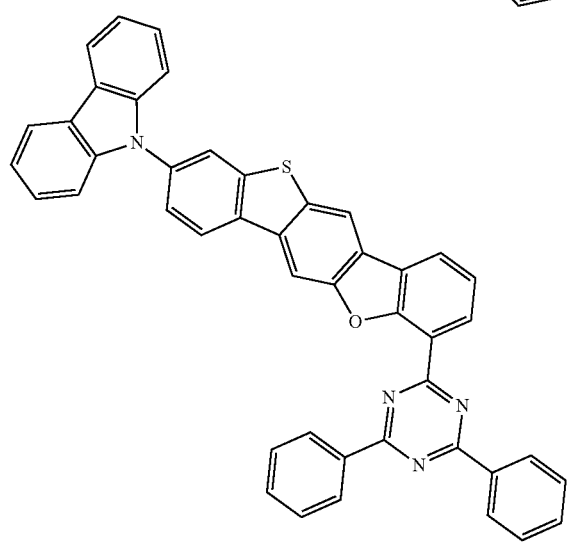
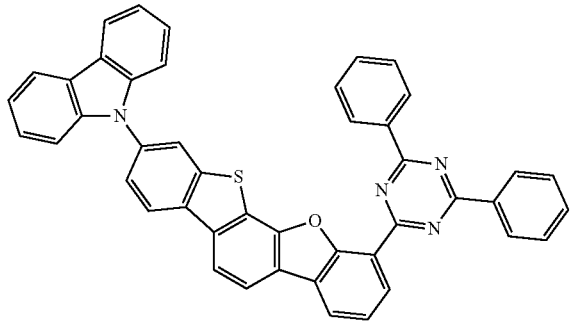
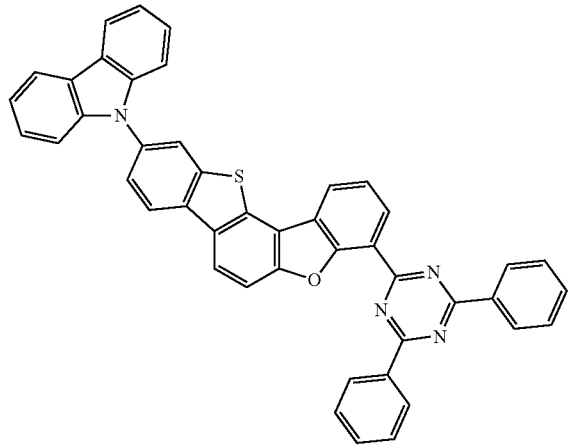
-continued
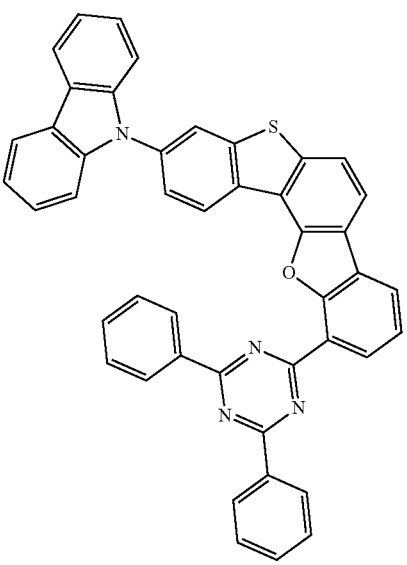
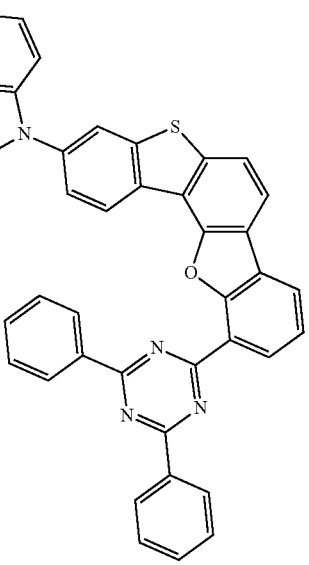
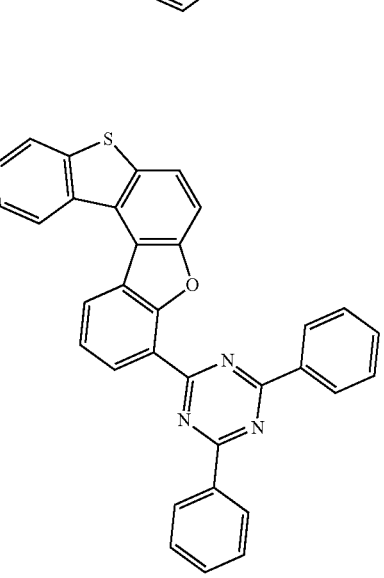
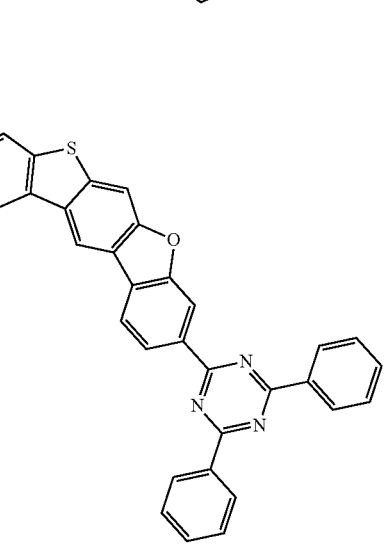

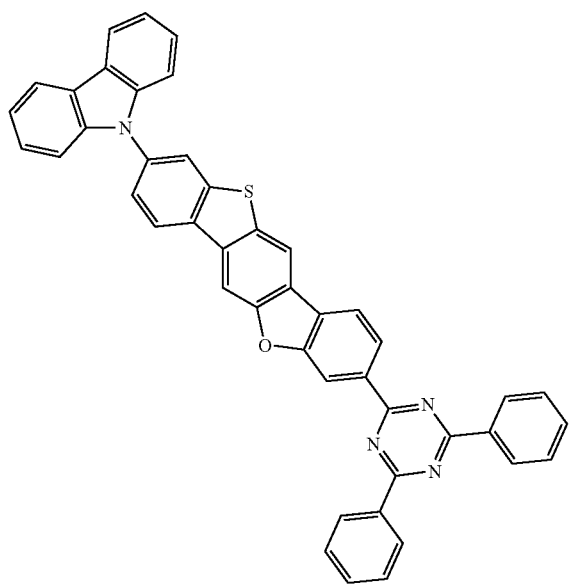
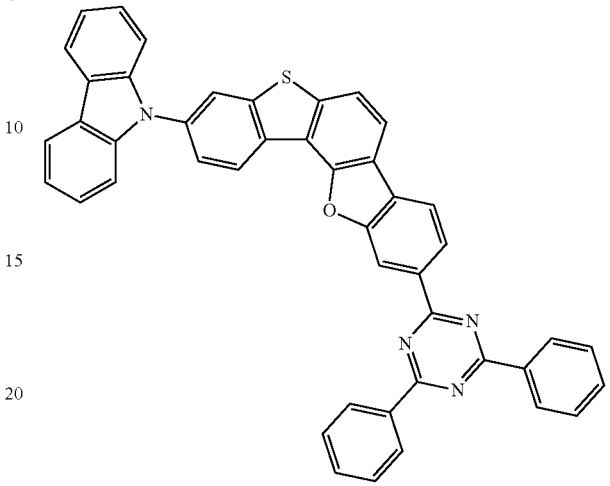
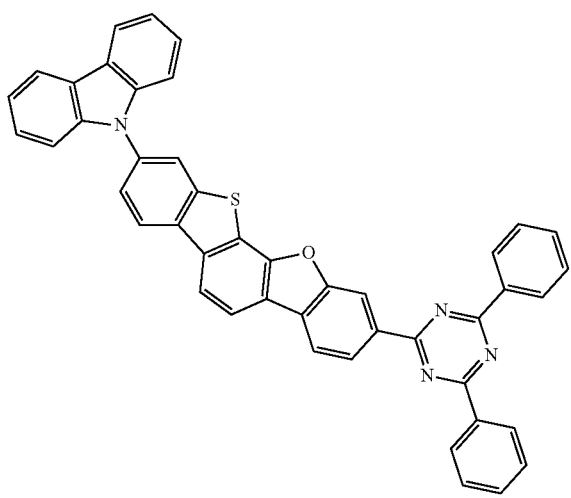
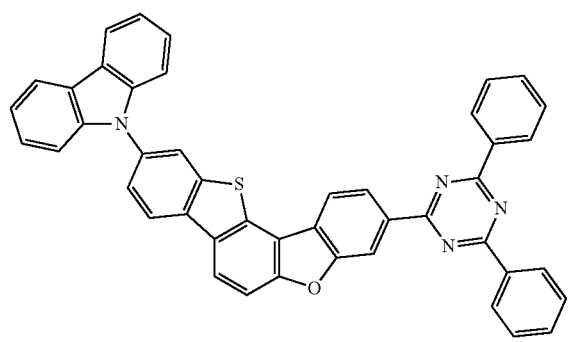
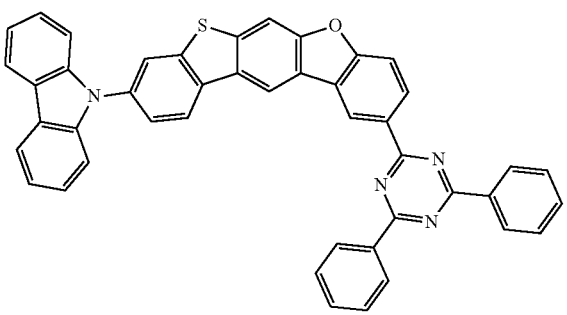

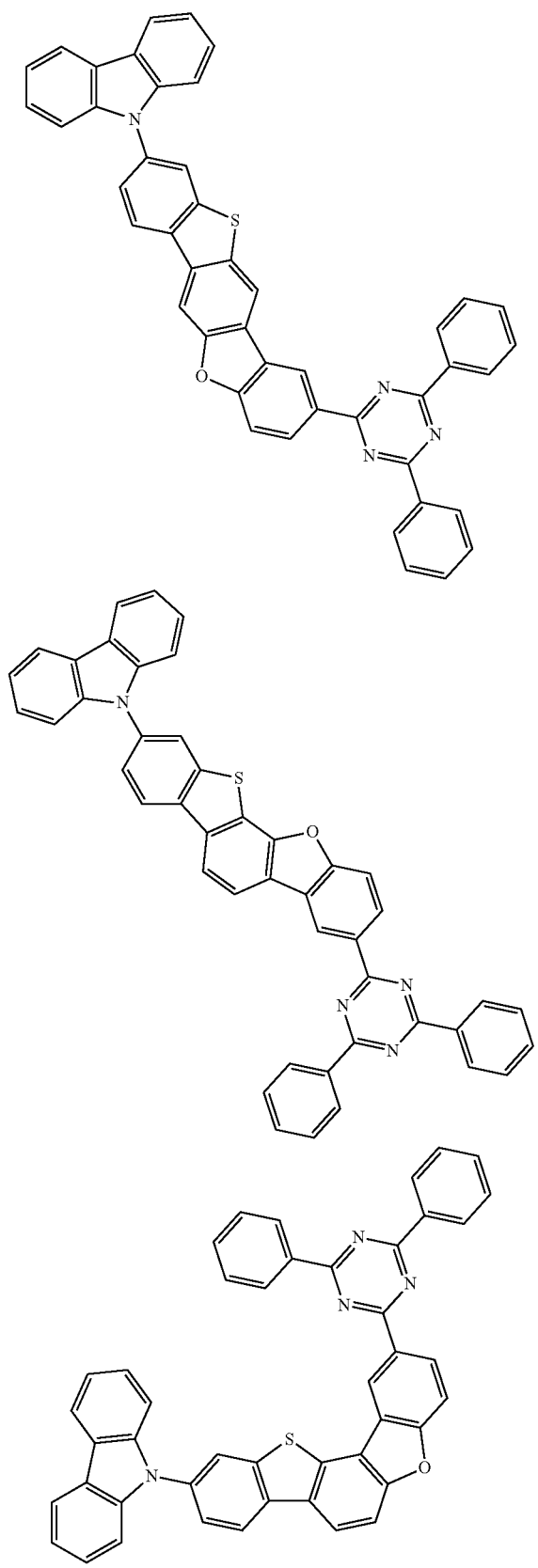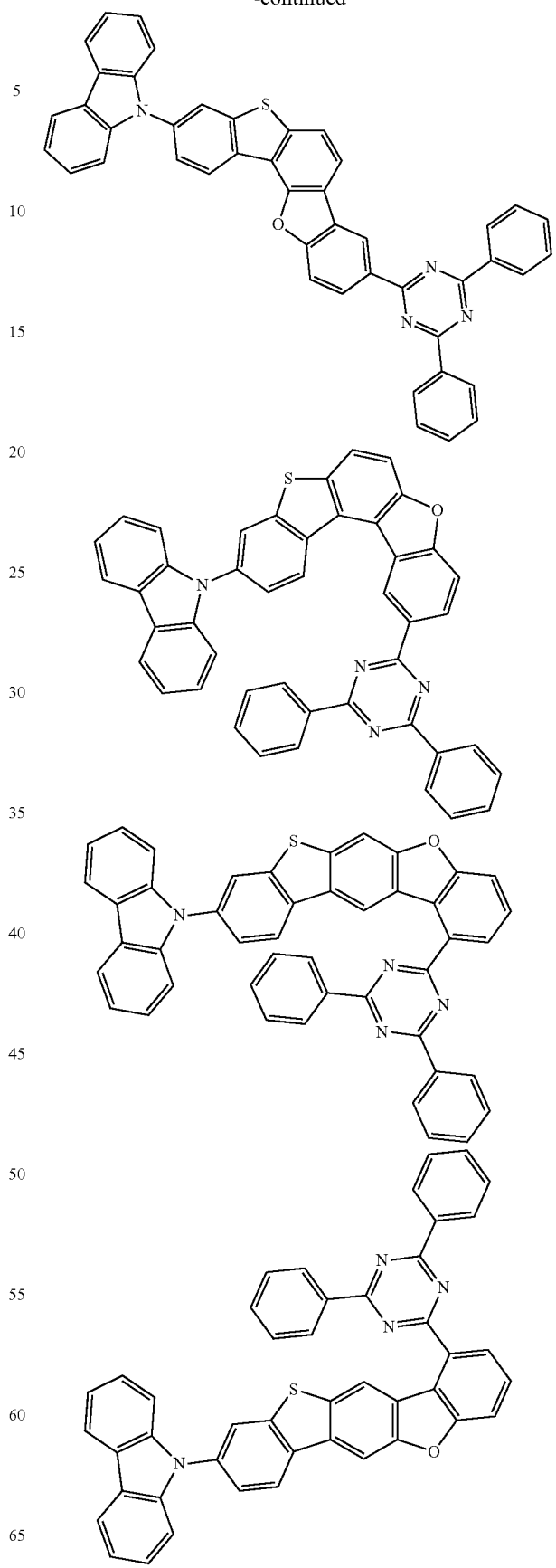

-continued
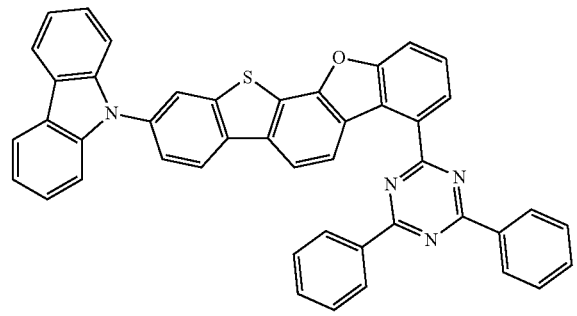
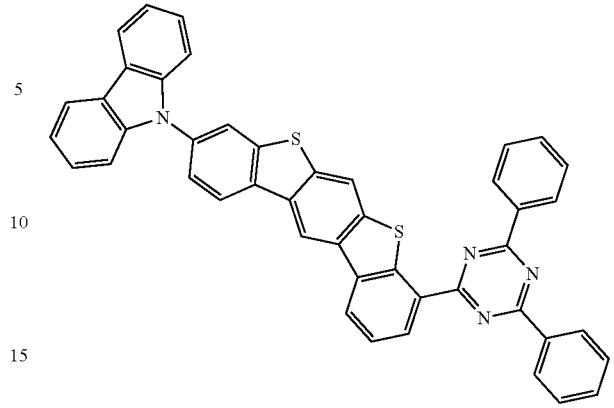
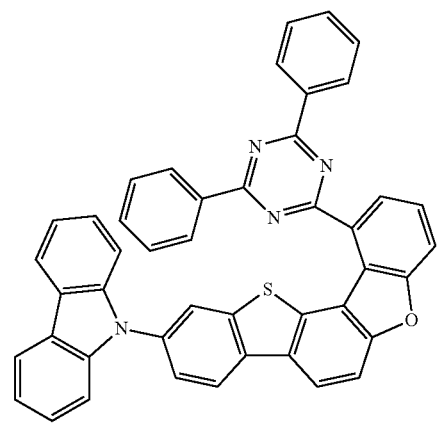
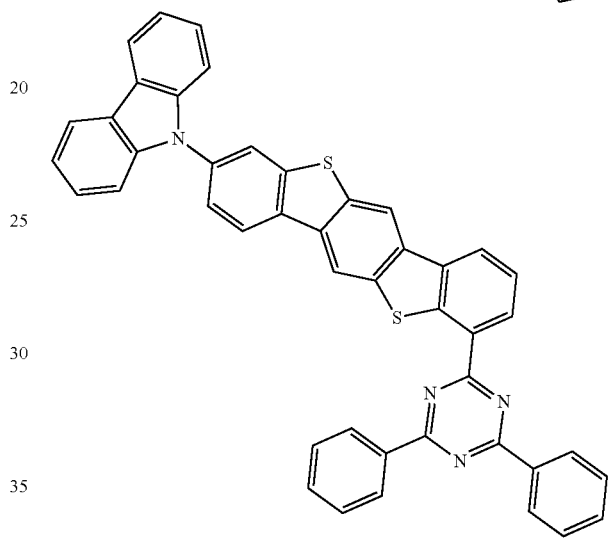
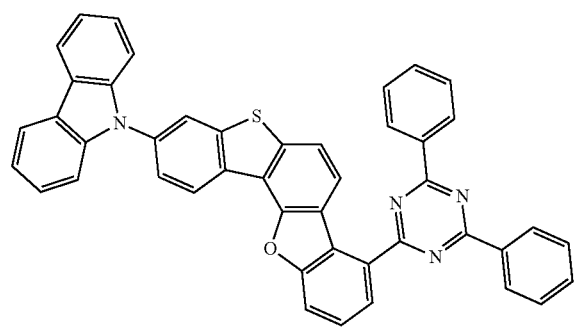
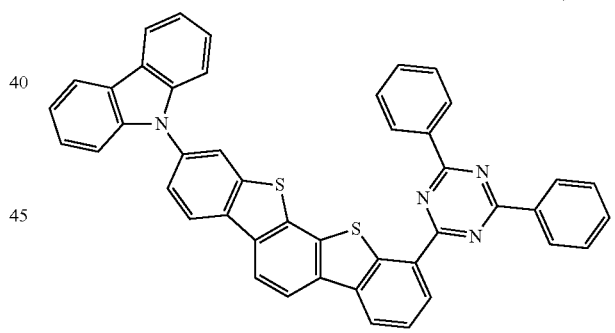
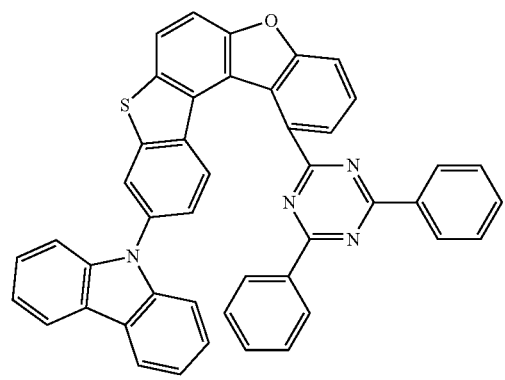
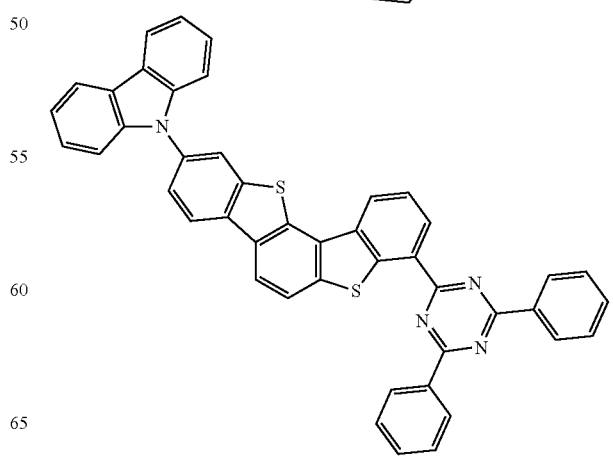

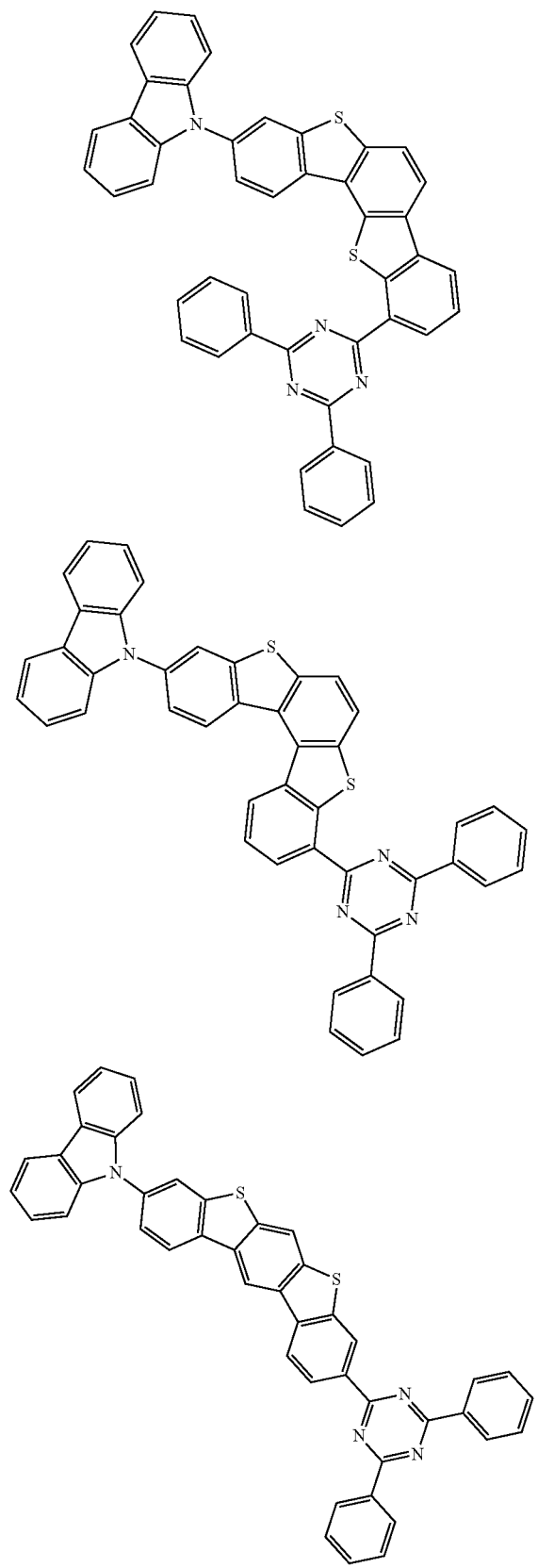
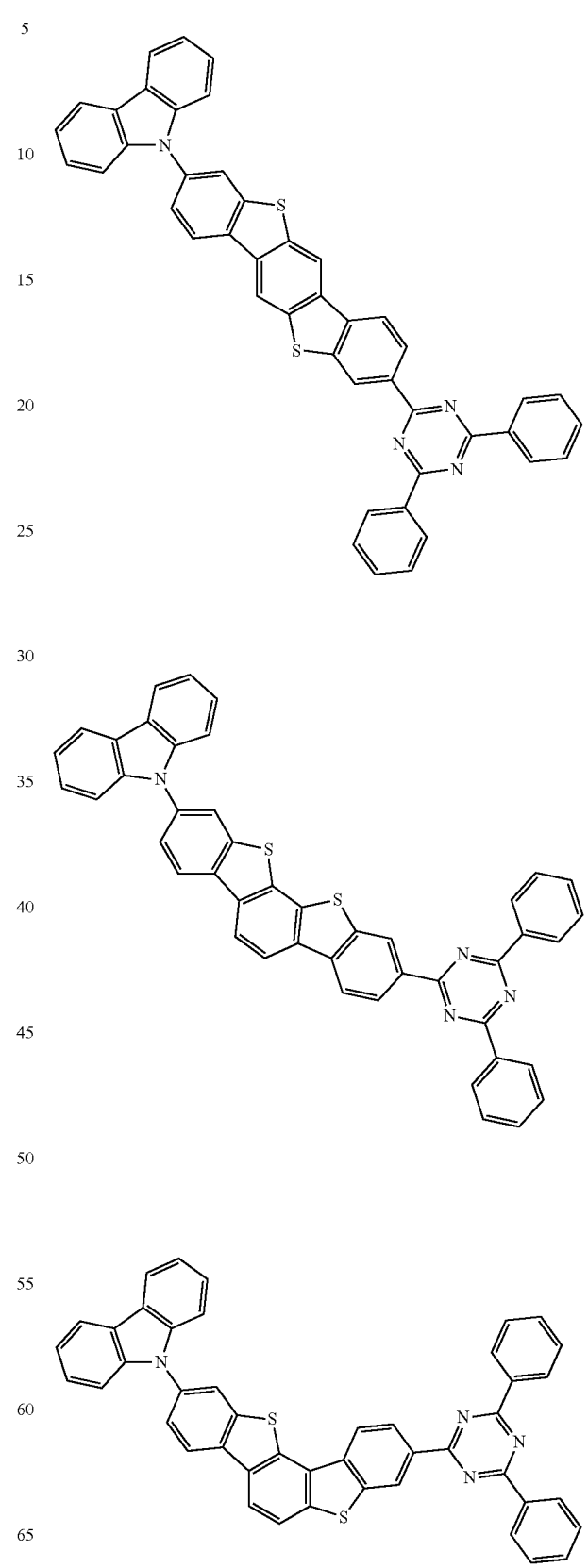

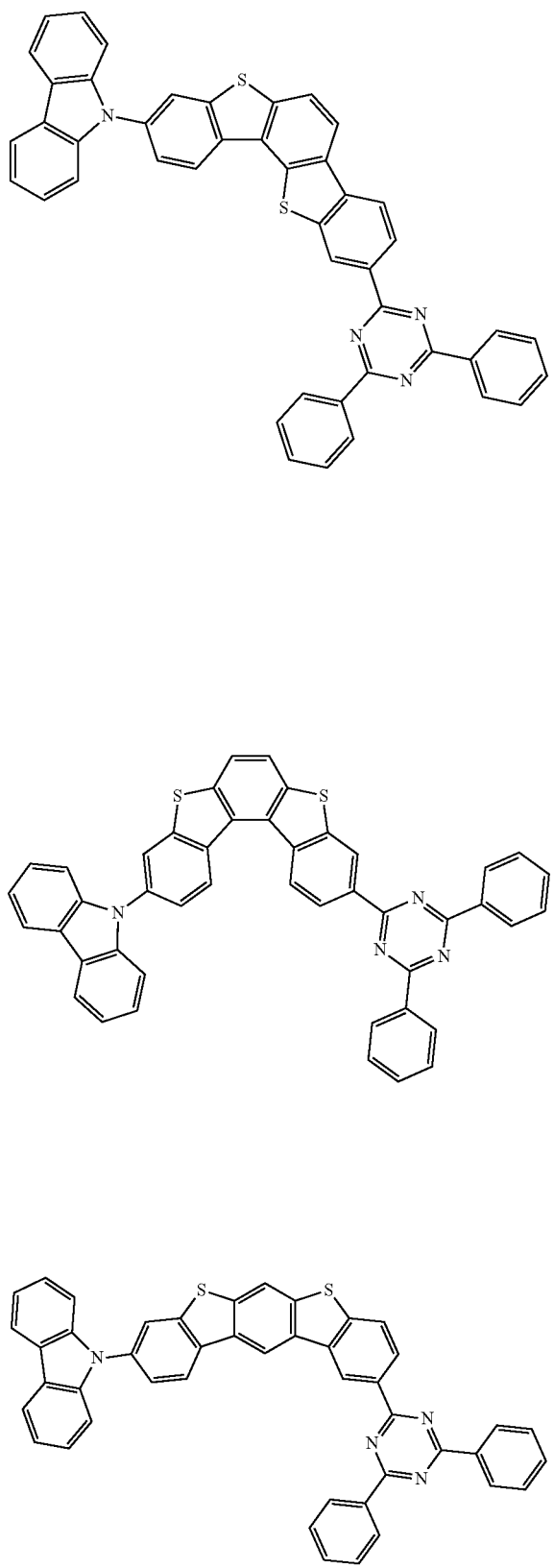
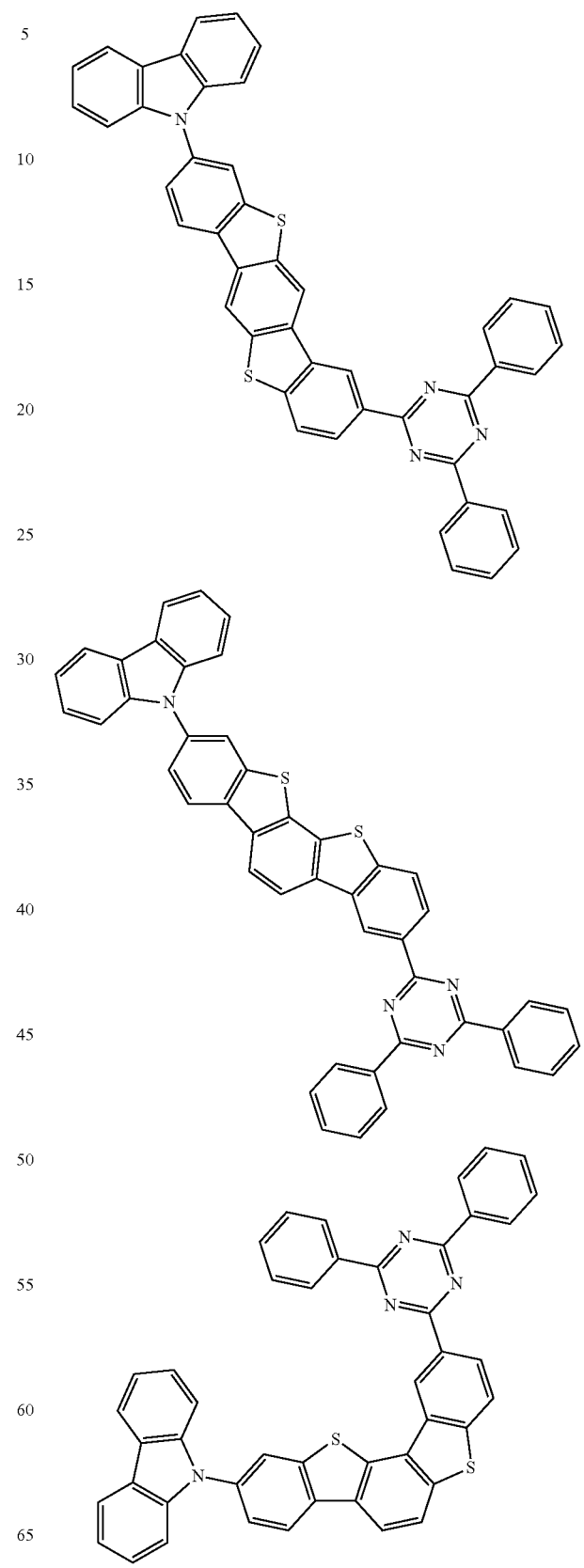

35
-continued
36
-continued
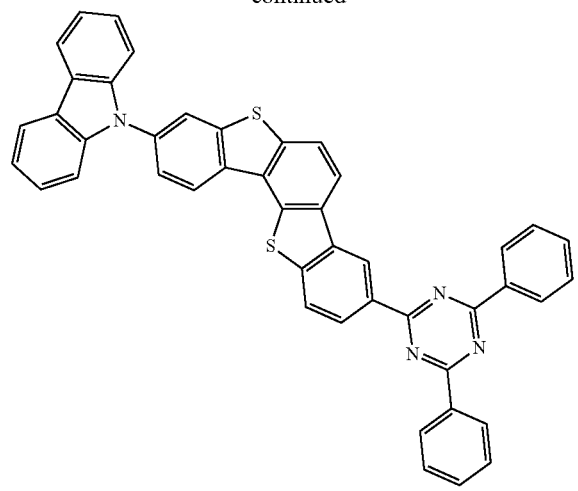
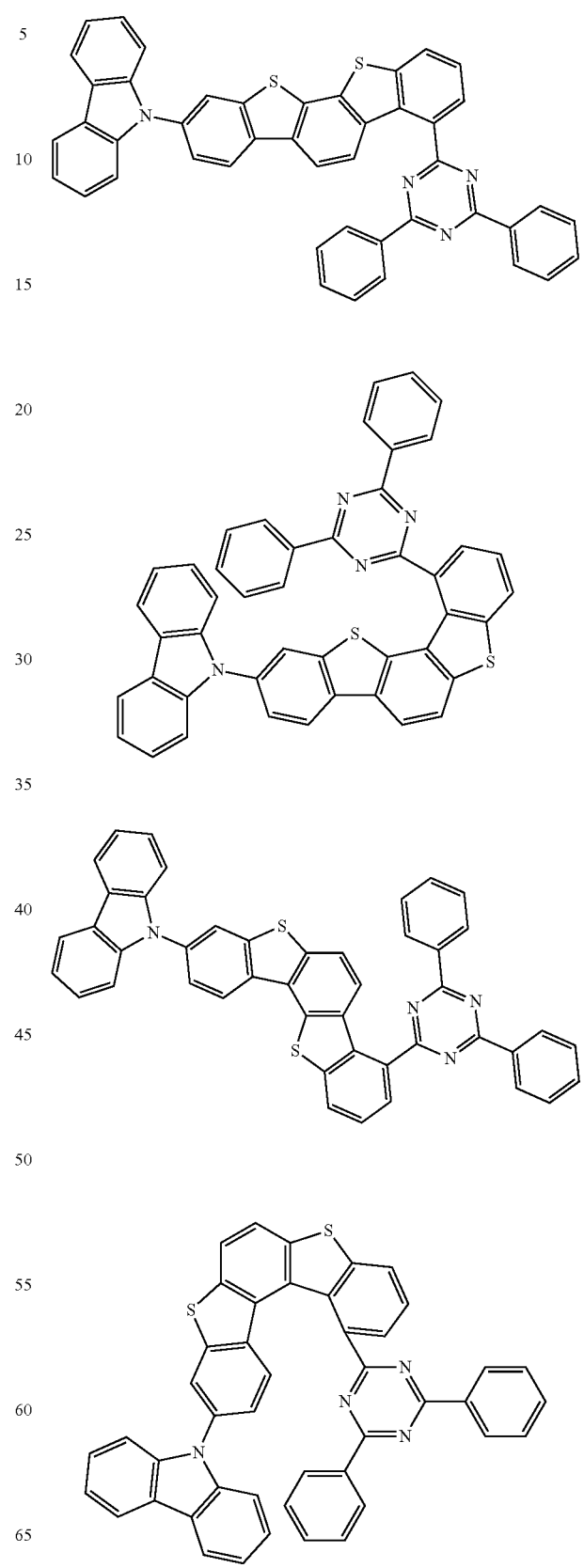

37
-continued
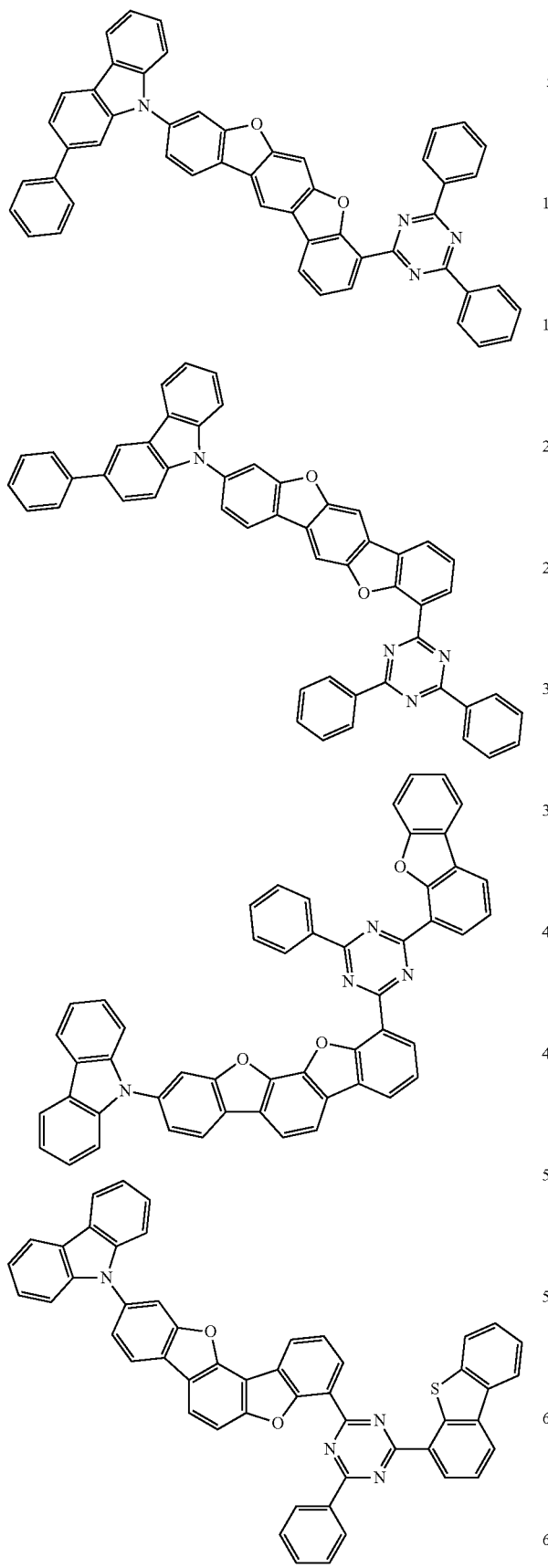
38
-continued
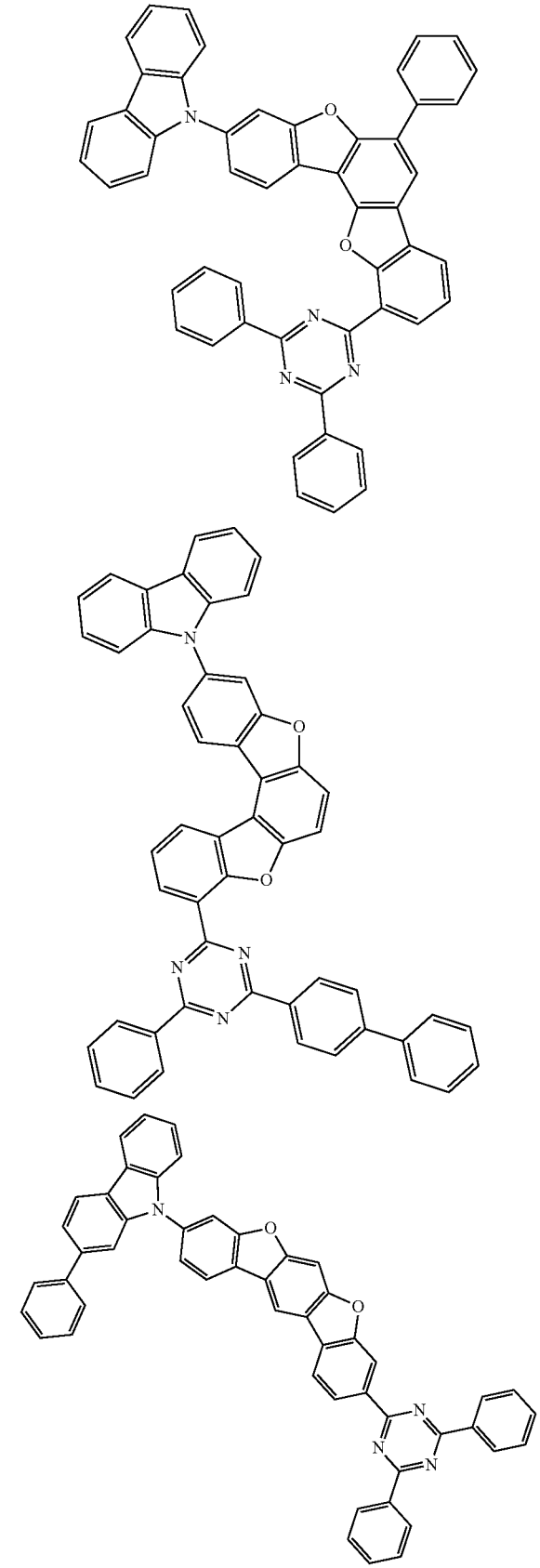

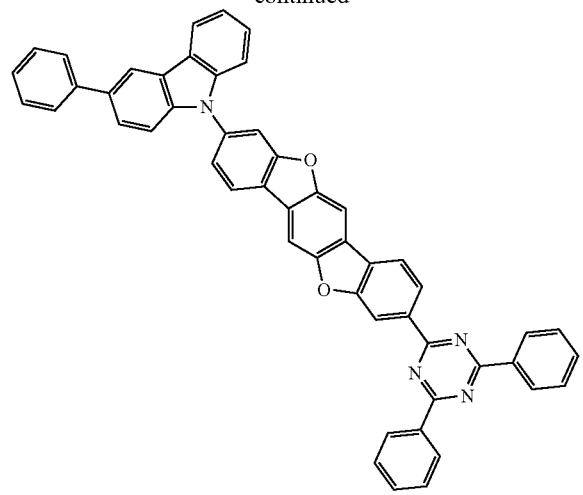
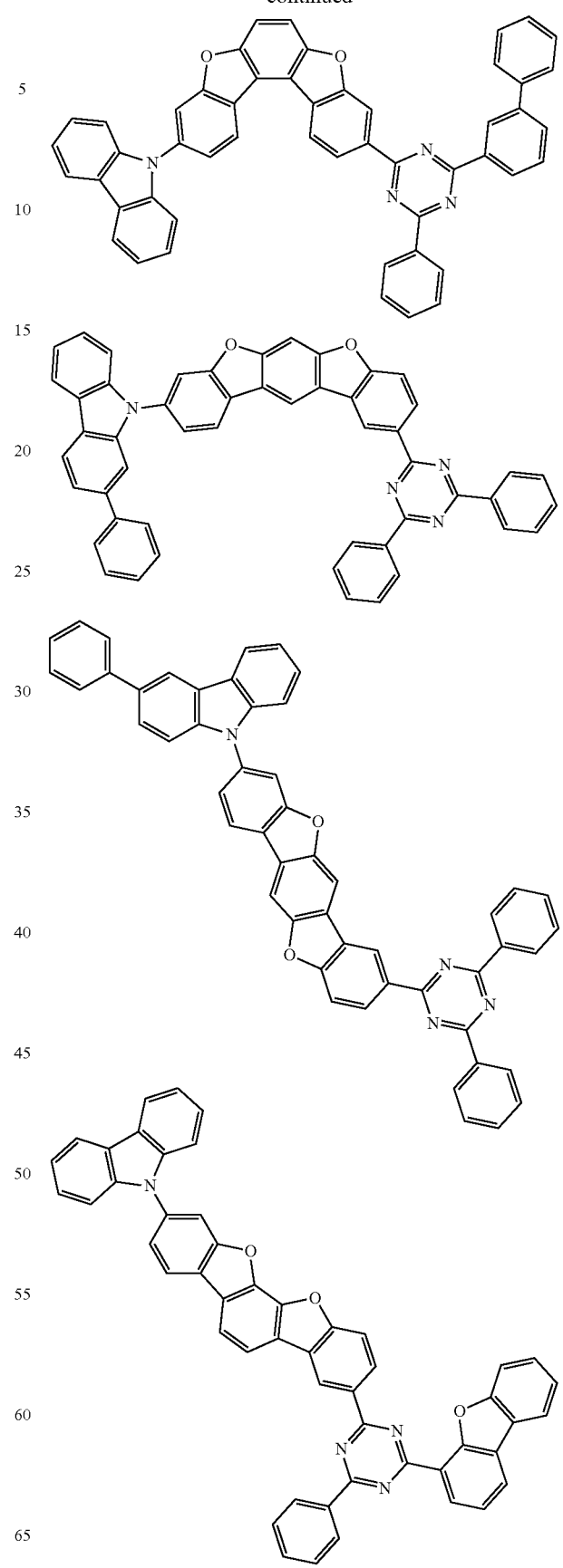

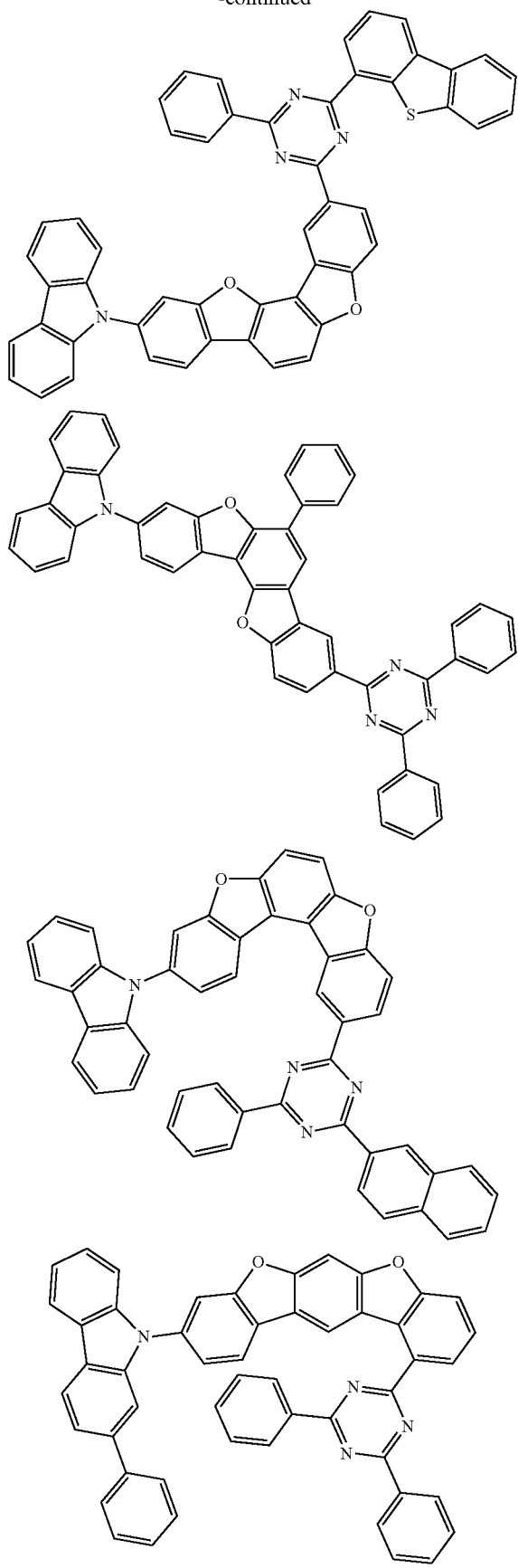
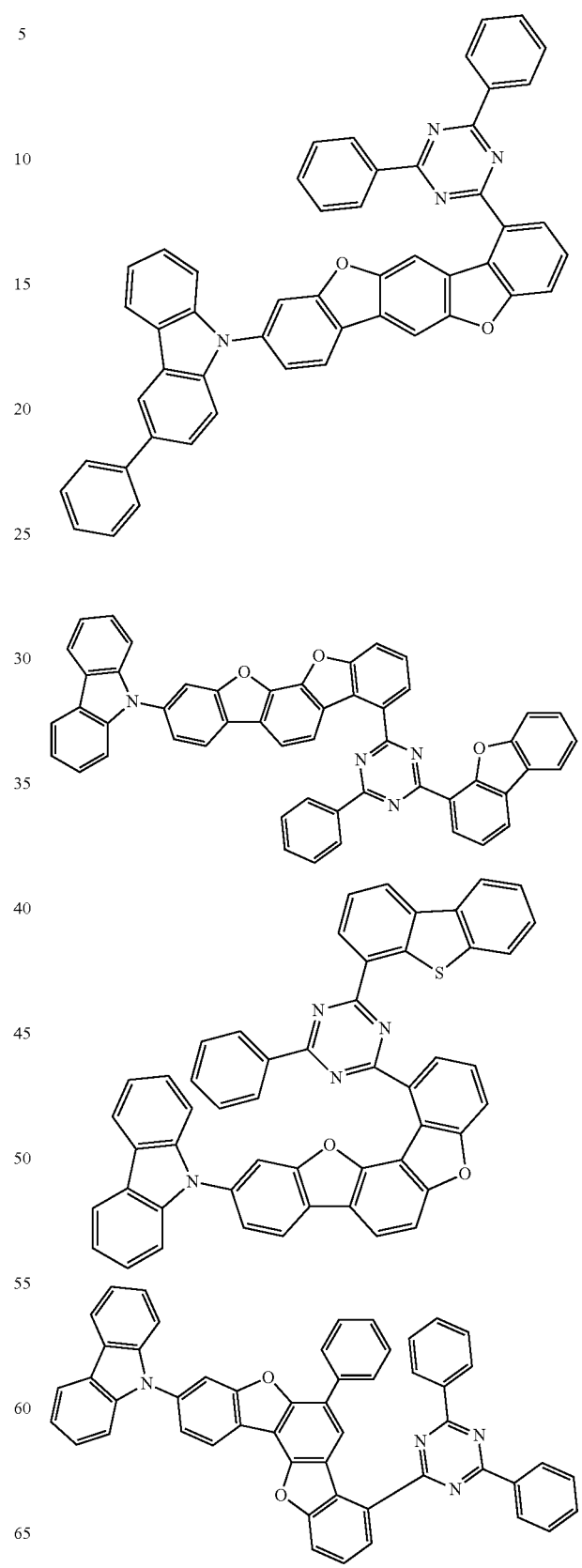

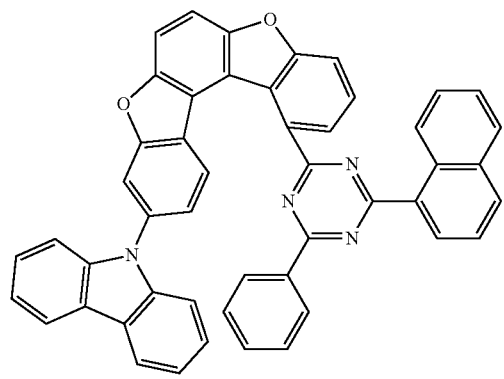
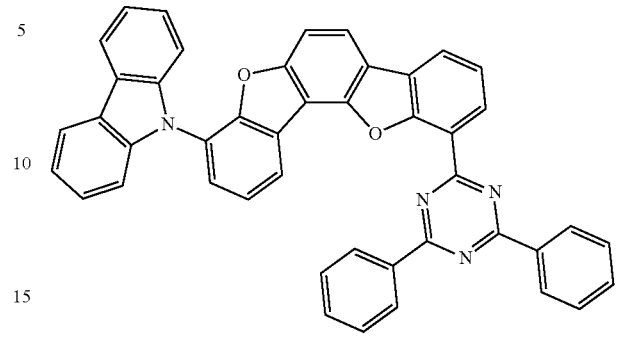
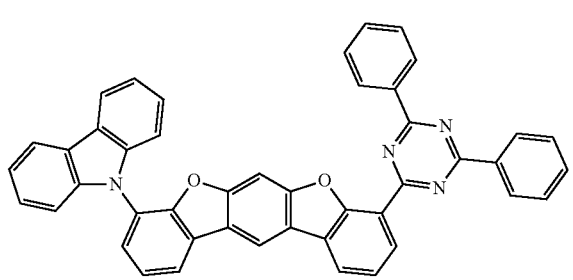
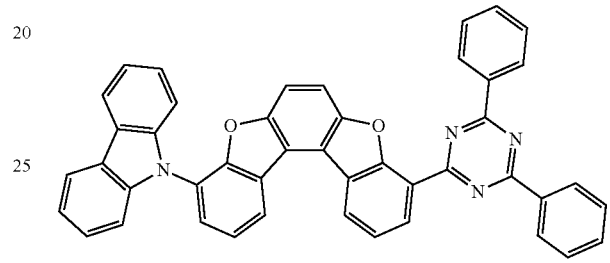
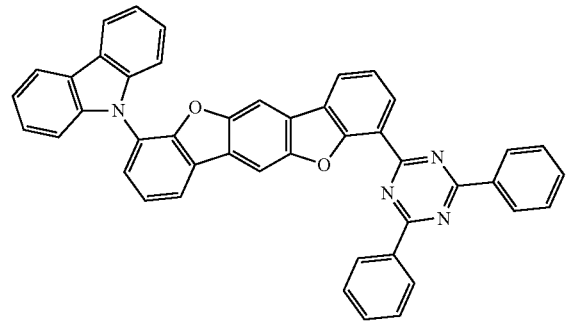
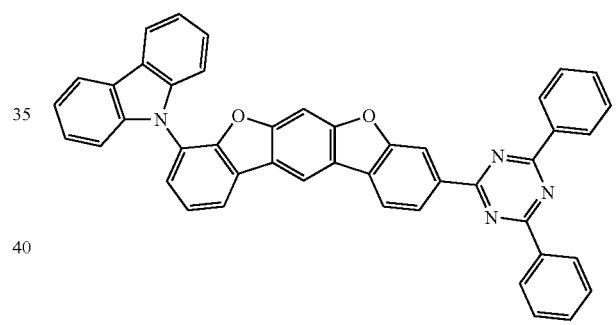
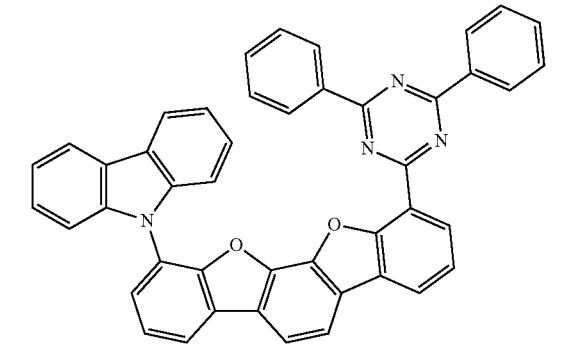
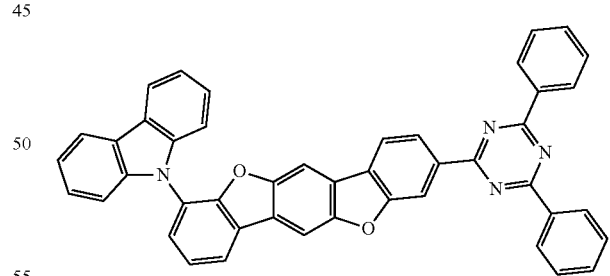
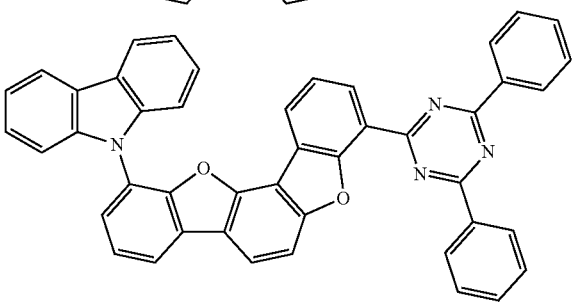
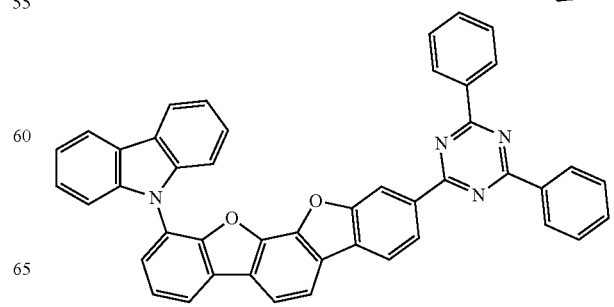

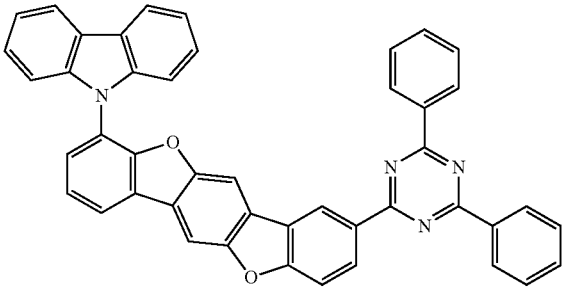
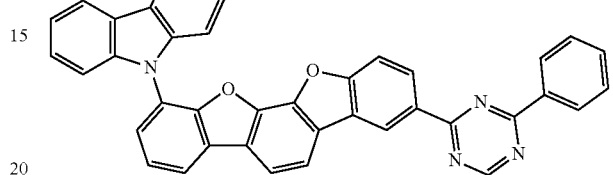
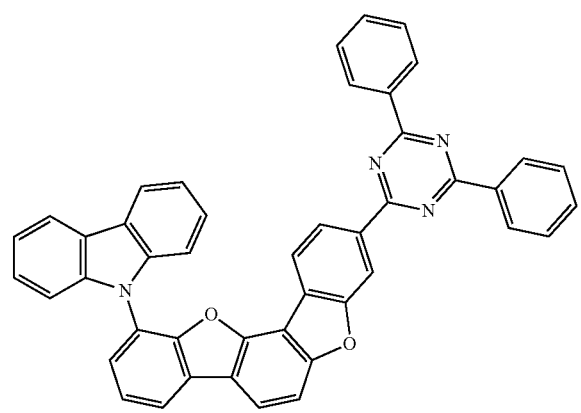
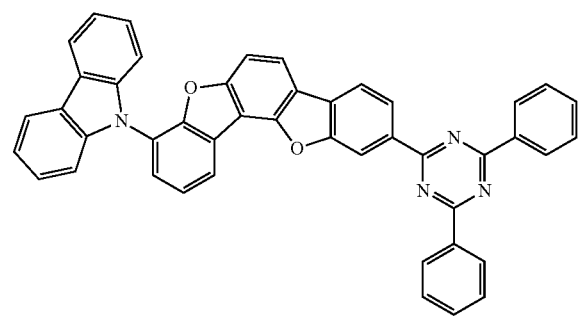
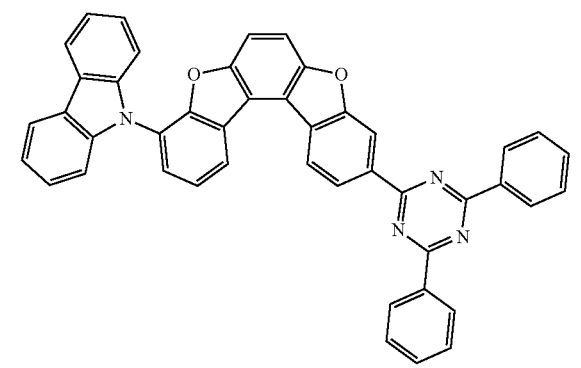
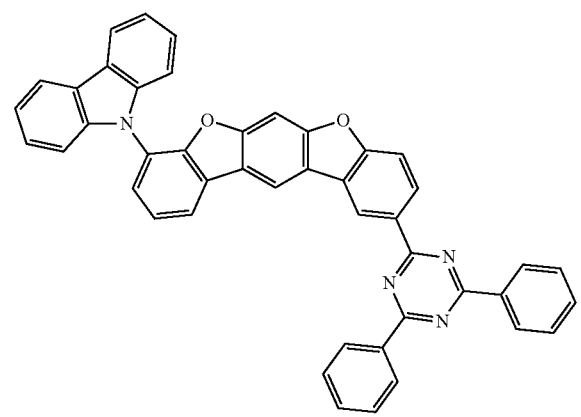

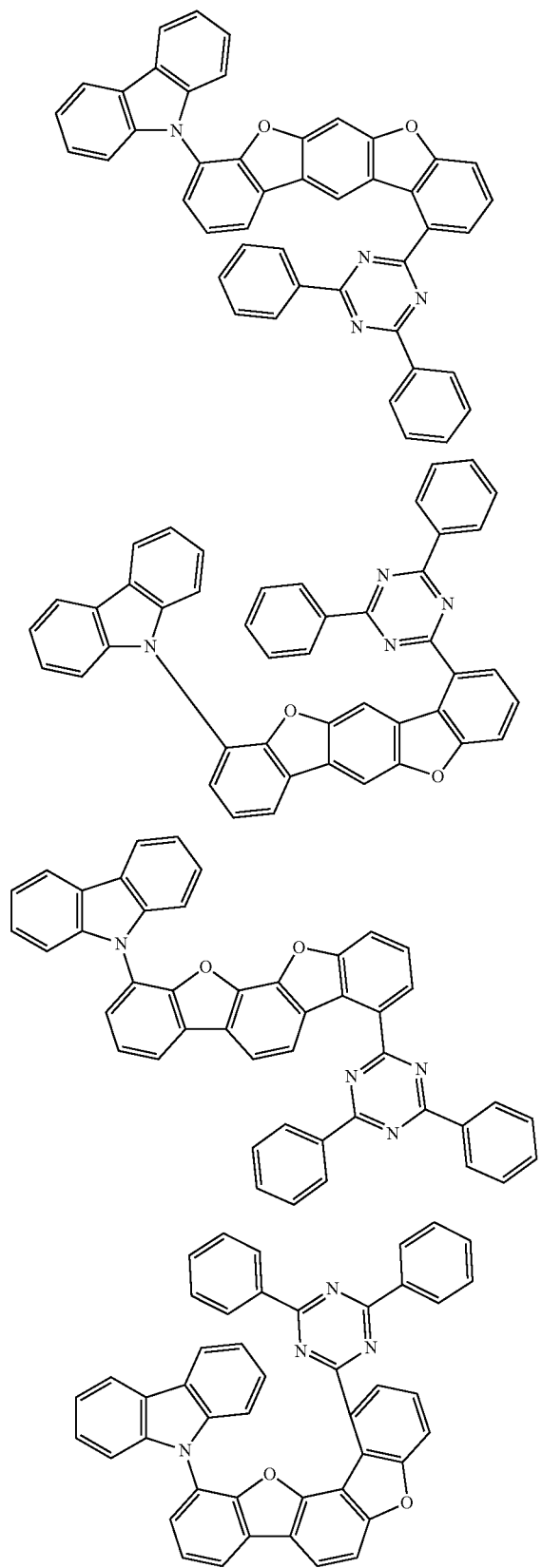
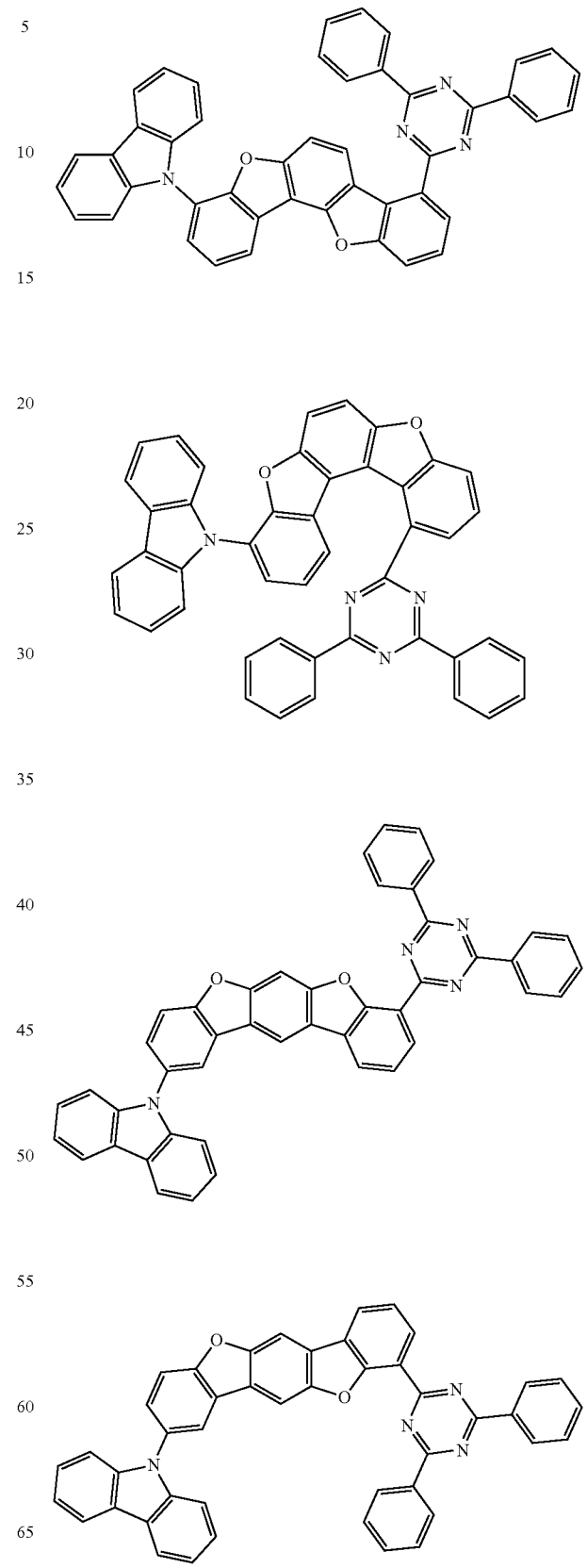

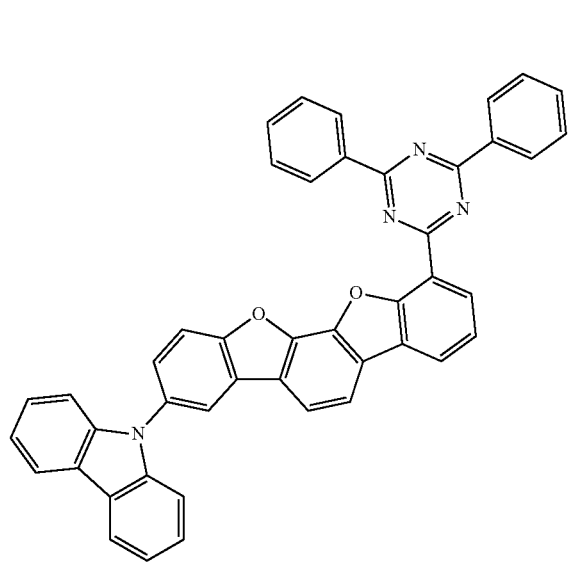
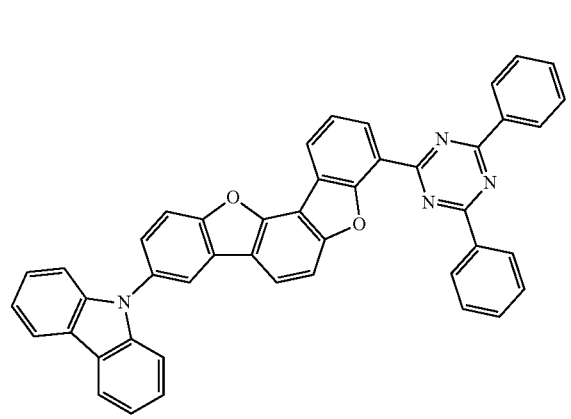
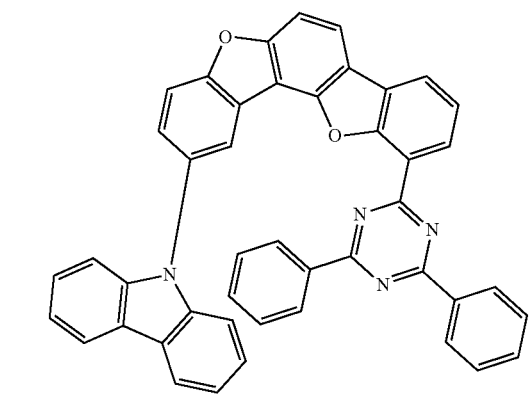
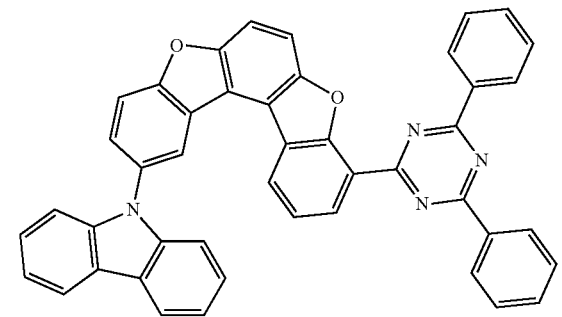
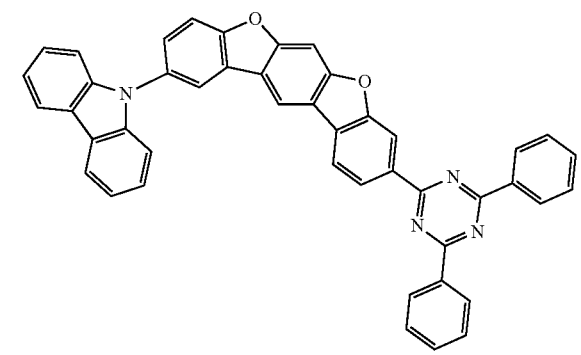
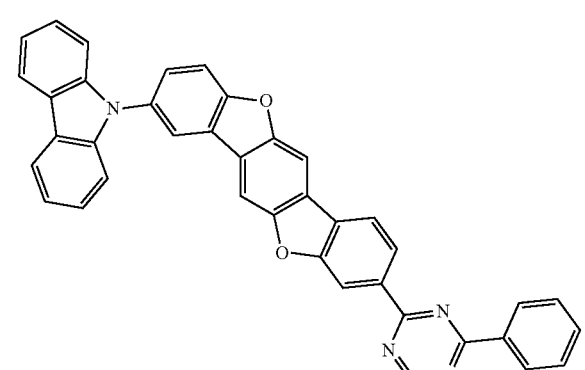
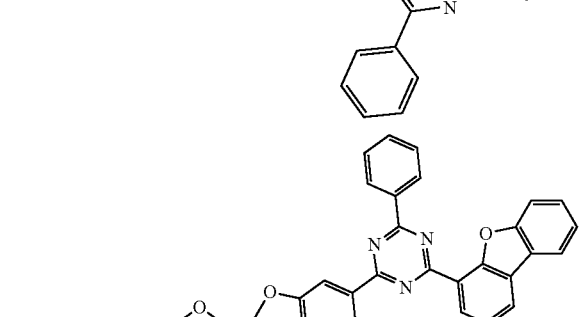
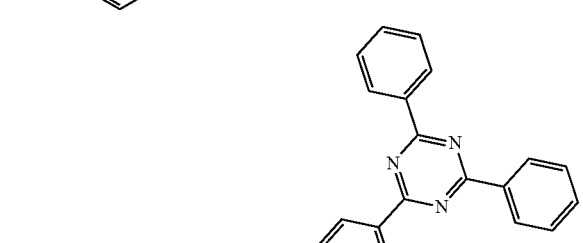
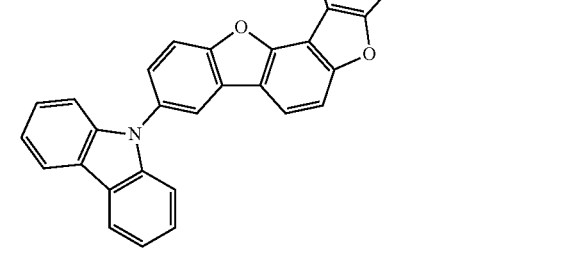

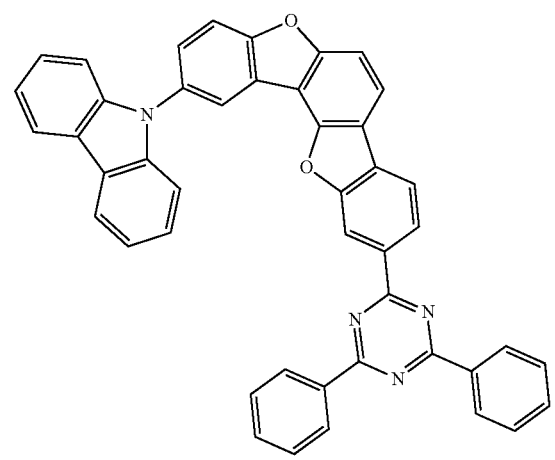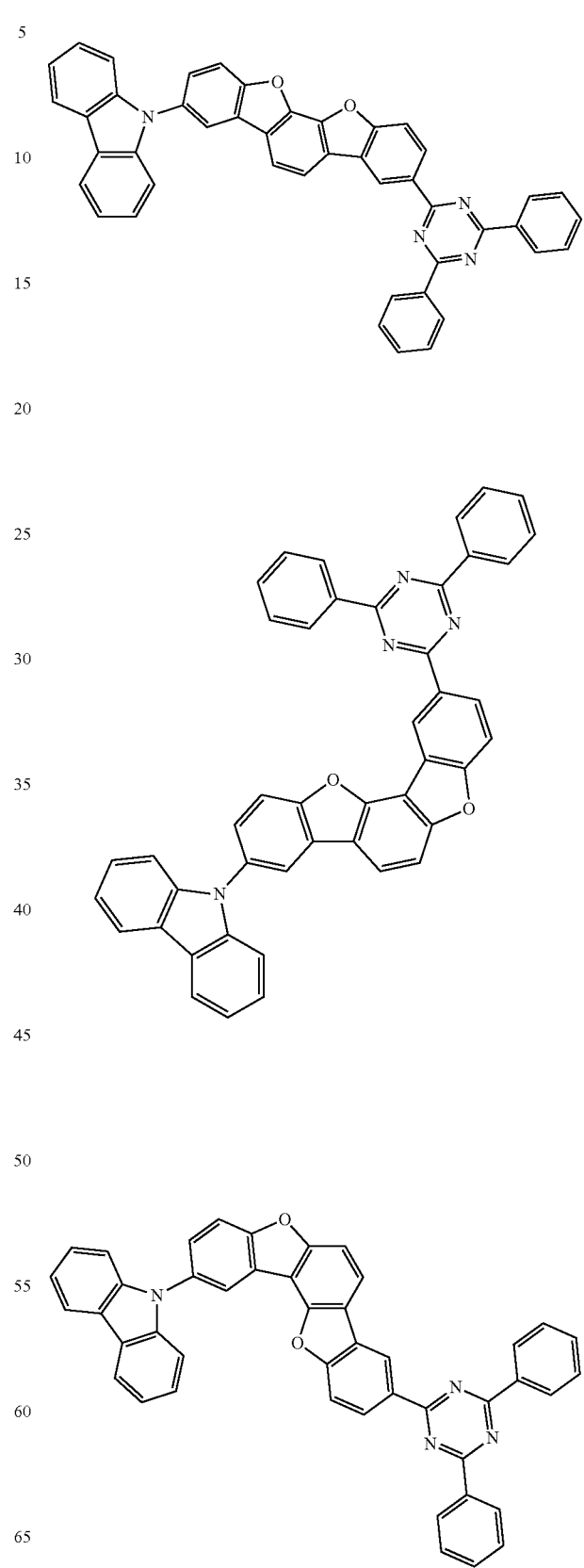

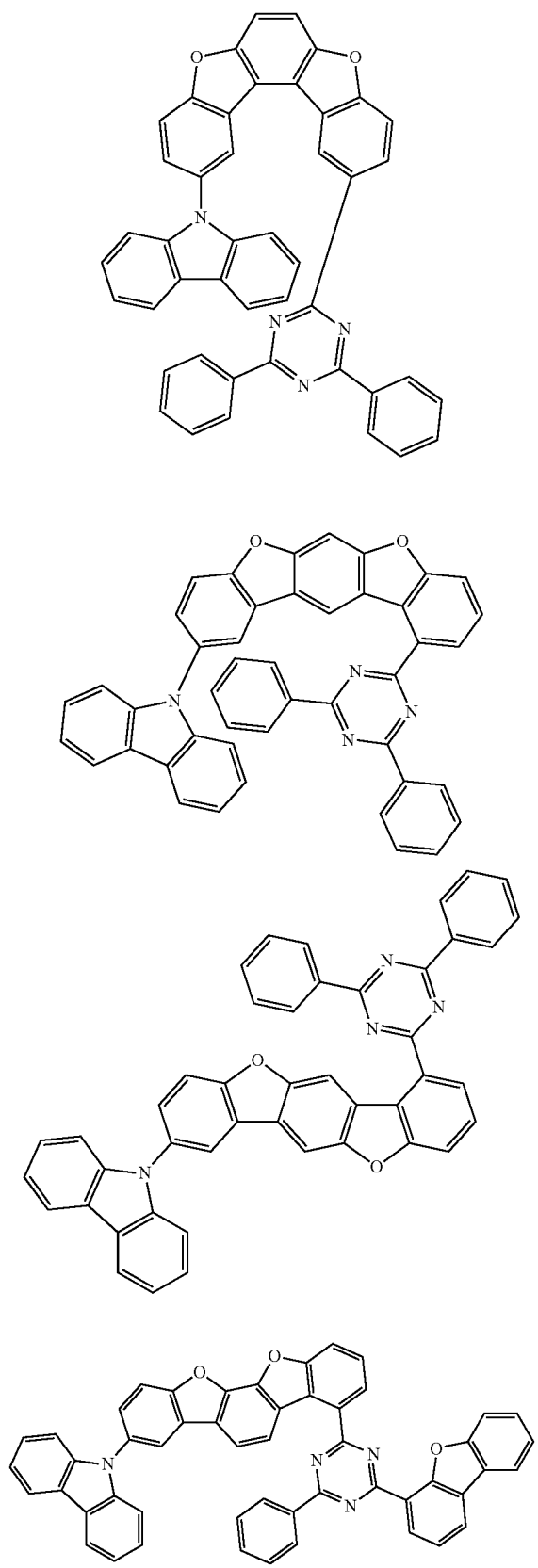
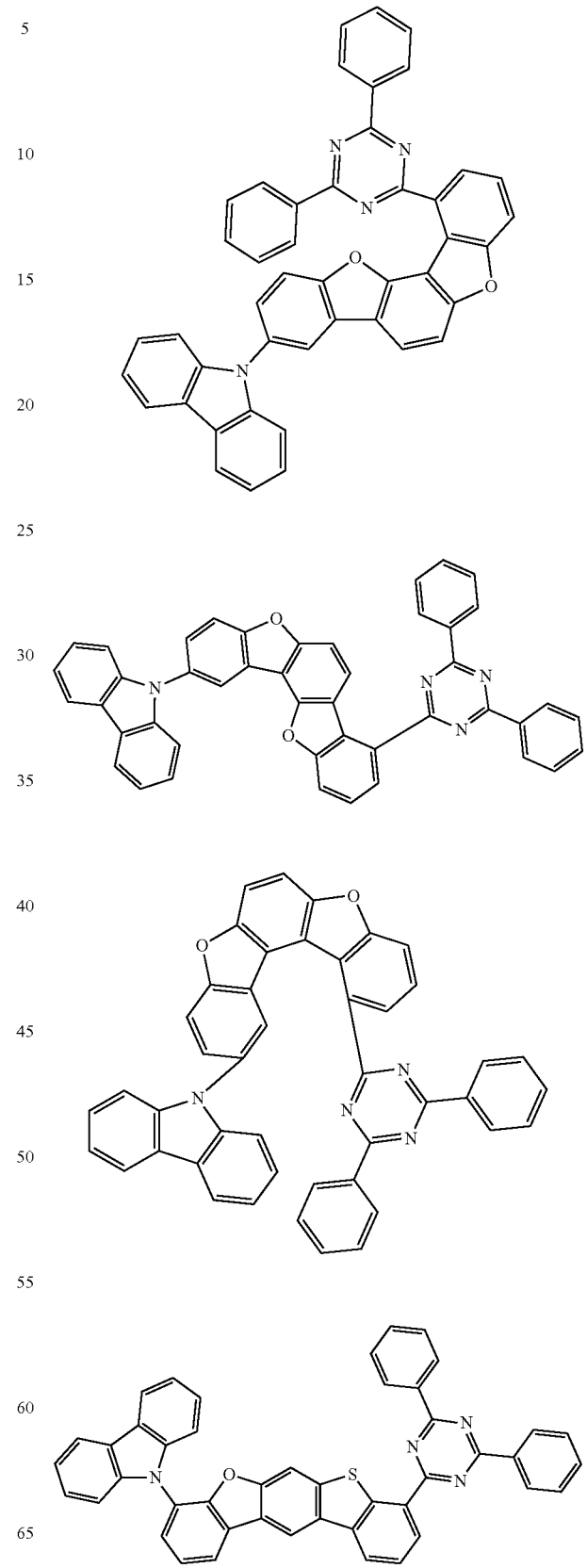

-continued
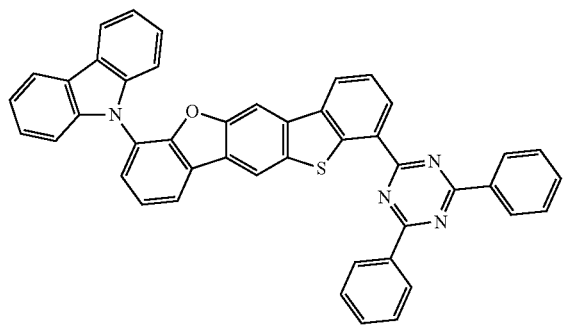
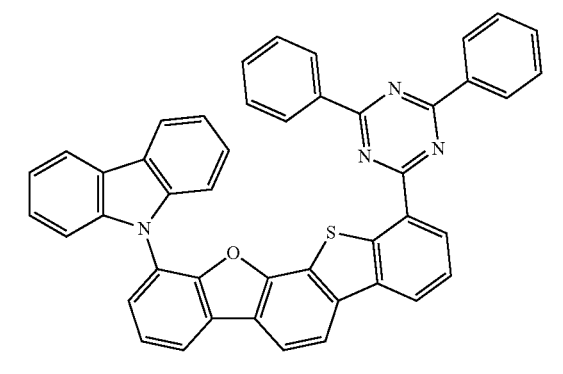
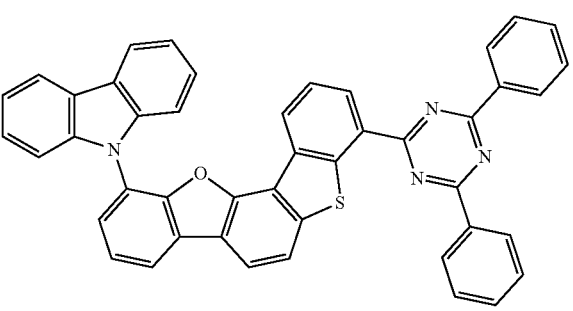
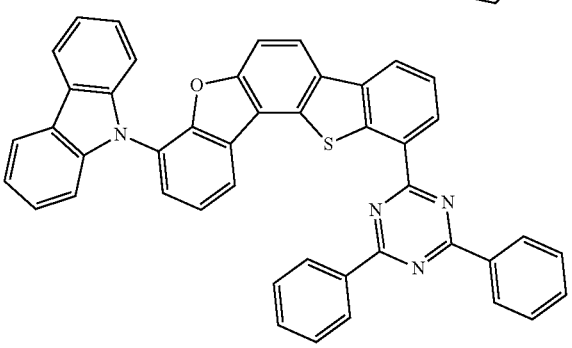
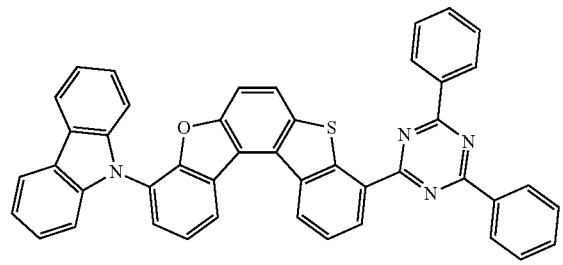
-continued
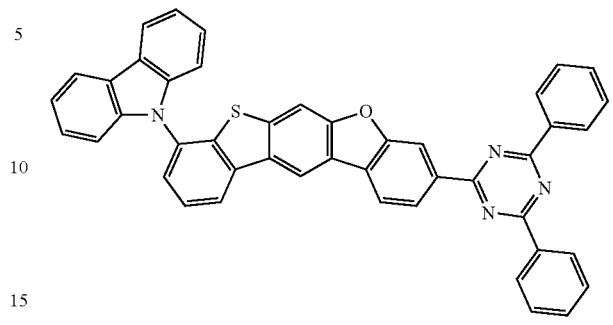
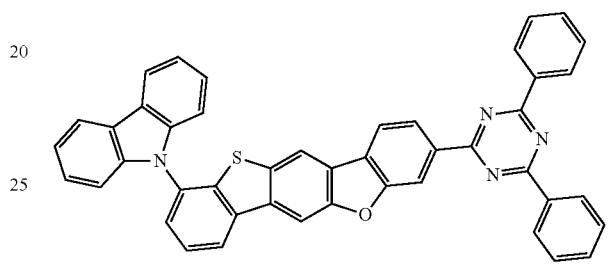
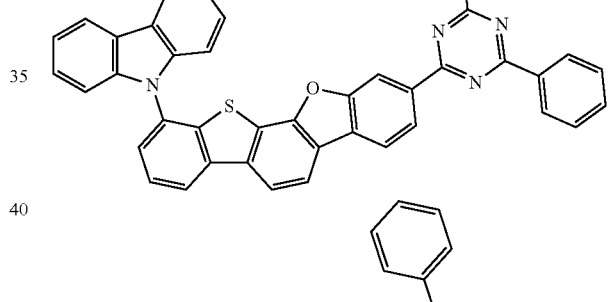
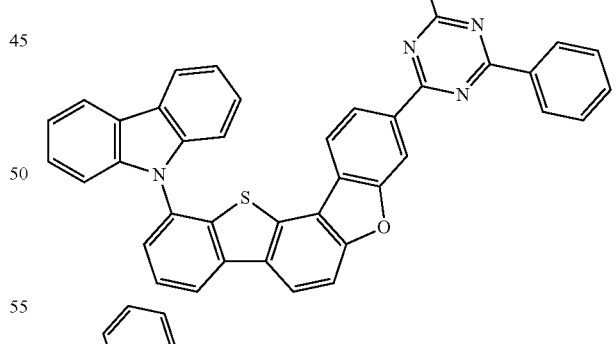
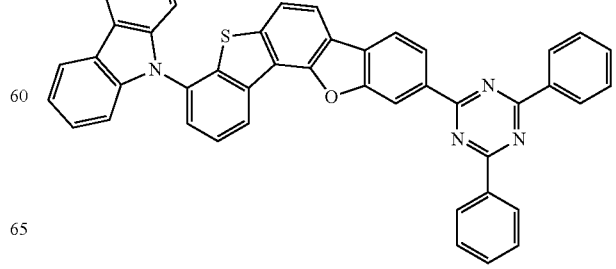

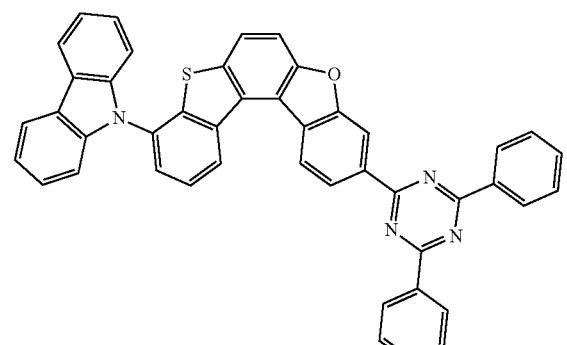
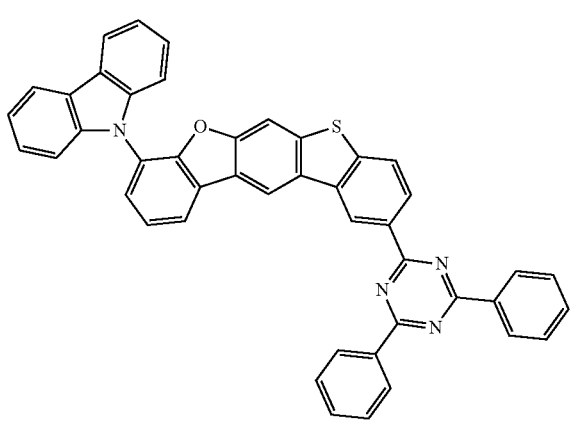
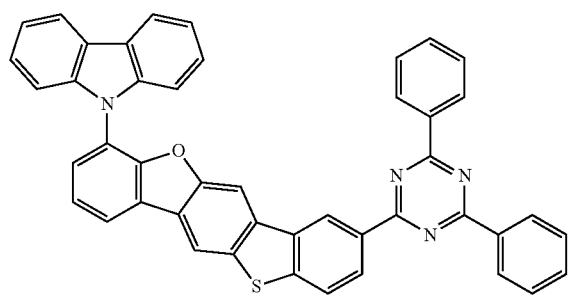
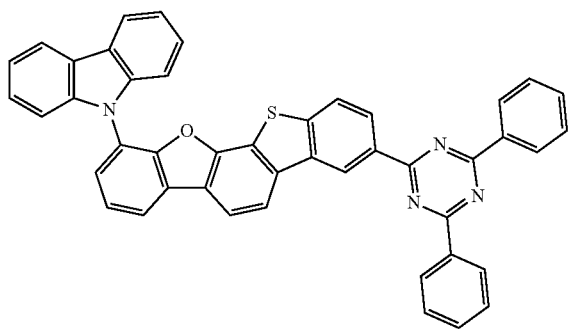
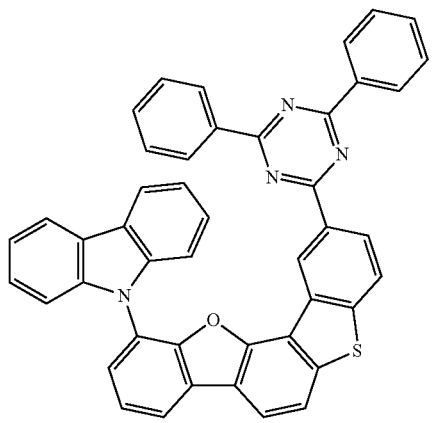
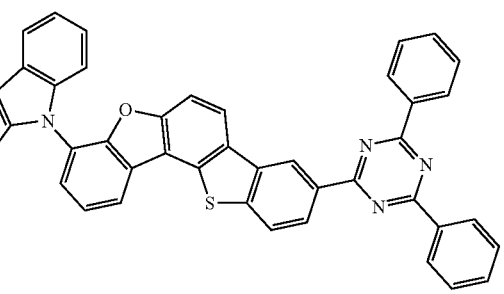
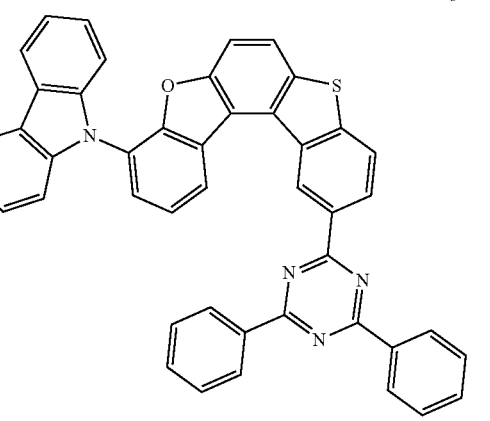
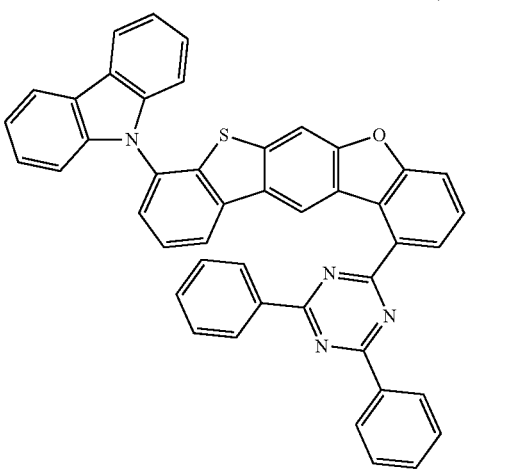

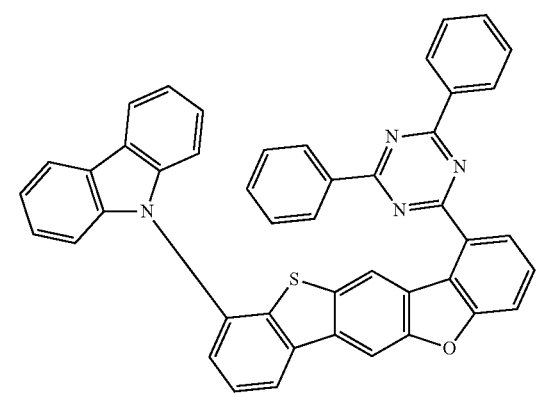
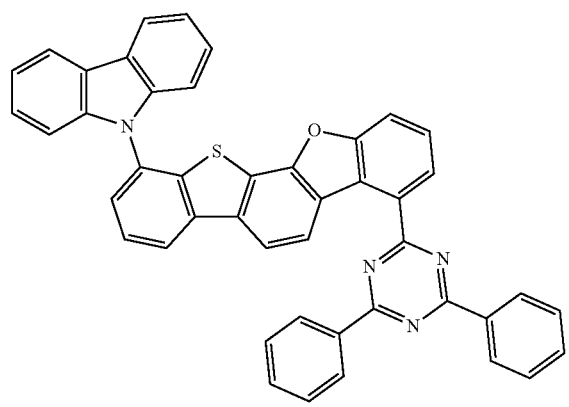
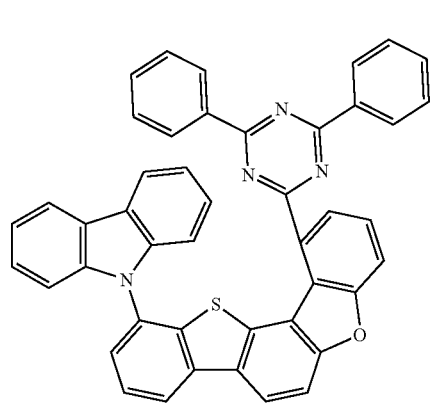
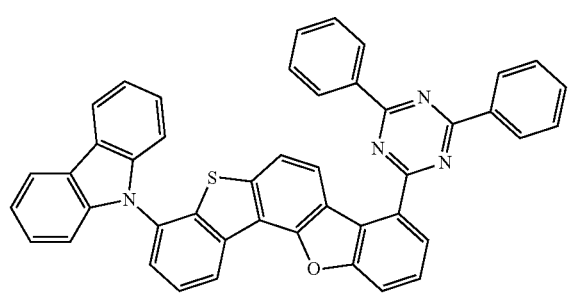
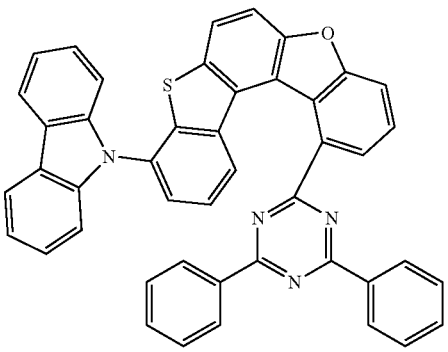
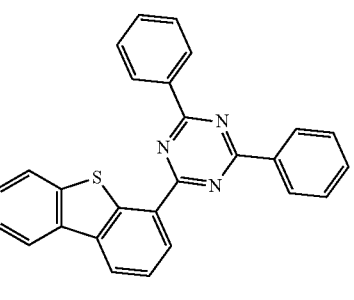
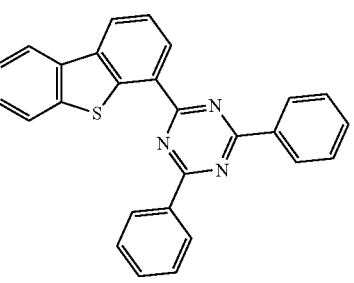
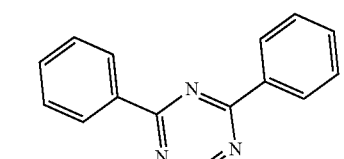
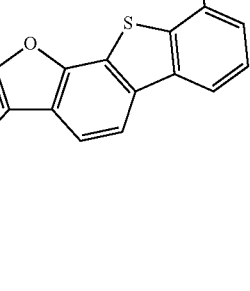

61
-continued
62
-continued
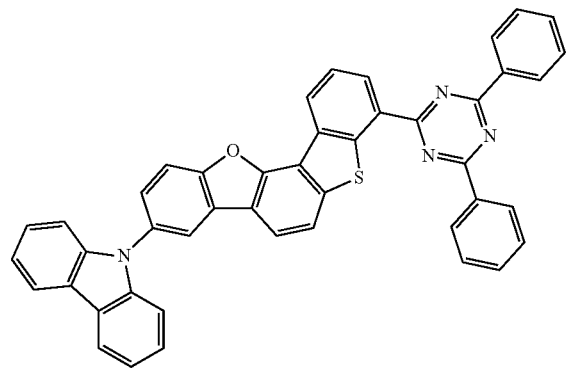
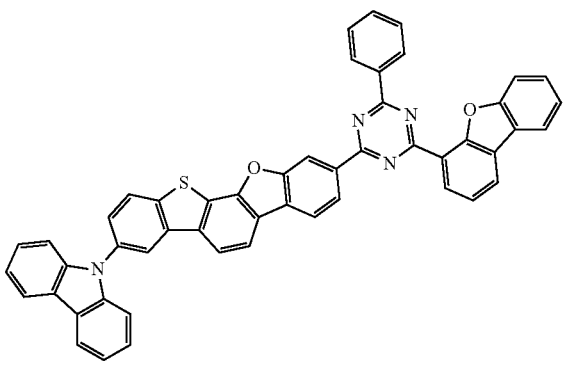
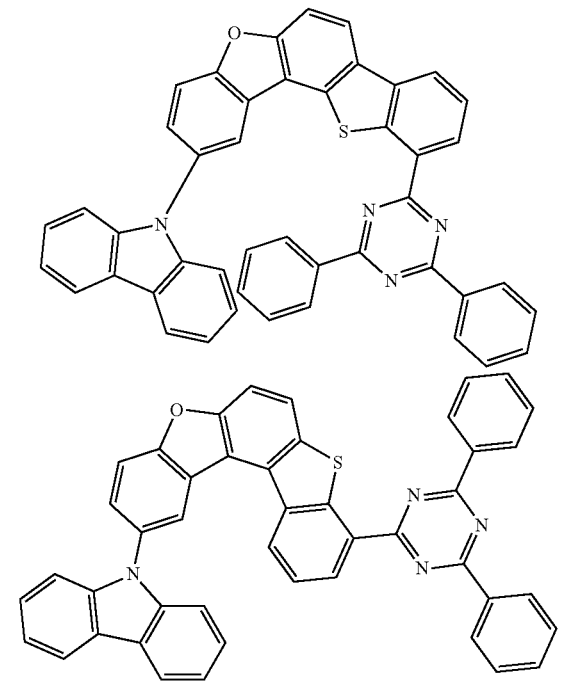
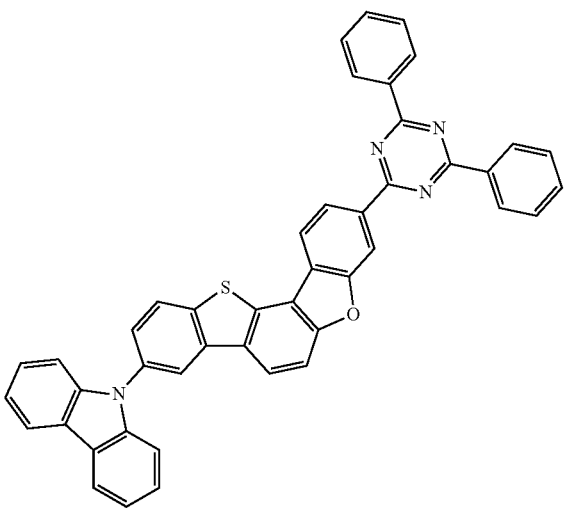
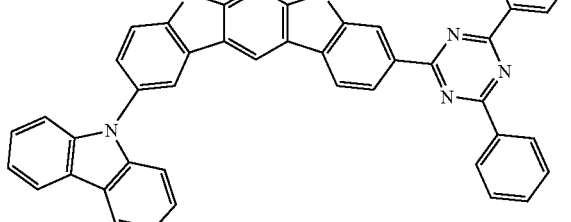
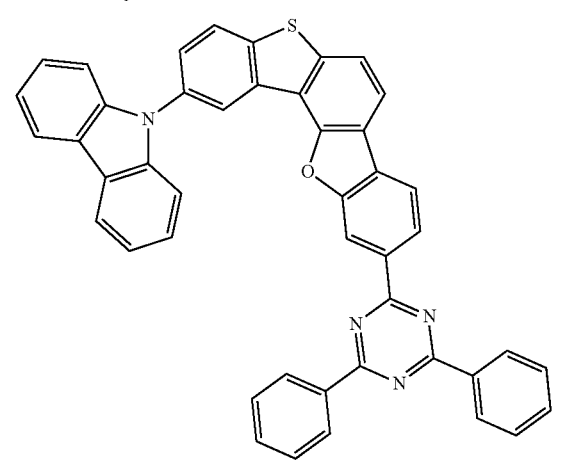
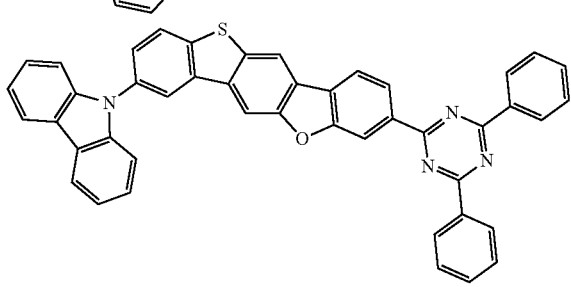
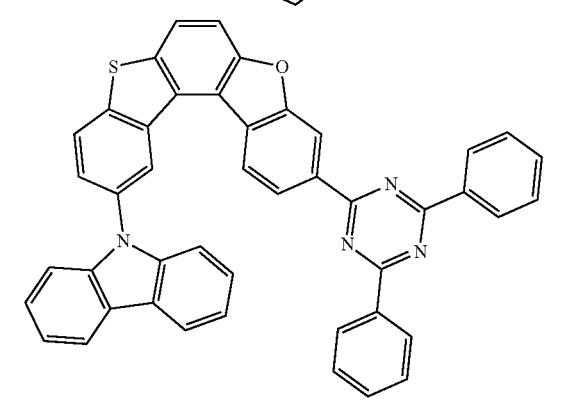

-continued
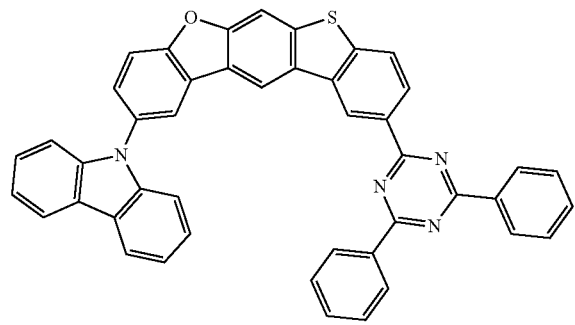
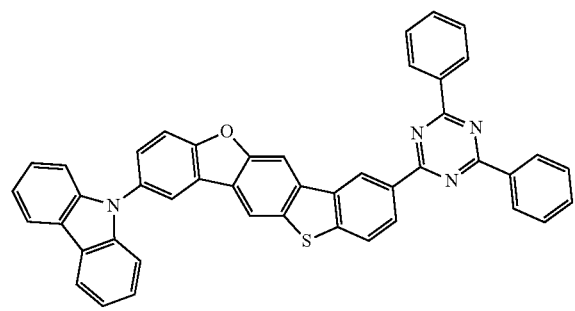
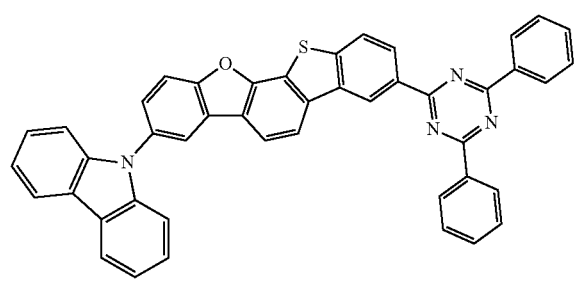
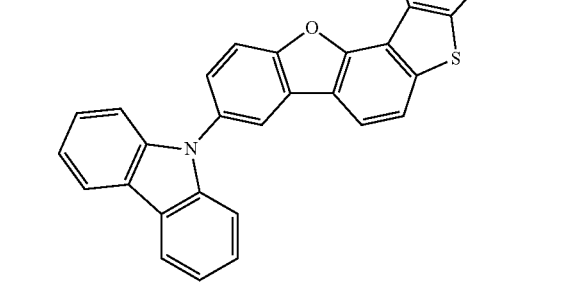
-continued
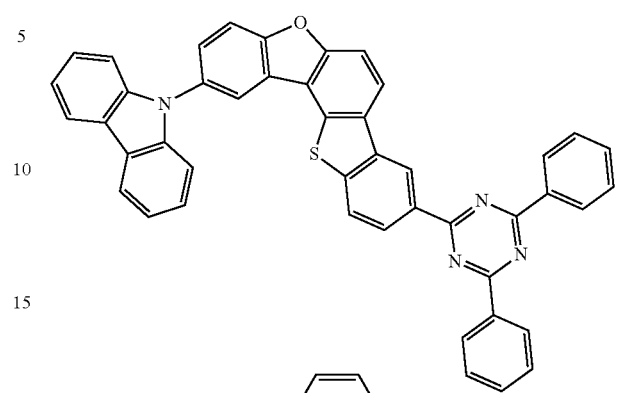
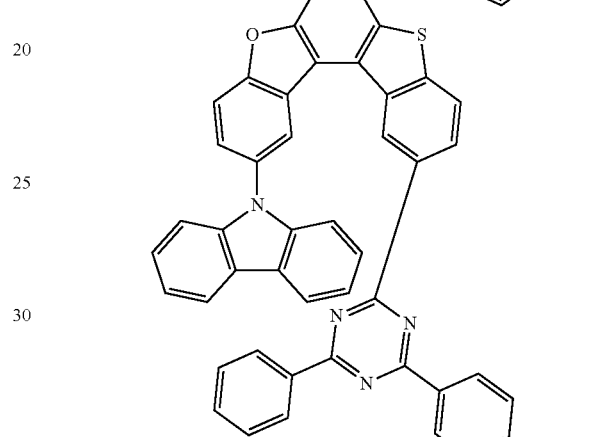
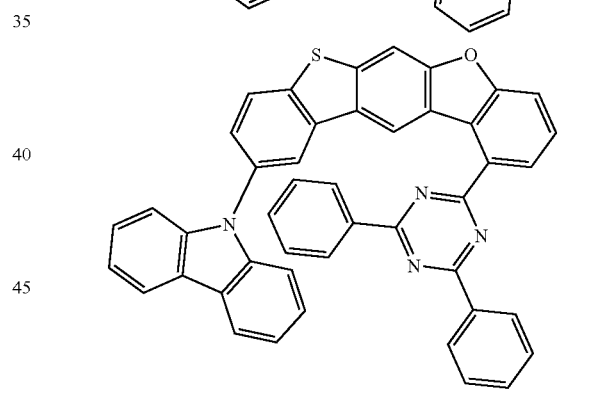
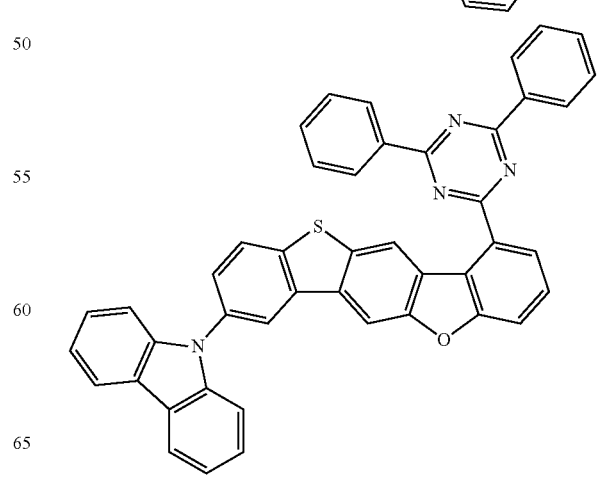

65
-continued
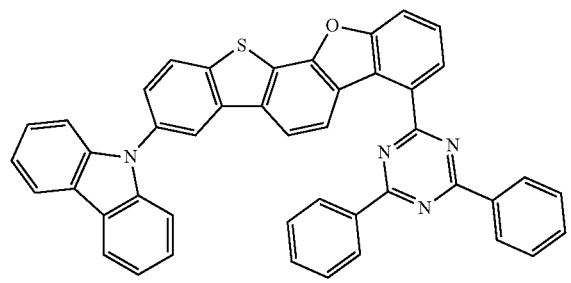
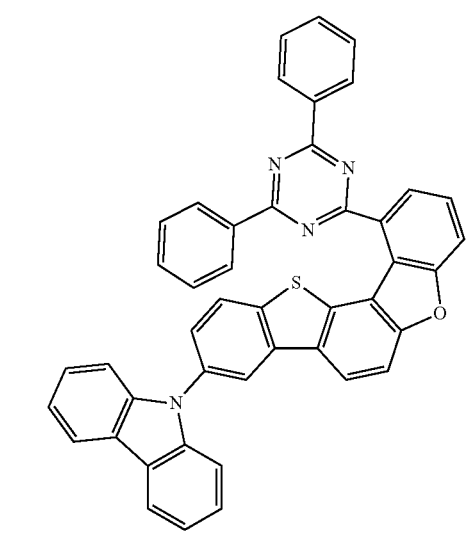
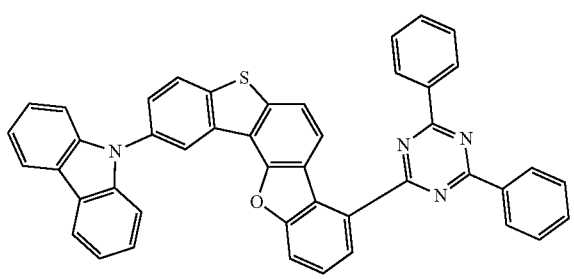
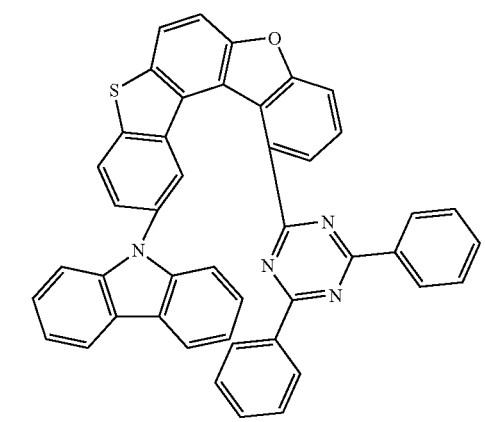
66
-continued
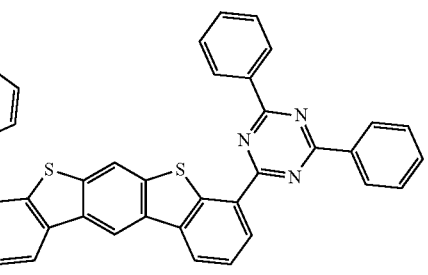
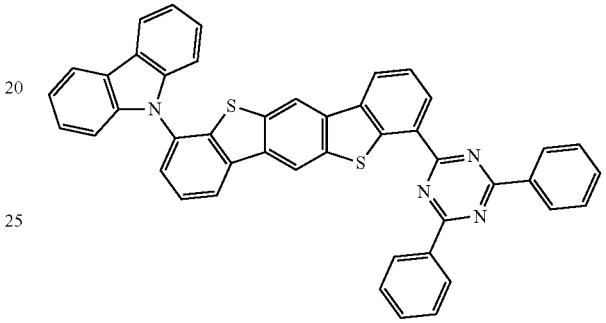
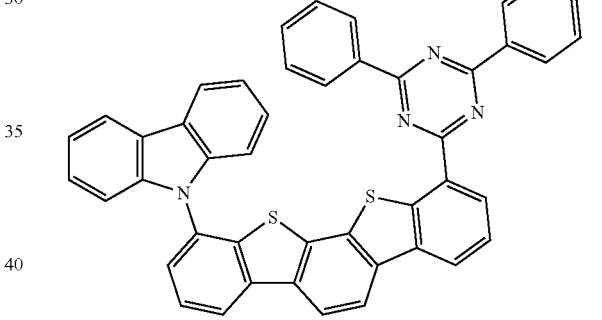
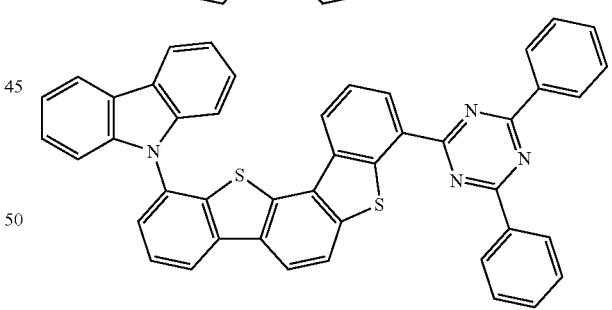
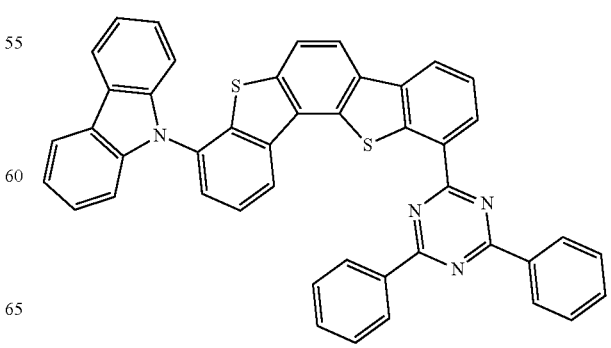

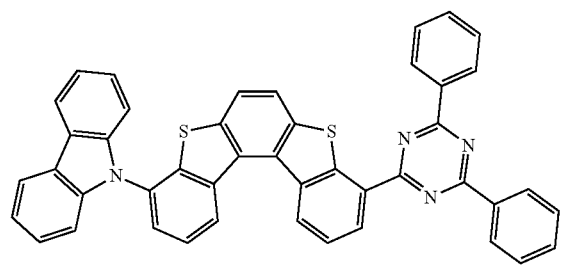
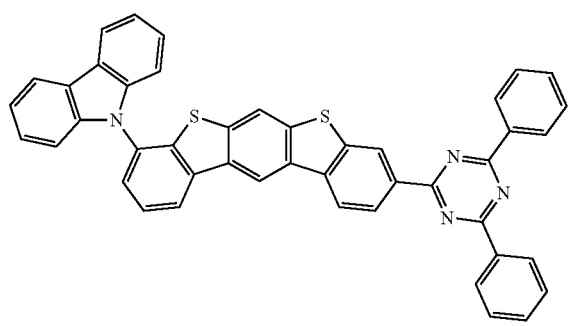
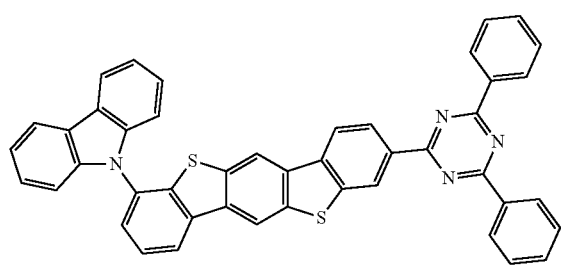
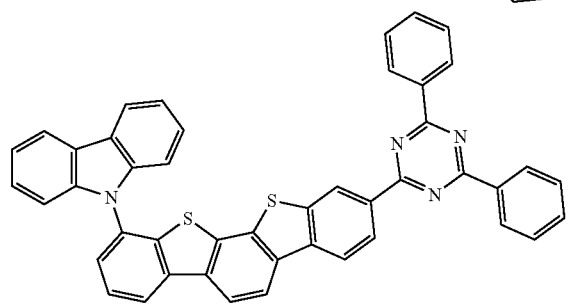
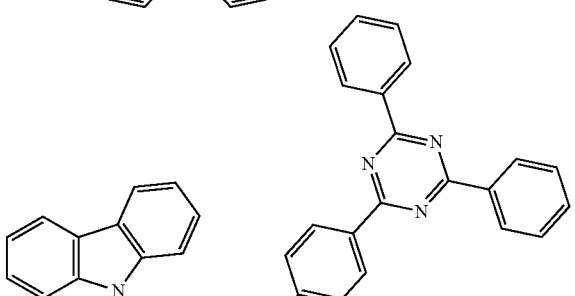
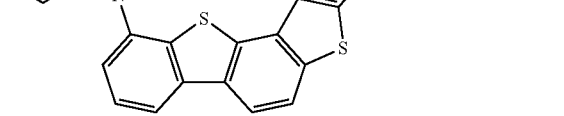
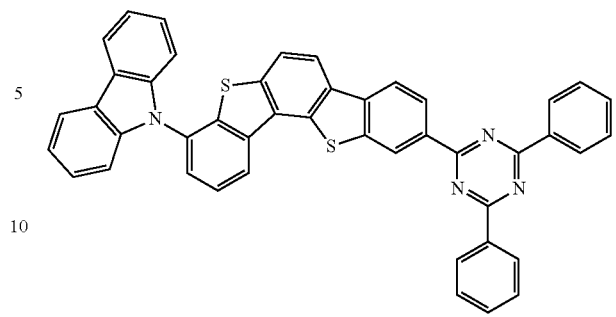
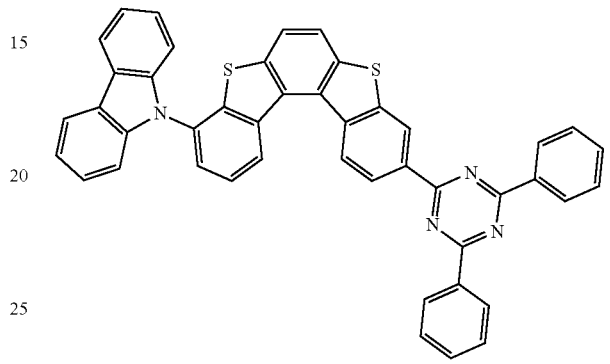
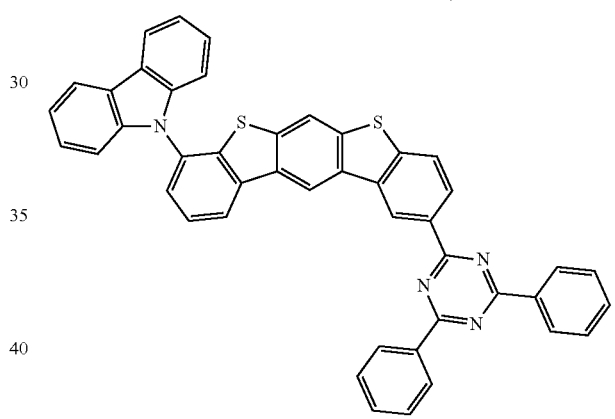
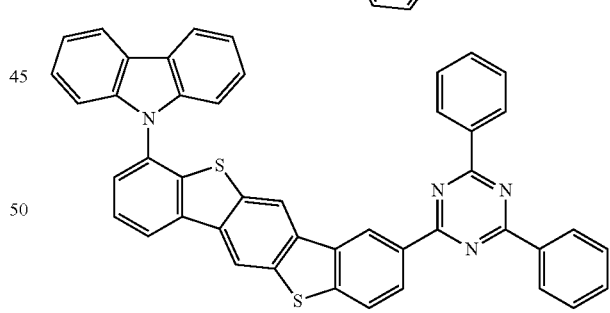
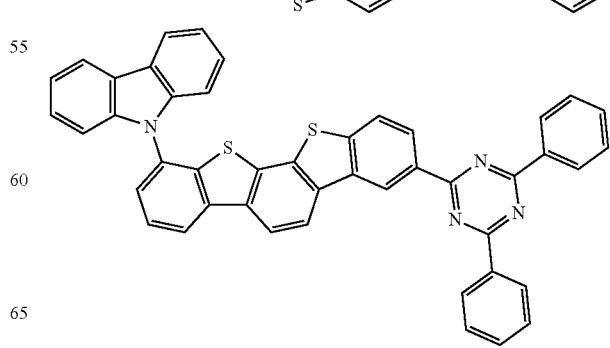

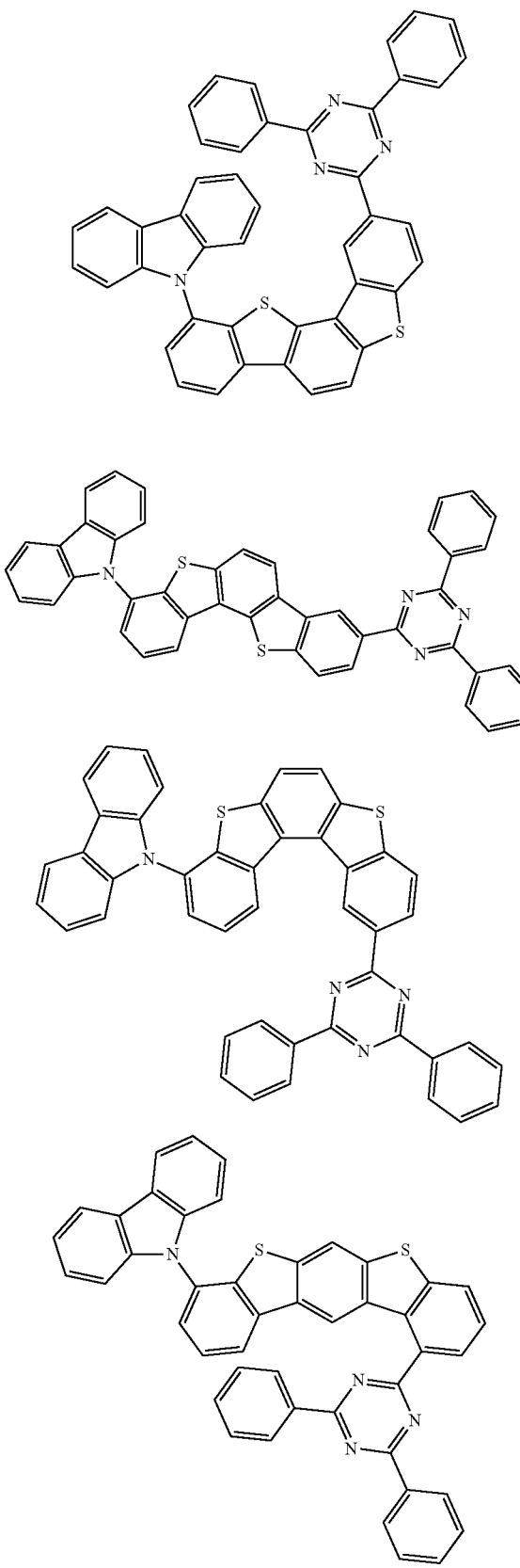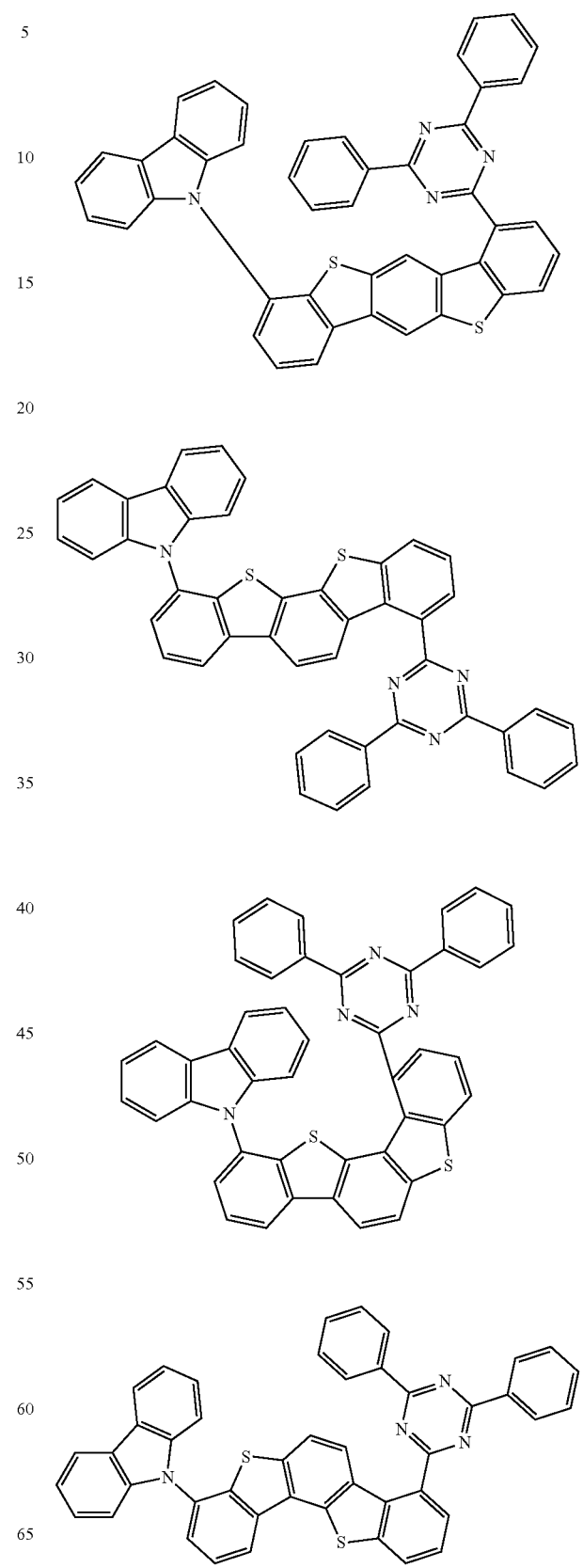

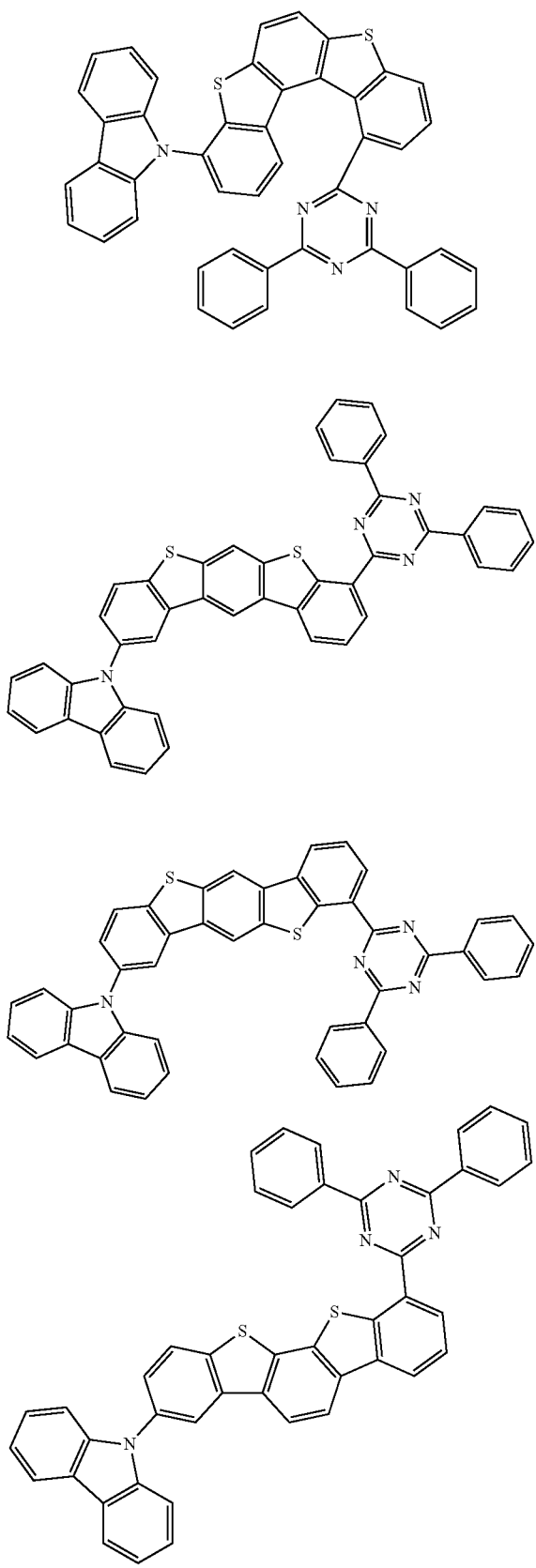
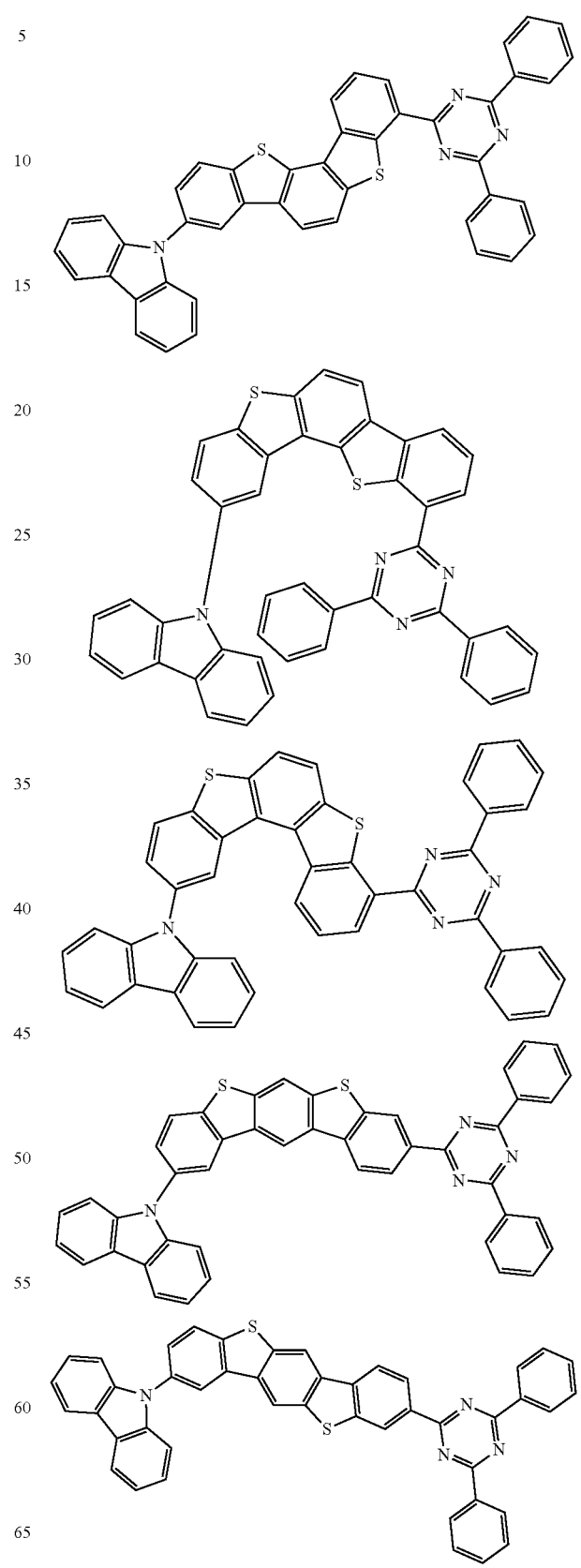

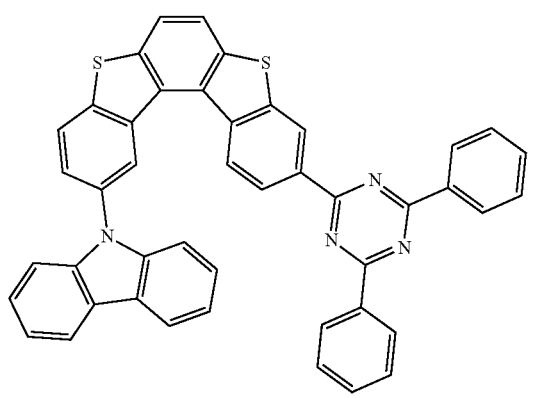
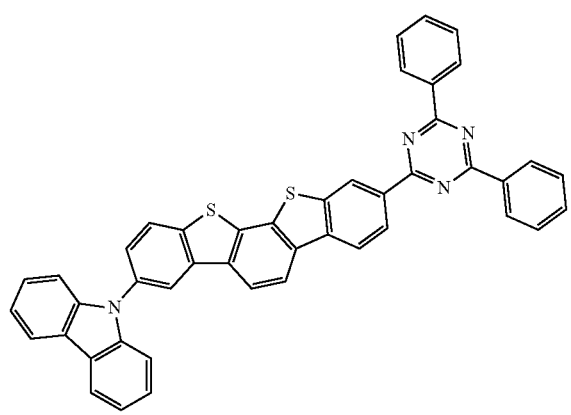
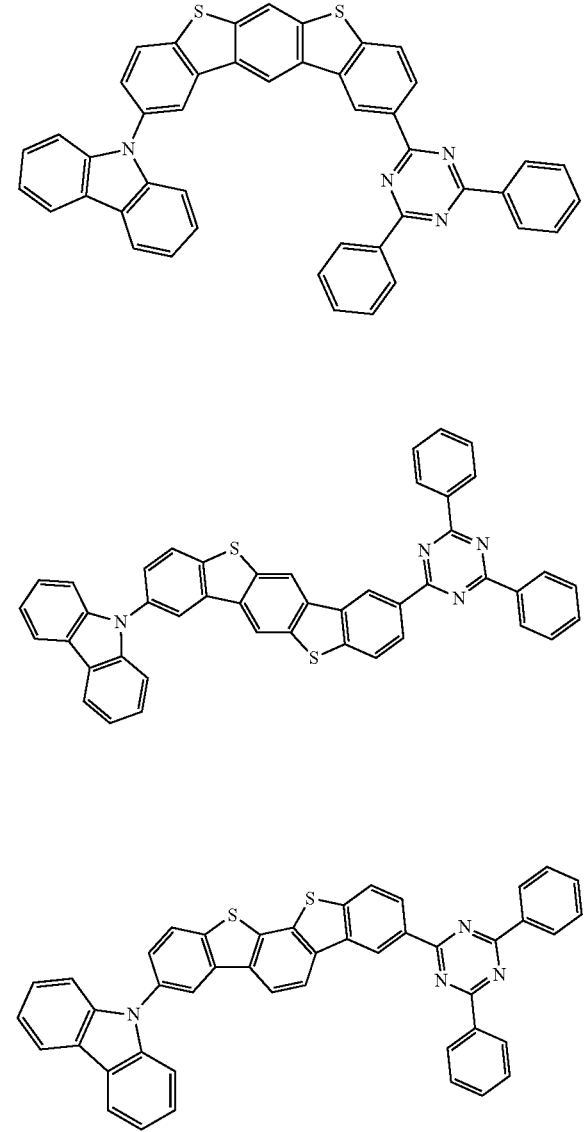
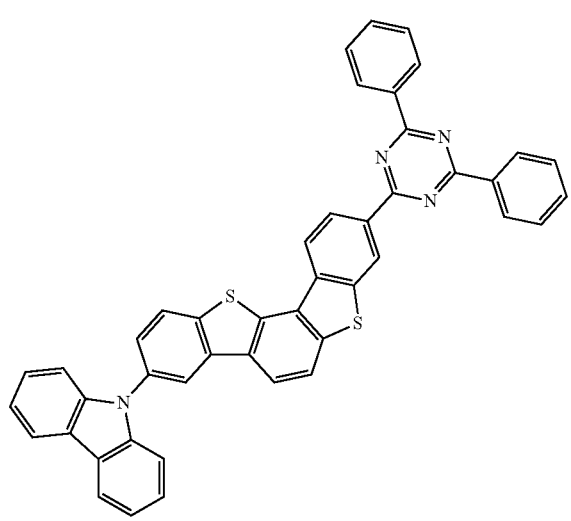
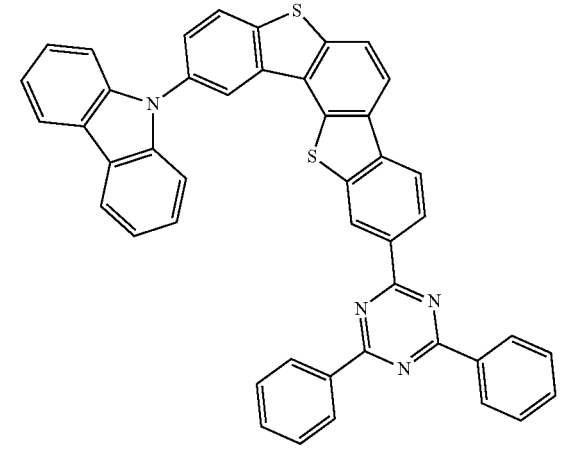

75
-continued
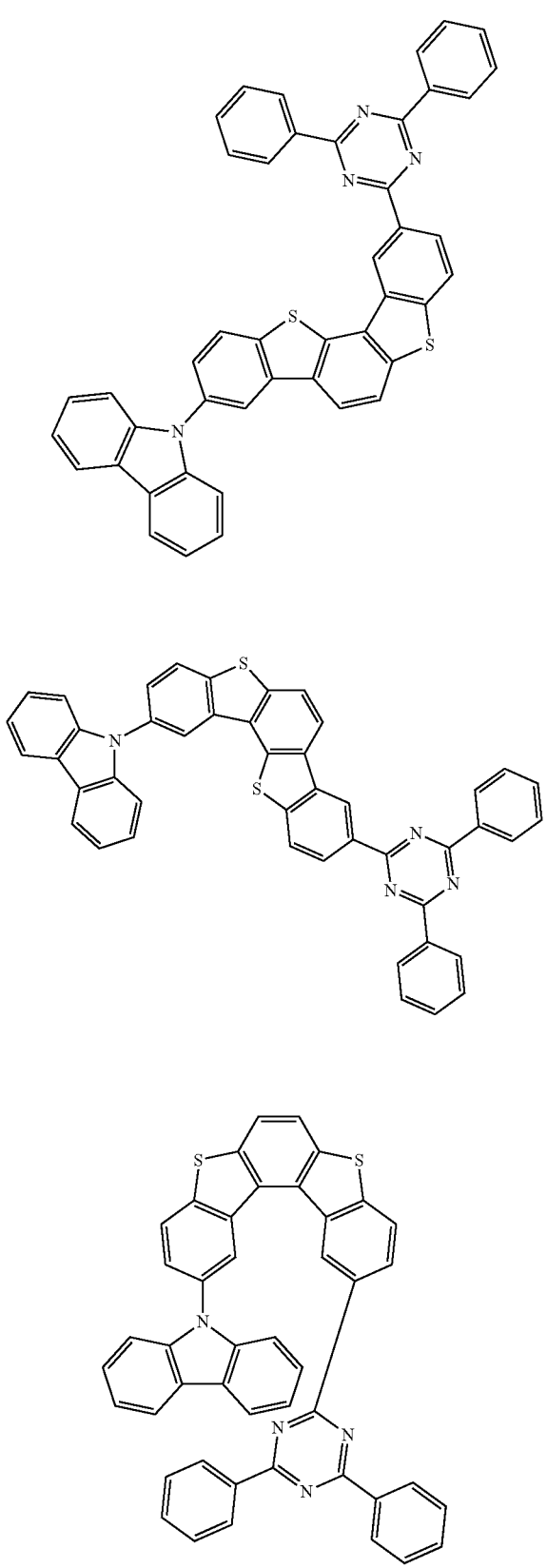
76
-continued
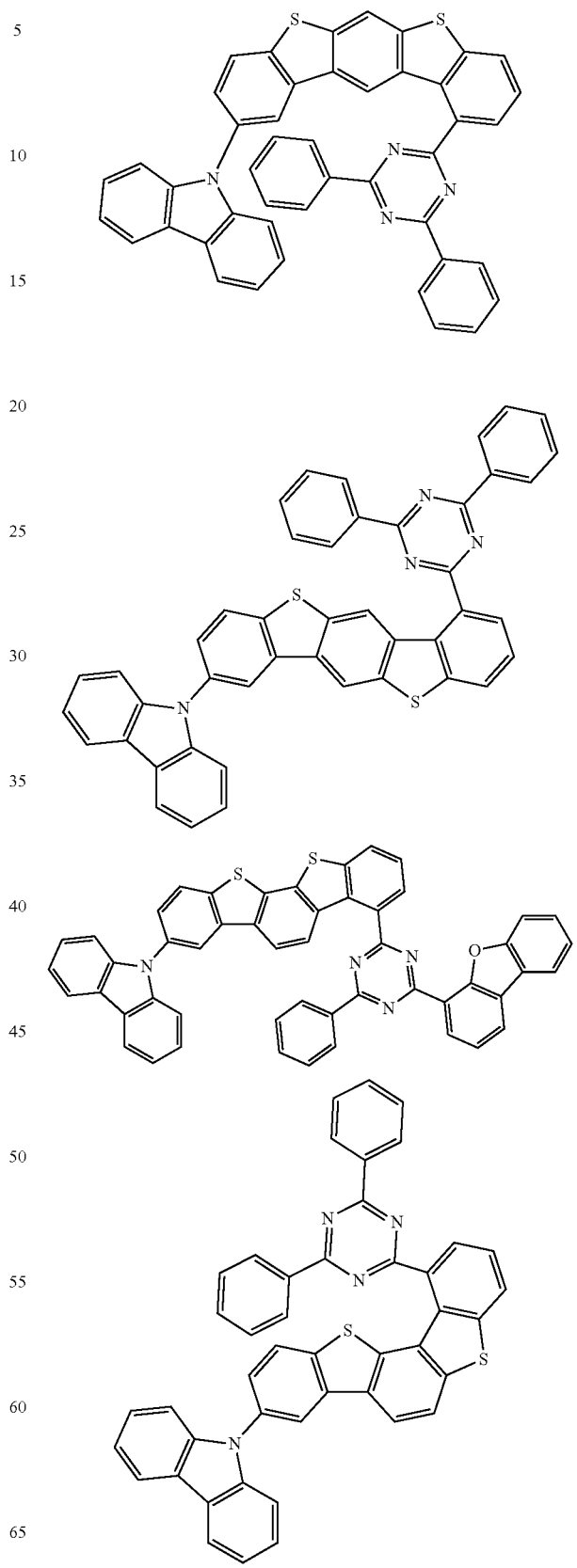

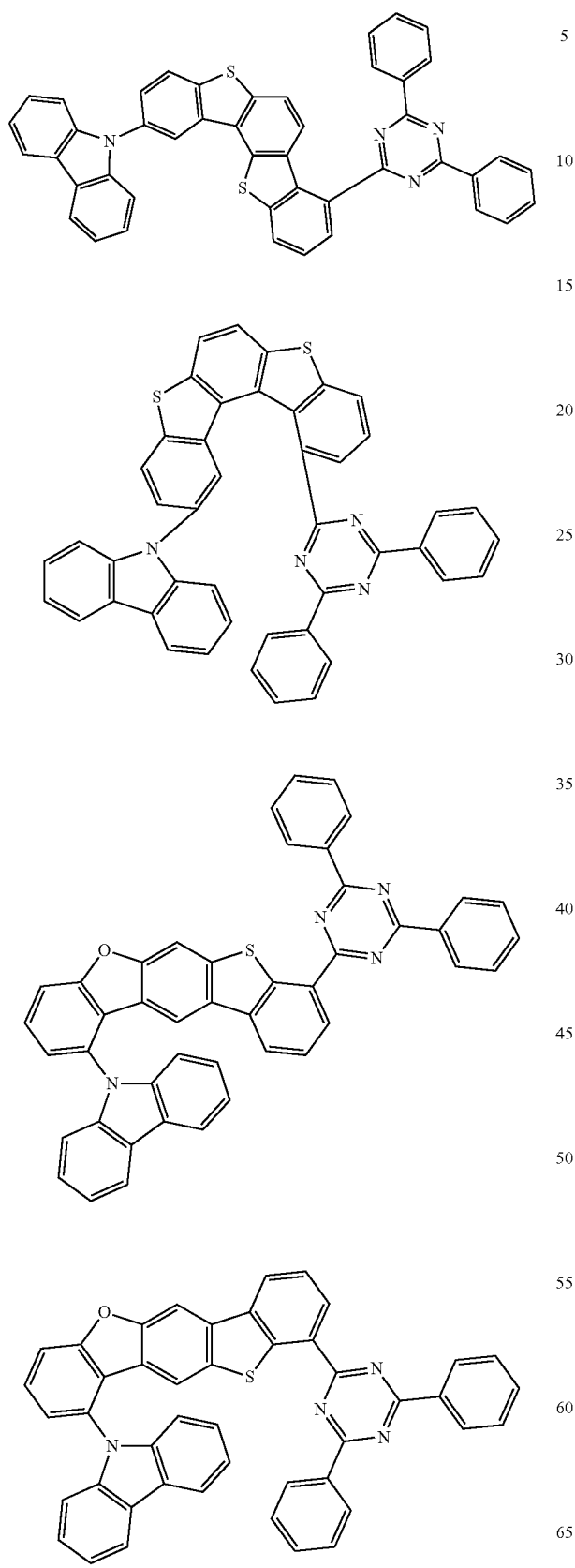
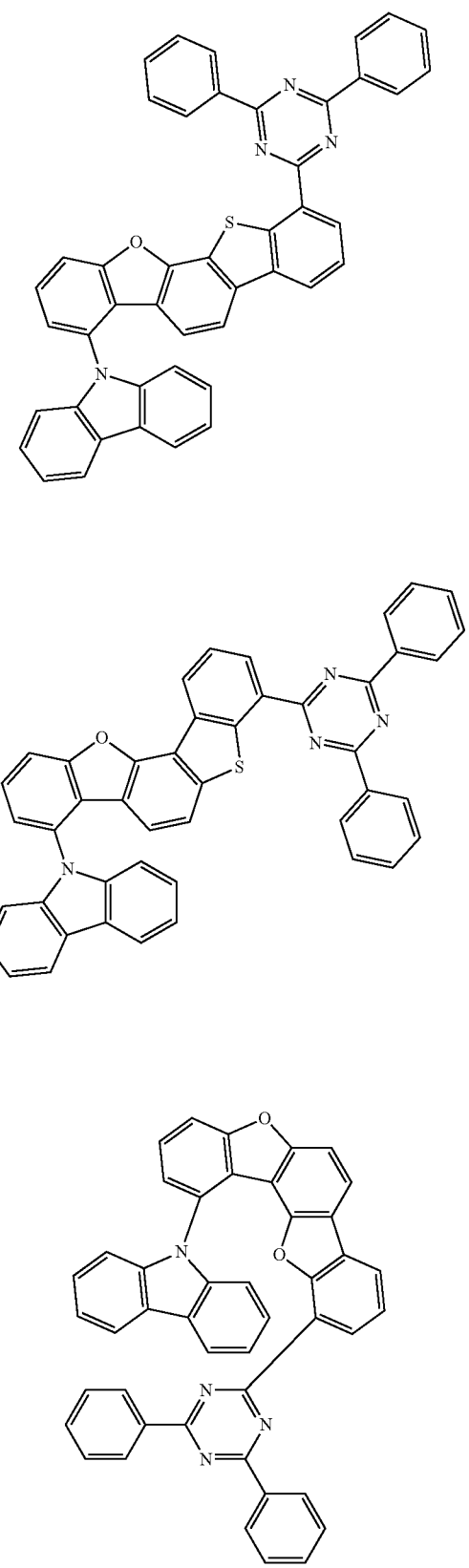

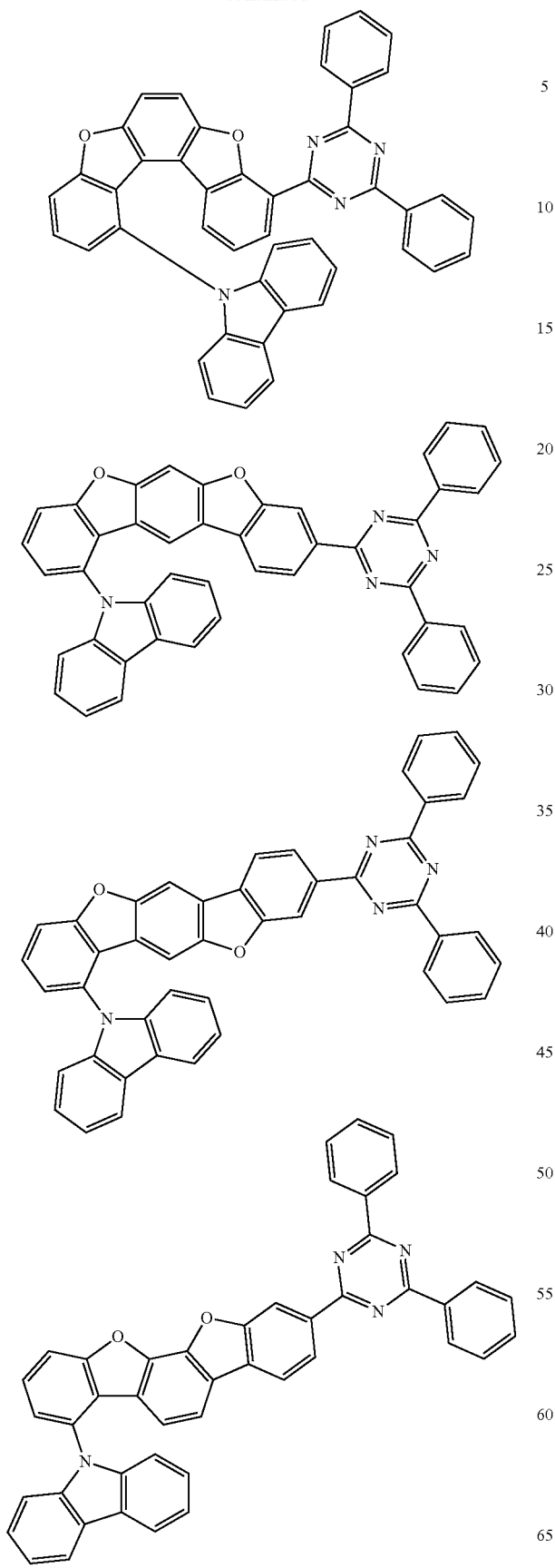
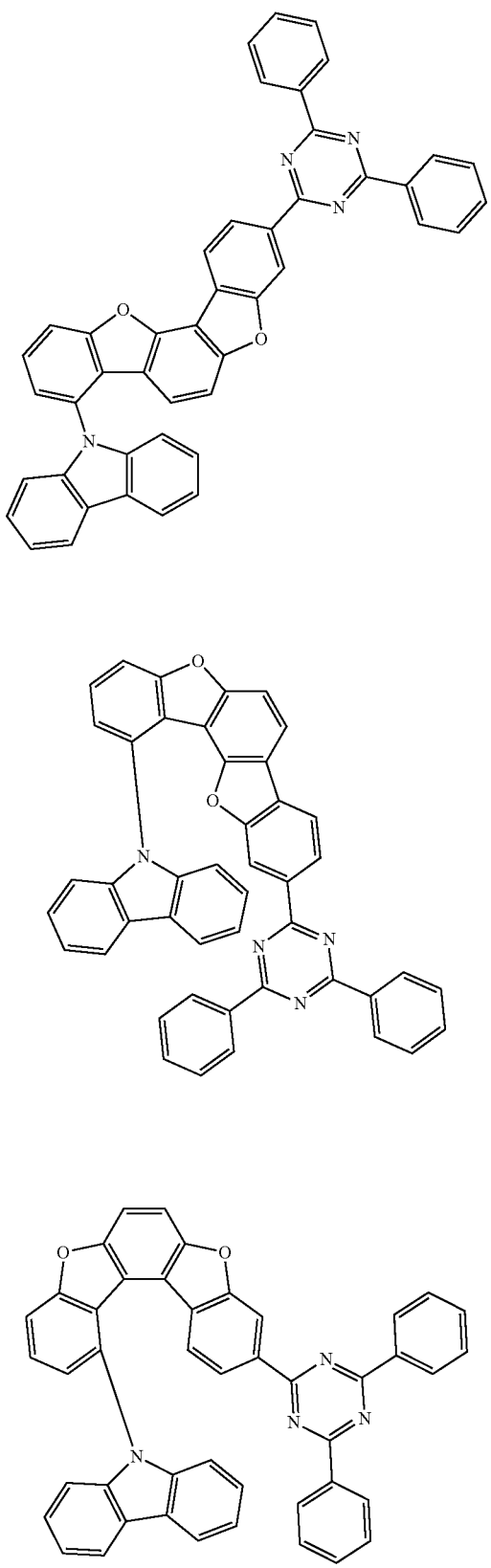

-continued
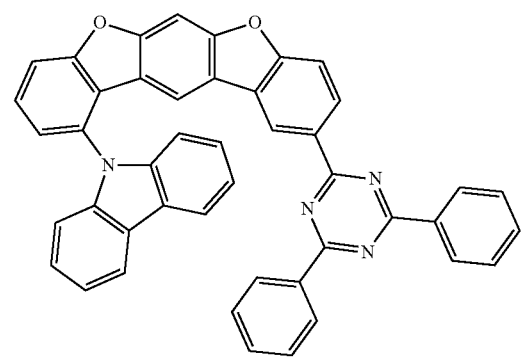
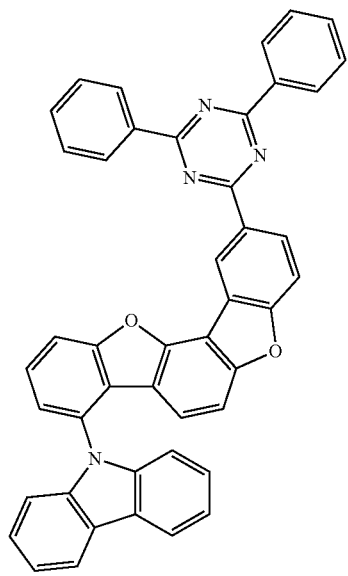
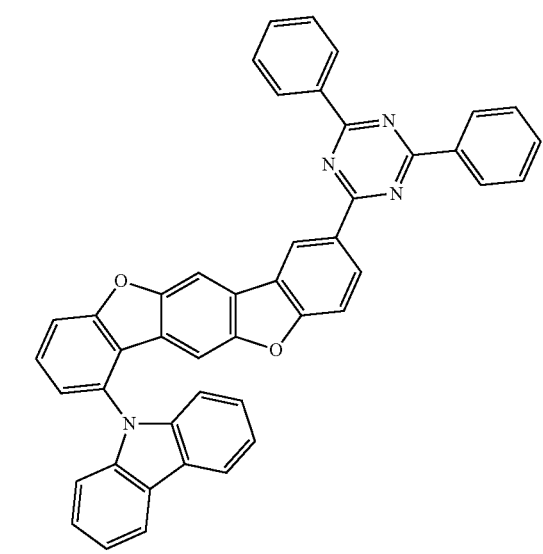
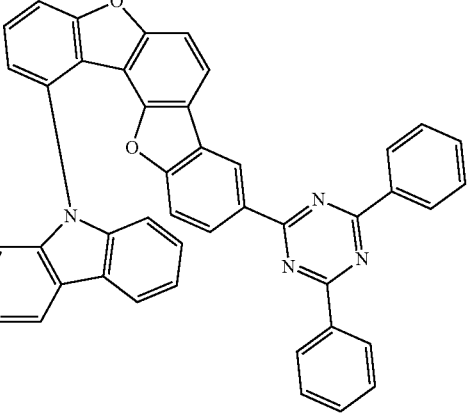
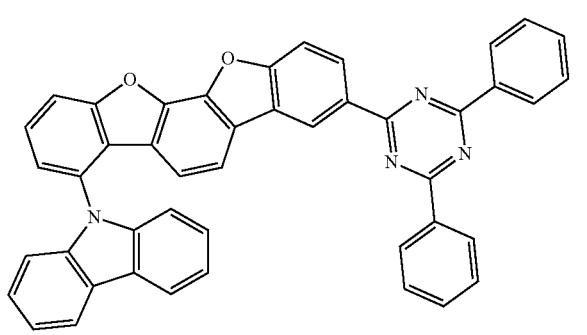
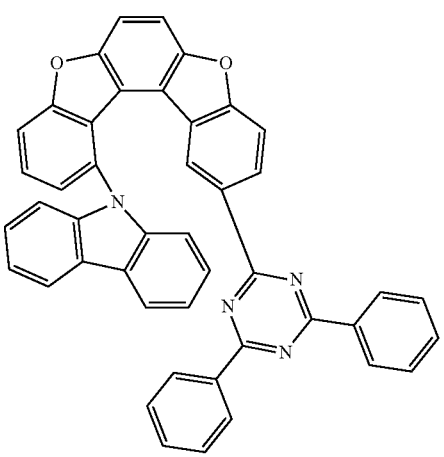

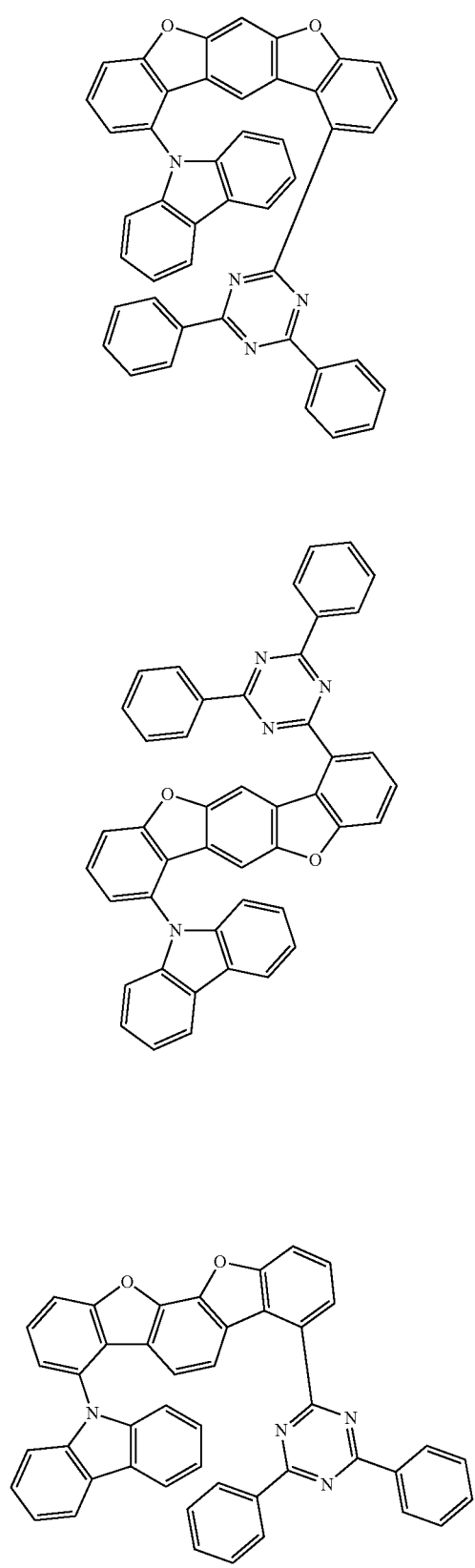
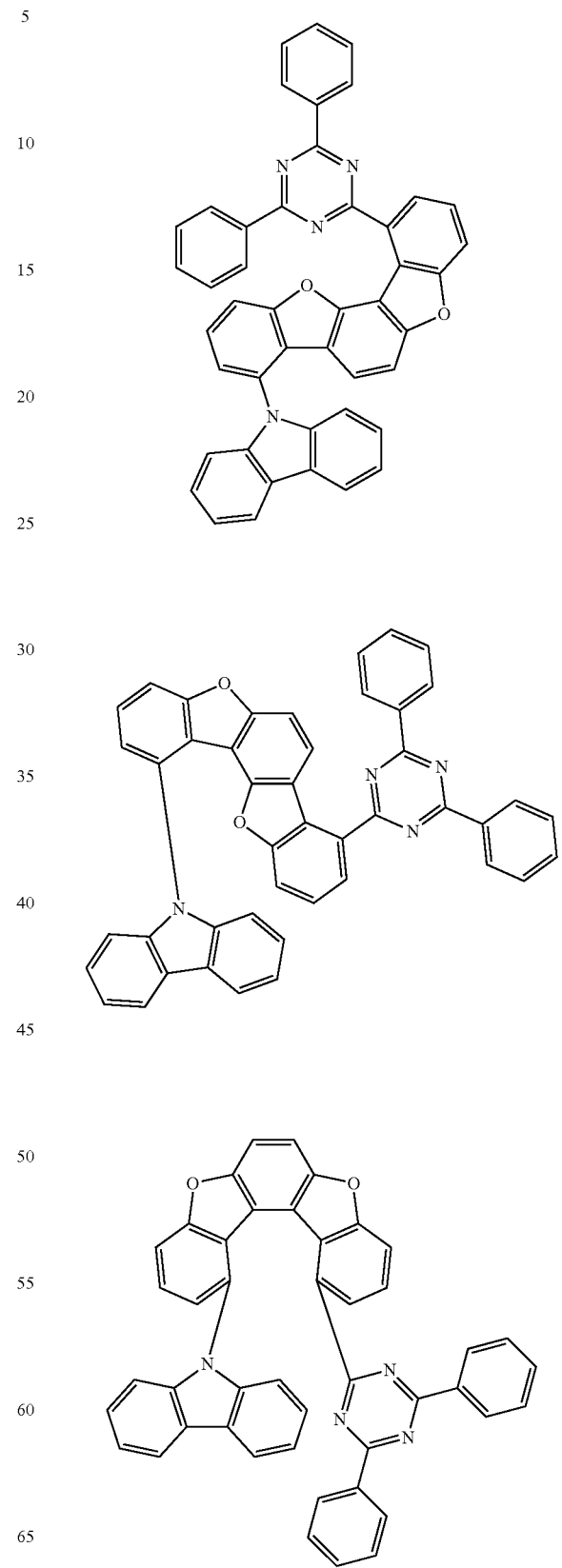

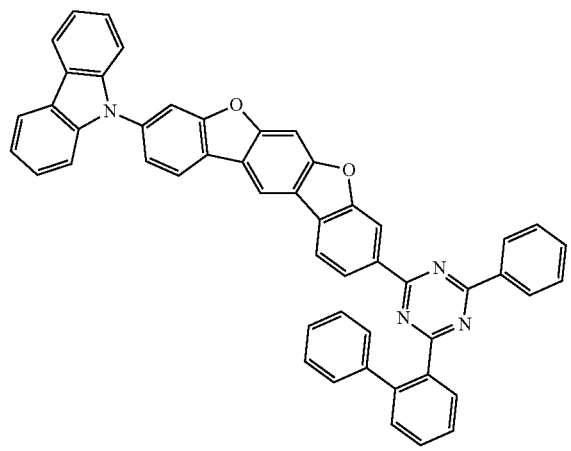
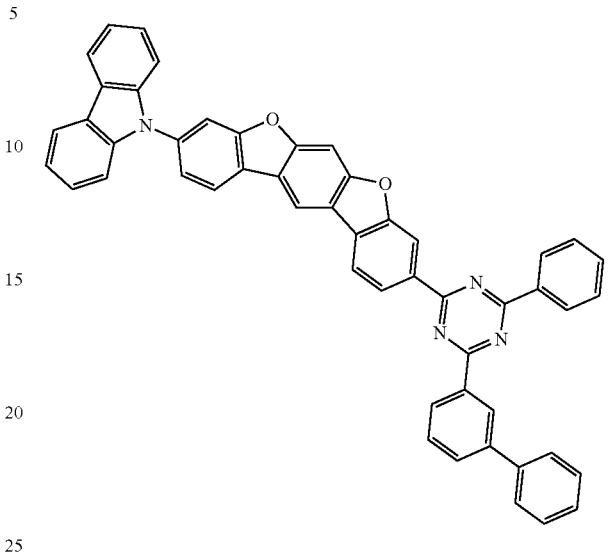
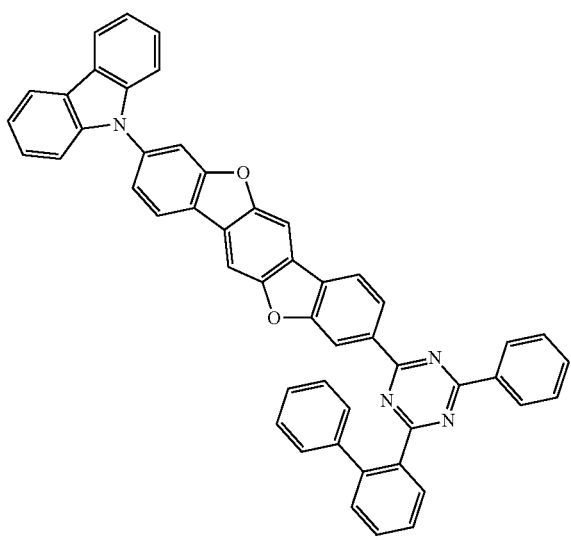
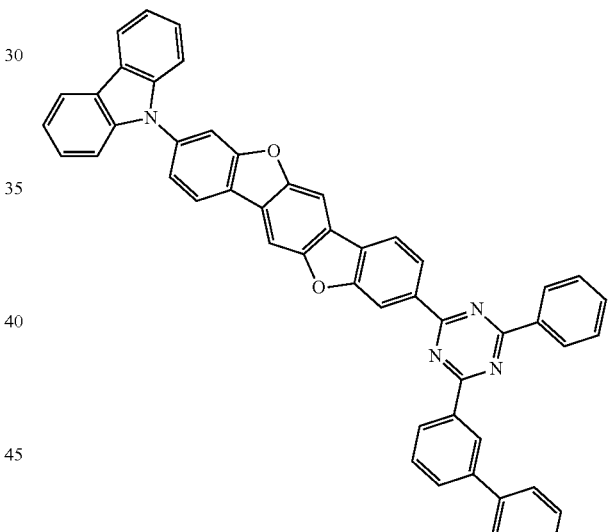
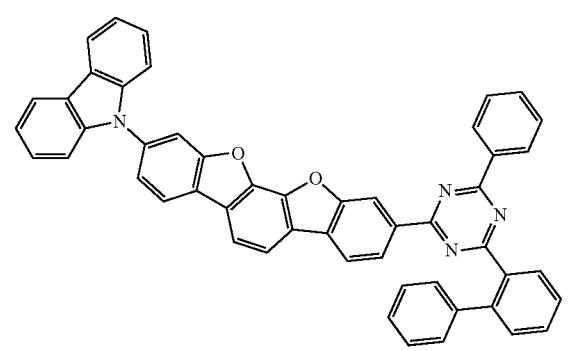
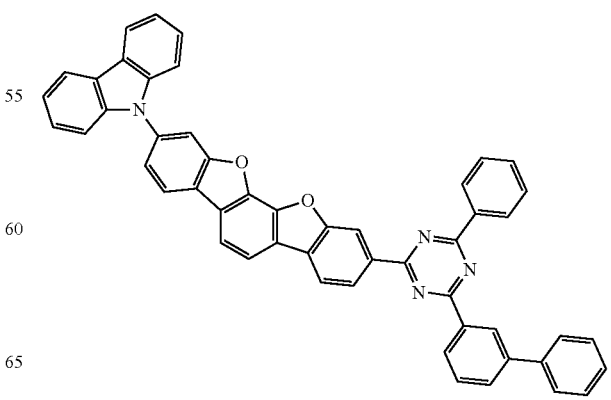

-continued
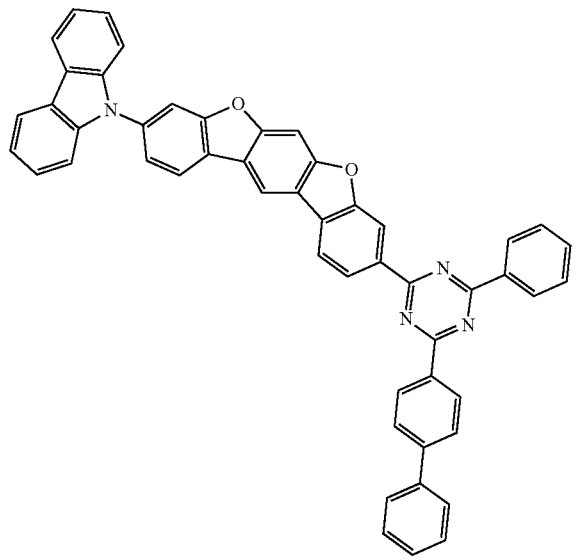
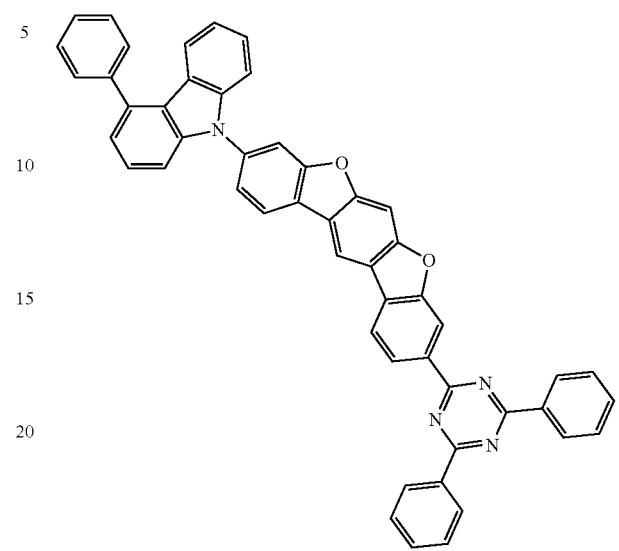
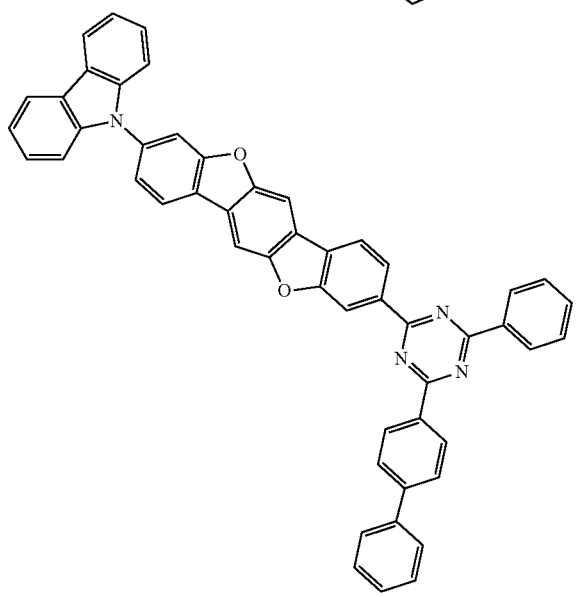
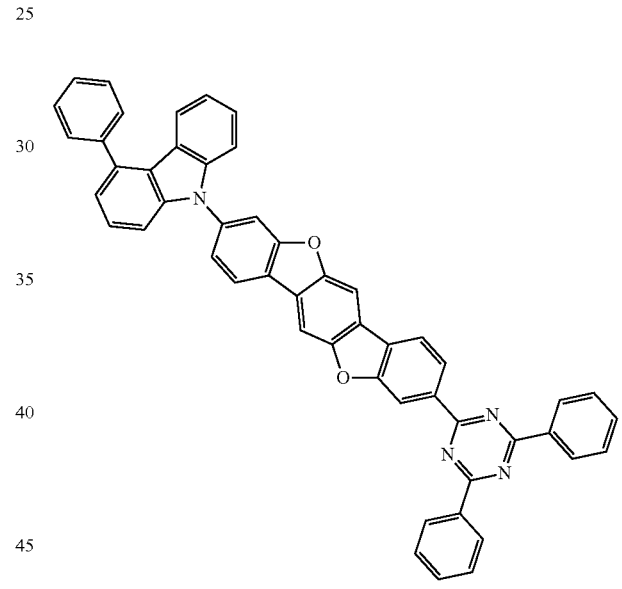
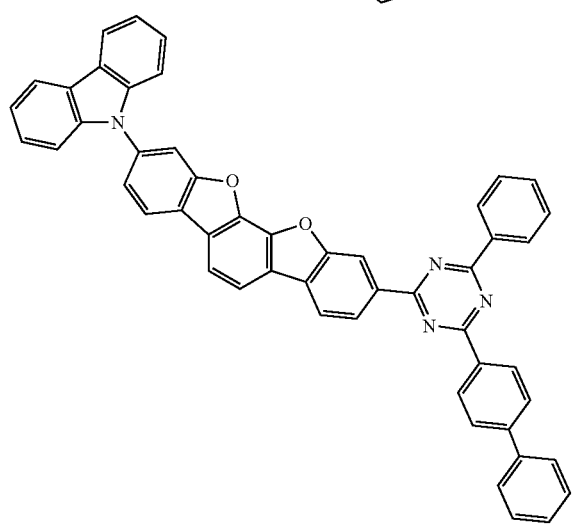
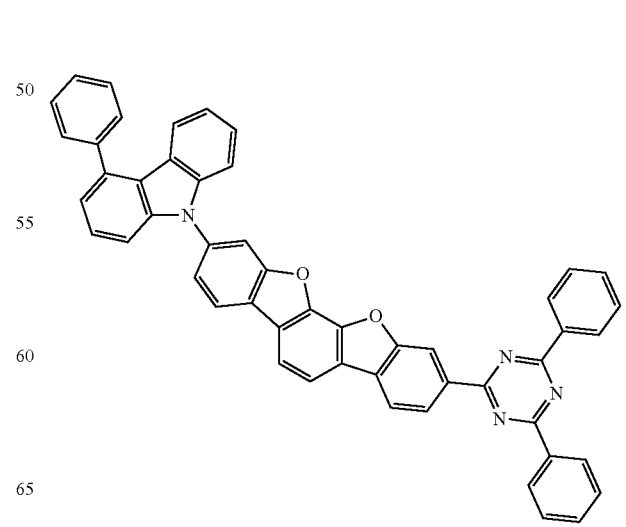

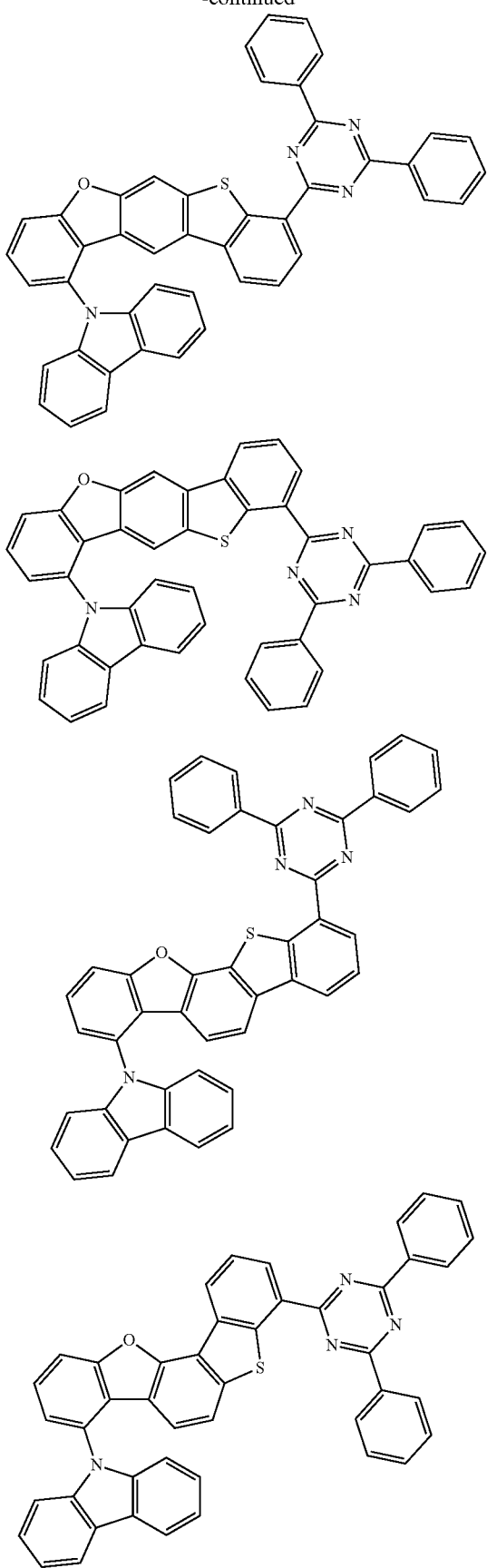
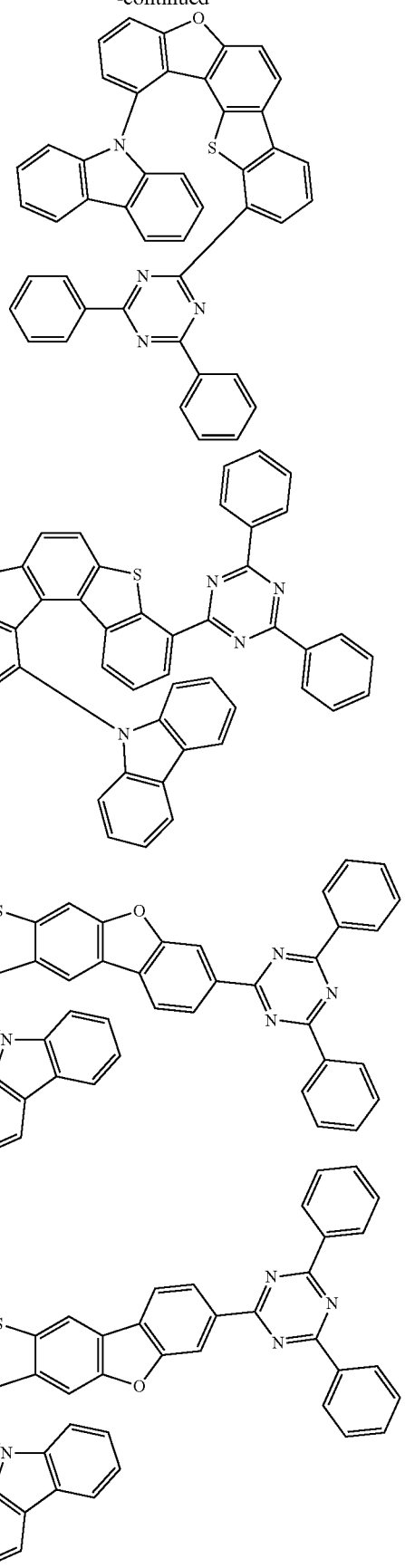

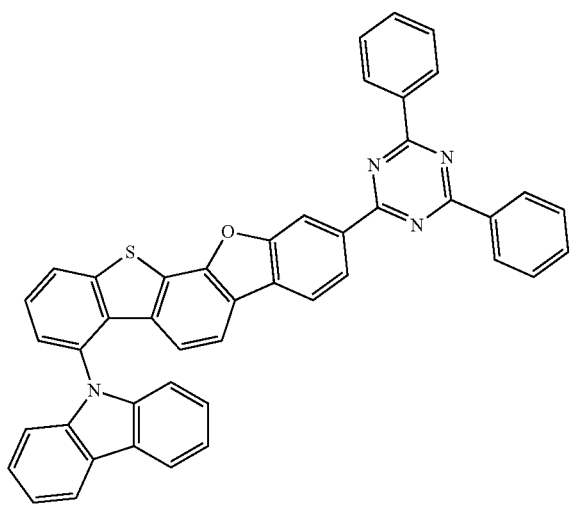
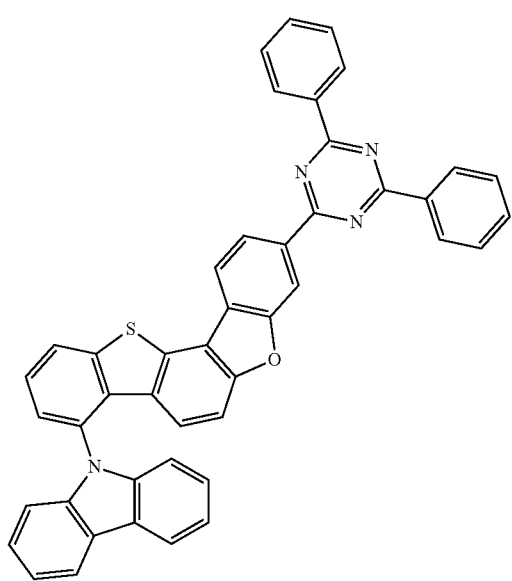
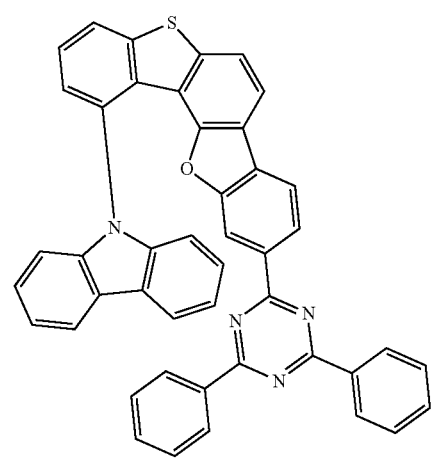
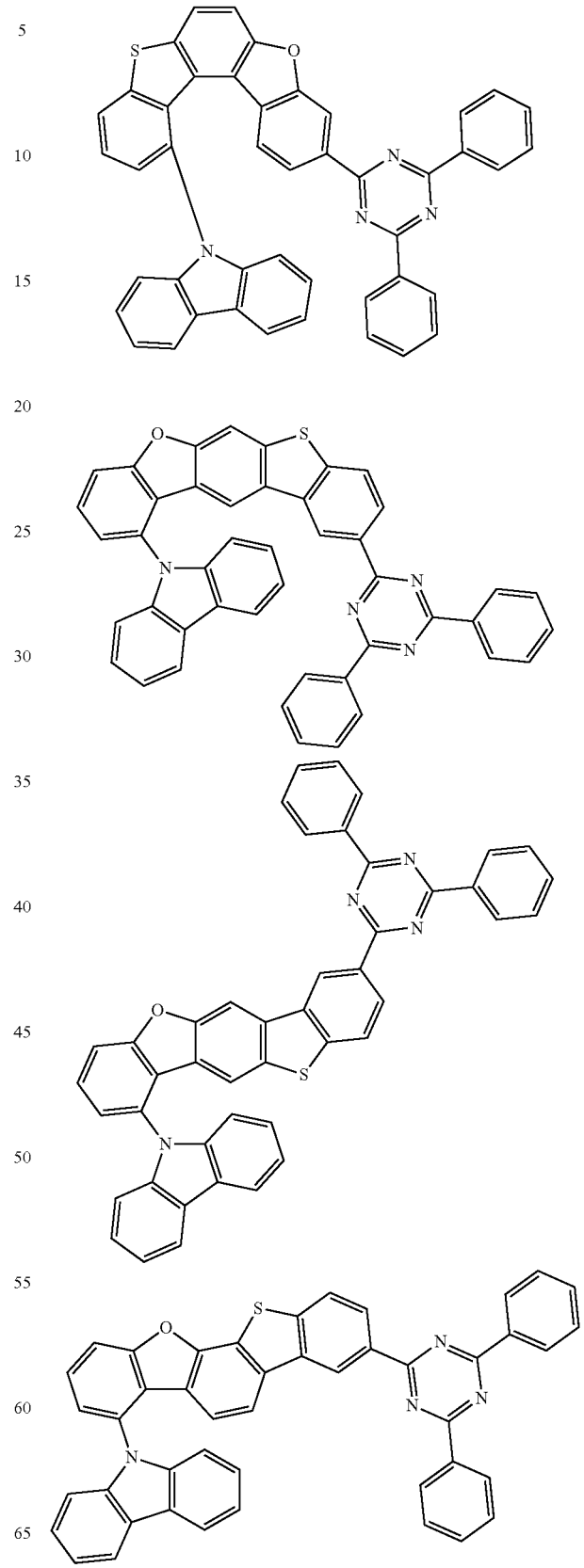

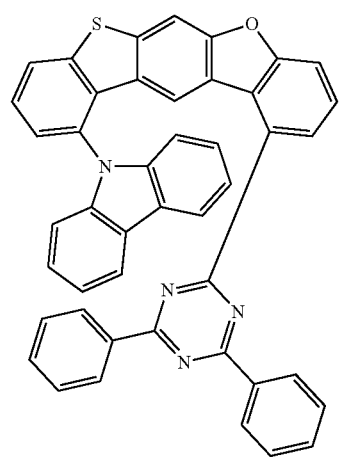
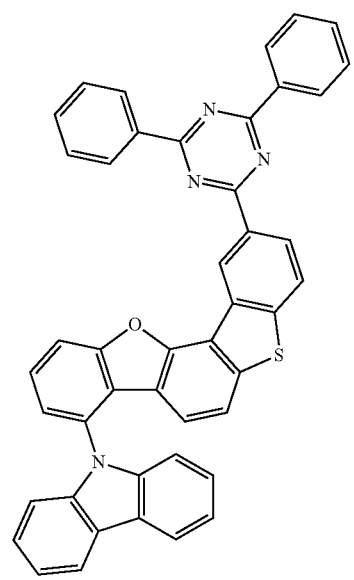
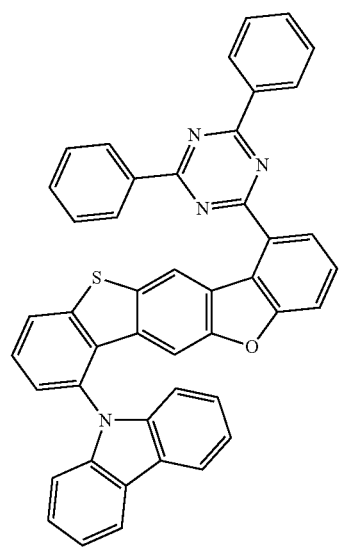
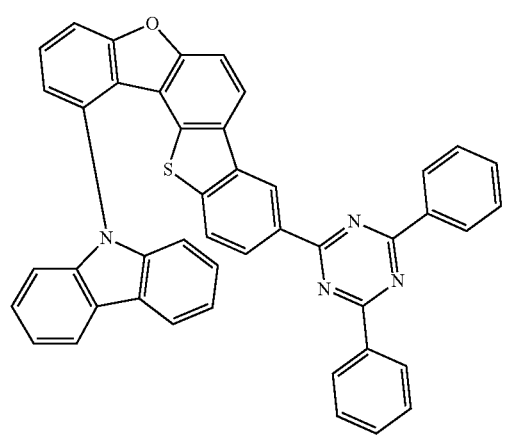
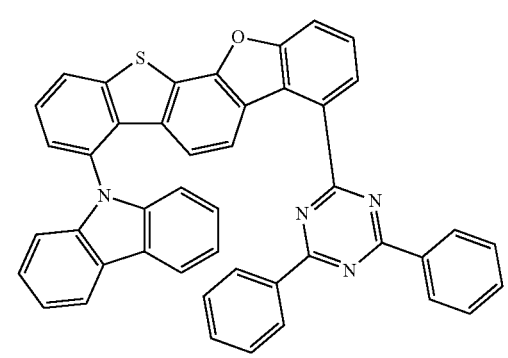
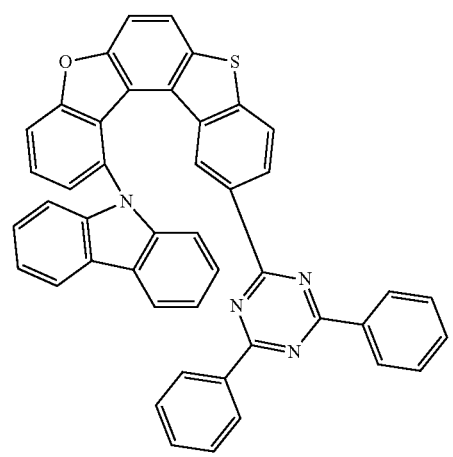

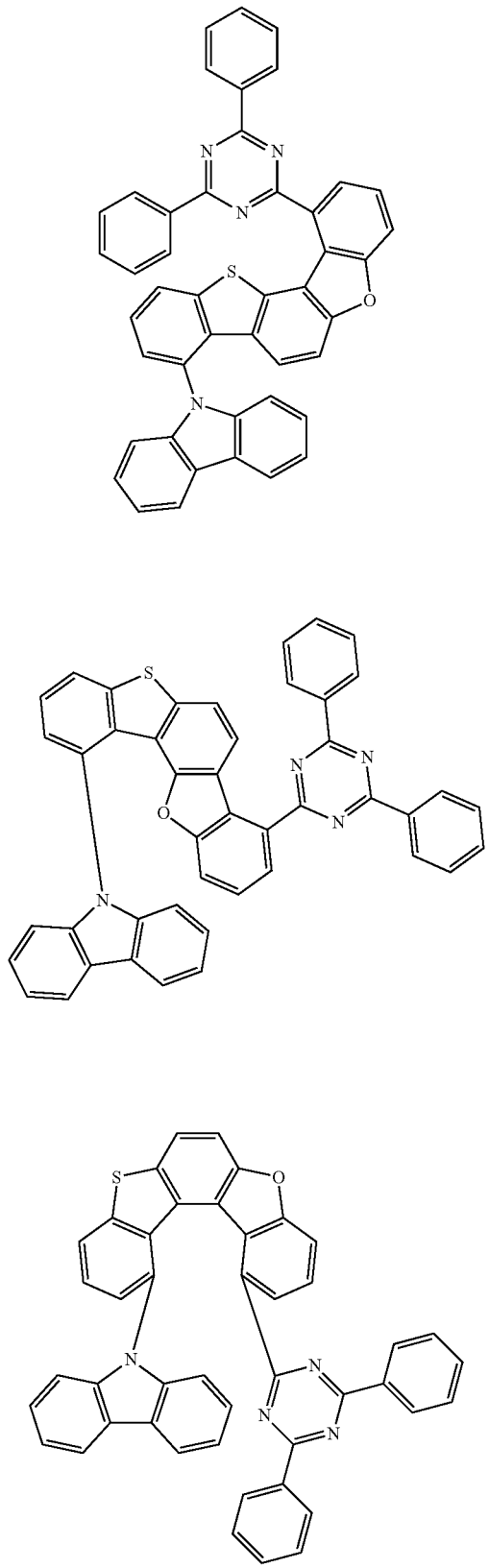
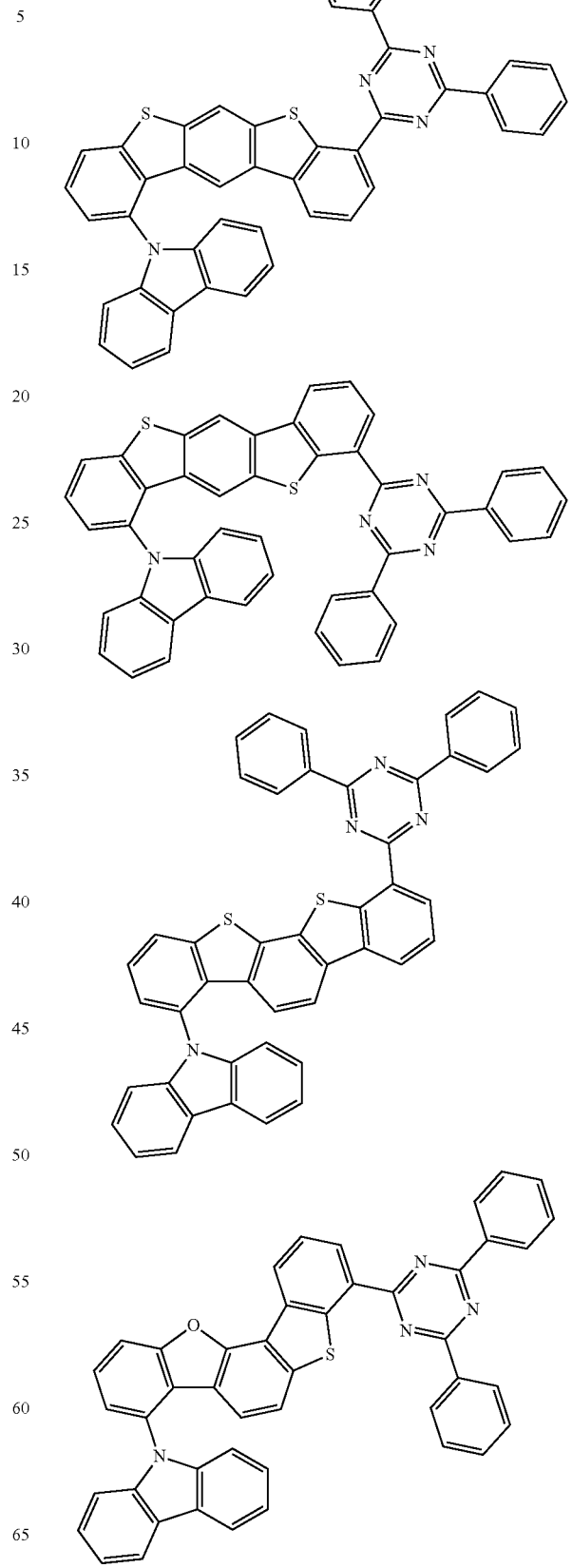

-continued
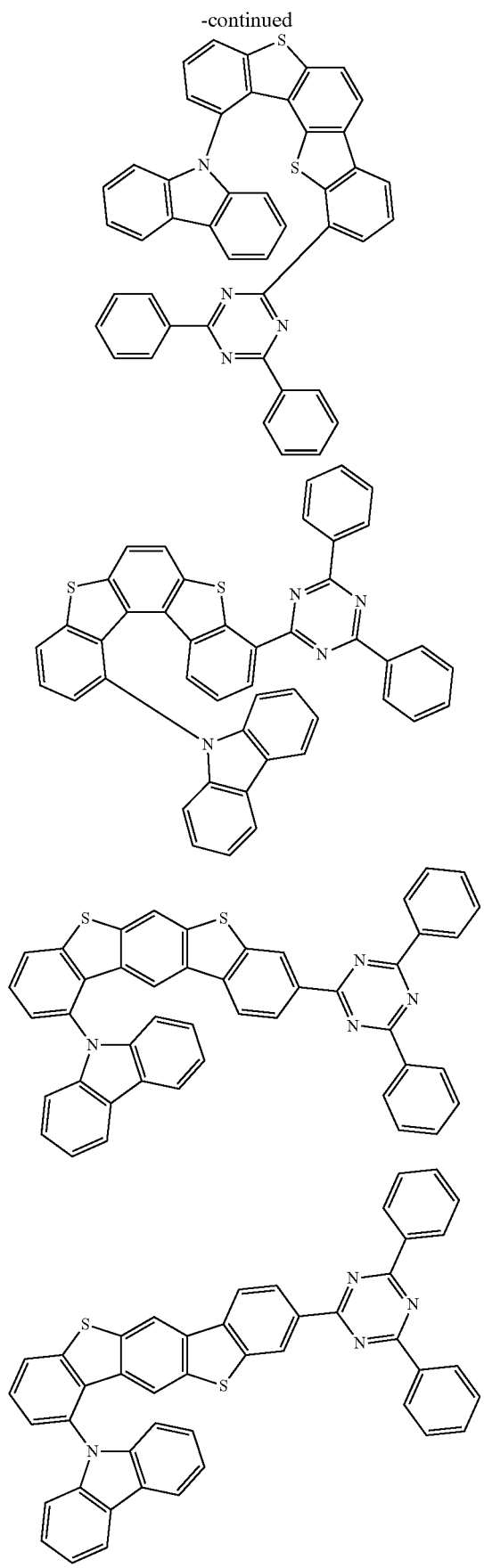
-continued
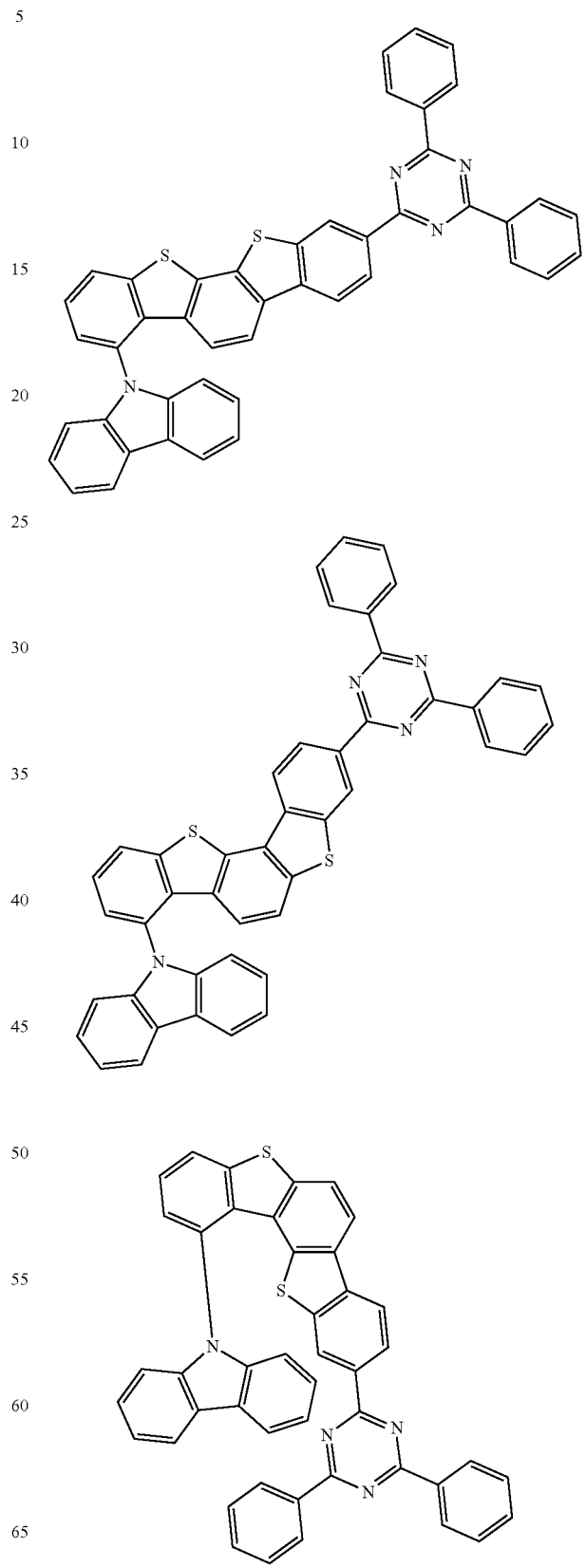

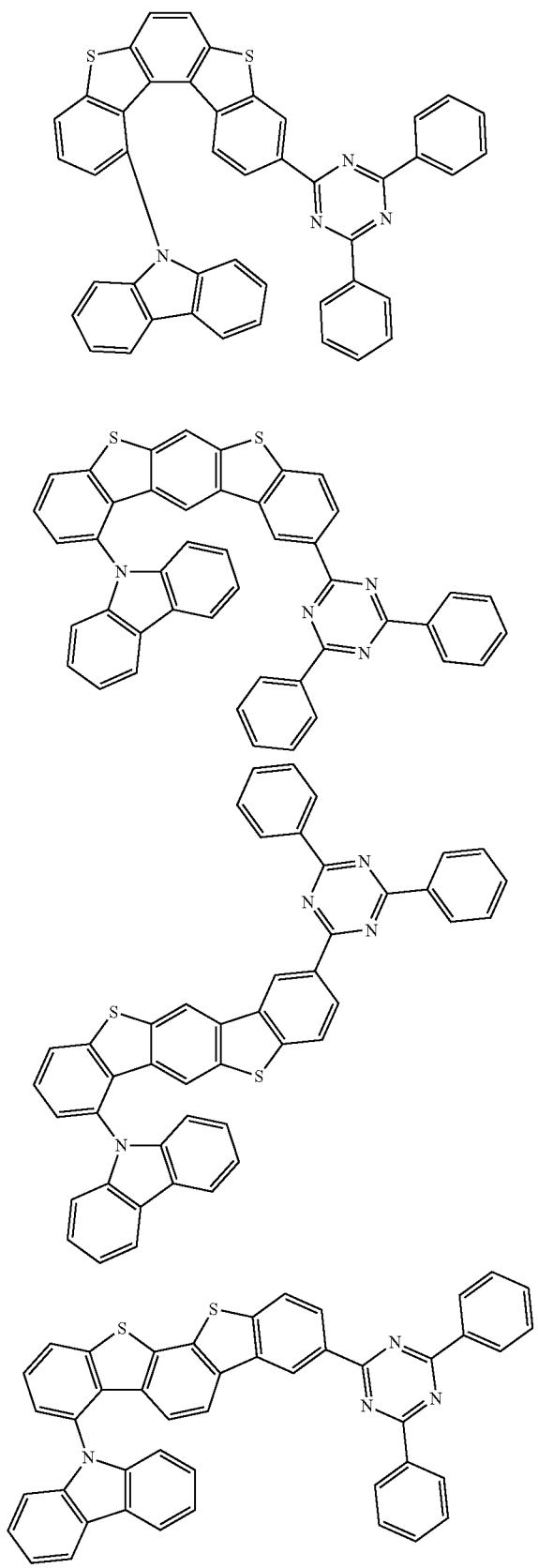
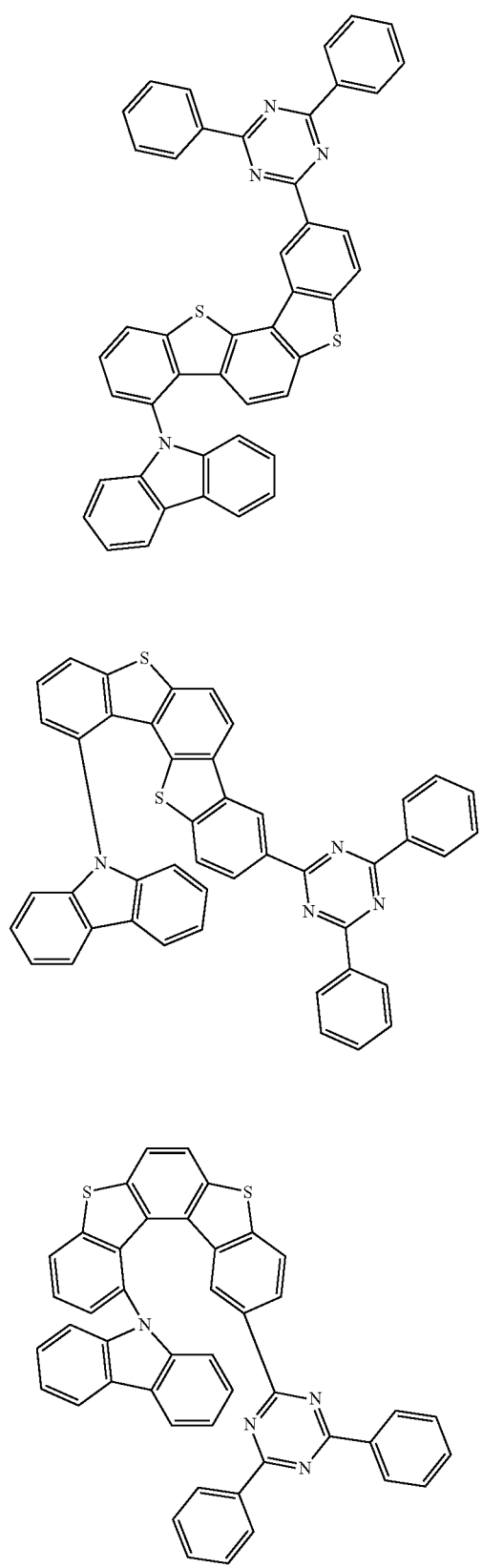

101
-continued
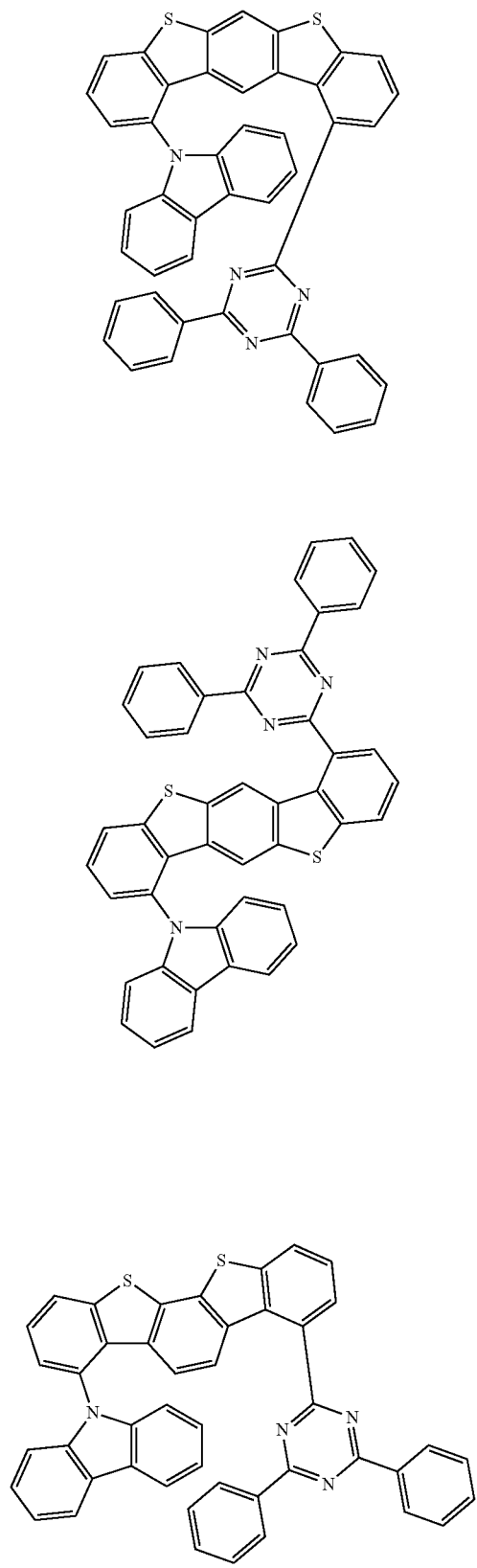
102
-continued
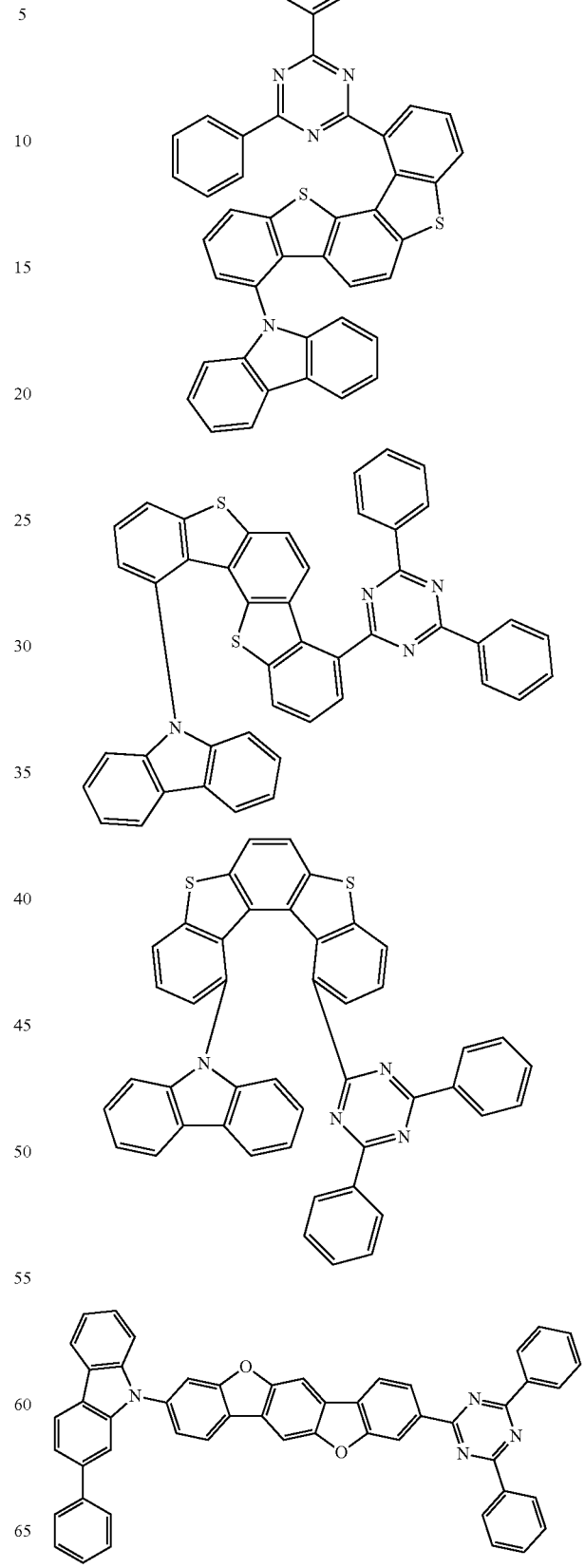

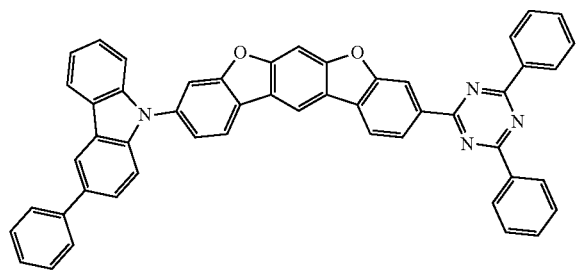
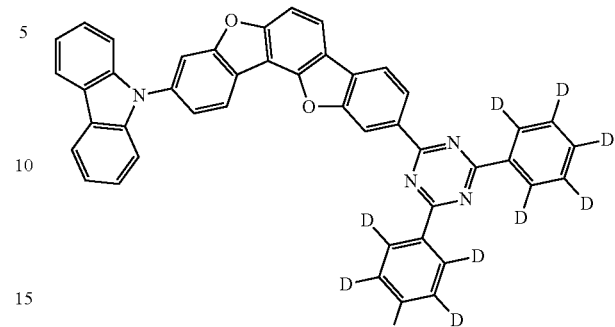
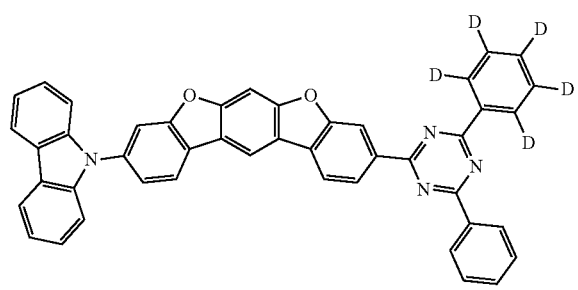
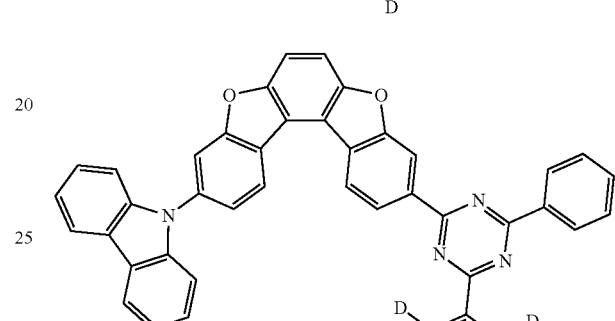
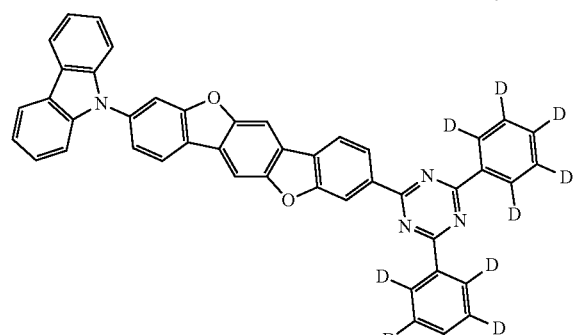
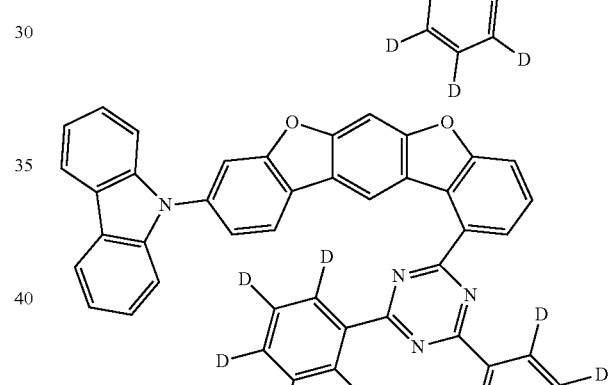
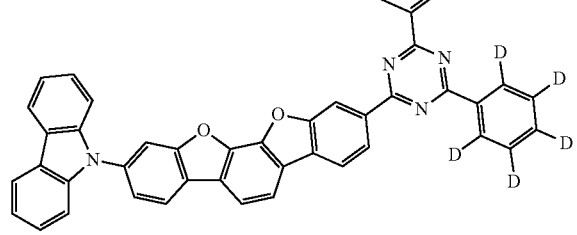
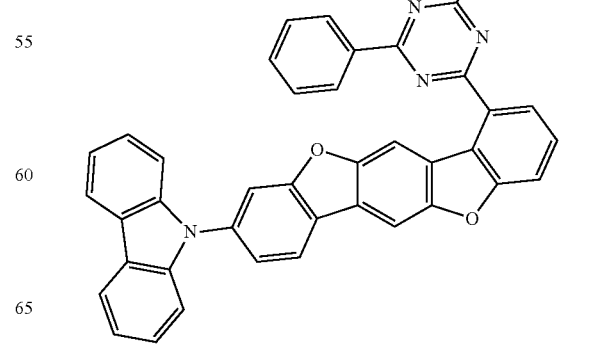

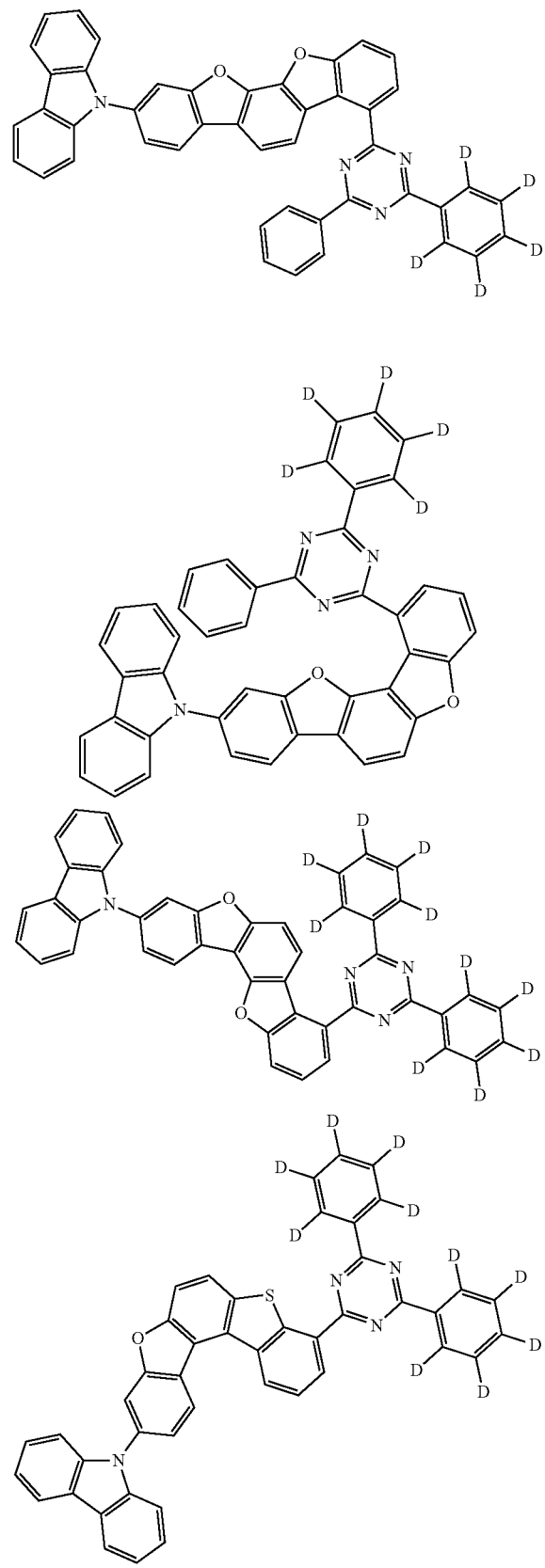
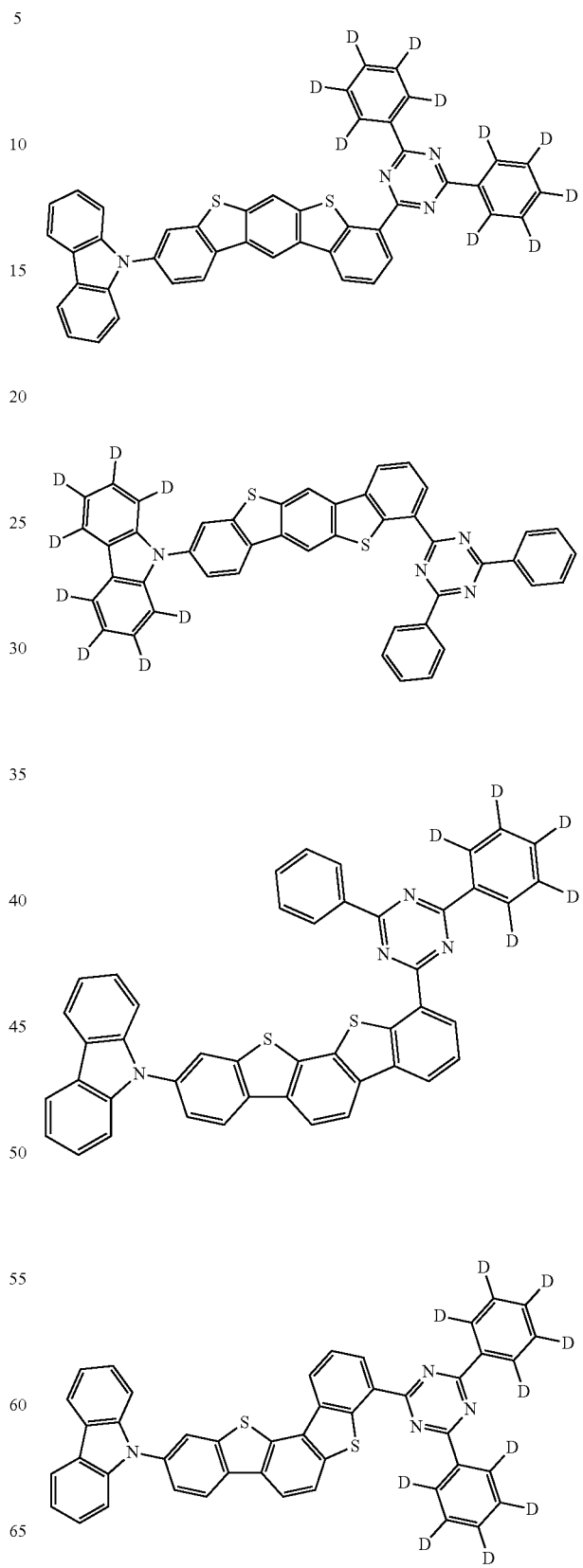

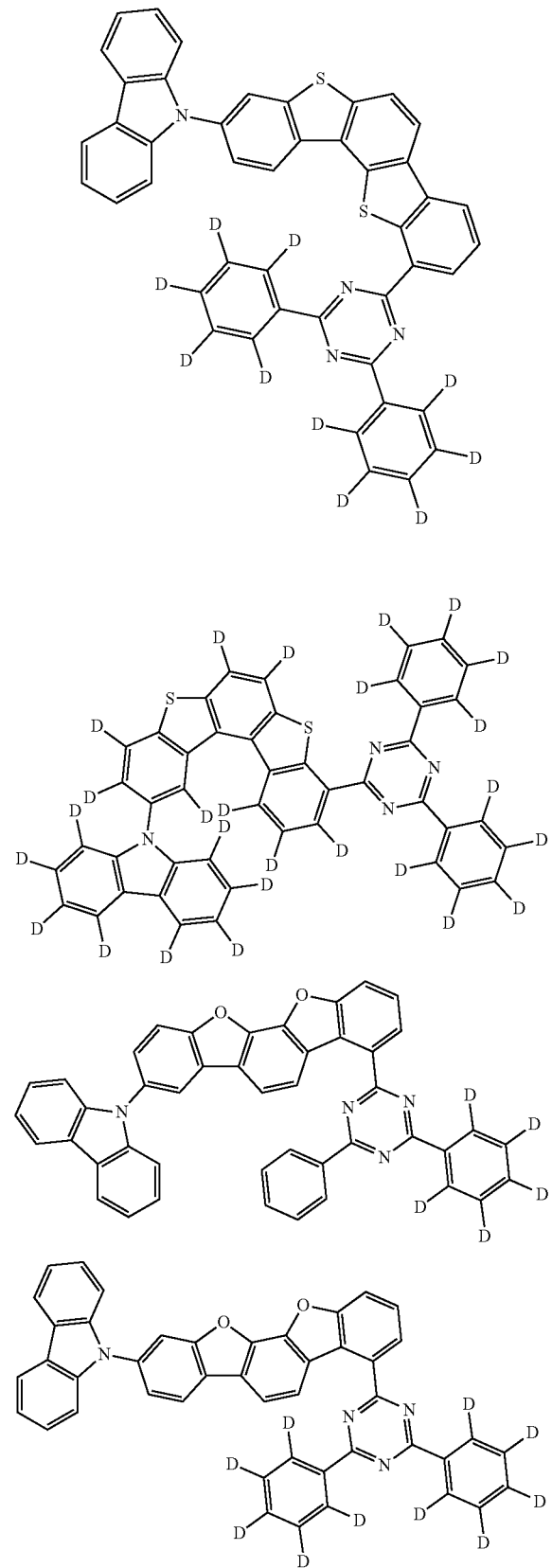
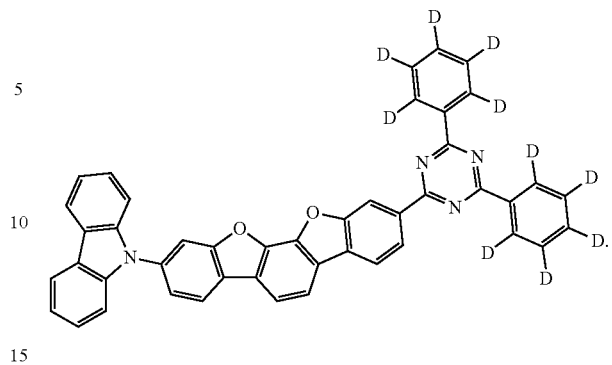
The compound of Chemical Formula 1 can be prepared, for example, according to a preparation method as shown in the following Reaction Schemes 1 and 2, and the other remaining compounds can be prepared in a similar manner.
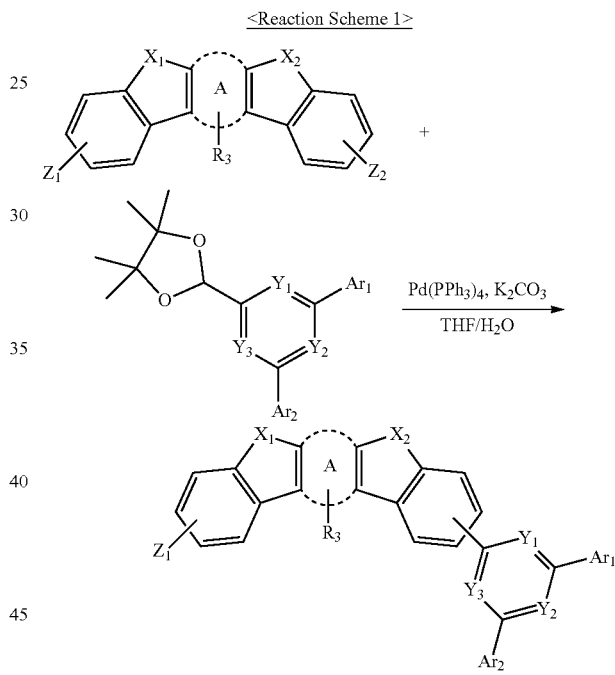
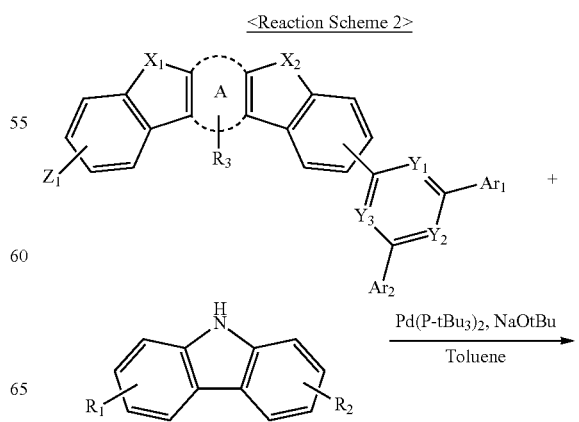

-continued

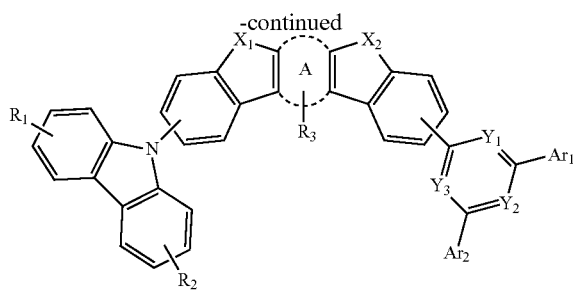

In Reaction Schemes 1 and 2, $X_1$, $X_2$, A, $Y_1$ to $Y_3$, $Ar_1$, $Ar_2$ and $R_1$ to $R_3$ are the same as defined in Chemical Formula 1, $Z_1$ and $Z_2$ are halogen, and more preferably $Z_1$ and $Z_2$ are bromo or chloro.

The Reaction Scheme 1 is a Suzuki coupling reaction, which is preferably carried out in the presence of a palladium catalyst and a base, and a reactive group for the Suzuki coupling reaction can be modified as known in the art. Also, the Reaction Scheme 2 is an amine substitution reaction, which is preferably carried out in the presence of a palladium catalyst and a base, and a reactive group for the amine substitution reaction can be modified as known in the art. The above preparation method can be further embodied in the Preparation Examples described hereinafter.

Another embodiment of the invention provides an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present invention can have a single-layer structure, or it can have a multilayered structure in which two or more organic material layers are stacked. For example, the organic light emitting device of the present invention can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic material layers.

Further, the organic material layer can include a light emitting layer, a hole transport layer, a hole injection layer, or a layer for simultaneously performing hole transport and hole injection, wherein the light emitting layer, the hole transport layer, the hole injection layer, or the layer for simultaneously performing hole transport and hole injection can include the compound of Chemical Formula 1.

Further, the organic material layer can include a light emitting layer, wherein the light emitting layer includes the compound of Chemical Formula 1. In particular, the compound according to the present invention can be used as a host of the light emitting layer.

Further, the organic material layer can include a light emitting layer, an electron transport layer, an electron injection layer, and a layer for simultaneously performing electron transport and electron injection, wherein the light emitting layer, the electron transport layer, the electron injection layer, and the layer for simultaneously performing electron transport and electron injection can include the compound of Chemical Formula 1.

In addition, the organic material layer includes a light emitting layer, an electron blocking layer and an electron transport layer, wherein the light emitting layer can include a compound of Chemical Formula 1.

Further, the organic light emitting device according to the present invention can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole transport layer 5, an electron blocking layer 6, a light emitting layer 3, a hole blocking layer 7, an electron transport layer 8, an electron injection layer 9, and a cathode 4. In such a structure, the compound of Chemical Formula 1 can be included in one or more layers of the hole transport layer, the electron blocking layer, the light emitting layer, the hole blocking layer, the electron transport layer and the electron injection layer.

The organic light emitting device according to the present invention can be manufactured by materials and methods known in the art, except that one or more layers of the organic material layers include the compound of Chemical Formula 1, In addition, when the organic light emitting device includes a plurality of organic material layers, the organic material layers can be formed of the same material or different materials.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole transport layer, the electron blocking layer, the light emitting layer, the hole blocking layer, the electron transport layer and the electron injection layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and the hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is a layer provided between the hole transport layer and the light emitting layer in order to prevent the electrons injected in the cathode from being transferred to the hole transport layer without being recombined in the light emitting layer, which can also be referred to as an electron inhibition layer. The electron blocking layer is preferably a material having a smaller electron affinity than the electron transport layer.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole, a benzothiazole, a benzimidazole-based compound; a poly(p-phenylenevinylene)(PPV)-based polymer, a spiro compound, polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. In particular, the compound of Chemical Formula 1 can be included as a host.

Preferably, the light emitting layer can further include a compound of Chemical Formula 27:

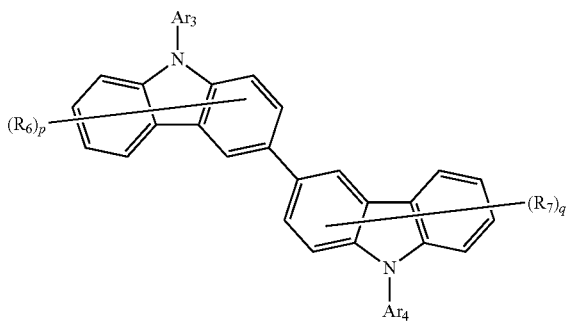

Chemical Formula 2 wherein in Chemical Formula 2;

$Ar_3$ and $Ar_4$ are each independently a substituted or unsubstituted $C_{6-60}$ aryl or a substituted or unsubstituted $C_{2-60}$ heteroaryl containing one or more heteroatoms selected from the group consisting of N, O, and S;

$R_6$ and $R_7$ are each independently hydrogen, deuterium, halogen, cyano, nitro, amino, a substituted or unsubstituted $C_{1-60}$ alkyl, a substituted or unsubstituted $C_{3-60}$ cycloalkyl, a substituted or unsubstituted $C_{2-60}$ alkenyl, a substituted or unsubstituted $C_{6-60}$ aryl, or a substituted or unsubstituted $C_{2-60}$ heteroaryl containing one or more heteroatoms selected from the group consisting of N, O, and S; and p and q are each independently an integer of 0 to 7.

Preferably, $Ar_3$ and $Ar_4$ can be each independently a substituted or unsubstituted $C_{6-20}$ aryl or a substituted or unsubstituted $C_{6-20}$ heteroaryl containing any one or more heteroatoms selected from the group consisting of N, O, and S.

More preferably, $Ar_3$ and $Ar_4$ can be each independently a phenyl, biphenylyl, terphenylyl, naphthyl, dibenzofuranyl, dibenzothiophenyl, or dimethylfluorenyl.

Most preferably, $Ar_3$ and $Ar_4$ are each independently phenyl, biphenylyl, terphenylyl, naphthyl, dibenzofuranyl, dibenzothiophenyl, or 9,9-dimethyl-9H-fluorenyl.

Preferably, $R_6$ and $R_7$ can be each independently hydrogen, a substituted or unsubstituted $C_{1-20}$ alkyl, a substituted or unsubstituted $C_{6-20}$ aryl, or a substituted or unsubstituted $C_{6-20}$ heteroaryl containing any one or more heteroatoms selected from the group consisting of N, O and S.

More preferably, $R_6$ and $R_7$ can each be hydrogen.

p and q represent the number of $R_6$ and $R_7$, respectively, and when p is 2 or more, two or more $R_6$ can be the same as or different from each other. When q is 2 or more, two or more $R_7$ can be the same as or different from each other.

Representative examples of the compound of Chemical Formula 2 are as follows:

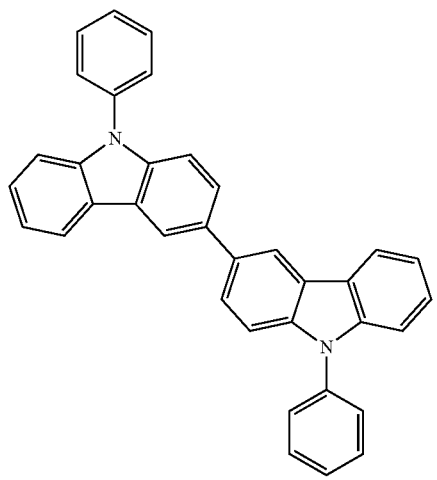

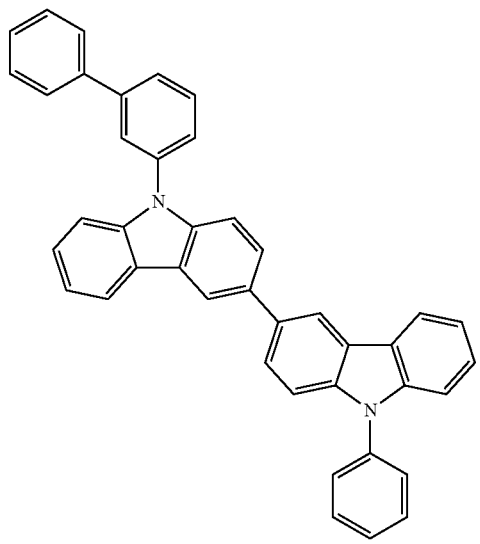

-continued

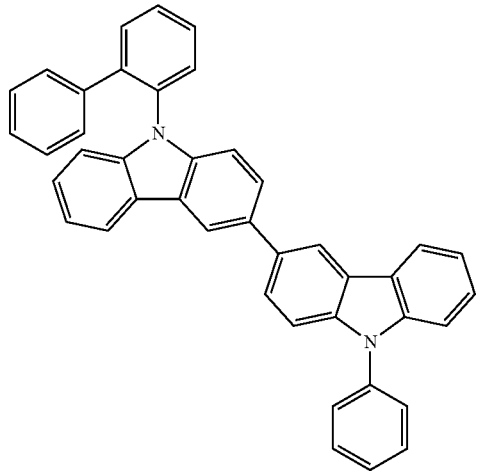

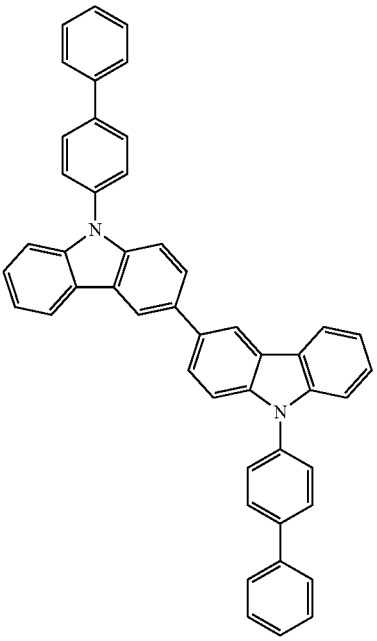

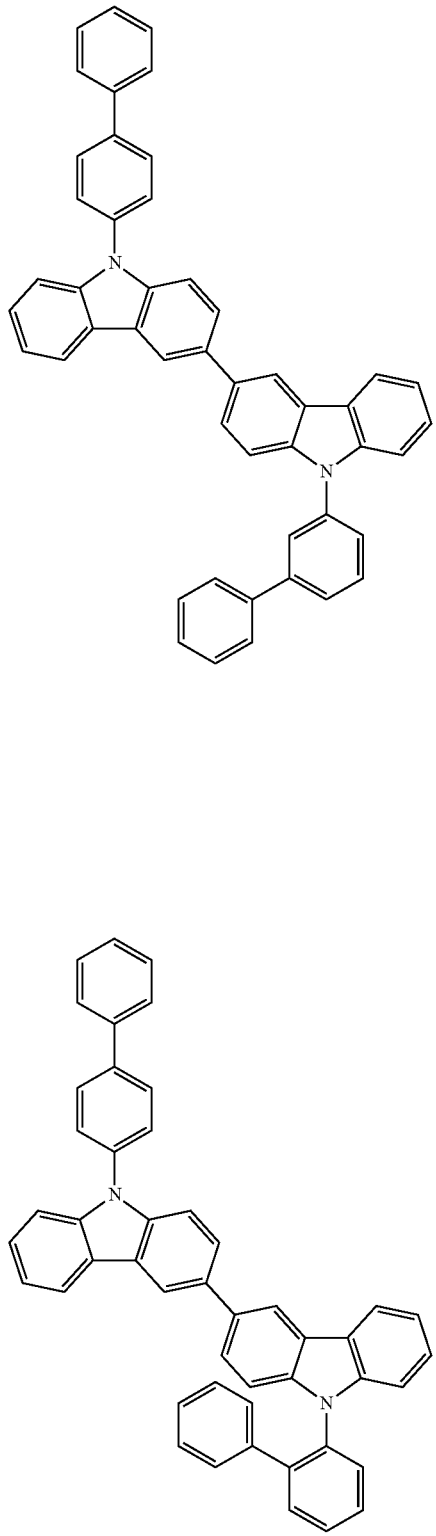
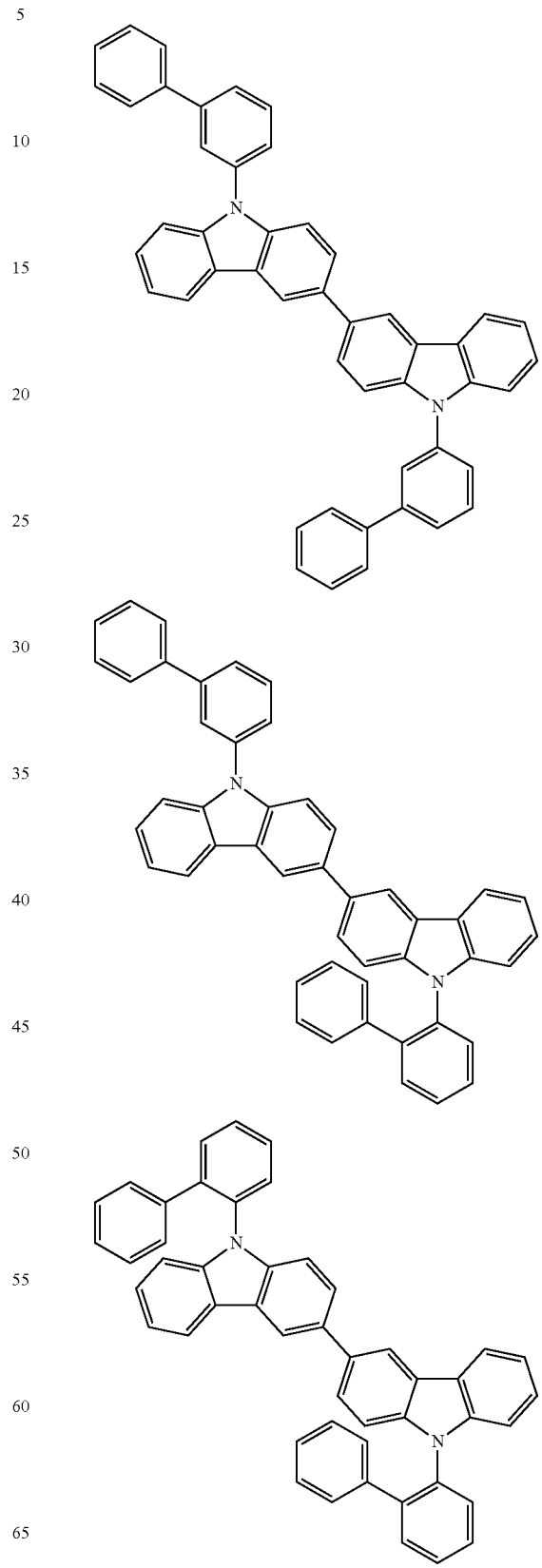

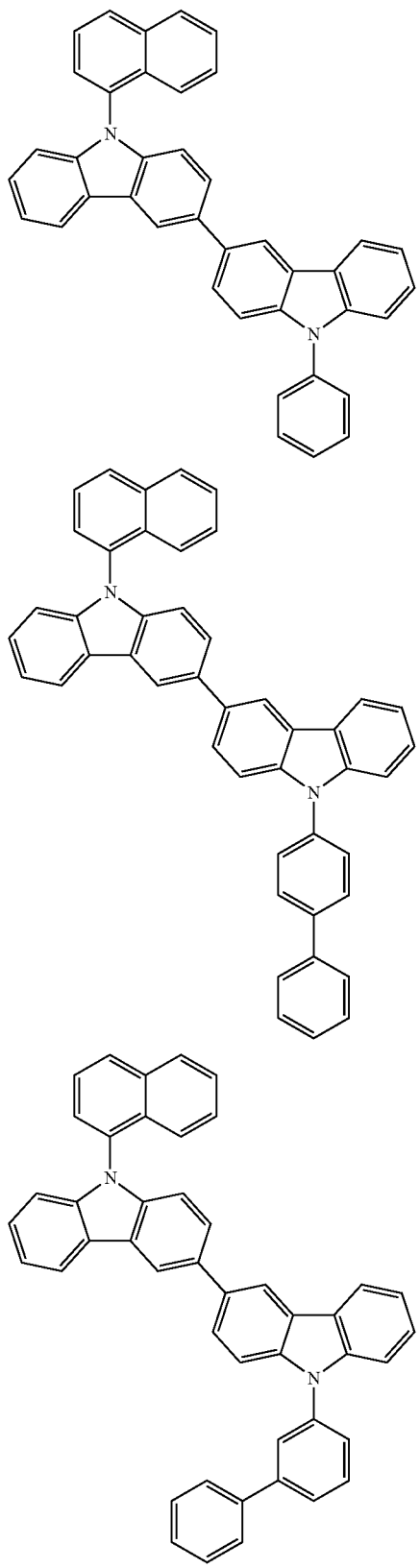
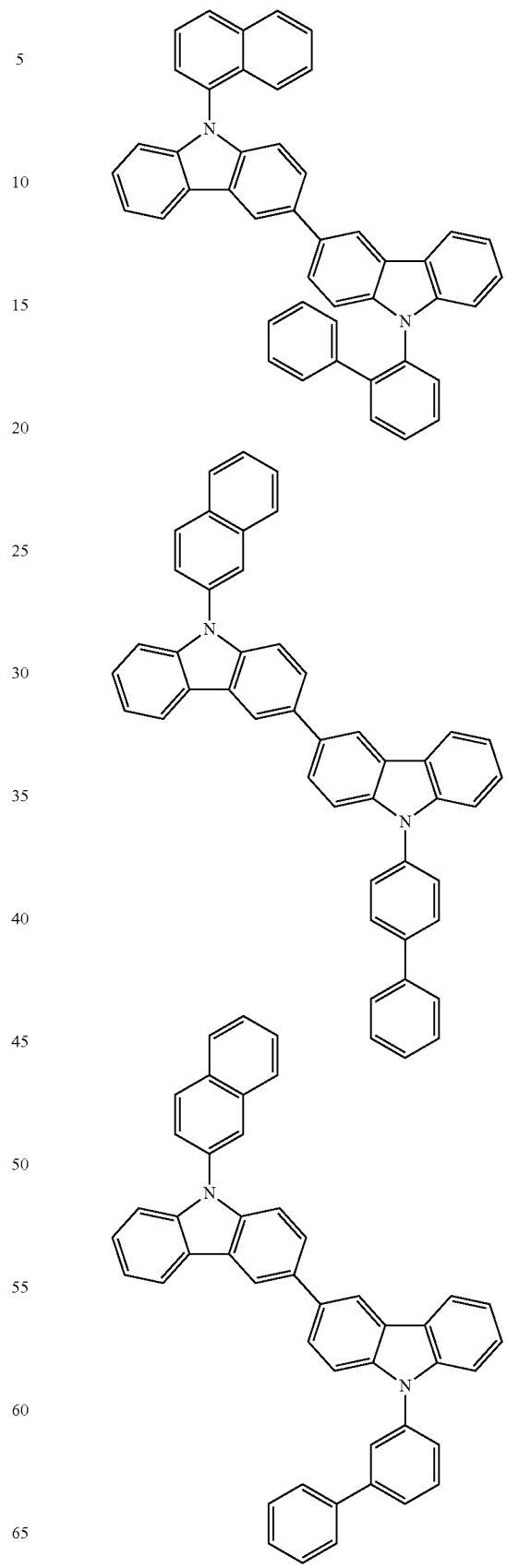

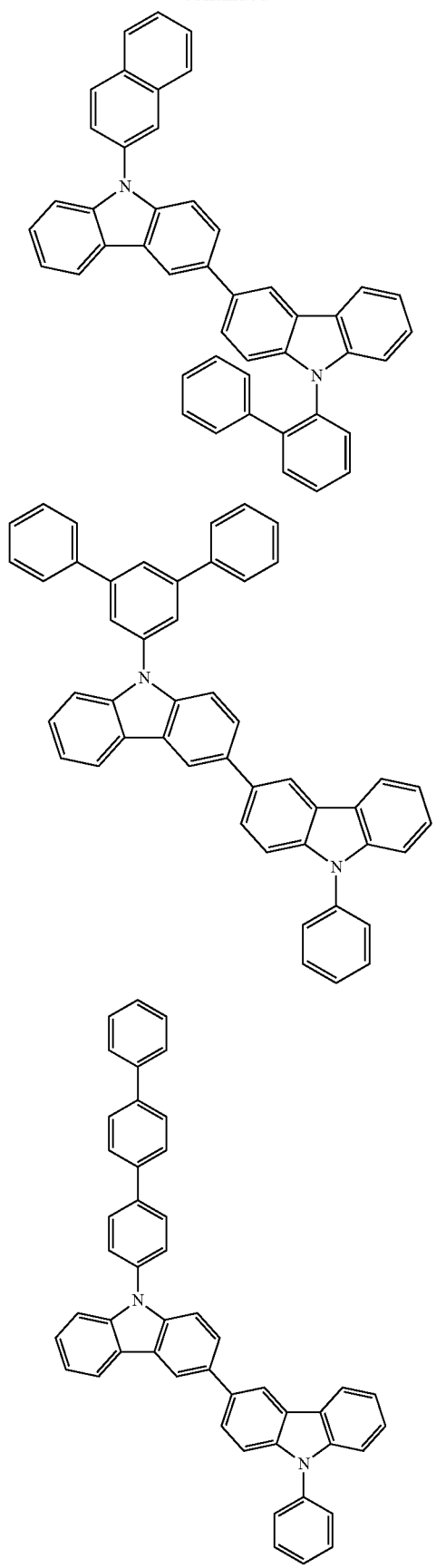
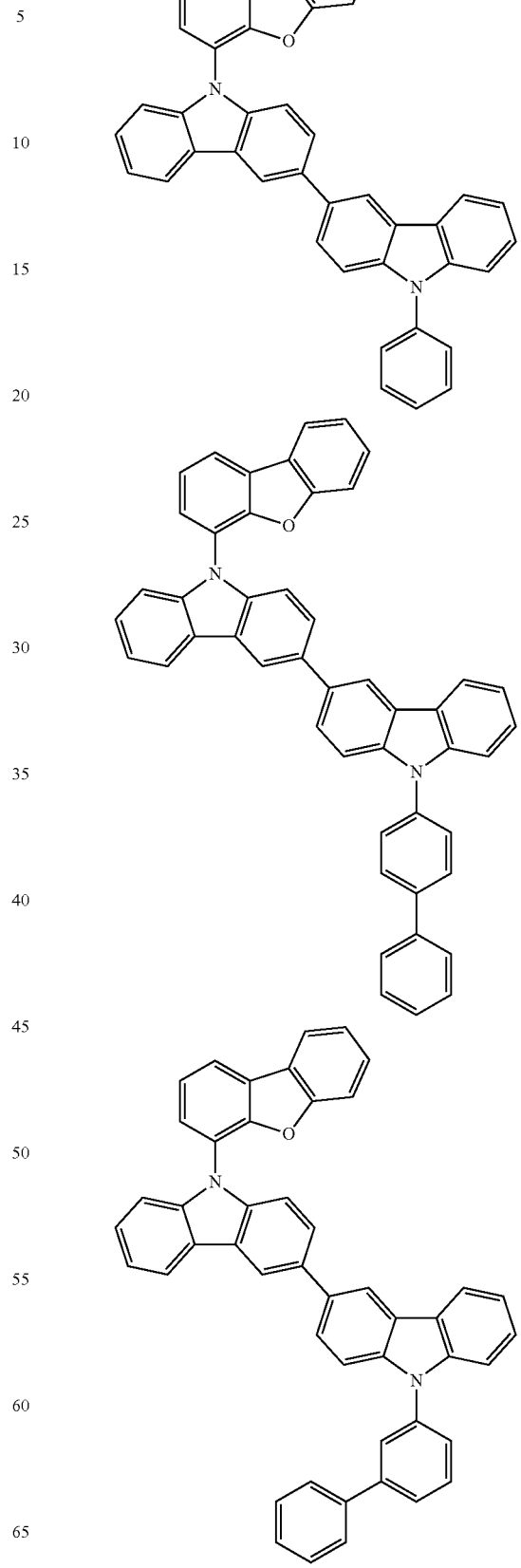

121
-continued
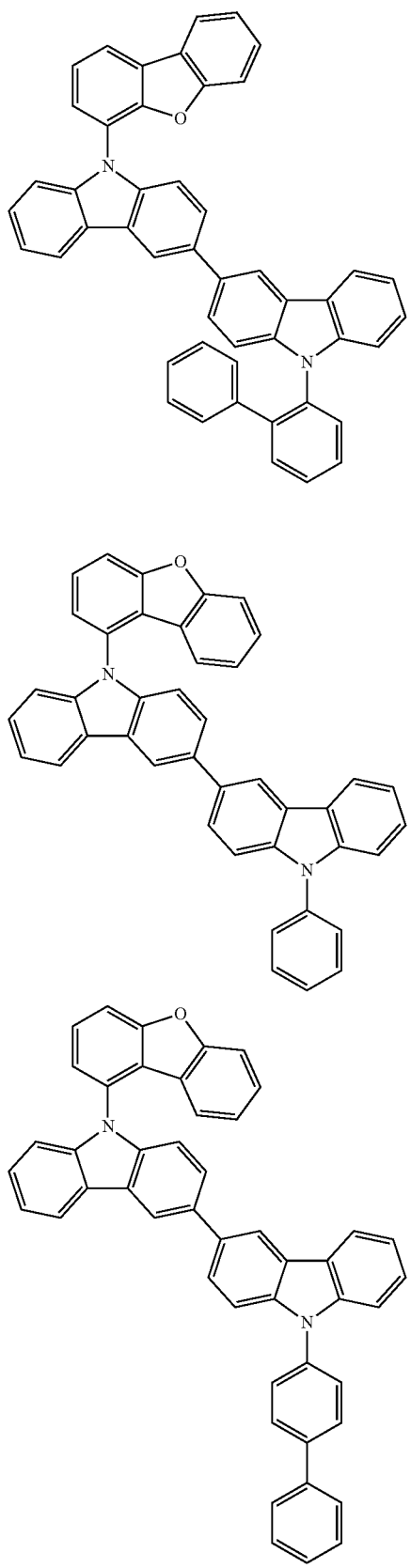
122
-continued
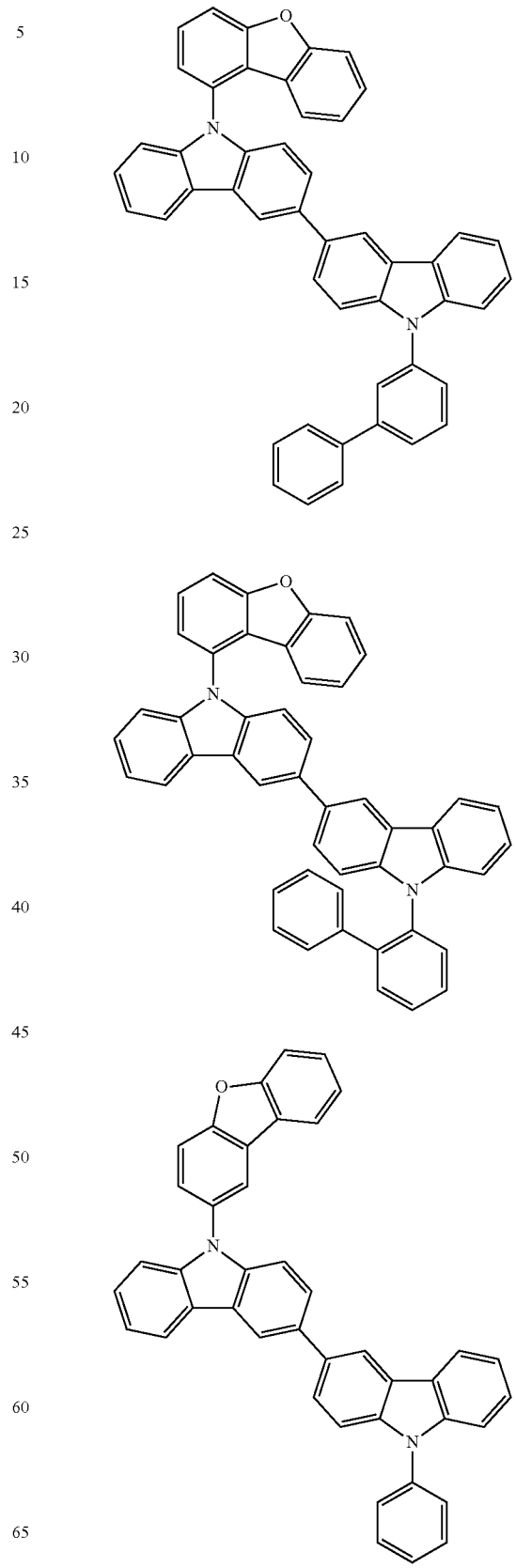

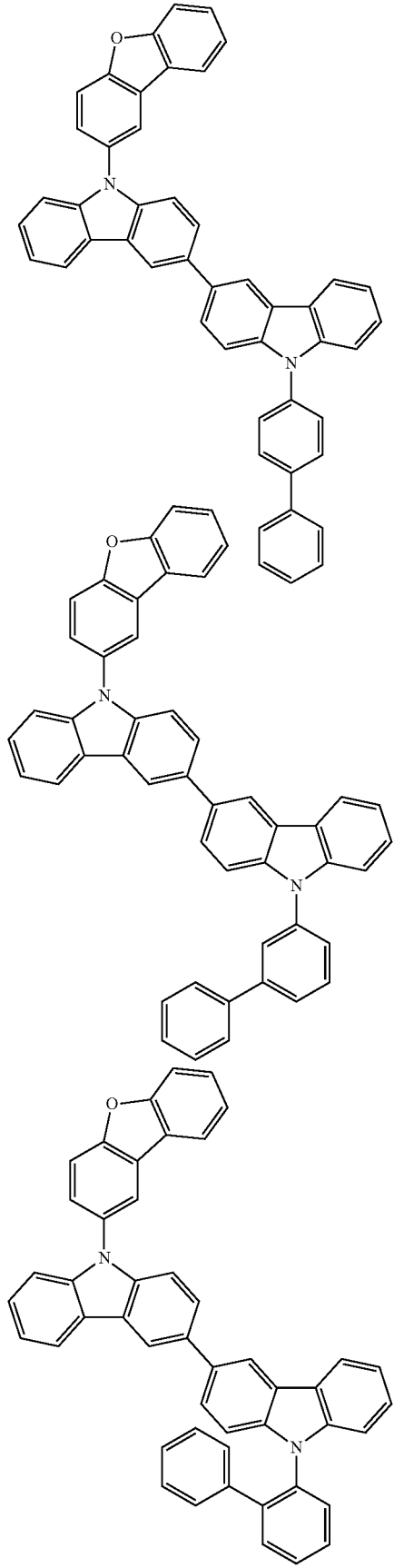
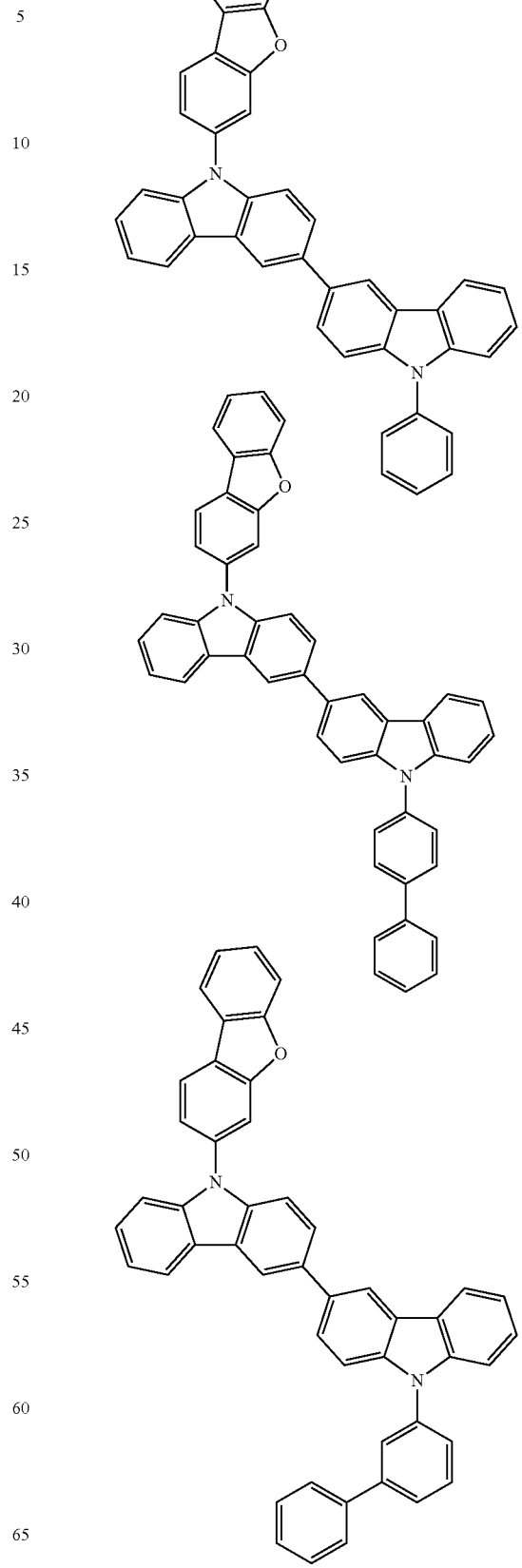

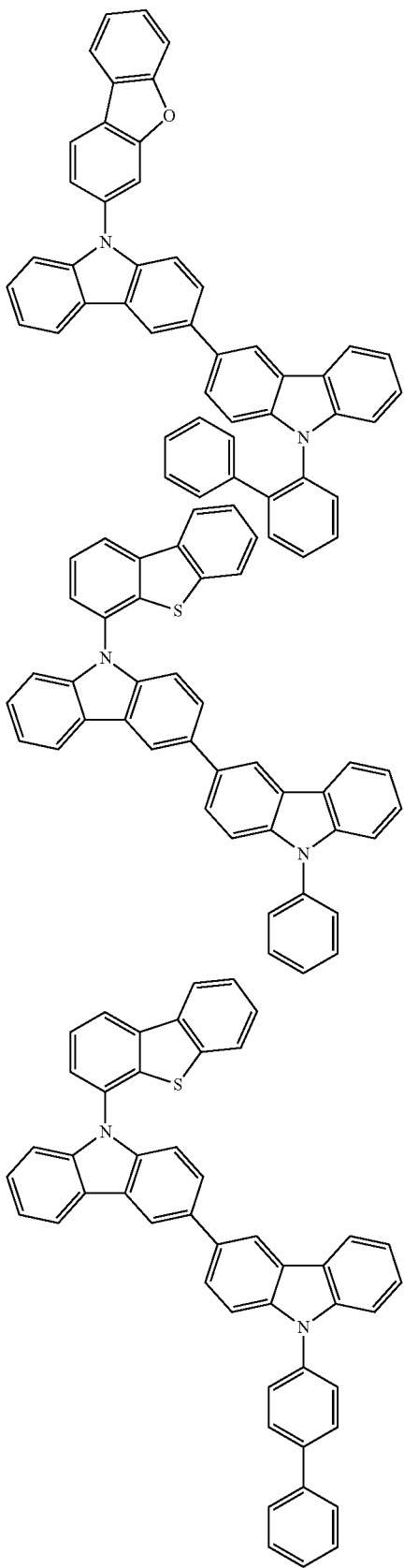
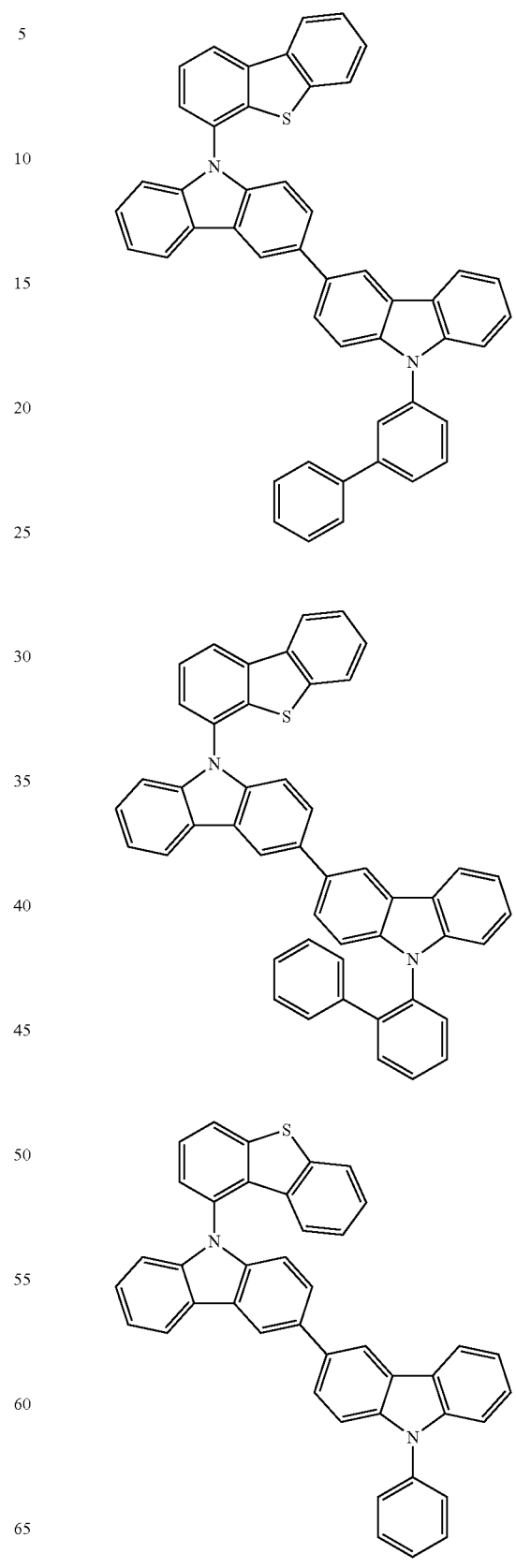

127
-continued
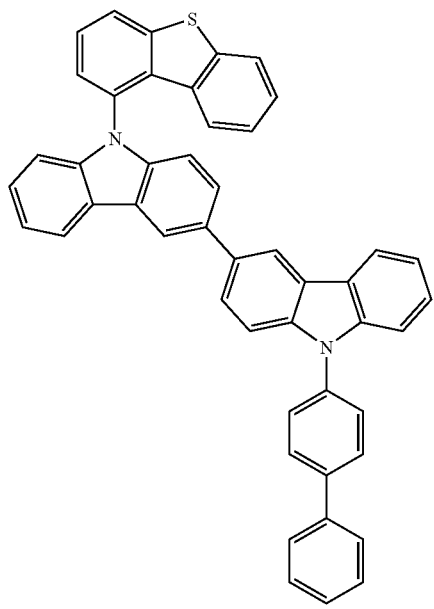
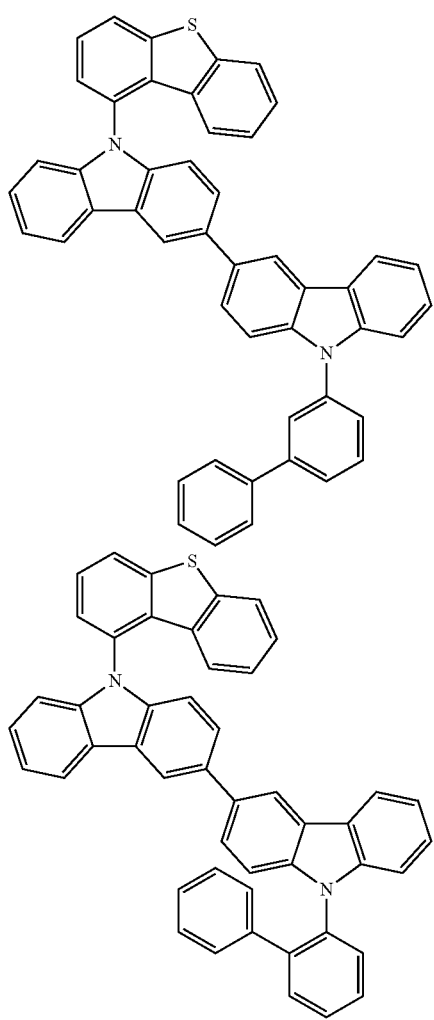
128
-continued
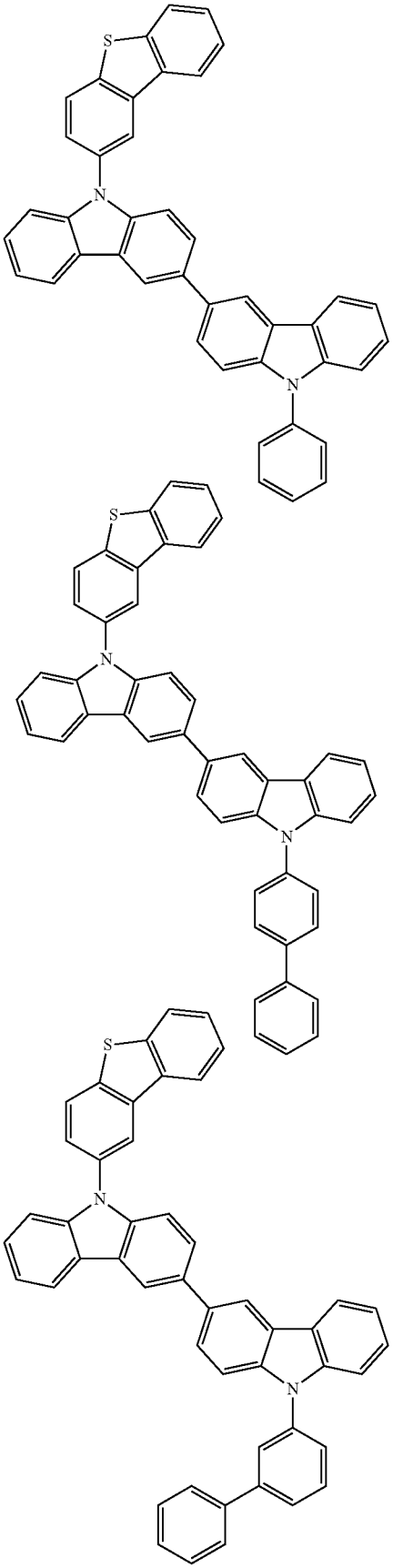

129
-continued
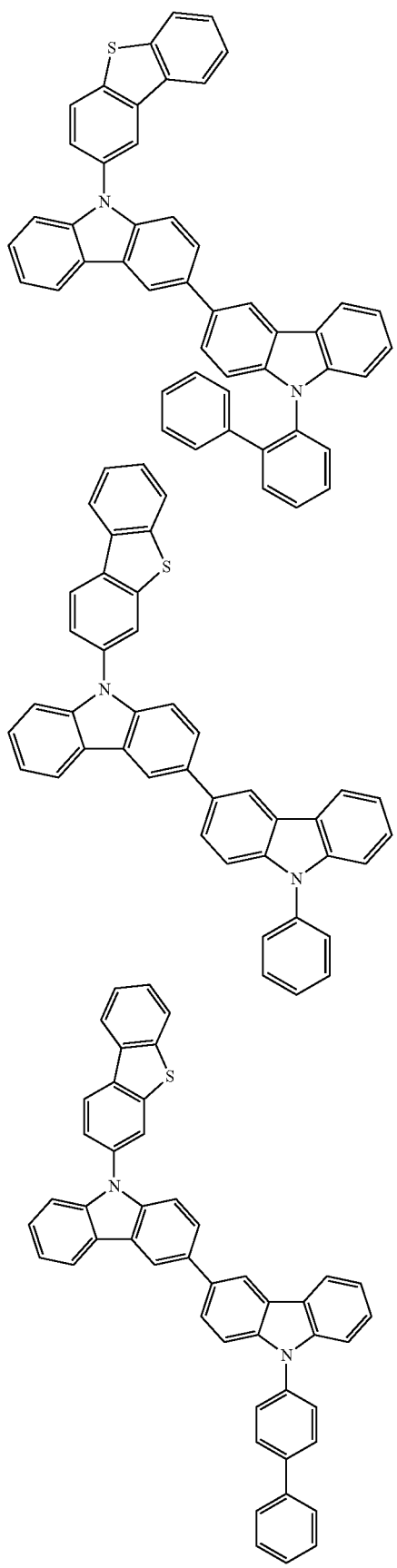
130
-continued
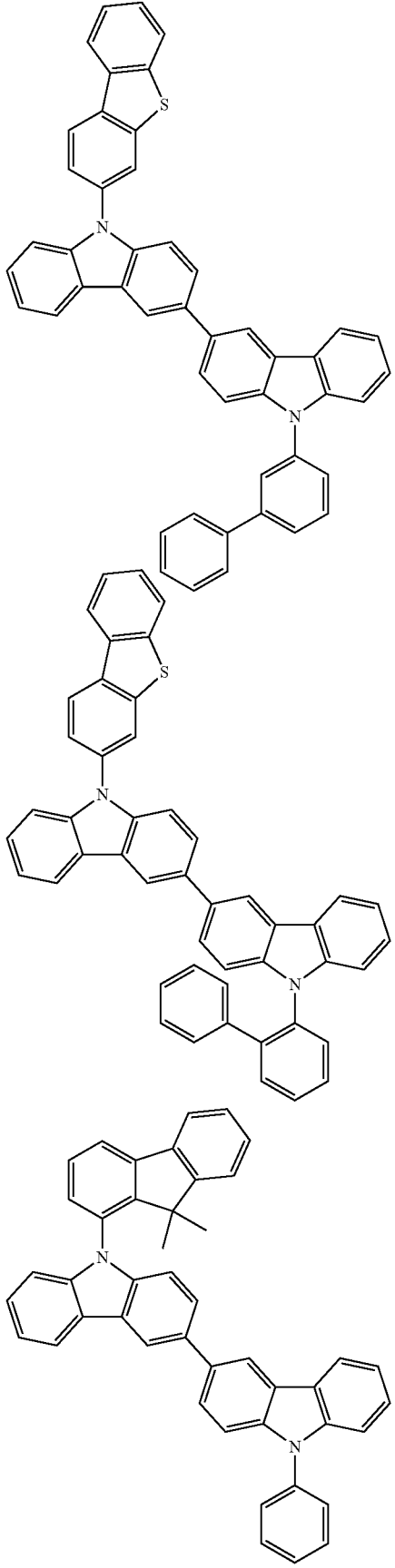

131
-continued
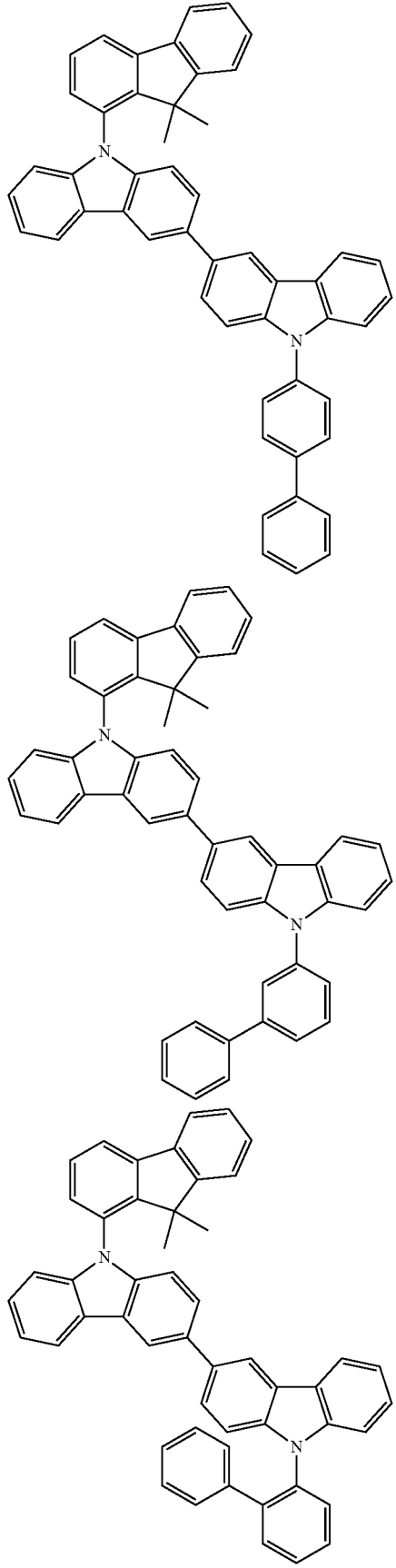
132
-continued
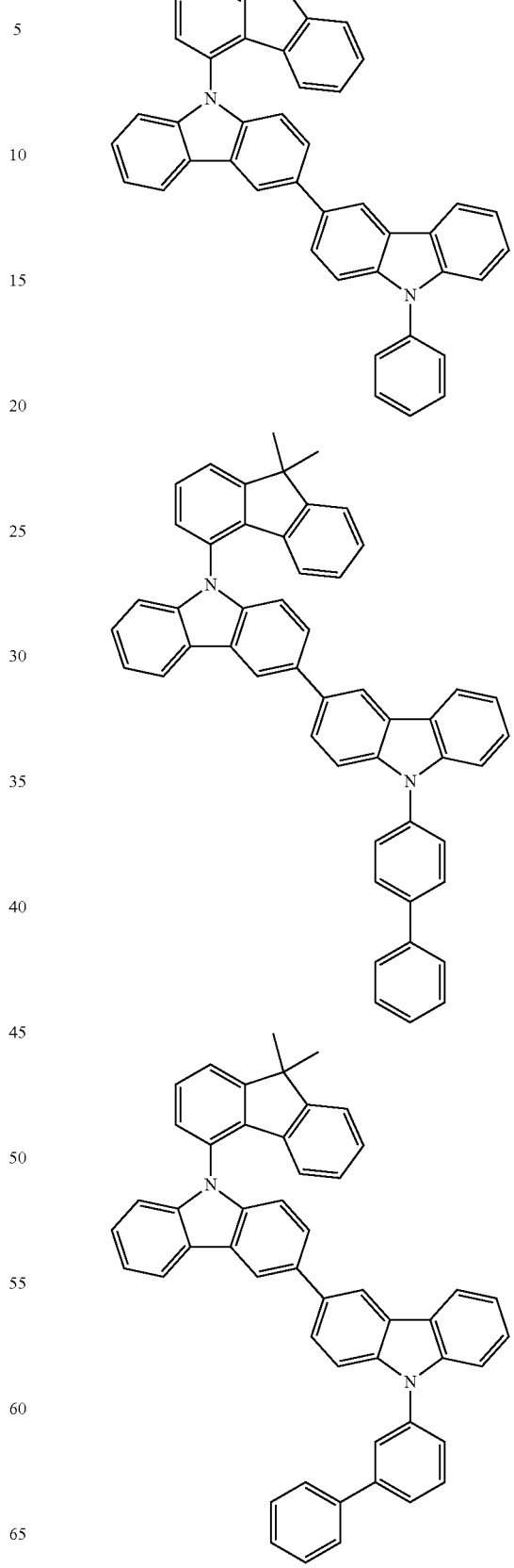

133
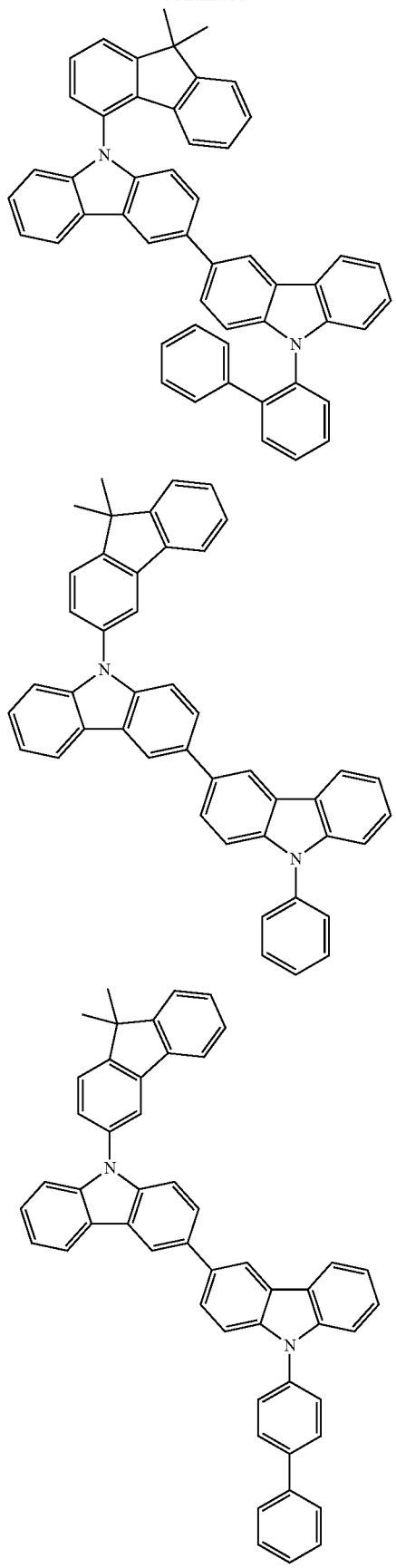
134
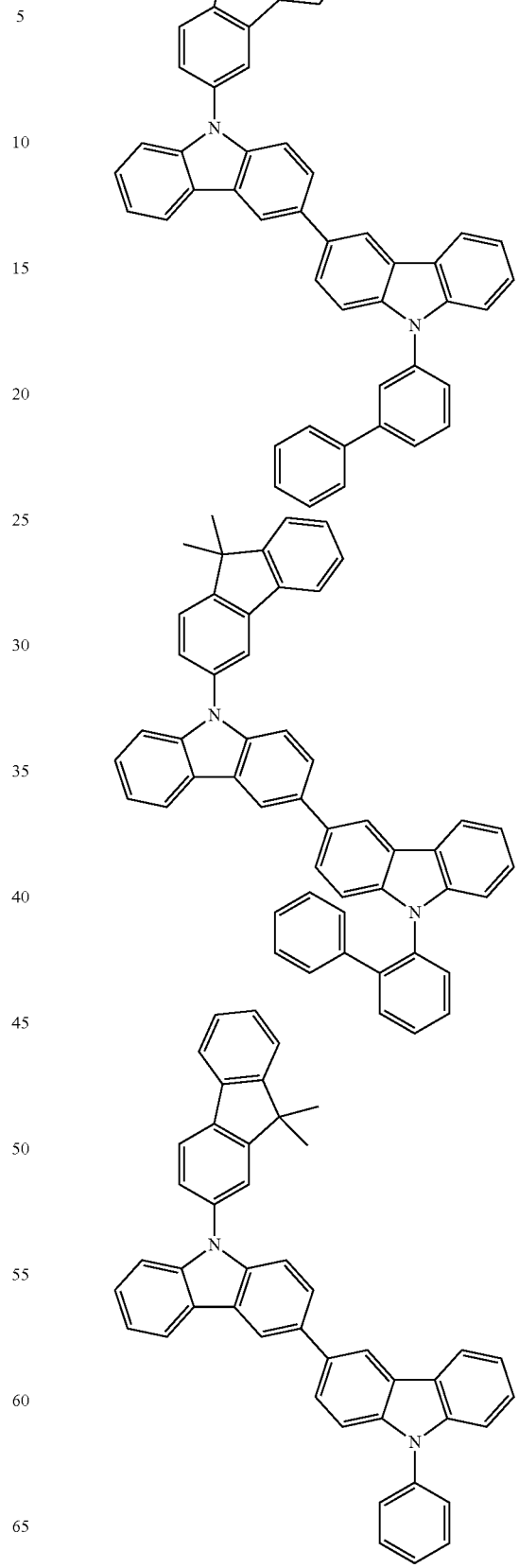

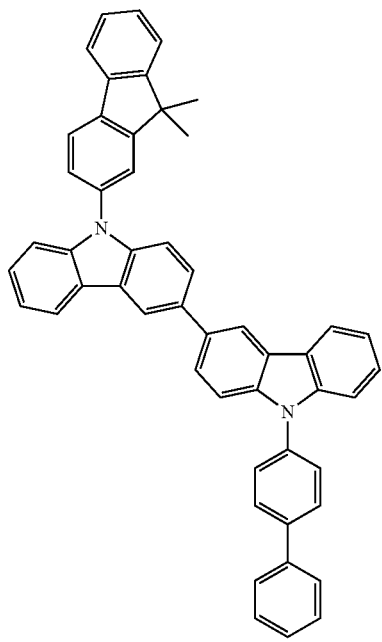

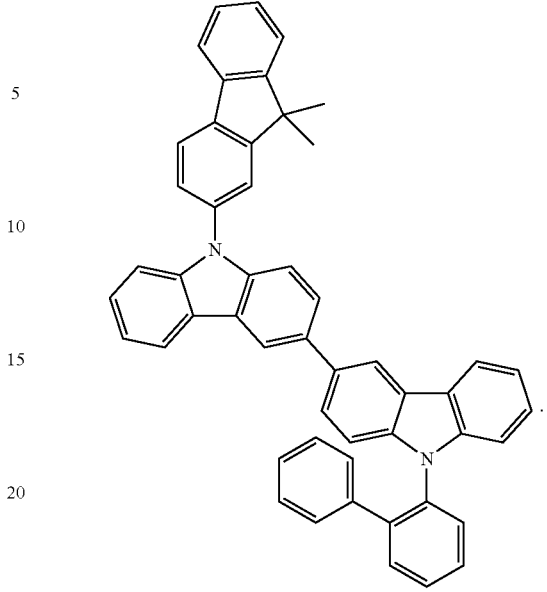

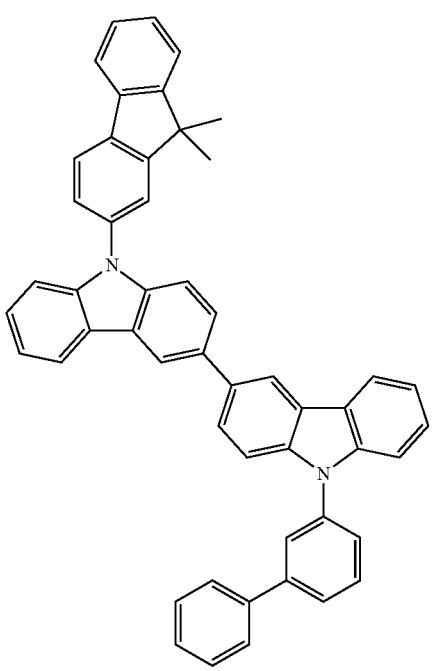

The compound of Chemical Formula 2 can be included in an organic material layer including the compound of Chemical Formula 1 at the same time.

Preferably, the weight ratio of the compound of Chemical Formula 1 to the compound of Chemical Formula 2 can be 1:99 to 99:1, and more preferably 10:90 to 90:10.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is a layer provided between the electron transport layer and the light emitting layer in order to prevent the holes injected in the anode from being transferred to the electron transport layer without being recombined in the light emitting layer, which can also be referred to as a hole inhibition layer. The hole blocking layer is preferably a material having the large ionization energy.

The electron transport layer is a layer which receives electrons from an electron injection layer and transports the electrons to a light emitting layer, and an electron transport material is suitably a material which can receive electrons well from a cathode and transfer the electrons to a light emitting layer, and has a large mobility for electrons. Specific examples of the electron transport material include: an Al complex of 8-hydroxyquinoline, a complex including $Alq_3$, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and the electron injection material is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection material include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium, and the like, but are not limited thereto.

The organic light emitting device according to the present invention can be a front side emission type, a back side emission type, or a double side emission type according to the used material.

In addition, the compound of Chemical Formula 1 can be included in an organic solar cell or an organic transistor in addition to an organic light emitting device.

Hereinafter, preferred embodiments of the present invention will be described in more detail to facilitate understanding of the invention. However, these examples are presented for illustrative purposes only and are not intended to limit the scope of the present invention.

Preparation Example 1: Synthesis of Intermediate A (Synthesis of Intermediate A-1)

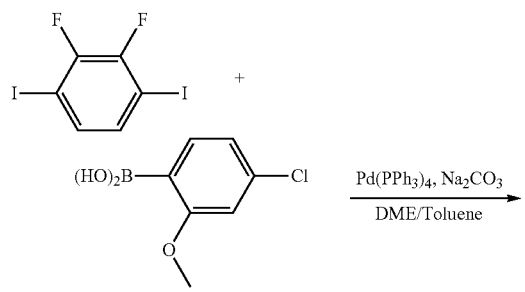

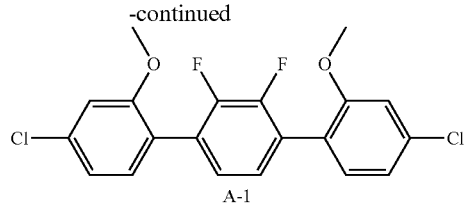

2,3-Difluoro-1,4-diiodobenzene (30.0 g, 82.0 mmol), (4-chloro-2-methoxyphenyl)boronic acid (36.7 g, 196.8 mmol), 2M aqueous $Na_2CO_3$ solution (164 mL, 328.0 mmol), DME (165 mL), toluene (165 mL), $Pd(PPh_3)_4$ (9.5 g, 8.2 mmol) were added to a three-necked flask, and the mixture was stirred at reflux for 8 hours under an argon atmosphere. After completion of the reaction, the reaction temperature was cooled down to room temperature and then the reaction solution was transferred to a separatory funnel. $H_2O$ (300 mL) was added and extracted with $CH_2Cl_2$. The extract was dried over $MgSO_4$, filtered and concentrated, and then the sample was purified by silica gel column chromatography to give Intermediate A-1 (21.1 g, yield: 65%).

$MS[M+H]^+=395$.

(Synthesis of Intermediate A-2)

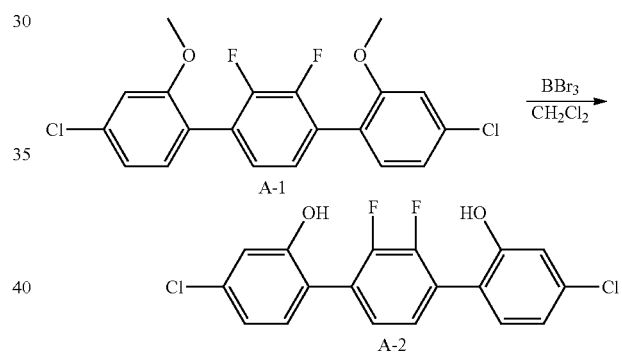

Intermediate A-1 (20.0 g, 50.6 mmol), 1M $BBr_3$ in $CH_2Cl_2$ solution (121 mL, 121.4 mmol), and $CH_2Cl_2$ (300 mL) were added to a two-necked flask, the temperature was adjusted to 0° C. under an argon atmosphere, and the mixture was stirred for 8 hours. Then, the reaction mixture was further stirred at room temperature for 4 hours, and then neutralized with saturated aqueous $NaHCO_3$ solution. The reaction solution was transferred to a separatory funnel and extracted with $CH_2Cl_2$. The extract was purified by silica gel column chromatography to give Intermediate A-2 (15.8 g, yield: 85%).

$MS[M+H]^+=367$.

(Synthesis of Intermediate A)

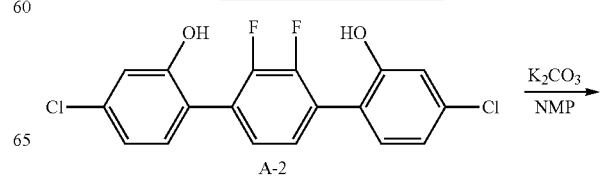

-continued

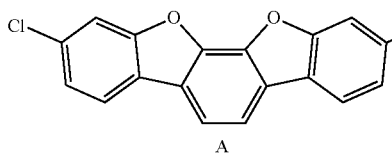

A

Intermediate A-2 (15.0 g, 40.9 mmol), K₂CO₃ (12.4 g, 89.9 mmol) and NMP (170 mL) were added to a two-necked flask, and the mixture was stirred at 150° C. for 8 hours under an argon atmosphere. After completion of the reaction, the reaction temperature was cooled down to room temperature and then the reaction solution was transferred to a separatory funnel. H₂O (100 mL) was added and extracted with ethyl acetate. The extract was purified by silica gel column chromatography to give Intermediate A (11.9 g, yield: 89%).

MS[M+H]⁺=327.

Preparation Example 2: Synthesis of Intermediate B (Synthesis of Intermediate B-1)

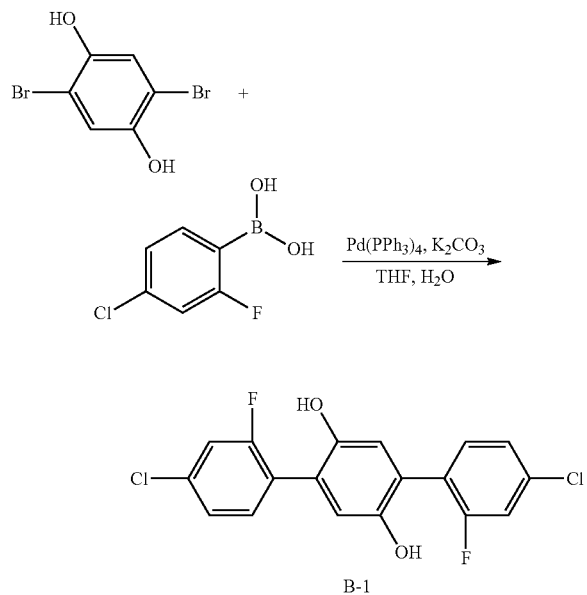

B-1

A solution in which 2,5-Dibromobenzene-1,4-diol (20.0 g, 74.7 mmol), (4-chloro-2-fluorophenyl)boronic acid (39.9 g, 156.8 mmol) were dissolved in THF (750 mL) and K₂CO₃ (61.9 g, 447.9 mmol) was dissolved in H₂O (375 mL) was added to a three-necked flask. Pd(PPh₃)₄ (1.7 g, 1.5 mmol) was added thereto, and the mixture was stirred at reflux for 8 hours under an argon atmosphere. After completion of the reaction, the reaction temperature was cooled down to room temperature and the reaction solution was transferred to a separatory funnel and extracted with CH₂Cl₂. The extract was dried over MgSO₄, filtered and concentrated, and then the sample was purified by silica gel column chromatography to give Intermediate B-1 (21.1 g, yield: 77%).

MS[M+H]⁺=367.

(Synthesis of Intermediate B)

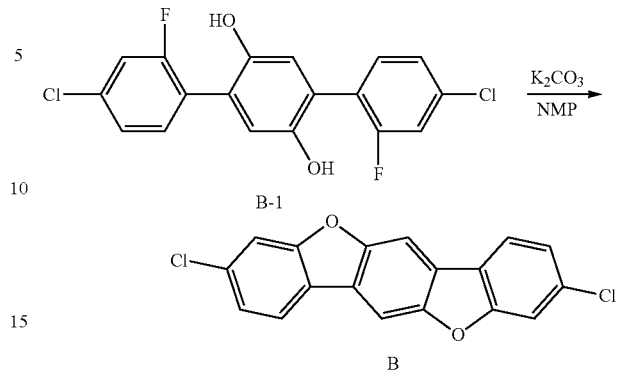

B

Intermediate B-1 (15.0 g, 40.9 mmol), K₂CO₃ (12.4 g, 89.9 mmol) and NMP (170 mL) were added to a two-necked flask, and the mixture was stirred at 150° C. for 8 hours under an argon atmosphere. After completion of the reaction, the reaction temperature was cooled down to room temperature, and then the sample was transferred to a separatory funnel. H₂O (100 mL) was added thereto and extracted with ethyl acetate. The extract was purified by silica gel column chromatography to give Intermediate B (10.8 g, yield: 81%).

MS[M+H]⁺=327.

Preparation Example 3: Synthesis of Intermediate C

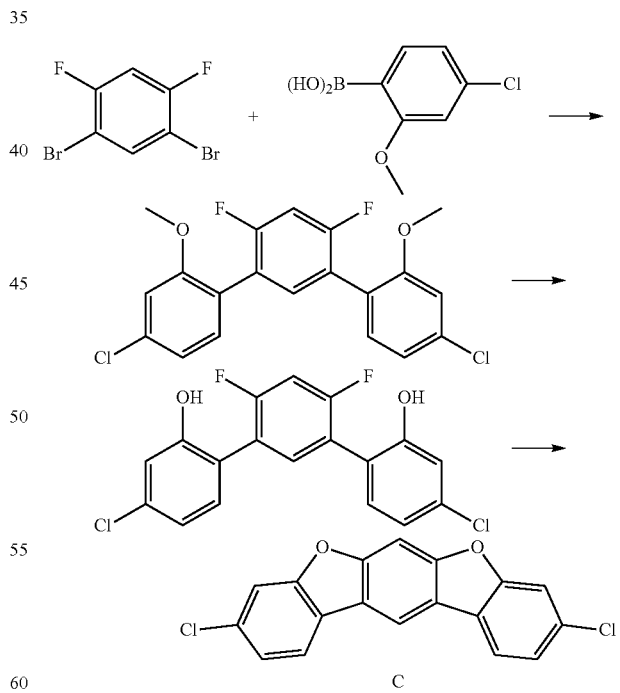

C

Intermediate C was prepared in the same manner as in the preparation method of Intermediate A, except for using 1,5-dibromo-2,4-difluorobenzene instead of 2,3-difluoro-1,4-diiodobenzene in Preparation Example 1.

MS[M+H]⁺=327.

Preparation Example 4: Synthesis of Intermediate D (Synthesis of Intermediate D-1)

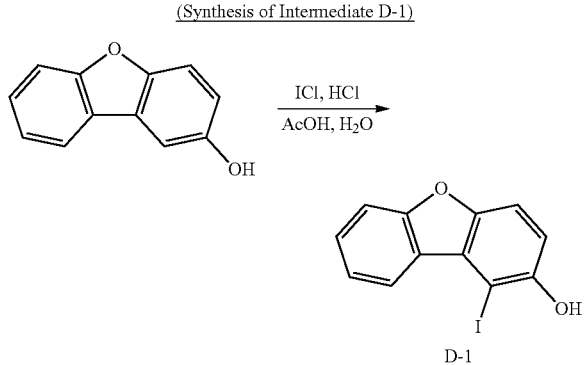

2-Hydroxydibenzo[b,d]furan (15.0 g, 81.4 mmol) and acetic acid (100 mL) were added to a three-necked flask, to which iodine monochloride (4.5 mL, 89.6 mmol), conc. HCl (55 mL) and acetic acid solution (34 mL) were added dropwise and then stirred at room temperature for 24 hours. After completion of the reaction, H₂O (300 mL) was added thereto, and the produced precipitate was filtered and washed with H₂O. The filtered solid was recrystallized from MeOH to give Intermediate D-1 (18.9 g, yield: 75%).
MS[M+H]⁺=310

(Synthesis of Intermediate D-2)

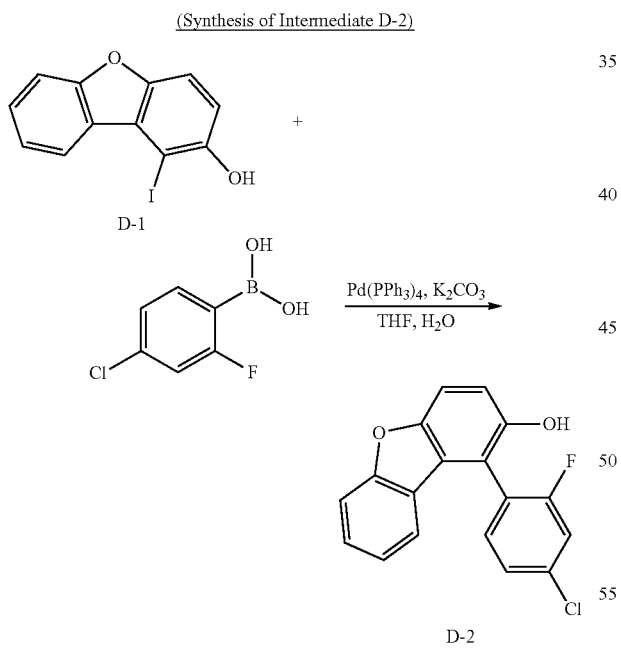

A solution in which Intermediate D-1 (18.0 g, 58.0 mmol) and (4-chloro-2-fluorophenyl)boronic acid (10.6 g, 61.0 mmol) were dissolved in THF (600 mL) and K₂CO₃ (32.1 g, 232.2 mmol) was dissolved in H₂O (300 mL) was added to a three-necked flask. Pd(PPh₃)₄ (0.7 g, 0.6 mmol) was added thereto, and the mixture was stirred at reflux for 8 hours under an argon atmosphere. After completion of the reaction, the reaction temperature was cooled down to room temperature and the reaction solution was transferred to a separatory funnel and extracted with CH₂Cl₂. The extract was dried over MgSO₄, filtered and concentrated, and then the sample was purified by silica gel column chromatography to give Intermediate D-2 (14.5 g, yield: 80%).
MS[M+H]⁺=313.

(Synthesis of Intermediate D)

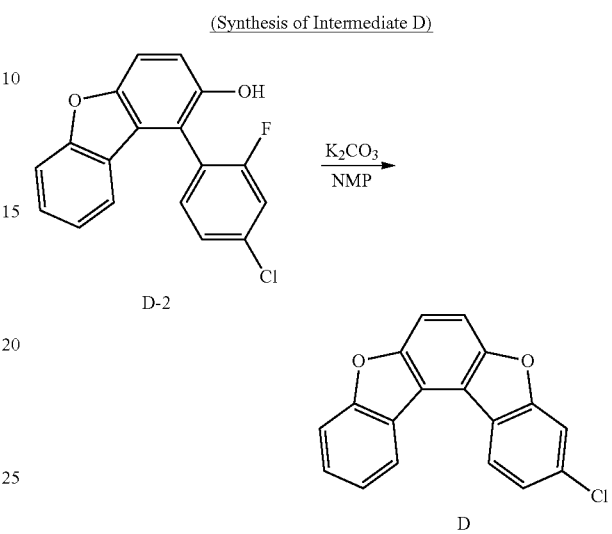

Intermediate D-2 (14.0 g, 44.8 mmol), K₂CO₃ (9.3 g, 67.2 mmol) and NMP (180 mL) were added to a two-necked flask, and the mixture was stirred at 150° C. for 8 hours under an argon atmosphere. After completion of the reaction, the reaction temperature was cooled down to room temperature, and then the sample was transferred to a separatory funnel. H₂O (200 mL) was added thereto and extracted with ethyl acetate. The extract was purified by silica gel column chromatography to give Intermediate D (10.6 g, yield: 81%).
MS[M+H]⁺=293.

Preparation Example 5: Synthesis of Intermediate E (Synthesis of Intermediate E-1)

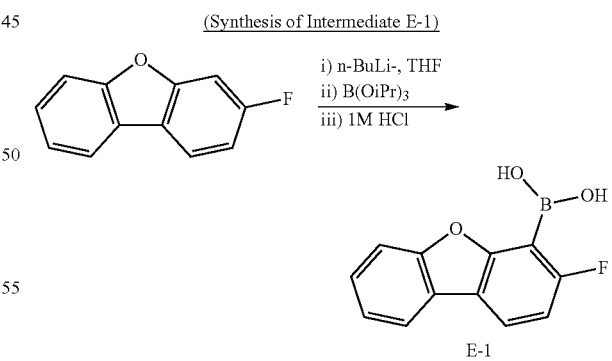

3-Fluorodibenzo[b,d]furan (15.0 g, 80.6 mmol) and THF (400 mL) were added to a three-necked flask and cooled to −78° C. n-BuLi (1.6M n-hexane solution, 55 mL, 88.6 mmol) was added dropwise and stirred at −78° C. for 20 minutes. Boric acid triisopropyl (45.5 g, 241.7 mmol) was added and stirred at −78° C. for 1 hour, and then further stirred at room temperature for 4 hours. Then, 1N HCl (130 mL) was added thereto and stirred at room temperature for 1 hour, and the reaction solution was concentrated and transferred to a separatory funnel. H₂O (200 mL) was added and extracted with CH₂Cl₂. The extract was dried over MgSO₄, filtered, concentrated, and recrystallized from toluene-hexane to give Intermediate E-1 (11.1 g, yield: 60%).

MS[M+H]⁺=230.

(Synthesis of Intermediate E-2)

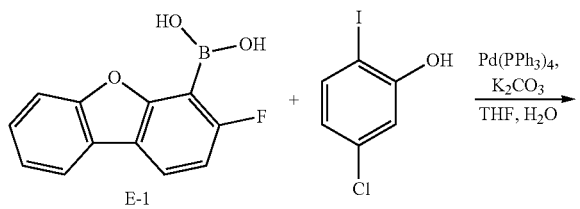

A solution in which Intermediate E-1 (10.0 g, 43.5 mmol) and 5-chloro-2-iodophenol (11.6 g, 45.7 mmol) were dissolved in THF (430 mL) and K₂CO₃ (24.0 g, 173.9 mmol) was dissolved in H₂O (220 mL) was added to a three-necked flask. Pd(PPh₃)₄ (0.5 g, 0.4 mmol) was added thereto, and the mixture was stirred at reflux for 8 hours under an argon atmosphere. After completion of the reaction, the reaction temperature was cooled down to room temperature and the reaction solution was transferred to a separatory funnel and extracted with CH₂Cl₂. The extract was dried over MgSO₄, filtered and concentrated, and then the sample was purified by silica gel column chromatography to give Intermediate E-2 (10.5 g, yield: 77%).

MS[M+H]⁺=313.

(Synthesis of Intermediate E)

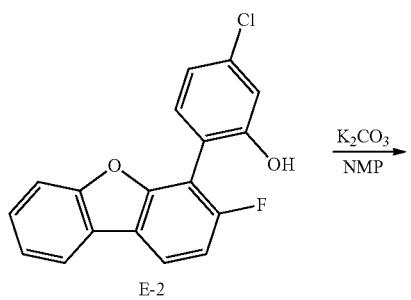

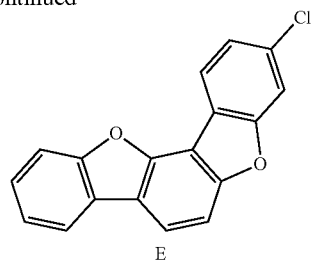

Compound E-2 (10.0 g, 32.0 mmol), K₂CO₃ (6.6 g, 48.0 mmol) and NMP (130 mL) were added to a two-necked flask, and the mixture was stirred at 150° C. for 8 hours under an argon atmosphere. After completion of the reaction, the reaction temperature was cooled down to room temperature, and then the sample was transferred to a separatory funnel. H₂O (100 mL) was added thereto and extracted with ethyl acetate. The extract was purified by silica gel column chromatography to give Intermediate E (6.2 g, yield: 66%).

MS[M+H]⁺=293.

Preparation Example 6: Synthesis of Intermediate F

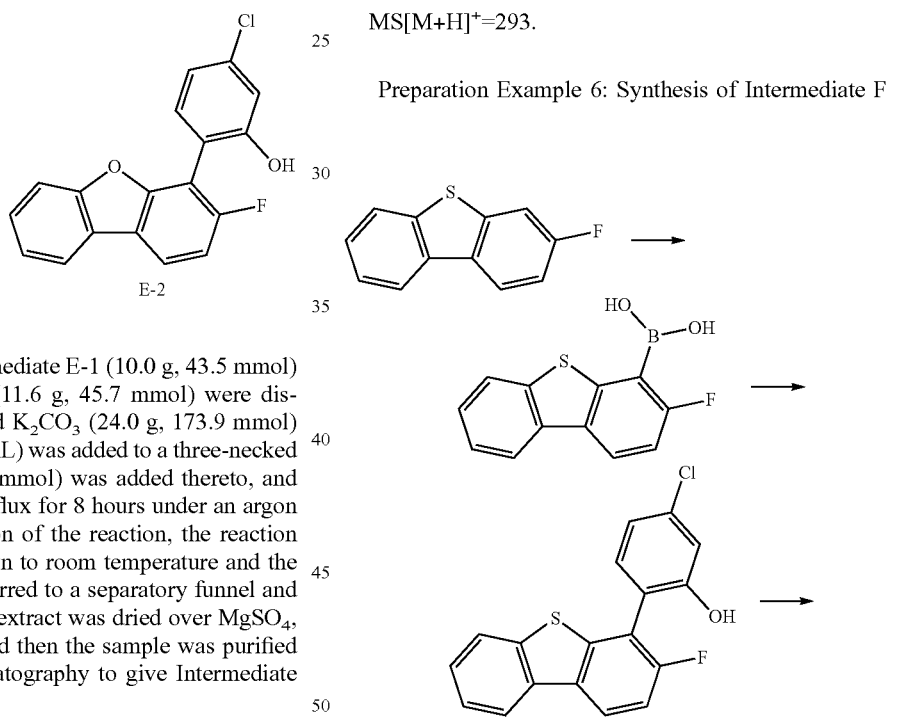

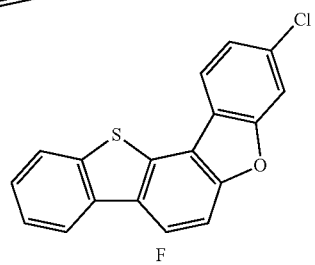

Intermediate F was prepared in the same manner as in the preparation method of intermediate E, except for using 3-fluorodibenzo[b,d]thiophene instead of 3-fluorodibenzo[b,d]furan in Preparation Example 5.

MS[M+H]⁺=309.

Preparation Example 7: Synthesis of Compound 1

(Synthesis of Compound 1-1)

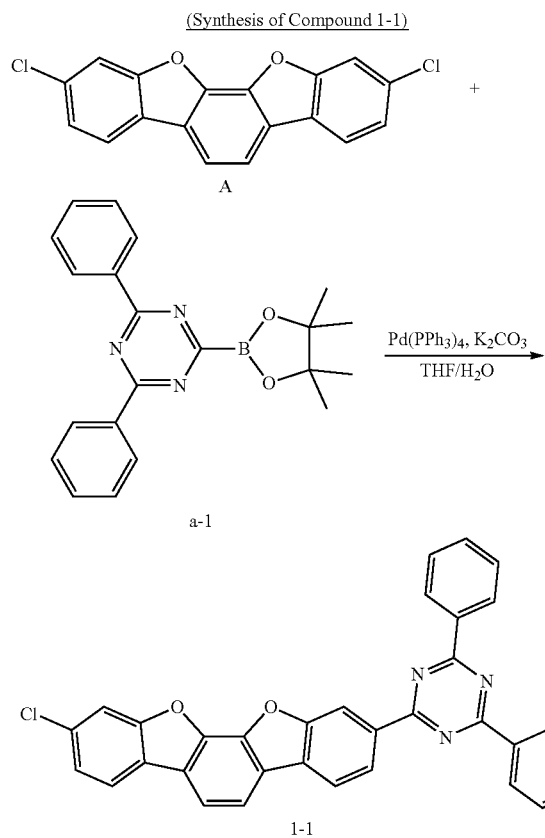

A solution in which Intermediate A (15.0 g, 45.8 mmol) and Intermediate a-1 (17.3 g, 48.1 mmol) were dissolved in THF (460 mL) and K₂CO₃ (25.3 g, 183.4 mmol) was dissolved in H₂O (230 mL) was added to a three-necked flask. Pd(PPh₃)₄ (0.5 g, 0.5 mmol) was added thereto, and the mixture was stirred at reflux for 8 hours under an argon atmosphere. After completion of the reaction, the reaction temperature was cooled down to room temperature, and the reaction solution was transferred to a separatory funnel and extracted with CH₂Cl₂. The extract was dried over MgSO₄, filtered and concentrated, and then the sample was purified by silica gel column chromatography to give Compound 1-1 (16.3 g, yield: 68%).

MS[M+H]⁺=524.

(Synthesis of Compound 1)

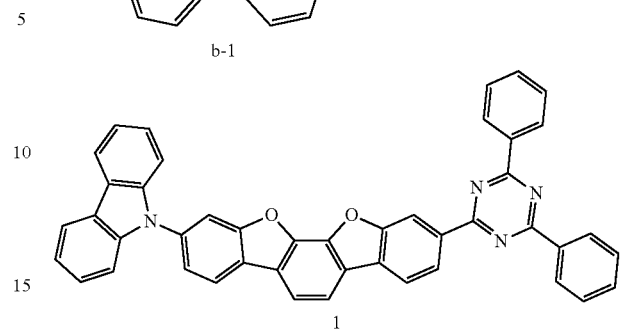

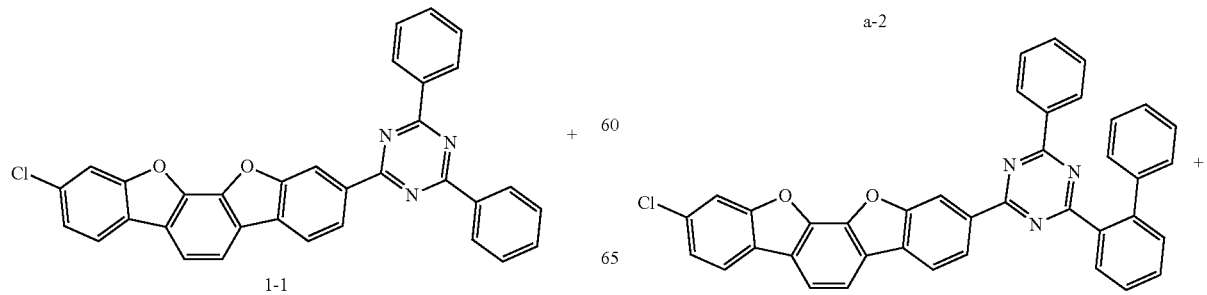

In a three-necked flask, Compound 1-1 (15.0 g, 28.6 mmol) and Intermediate b-1 (5.3 g, 31.5 mmol) were dissolved in toluene (285 mL), and sodium tert-butoxide (4.1 g, 42.9 mmol) and bis(tri-tert-butylphosphine)palladium(0) (0.3 g, 0.6 mmol) were added thereto. The mixture was stirred at reflux for 6 hours under an argon atmosphere. After completion of the reaction, the reaction temperature was cooled down to room temperature, H₂O (160 mL) was added thereto, and the reaction solution was transferred to a separatory funnel and extracted. The extract was dried over MgSO₄ and concentrated. The sample was purified by silica gel column chromatography and then subjected to sublimation purification to give Compound 1 (6.0 g, yield: 32%).

MS[M+H]⁺=655.

Preparation Example 8: Synthesis of Compound 2

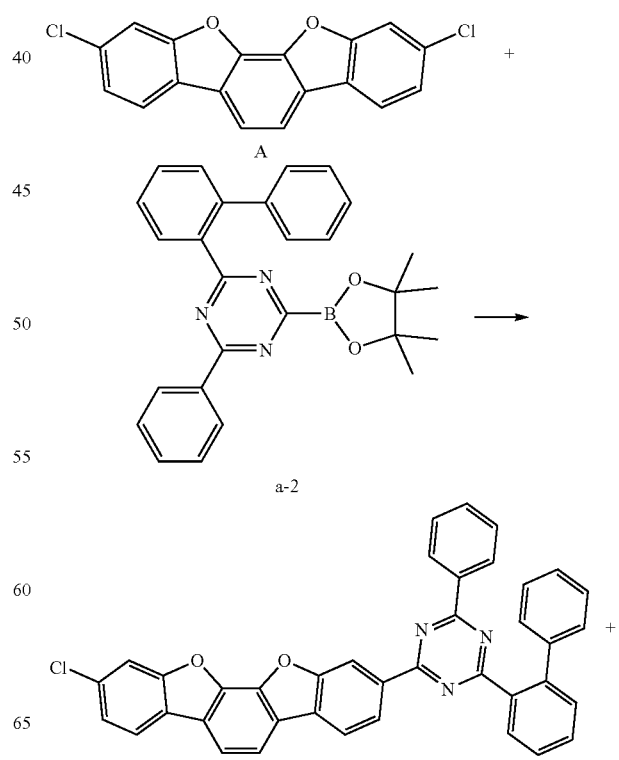

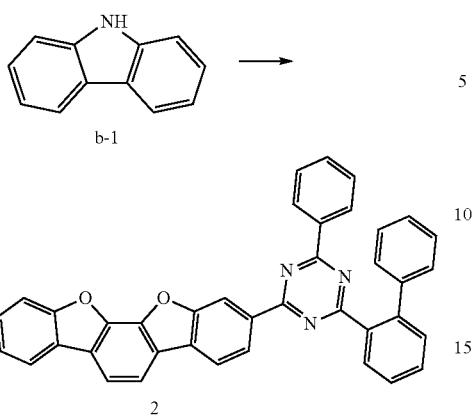
Compound 2 was prepared in the same manner as in the preparation method of Compound 1, except for using Intermediate a-2 instead of Intermediate a-1 in Preparation Example 7.
MS[M+H]$^+$=731
Preparation Example 9: Synthesis of Compound 3
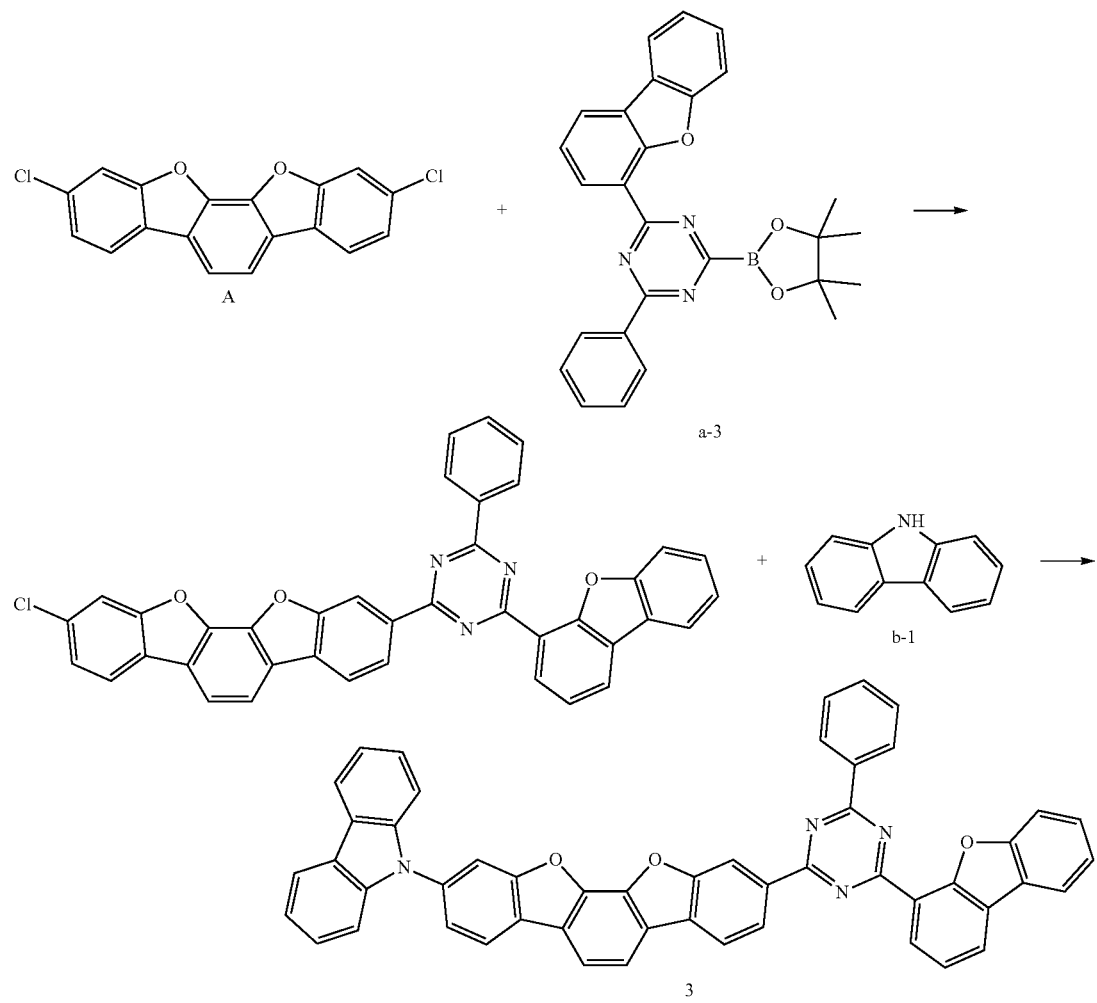

Compound 3 was prepared in the same manner as in the preparation method of Compound 1, except that Intermediate a-3 was used instead of Intermediate a-1 in Preparation Example 7.

MS[M+H]$^+$=745

Preparation Example 10: Synthesis of Compound 4

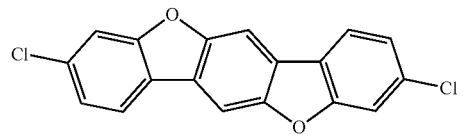

B

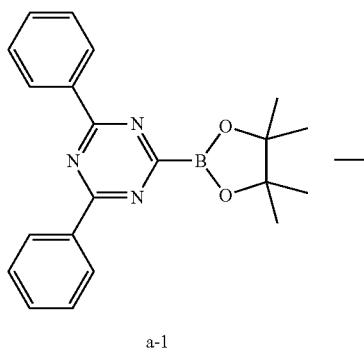

a-1

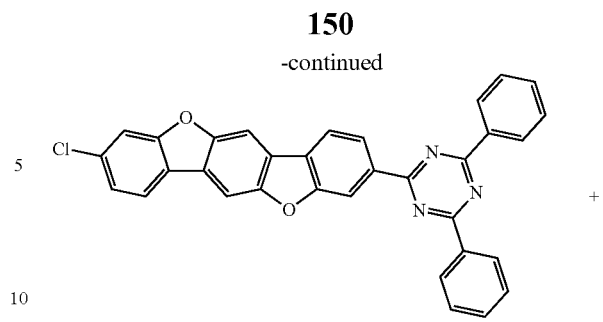

-continued

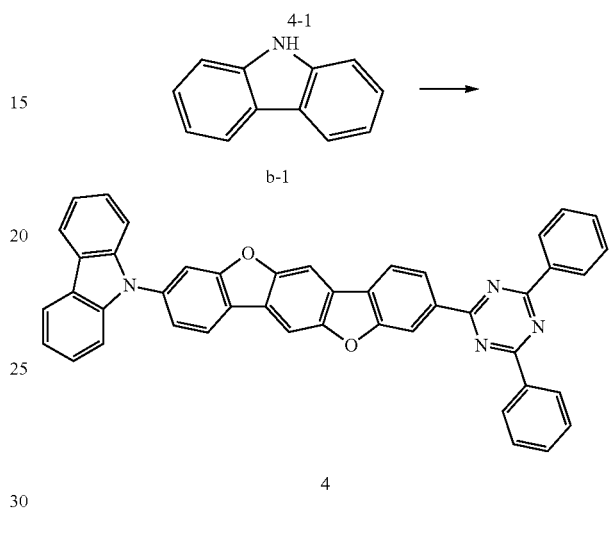

4

Compound 4 was prepared in the same manner as in the preparation method of Compound 1, except for using Intermediate B instead of Intermediate A in Preparation Example 7.

MS[M+H]$^+$=655

Preparation Example 11: Synthesis of Compound 5

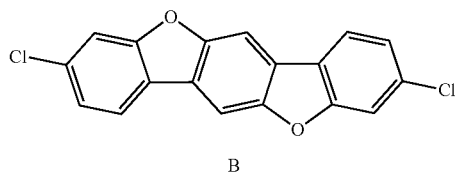

B

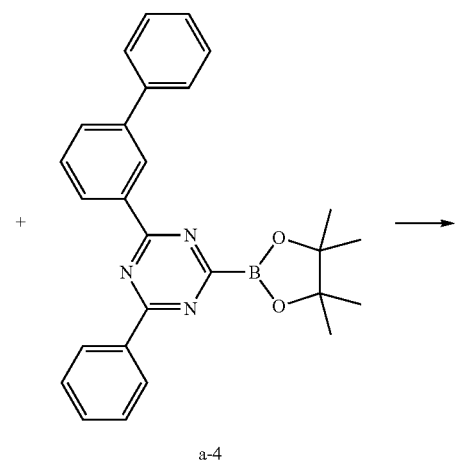

a-4

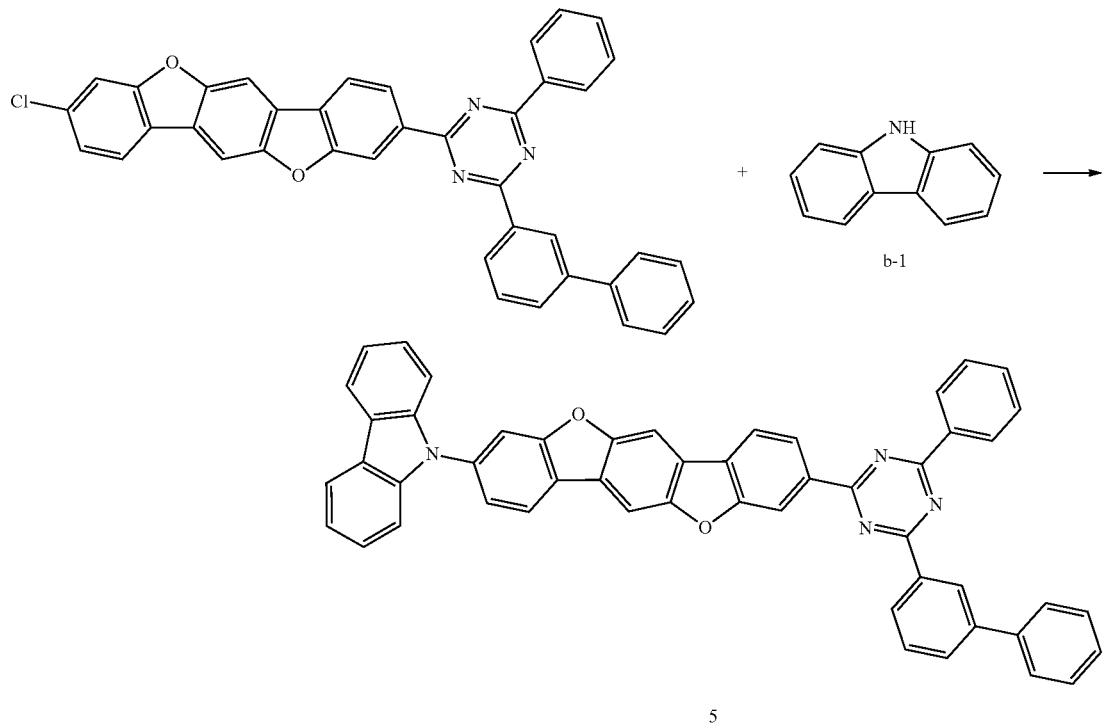

5

Compound 5 was prepared in the same manner as in the preparation method of Compound 1, except for using Intermediate B instead of Intermediate A and Intermediate a-4 instead of Intermediate a-1 in Preparation Example 7.

MS[M+H]$^+$=731

Preparation Example 12: Synthesis of Compound 6

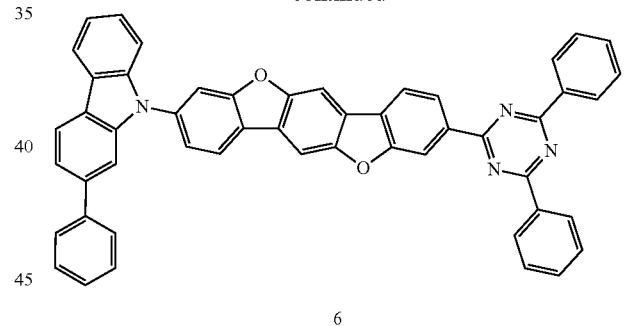

-continued

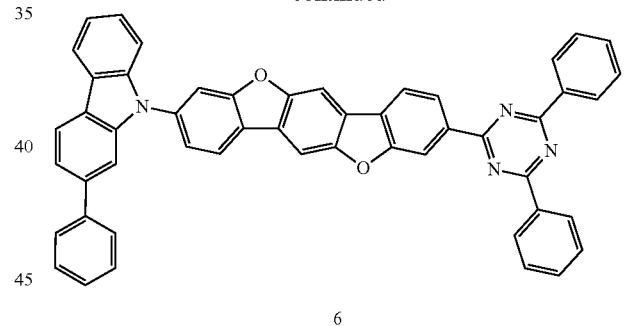

6

Compound 6 was prepared in the same manner as in the preparation method of Compound 1, except for using Intermediate 4-1 instead of Intermediate 1-1 and Intermediate b-2 instead of Intermediate b-1 in Preparation Example 7.

MS[M+H]$^+$=731

Preparation Example 13: Synthesis of Compound 7

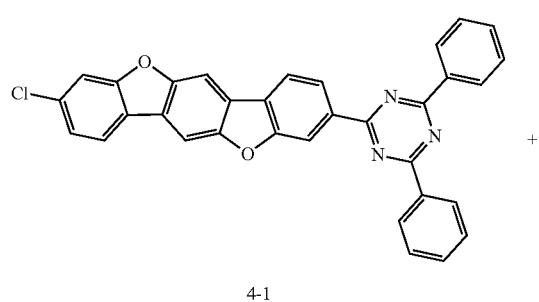

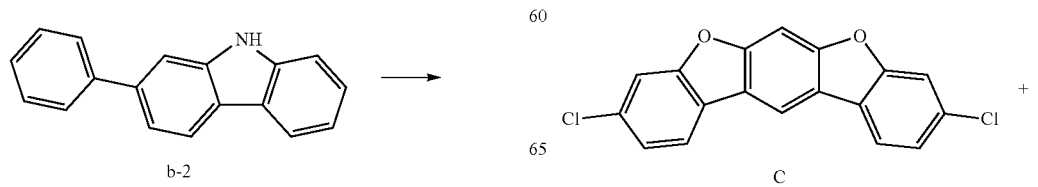

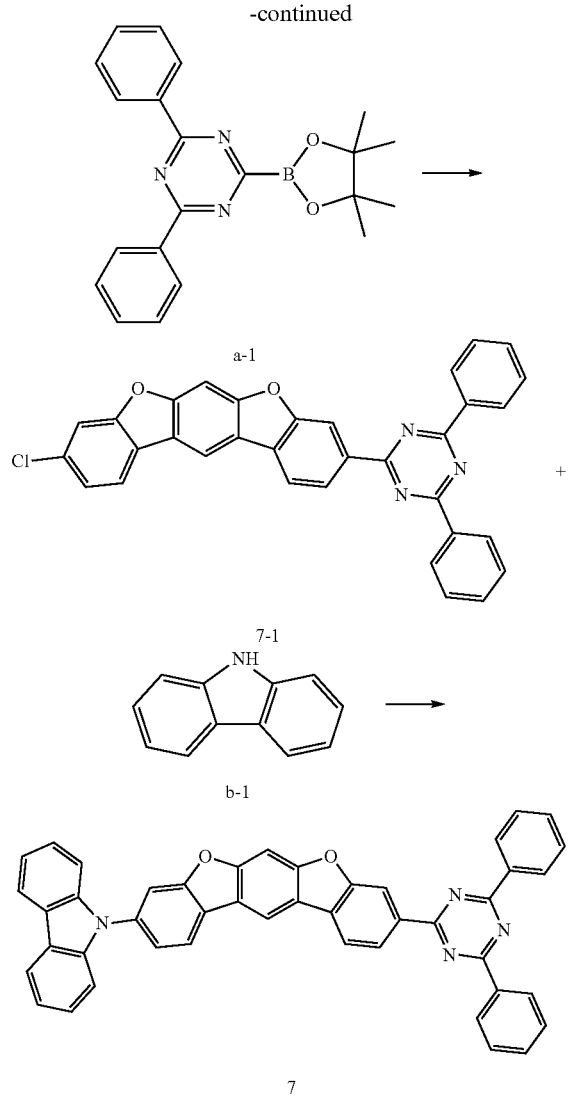

Compound 7 was prepared in the same manner as in the preparation method of Compound 1, except for using Intermediate C instead of Intermediate A in Preparation Example 7.

MS[M+H]$^+$=655

Preparation Example 14: Synthesis of Compound 8

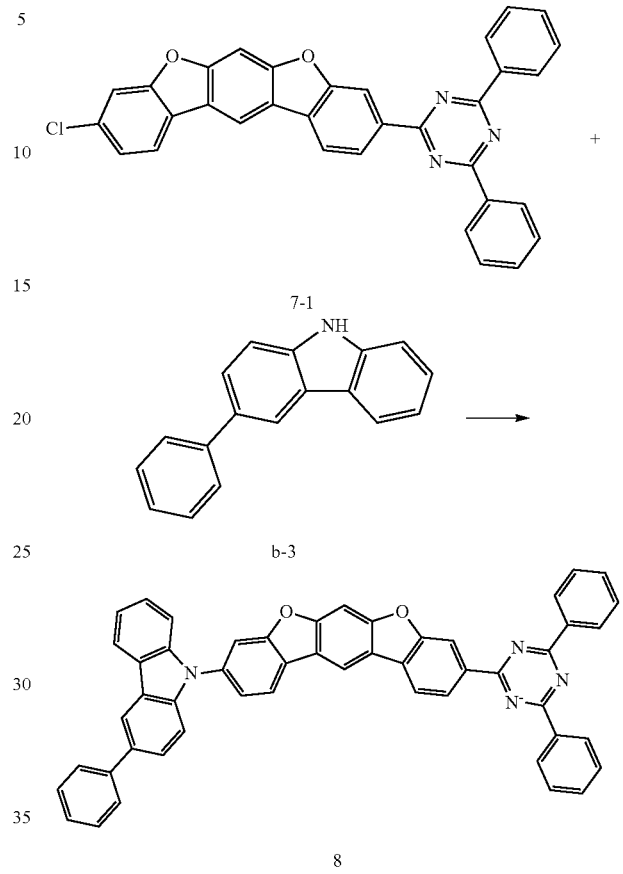

Compound 8 was prepared in the same manner as in the preparation method of Compound 1, except for using Intermediate 7-1 instead of Intermediate 1-1 and Intermediate b-3 instead of Intermediate b-1 in Preparation Example 7.

MS[M+H]$^+$=731

Preparation Example 15: Synthesis of Compound 9

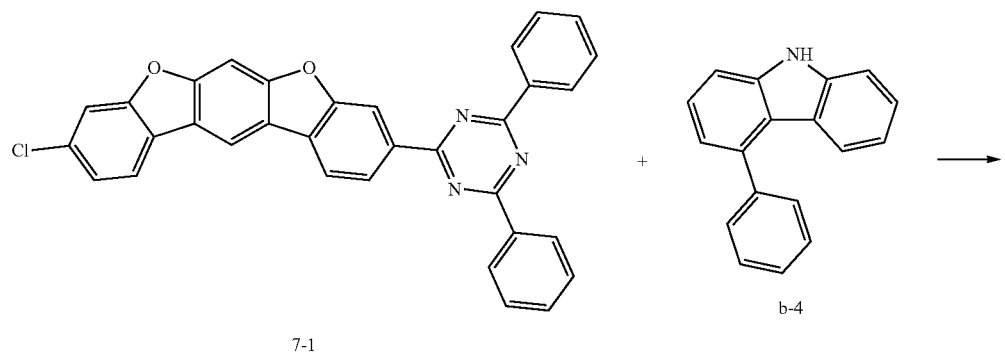

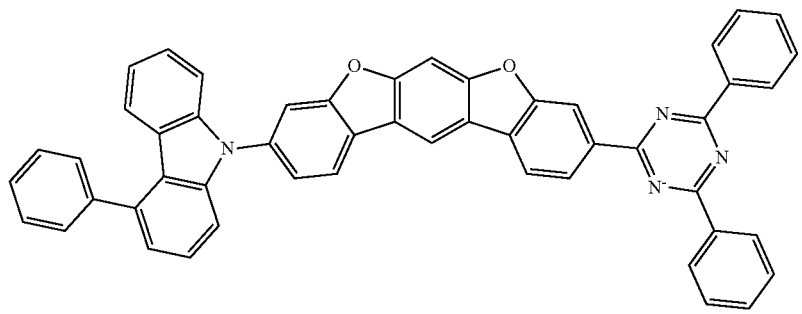

9

Compound 9 was prepared in the same manner as in the preparation method of Compound 1, except for using Intermediate 7-1 instead of Intermediate 1-1 and Intermediate b-4 instead of Intermediate b-1 in Preparation Example 7.

MS[M+H]$^+$=731

Preparation Example 16: Synthesis of Compound 10

{Synthesis of Compound 10-1}

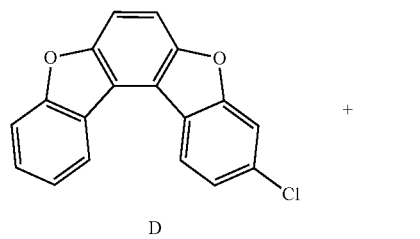

D

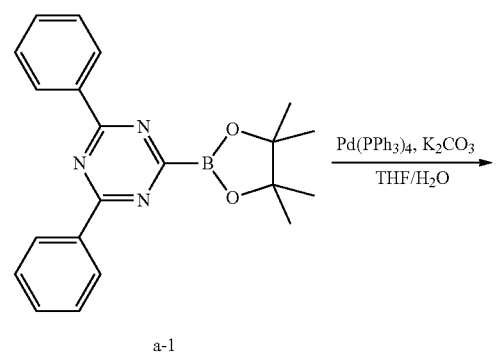

a-1

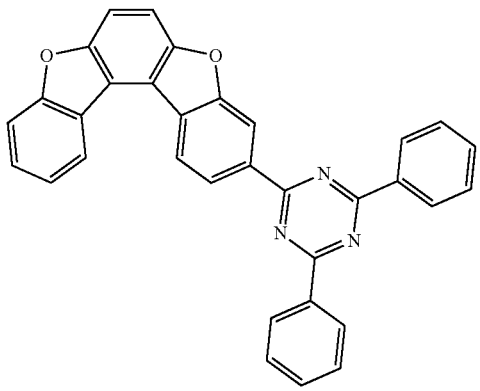

10-1

A solution in which Intermediate D (20.0 g, 68.3 mmol) and Intermediate a-1 (25.8 g, 71.7 mmol) were dissolved in THF (680 mL), and K$_2$CO$_3$ (37.8 g, 273.3 mmol) was dissolved in H$_2$O (340 mL) was added to a three-necked flask. Pd(PPh$_3$)$_4$ (0.8 g, 0.7 mmol) was added thereto, and the mixture was stirred at reflux for 8 hours under an argon atmosphere. After completion of the reaction, the reaction temperature was cooled down to room temperature and the reaction solution was transferred to a separatory funnel and extracted with CH$_2$Cl$_2$. The extract was dried over MgSO$_4$, filtered and concentrated, and then the sample was purified by silica gel column chromatography to give Compound 10-1 (22.4 g, yield: 67%).

MS[M+H]$^+$=490.

(Synthesis of Compound 10-2)

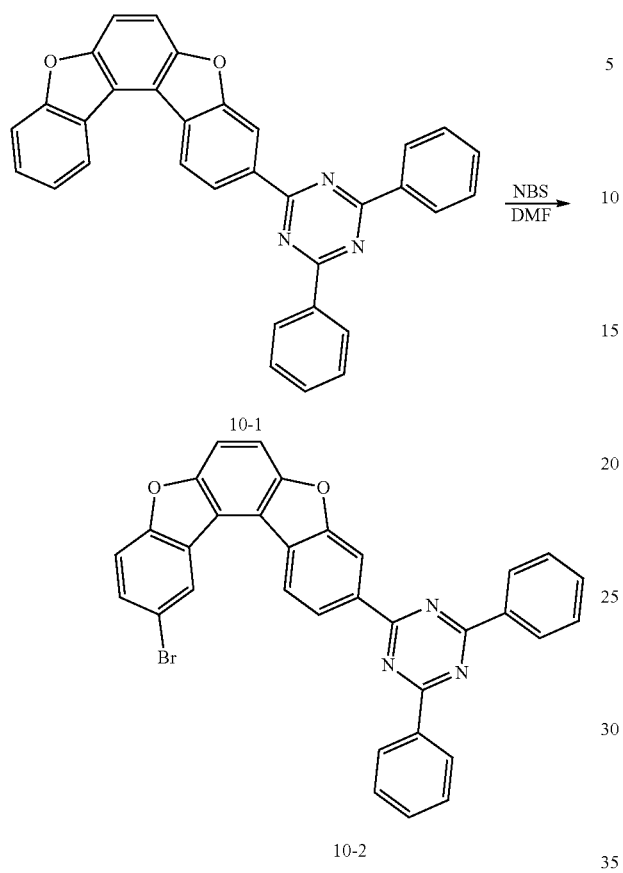

Compound 10-1 (20.0 g, 40.9 mmol), NBS (8.0 g, 44.9 mmol) and DMF (410 mL) were added to a two-necked flask, and the mixture was stirred at room temperature for 8 hours under an argon atmosphere. After completion of the reaction, the reaction solution was transferred to a separatory funnel. H$_2$O (200 mL) was added thereto and extracted with ethyl acetate. The sample was purified by silica gel column chromatography to give Compound 10-2 (19.0 g, yield: 82%).

MS[M+H]$^+$=568.

(Synthesis of Compound 10)

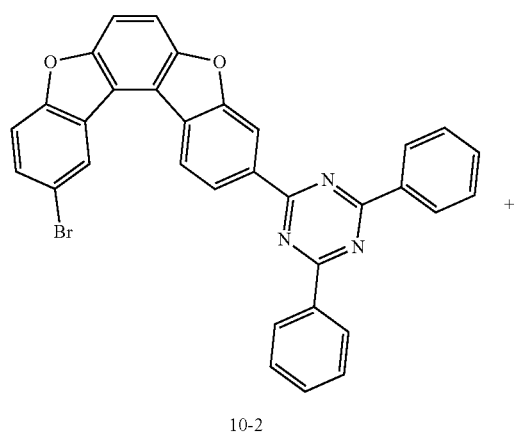

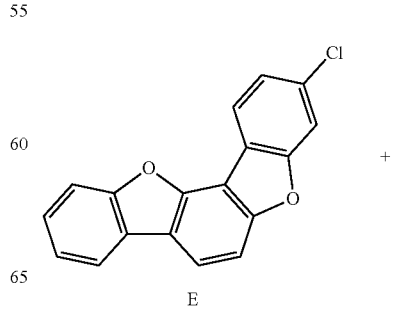

Compound 10-2 (18.0 g, 31.7 mmol) and Intermediate b-1 (5.8 g, 34.8 mmol) were dissolved in toluene (320 mL) in a three-necked flask. Sodium tert-butoxide (4.6 g, 47.5 mmol) and bis(tri-tert-butylphosphine)palladium(0) (0.3 g, 0.6 mmol) were added thereto and the mixture was stirred at reflux for 6 hours under an argon atmosphere. After completion of the reaction, the reaction temperature was cooled down to room temperature, H$_2$O (200 mL) was added thereto, and the reaction solution was transferred to a separatory funnel and extracted. The extract was dried over MgSO$_4$ and concentrated. The sample was purified by silica gel column chromatography and then subjected to sublimation purification to give Compound 10 (5.8 g, yield: 28%).

MS[M+H]$^+$=655.

Preparation Example 17: Synthesis of Compound 11

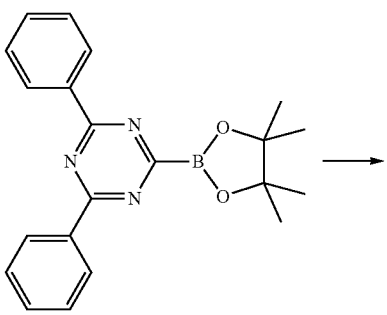

a-1

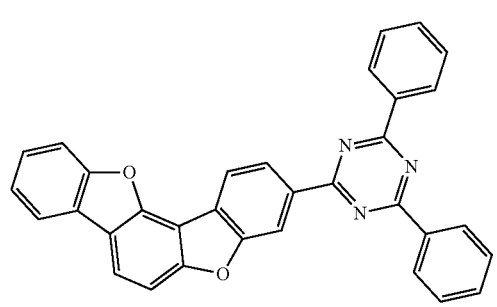

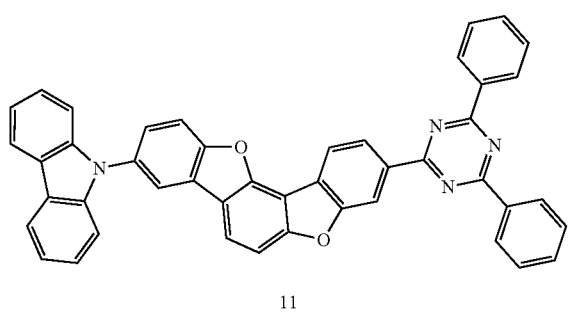

11

Compound 11 was prepared in the same manner as in the preparation method of Compound 10, except for using Intermediate E instead of Intermediate D in Preparation Example 16.

MS[M+H]$^+$=655

Preparation Example 18: Synthesis of Compound 12

(Synthesis of Compound 12-1)

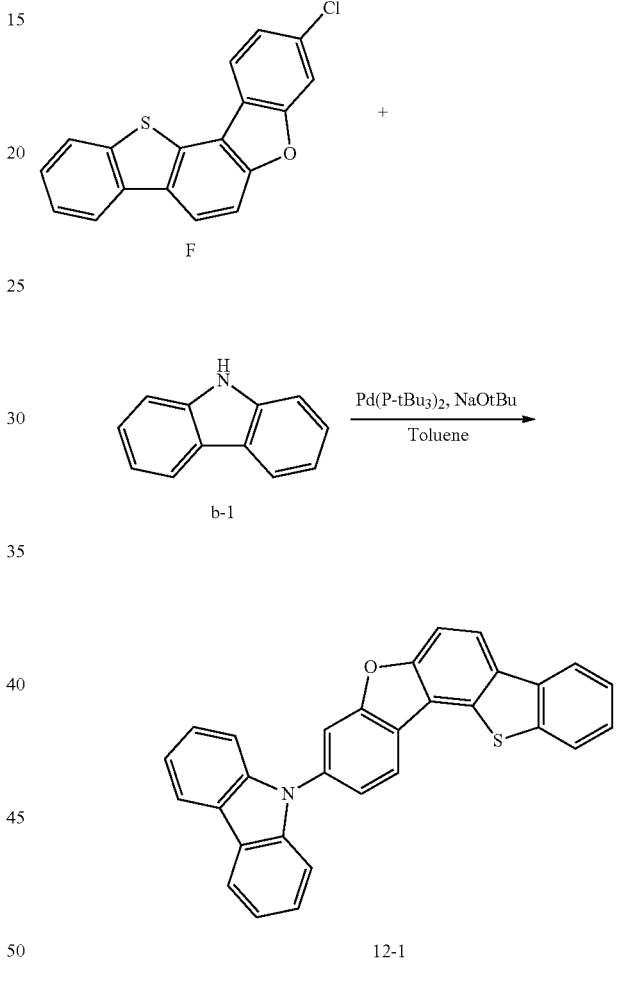

12-1

Compound F (15.0 g, 48.6 mmol) and Intermediate b-1 (8.9 g, 53.4 mmol) were dissolved in toluene (480 mL) in a three-necked flask. Sodium tert-butoxide (7.0 g, 72.9 mmol) and bis(tri-tert-butylphosphine)palladium(0) (0.5 g, 1.0 mmol) were added thereto and the mixture was stirred at reflux for 6 hours under an argon atmosphere. After completion of the reaction, the reaction temperature was cooled down to room temperature, H$_2$O (200 mL) was added thereto, and the reaction solution was transferred to a separatory funnel and extracted. The extract was dried over MgSO$_4$ and concentrated. The sample was purified by silica gel column chromatography to give Compound 12-1 (16.7 g, yield: 78%).

MS[M+H]$^+$=440.

(Synthesis of Compound 12-2)

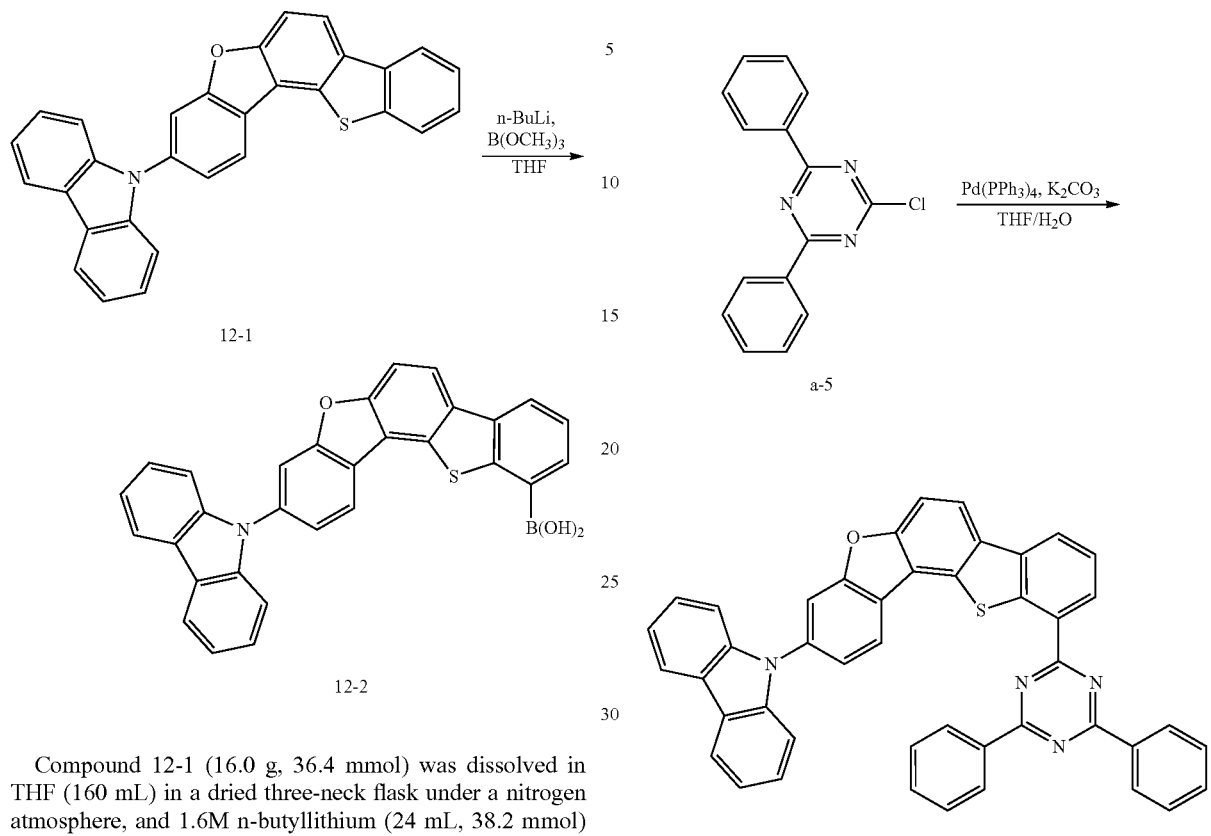

Compound 12-1 (16.0 g, 36.4 mmol) was dissolved in THF (160 mL) in a dried three-neck flask under a nitrogen atmosphere, and 1.6M n-butyllithium (24 mL, 38.2 mmol) was slowly added dropwise with stirring at −10° C. After completion of the dropwise addition, the mixture was further stirred for 4 hours at the same temperature, and then the temperature was lowered to −78° C., trimethyl borate (4.9 g, 47.3 mmol) was slowly added dropwise, the reaction temperature was raised up to room temperature and then the mixture was stirred overnight. After completion of the reaction, 2N HCl aqueous solution was added dropwise and acidified, and then stirred for 30 minutes. The reaction solution was transferred to a separatory funnel, the organic layer was extracted with water and ethyl acetate, concentrated under reduced pressure, and recrystallized to give Compound 12-2 (10.6 g, yield: 60%).

MS[M+H]$^+$=483.

(Synthesis of Compound 12)

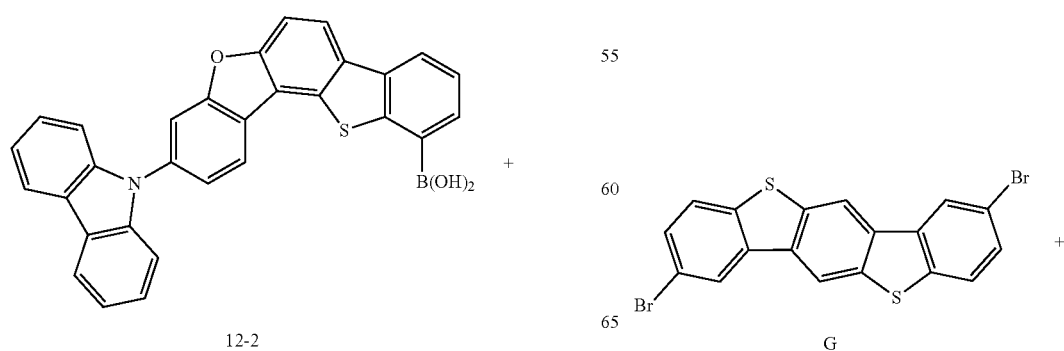

A solution in which Compound 12-2 (10.0 g, 20.7 mmol) and Intermediate a-5 (5.8 g, 21.7 mmol) were dissolved in THF (200 mL) and K$_2$CO$_3$ (11.4 g, 82.8 mmol) were dissolved in H$_2$O (100 mL) was added to a three-necked flask. Pd(PPh$_3$)$_4$ (0.2 g, 0.2 mmol) was added thereto and the mixture was stirred at reflux for 8 hours under an argon atmosphere. After completion of the reaction, the reaction temperature was cooled down to room temperature and the reaction solution was transferred to a separatory funnel and extracted with CH$_2$Cl$_2$. The extract was dried over MgSO$_4$, filtered and concentrated. The sample was purified by silica gel column chromatography and then subjected to sublimation purification to give Compound 12 (4.6 g, yield: 33%).

MS[M+H]$^+$=671

Preparation Example 19: Synthesis of Compound 13

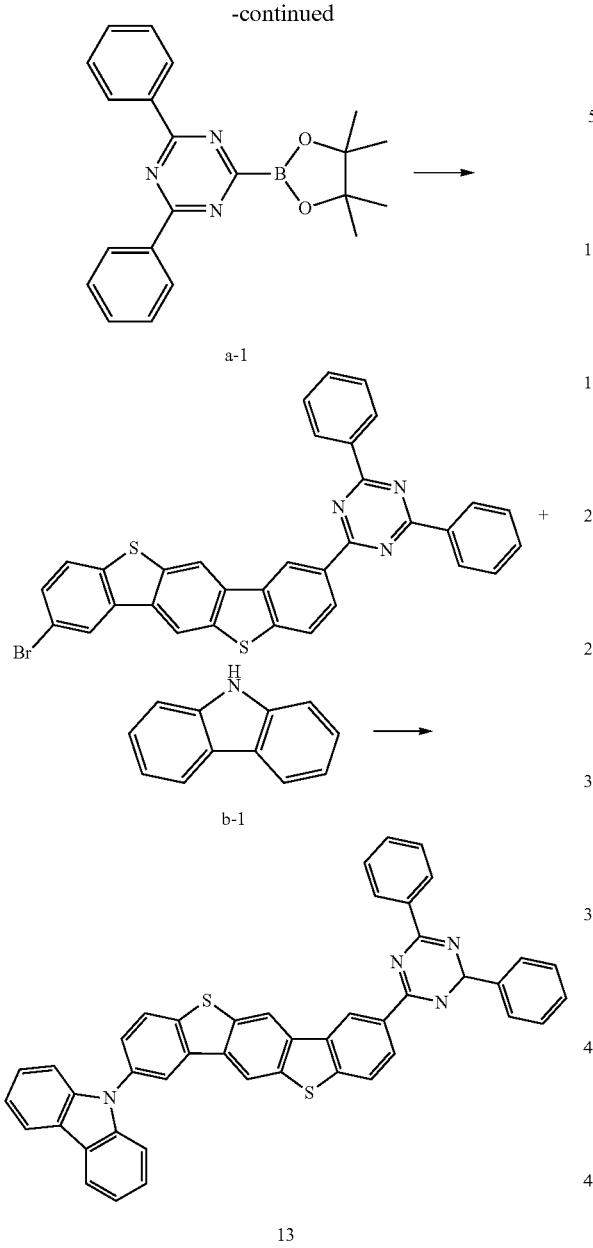

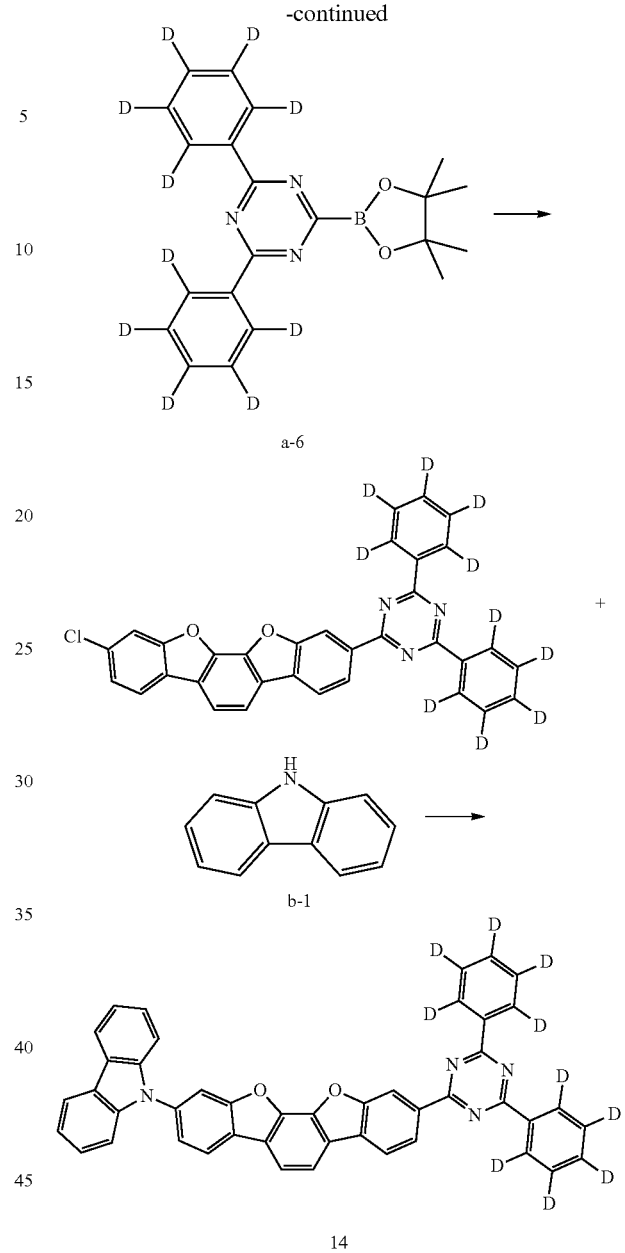

Compound 13 was prepared in the same manner as in the preparation method of Compound 1, except for using Intermediate G instead of Intermediate A in Preparation Example 7.

MS[M+H]⁺=687

Preparation Example 20: Synthesis of Compound 14

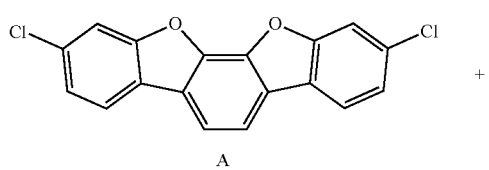

Compound 14 was prepared in the same manner as in the preparation method of Compound 1, except for using Intermediate a-6 instead of Intermediate a-1 in Preparation Example 7.

MS[M+H]⁺=665

Example 1

A glass substrate on which ITO (indium tin oxide) was coated as a thin film to a thickness of 1,400 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, a compound HT-A below and 5 wt % of a compound PD below were thermally vacuum-deposited to a thickness of 100 Å, and then only a compound HT-A below was deposited to a thickness of 1150 Å to form a hole transport layer. A compound HT-B below was thermally vacuum-deposited to a thickness of 450 Å thereon as an electronic blocking layer. Then, vacuum deposition was performed to a thickness of 400 Å by using a host containing a compound PGH-1 below as a first host and the compound 1 of Preparation Example 7 as a second host in a weight ratio of 60:40, and 15 wt % of a compound GD below as a dopant. Then, a compound ET-A below was vacuum-deposited to a thickness of 50 Å as a hole blocking layer. Then, a compounds ET-B and Liq below were thermally vacuum-deposited in a ratio of 2:1 to a thickness of 250 Å as an electron transport and injection layer, and LiF and magnesium were then vacuum-deposited in a ratio of 1:1 to a thickness of 30 Å. Magnesium and silver were deposited in a ratio of 1:4 to a thickness of 160 Å on the electron transport and injection layer to form a cathode, thereby completing the manufacture of an organic light emitting device.

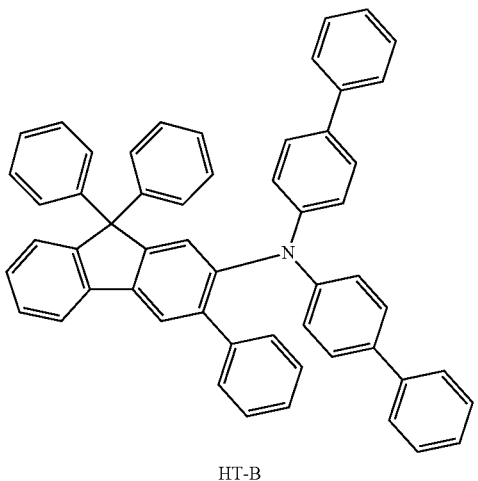

HT-B

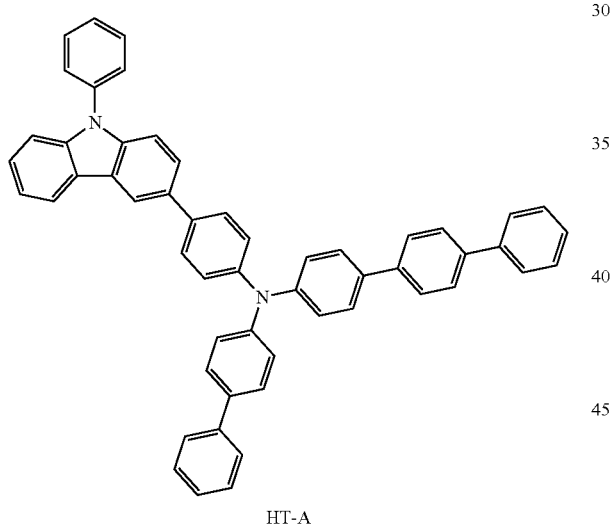

HT-A

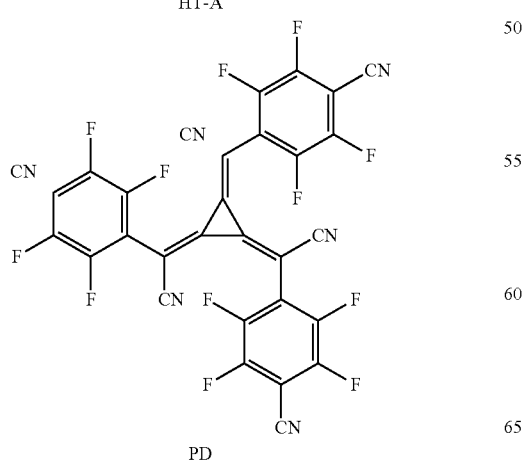

PD

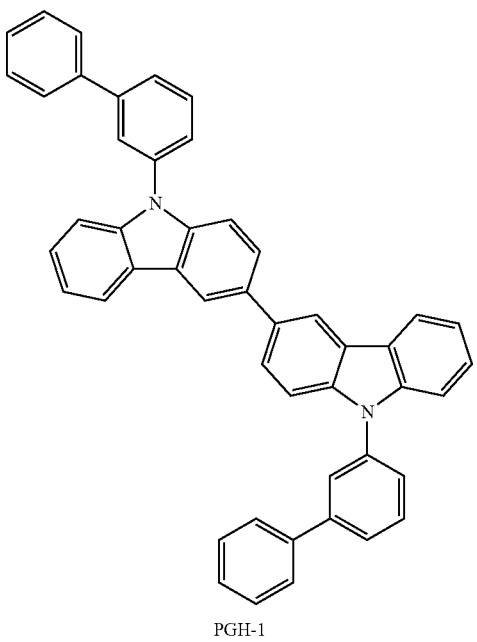

PGH-1

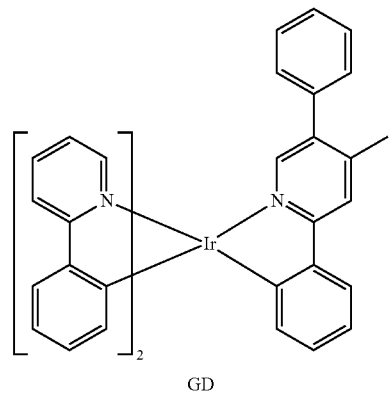

GD

-continued

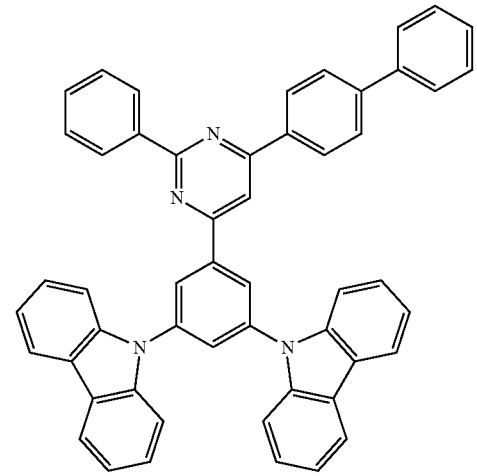

ET-A

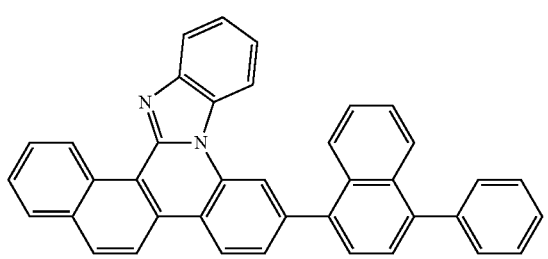

ET-B

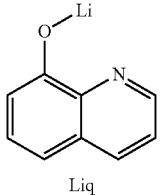

Liq

Examples 2 to 20

The organic light emitting devices of Examples 2 to 20 were manufactured in the same manner as in Example 1, except that the host material was changed as shown in Table 1 below. In this case, when a mixture of two kinds of compounds was used as the host, the parenthesis means the weight ratio between the host compounds.

Comparative Examples 1 to 6

The organic light emitting devices of Comparative Examples 1 to 6 were manufactured in the same manner as in Example 1, except that the host material was changed as shown in Table 1 below. In this case, when a mixture of two kinds of compounds was used as the host, the parenthesis means the weight ratio between the host compounds. Compounds GH-A, GH-B, GH-C and GH-D in Table 1 are as follows.

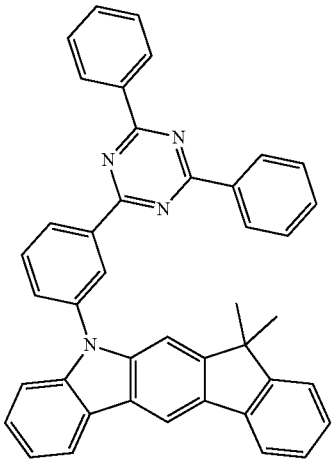

GH-A

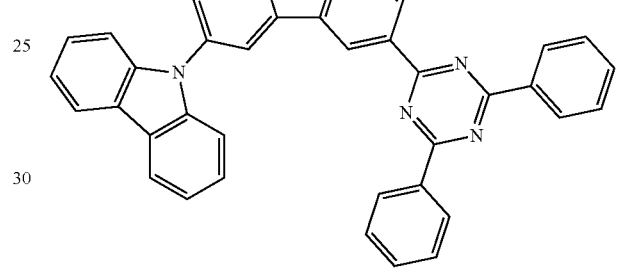

GH-B

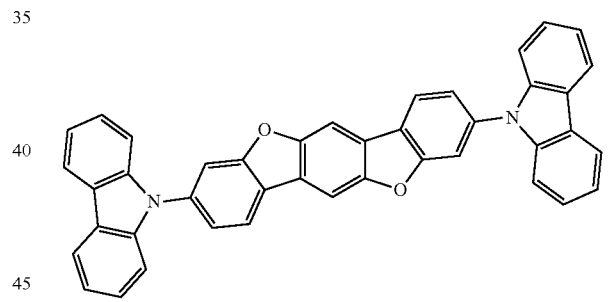

GH-C

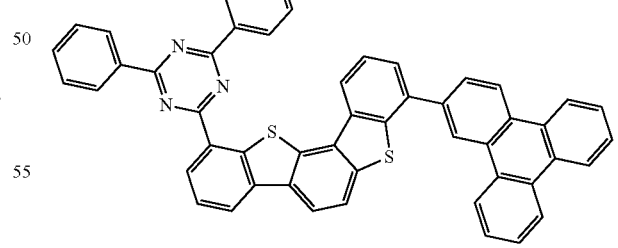

GH-D

Experimental Example

The voltage, efficiency and lifetime (T95) were measured by applying a current to the organic light emitting devices manufactured in Examples 1 to 20 and Comparative Examples 1 to 6, and the results are shown in Table 1 below. At this time, the voltage and efficiency were measured by applying a current density of 10 mA/cm², and the lifetime (T95) means the time required for the luminance to be reduced to 95% of the initial luminance at a current density of 20 mA/cm².

TABLE 1

|  | Host material (weight ratio) | @ 10 mA/cm² Voltage (V) | @ 10 mA/cm² Efficiency (cd/A) | @ 20 mA/cm² Lifetime (T95, hr) |
|---|---|---|---|---|
| Example 1 | PGH-1:Compound 1 (60:40) | 4.38 | 56.5 | 130 |
| Example 2 | PGH-1:Compound 2 (60:40) | 4.39 | 56.1 | 130 |
| Example 3 | PGH-1:Compound 3 (60:40) | 4.33 | 55.9 | 115 |
| Example 4 | PGH-1:Compound 4 (60:40) | 4.40 | 55.2 | 140 |
| Example 5 | PGH-1:Compound 5 (60:40) | 4.42 | 53.0 | 130 |
| Example 6 | PGH-1:Compound 6 (60:40) | 4.43 | 54.1 | 125 |
| Example 7 | PGH-1:Compound 7 (60:40) | 4.39 | 55.5 | 140 |
| Example 8 | PGH-1:Compound 8 (60:40) | 4.37 | 57.1 | 130 |
| Example 9 | PGH-1:Compound 9 (60:40) | 4.35 | 58.4 | 125 |
| Example 10 | PGH-1:Compound 10 (60:40) | 4.38 | 58.2 | 135 |
| Example 11 | PGH-1:Compound 11 (60:40) | 4.54 | 54.1 | 115 |
| Example 12 | PGH-1:Compound 12 (60:40) | 4.57 | 53.4 | 120 |
| Example 13 | PGH-1:Compound 13 (60:40) | 4.51 | 54.2 | 110 |
| Example 14 | Compound 1 | 4.78 | 48.1 | 110 |
| Example 15 | Compound 6 | 4.87 | 48.7 | 110 |
| Example 16 | Compound 9 | 4.80 | 49.1 | 105 |
| Example 17 | Compound 11 | 4.91 | 46.4 | 95 |
| Example 18 | Compound 12 | 4.96 | 45.1 | 100 |
| Example 19 | Compound 13 | 4.93 | 46.3 | 90 |
| Example 20 | Compound 14 | 4.83 | 19.4 | 120 |
| Comparative Example 1 | PGH-1:GH-A (60:40) | 4.88 | 40.1 | 80 |
| Comparative Example 2 | PGH-1:GH-B (60:40) | 4.97 | 38.1 | 70 |
| Comparative Example 3 | PGH-1:GH-C (60:40) | 6.71 | 21.0 | 5 |
| Comparative Example 4 | GH-B | 6.51 | 28.0 | 9 |
| Comparative Example 5 | GH-C | 7.23 | 10.3 | 3 |
| Comparative Example 6 | GH-D | 5.82 | 31.7 | 45 |

As shown in Table 1 above, it was confirmed that when the compound of Chemical Formula 1 was used as a host of the organic light emitting device, it exhibited low voltage, high efficiency, and long lifetime characteristics. In particular, when used in combination with a compound of Chemical Formula 2 such as PGH-1, the effect became more prominent and it exhibited more excellent effect than when used in combination with a compound of Chemical Formula 2.

DESCRIPTION OF SYMBOLS

1: substrate
2: anode
3: light emitting layer
4: cathode
5: hole transport layer
6: electron blocking layer
7: hole blocking layer
8: electron transport layer
9: electron injection layer

The invention claimed is:

1. A compound of Chemical Formula 1:

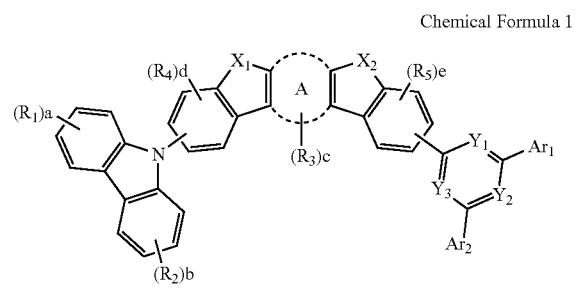

Chemical Formula 1 wherein, in Chemical Formula 1

A is a benzene ring;

$X_1$ and $X_2$ are each independently O or S;

$Y_1$ to $Y_3$ are each N;

$Ar_1$ and $Ar_2$ are each independently a substituted or unsubstituted $C_{6-60}$ aryl or a substituted or unsubstituted $C_{2-60}$ heteroaryl containing at least one heteroatom selected from the group consisting of N, O, and S;

$R_1$ to $R_3$ are each independently hydrogen, deuterium, halogen, cyano, nitro, amino, a substituted or unsubstituted $C_{1-60}$ alkyl, a substituted or unsubstituted $C_{3-60}$ cycloalkyl, a substituted or unsubstituted $C_{2-60}$ alkenyl, a substituted or unsubstituted $C_{6-60}$ aryl, or a substituted or unsubstituted $C_{2-60}$ heteroaryl containing at least one heteroatom selected from the group consisting of N, O, and S;

$R_4$ and $R_5$ are each independently hydrogen, deuterium, halogen, cyano, nitro, amino, a substituted or unsubstituted $C_{1-60}$ alkyl, a substituted or unsubstituted $C_{3-60}$ cycloalkyl, a substituted or unsubstituted $C_{2-60}$ alkenyl, a substituted or unsubstituted $C_{6-60}$ aryl, or a substituted or unsubstituted $C_{2-60}$ heteroaryl containing at least one heteroatom selected from the group consisting of N, O, and S;

a and b are each independently an integer of 0 to 4;

c is an integer of 0 to 2; and d and e are each independently an integer of 0 to 3.

2. The compound according to claim 1, wherein:

Chemical Formula 1 is any one of the following Chemical Formulas 1-1 to 1-6:

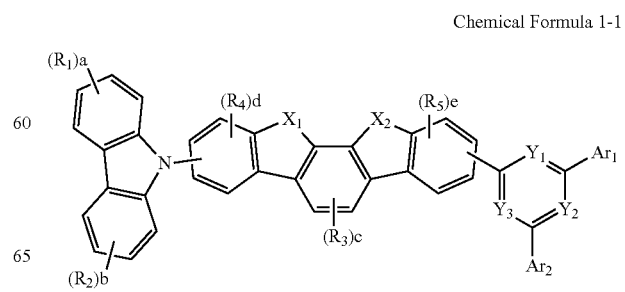

Chemical Formula 1-1

Chemical Formula 1-2

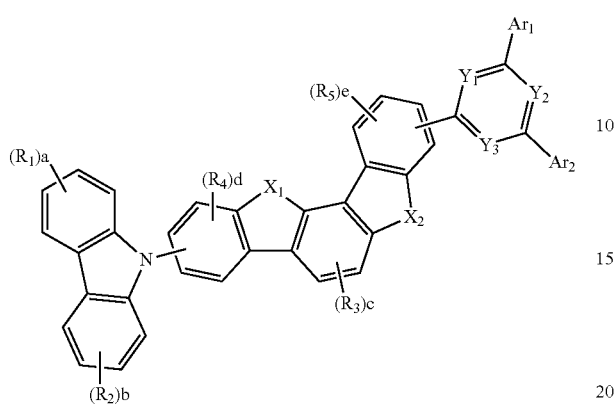

Chemical Formula 1-3

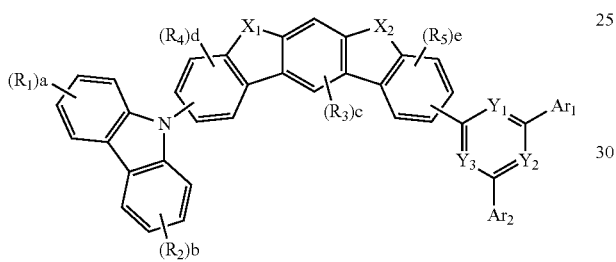

Chemical Formula 1-4

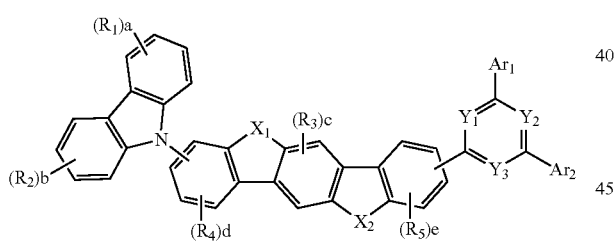

Chemical Formula 1-5

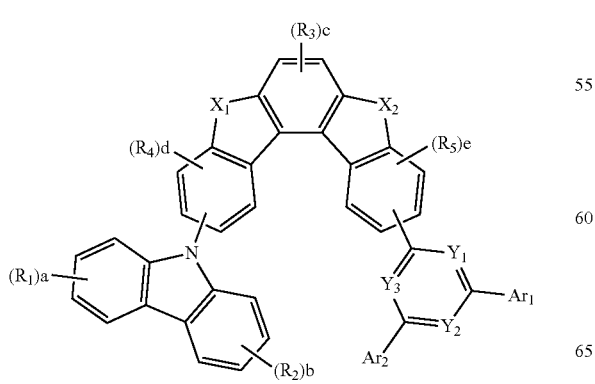

Chemical Formula 1-6

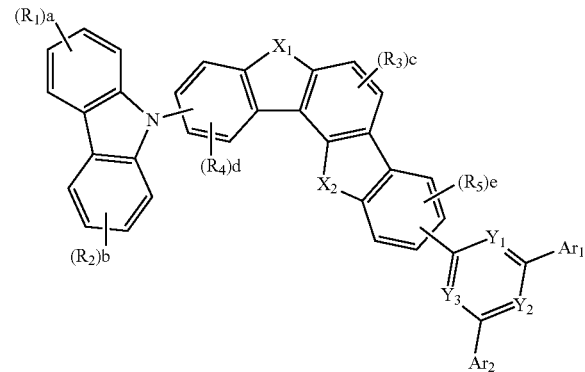

wherein, in Chemical Formulas 1-1 to 1-6:

$X_1$, $X_2$, $Y_1$ to $Y_3$, $Ar_1$, $Ar_2$, $R_1$ to $R_5$ and a to e are as the same as defined for Chemical Formula 1 in claim 1.

3. The compound according to claim 1, wherein:

$Ar_1$ and $Ar_2$ are each independently a phenyl, biphenylyl, terphenylyl, naphthyl, anthracenyl, phenanthrenyl, triphenylenyl, fluorenyl, dibenzofuranyl, dibenzothiophenyl, or phenyl substituted with five deuteriums.

4. The compound according to claim 1, wherein:

at least one of $Ar_1$ and $Ar_2$ is a substituted or unsubstituted $C_{6-60}$ aryl.

5. The compound according to claim 1, wherein:

$R_1$ to $R_3$ are each independently hydrogen, deuterium, or phenyl.

6. The compound according to claim 1, wherein:

$R_4$ and $R_5$ are each independently hydrogen or deuterium.

7. The compound according to claim 1, wherein:

the compound of Chemical Formula 1 is any one compound selected from the group consisting of the following compounds:

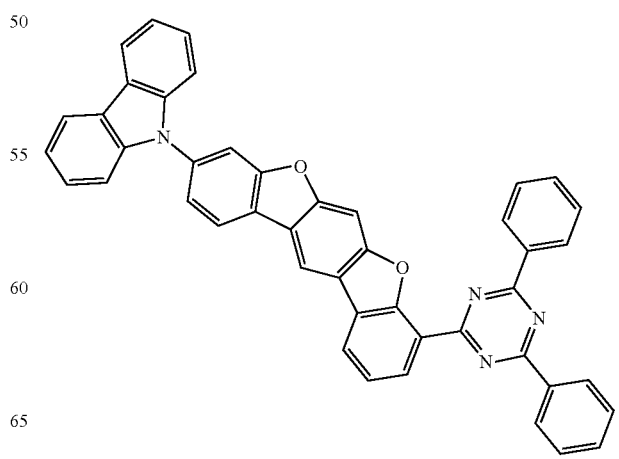

173
-continued
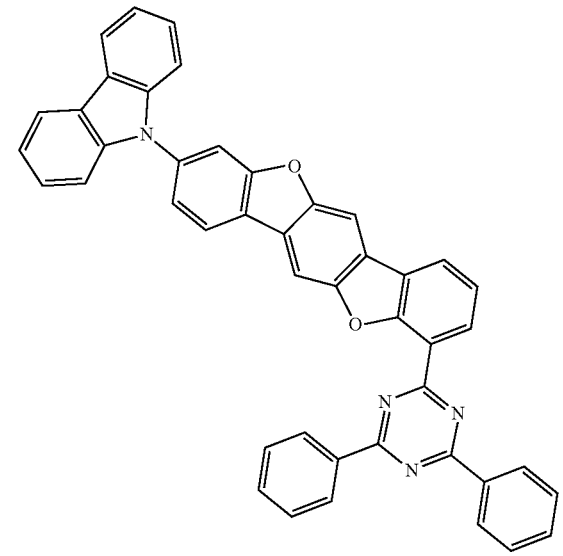
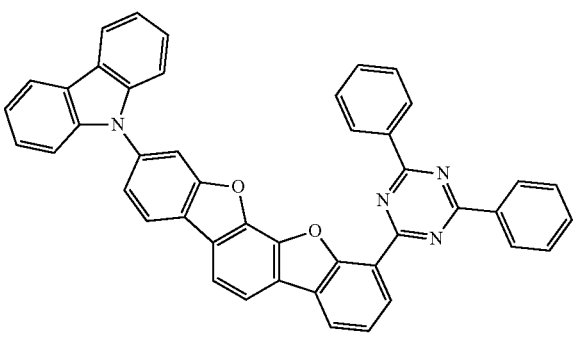
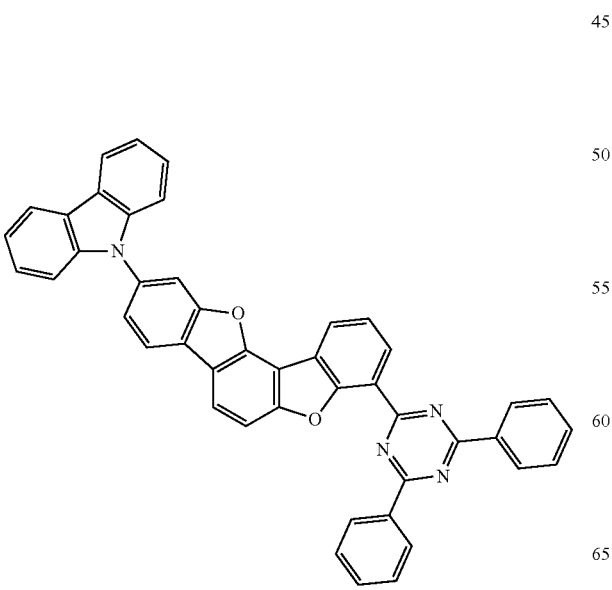
174
-continued
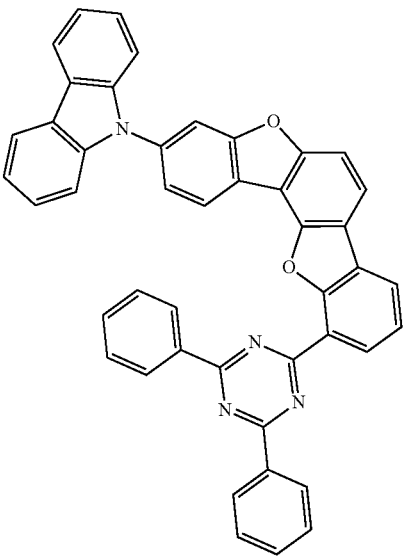
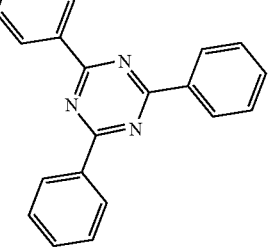

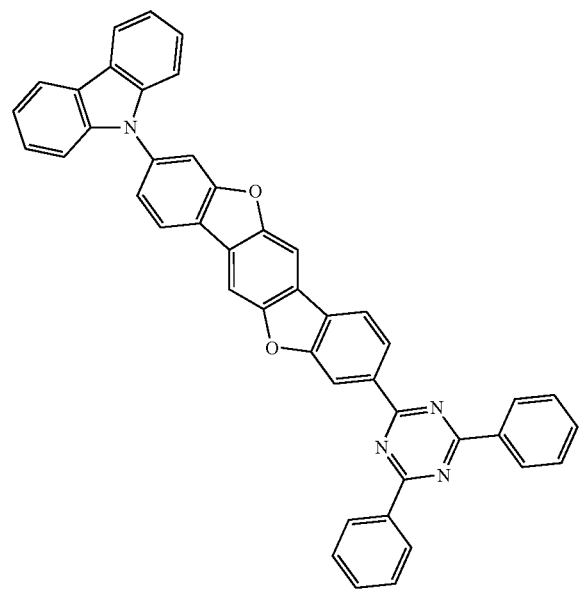
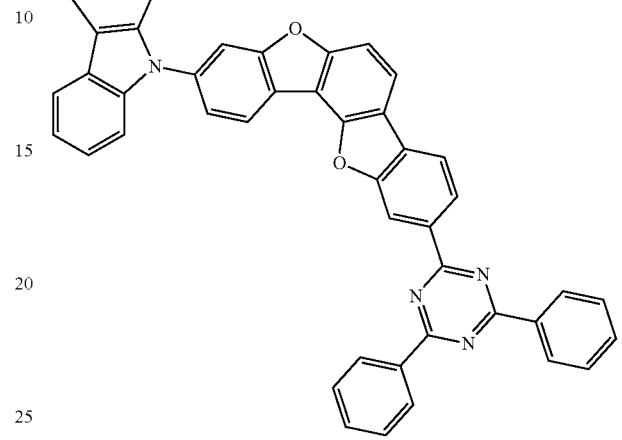
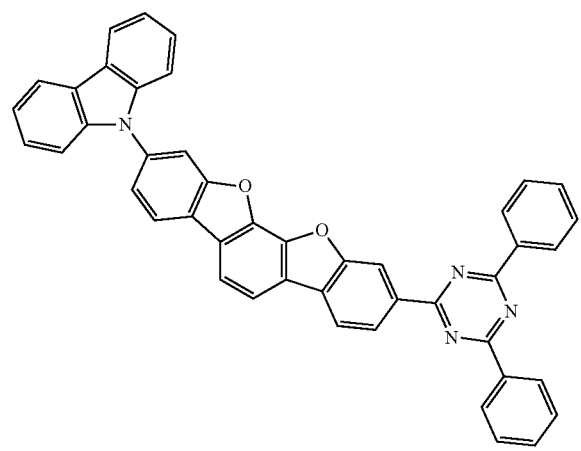
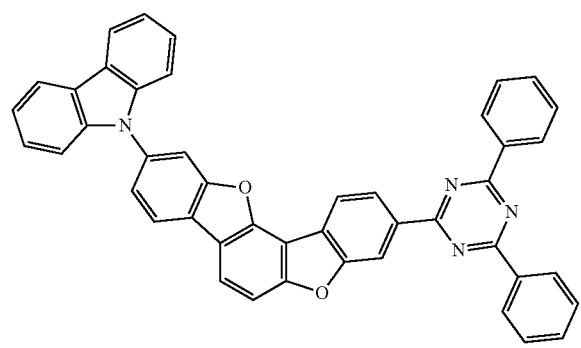
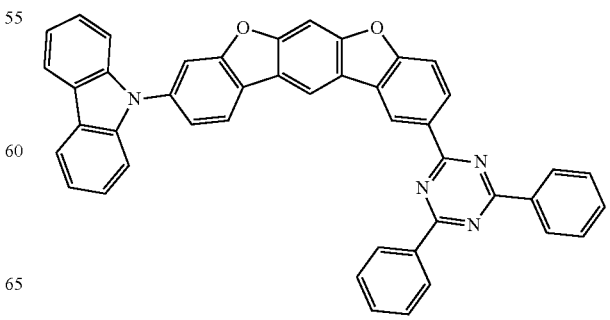

177
-continued
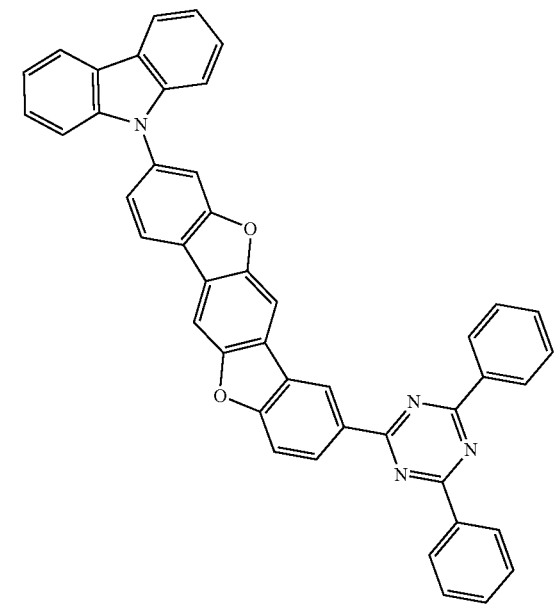
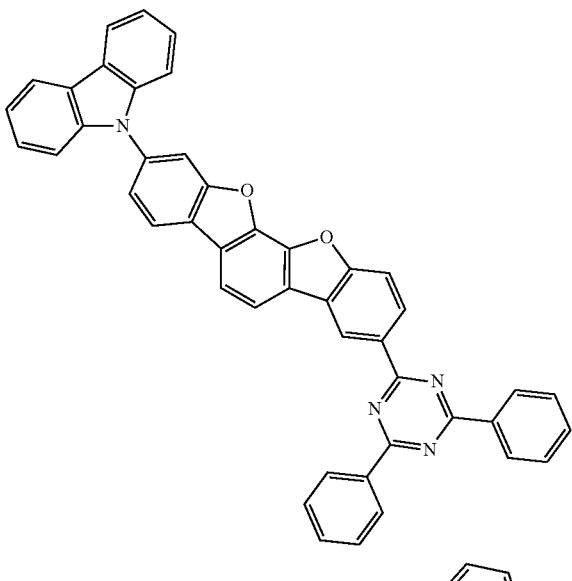
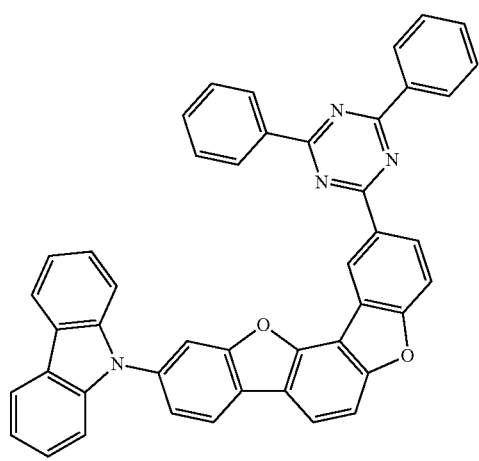
178
-continued
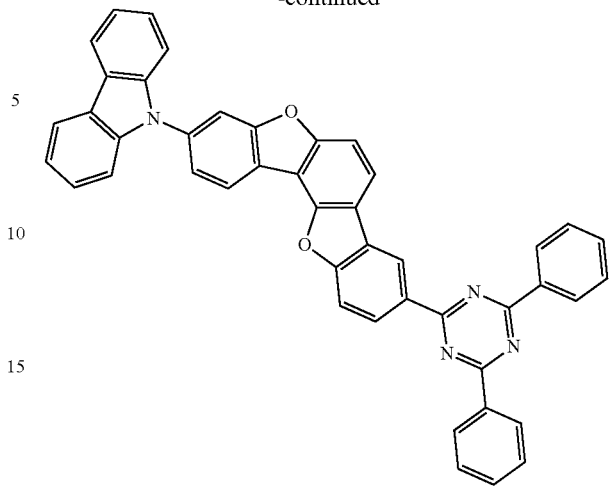
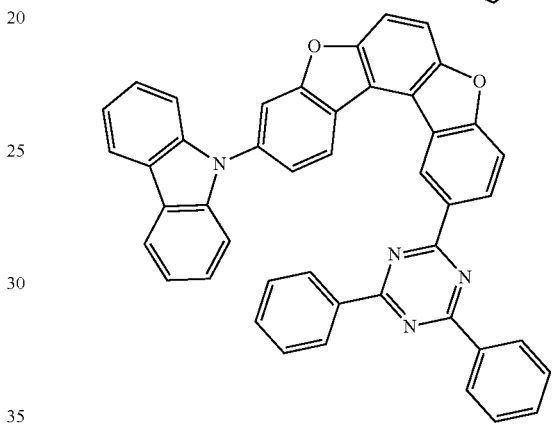
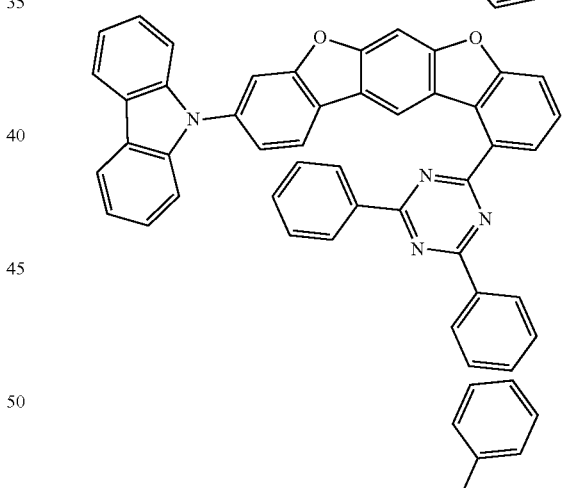
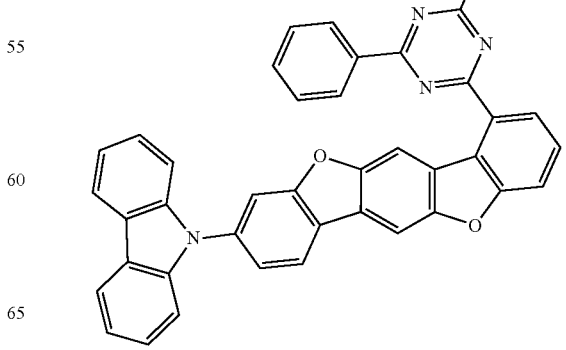

-continued
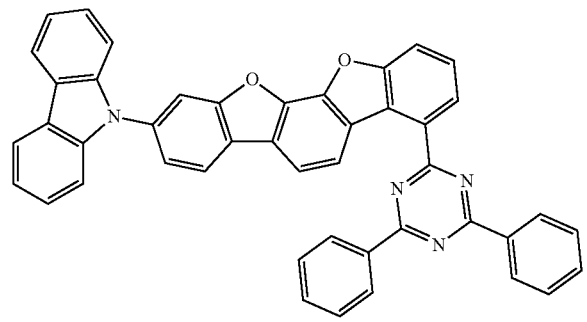
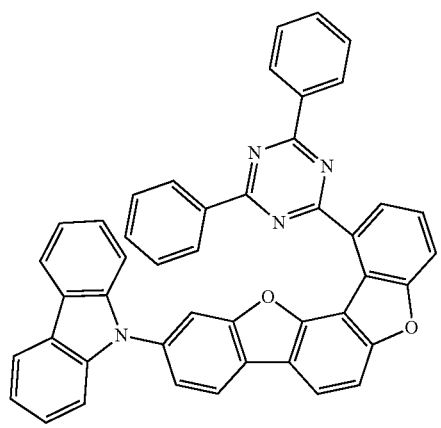
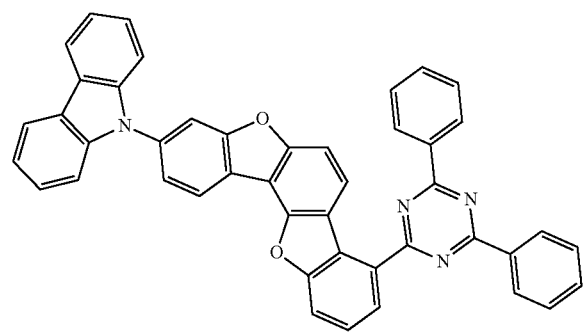
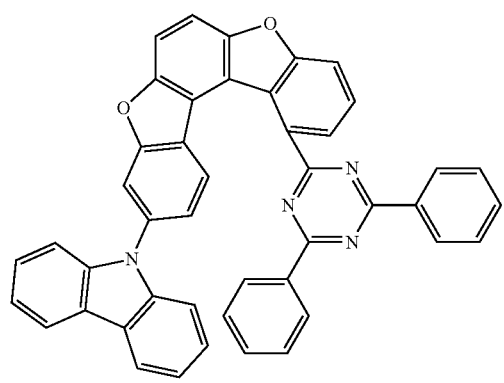
-continued
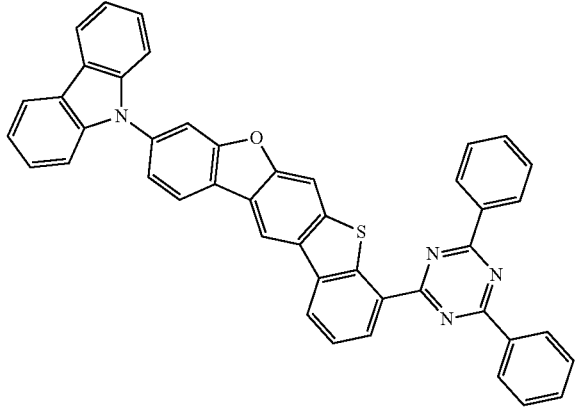
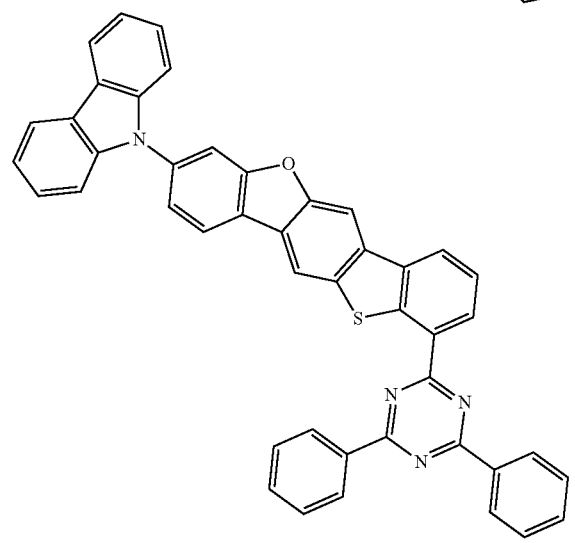
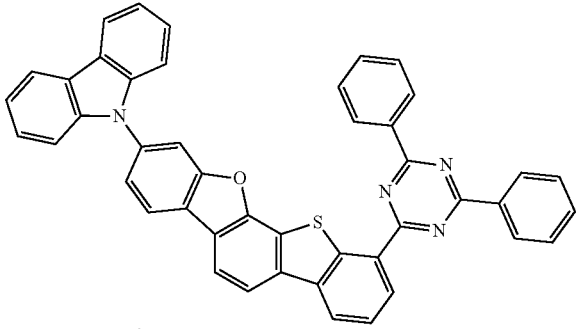
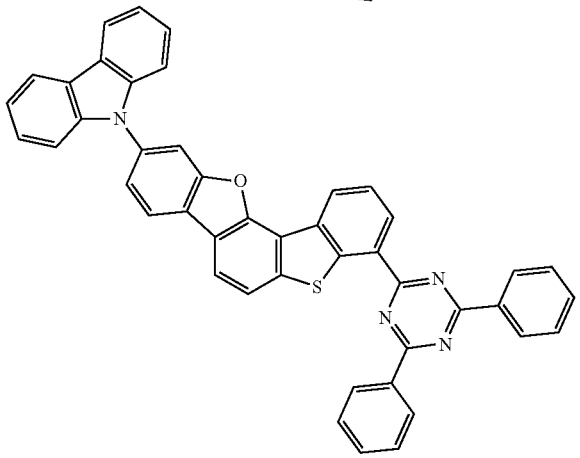

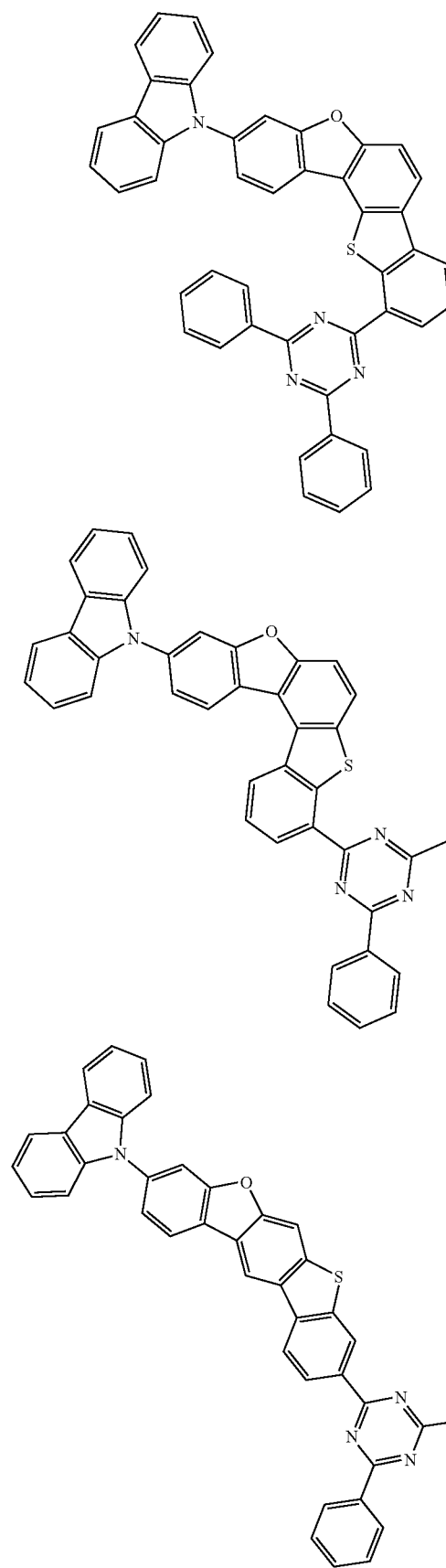
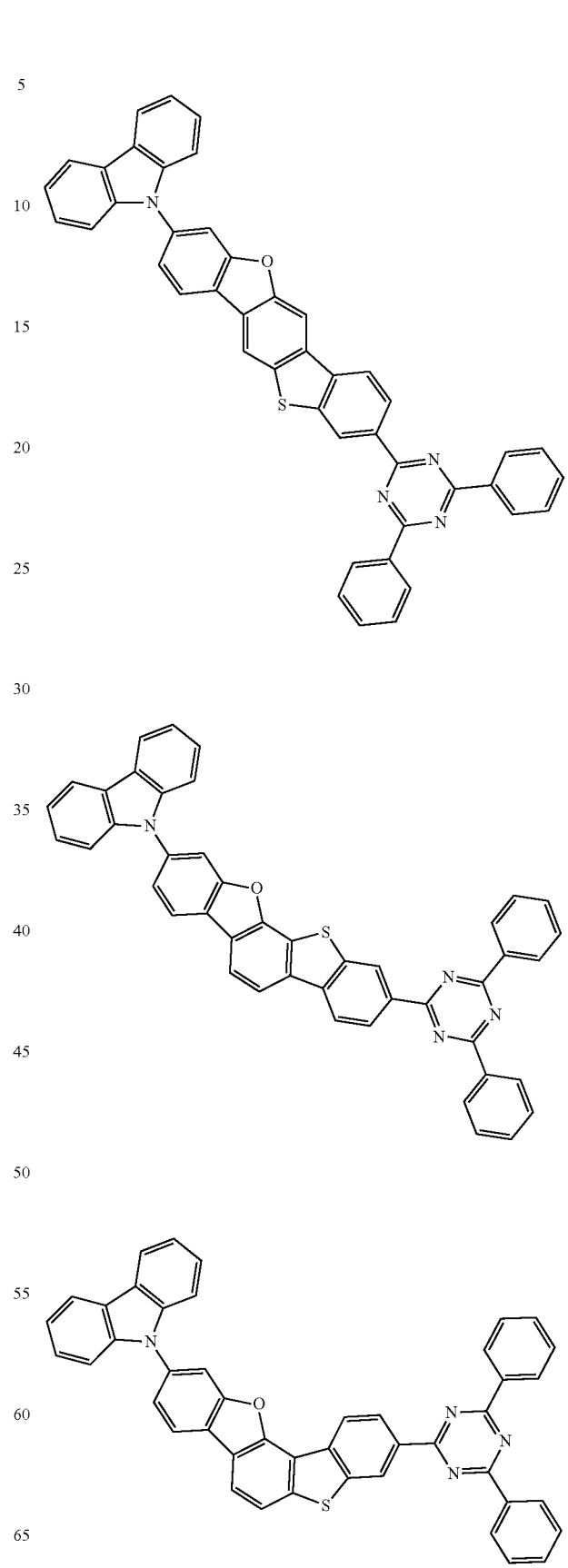

183
-continued
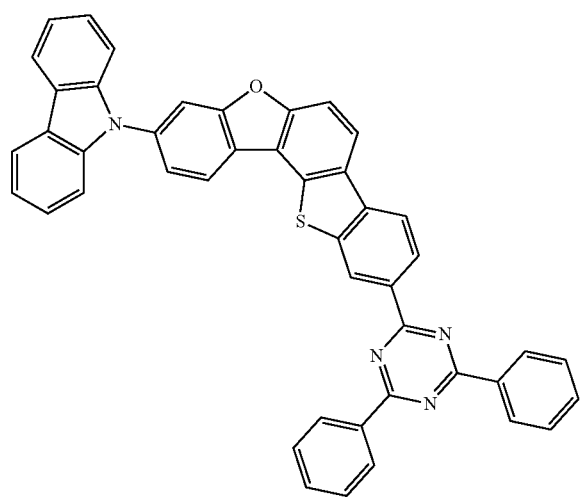
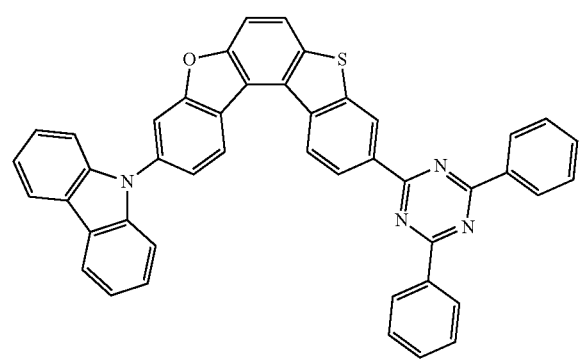
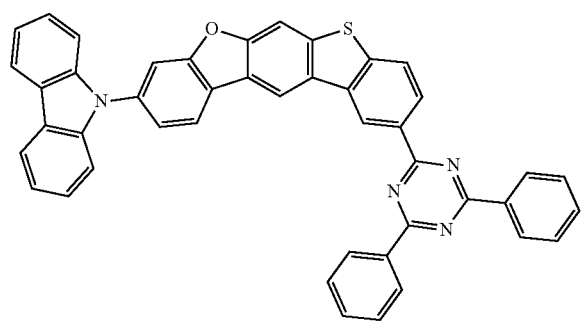
184
-continued
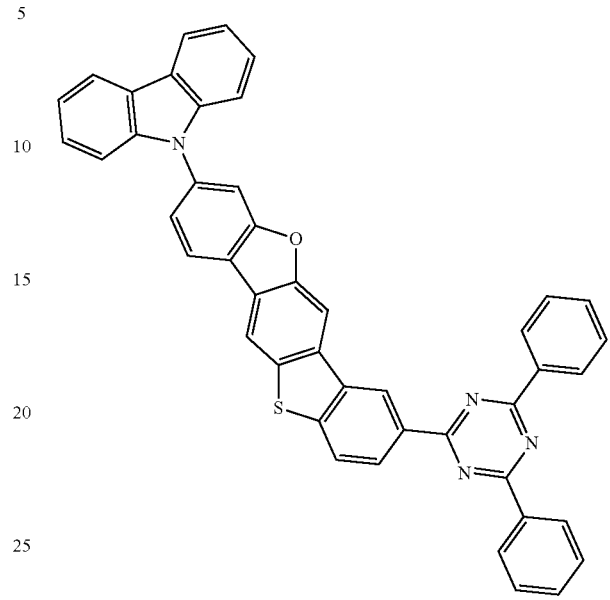
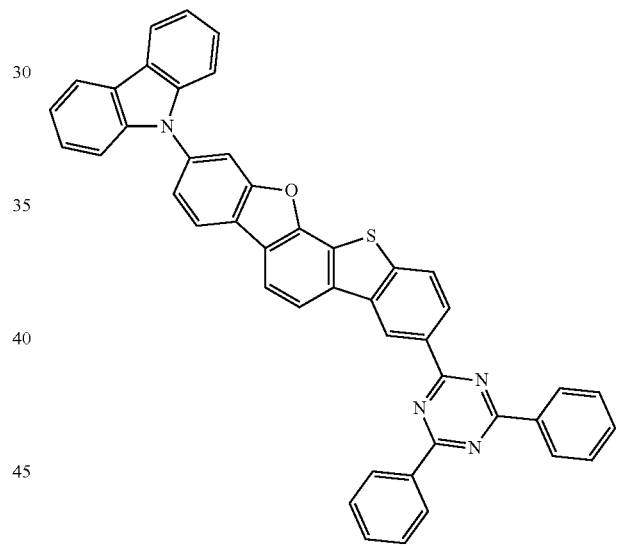
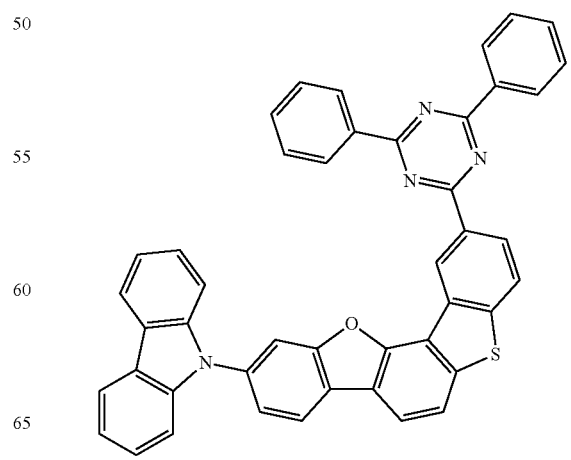

185
-continued
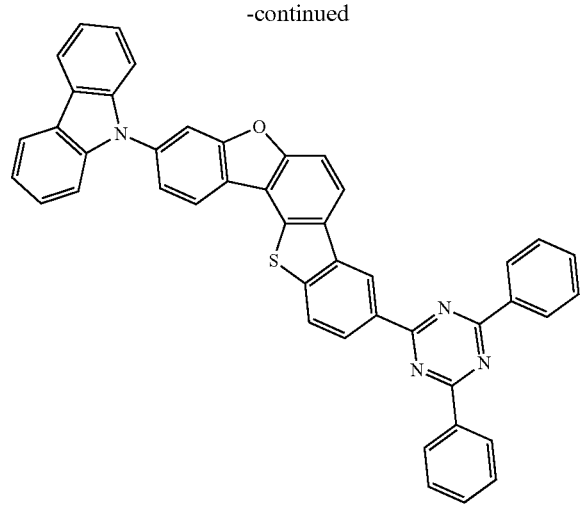
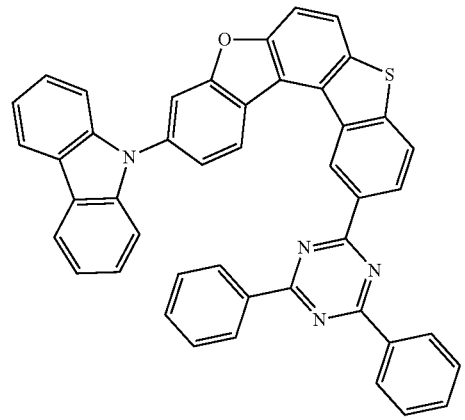
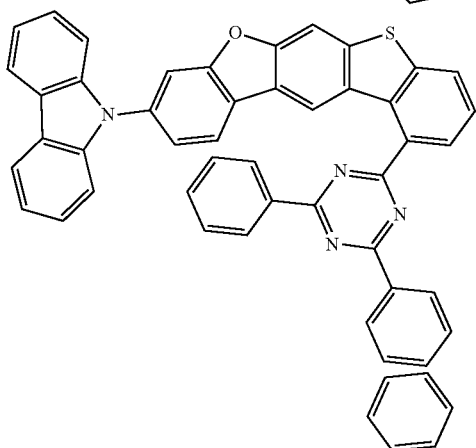
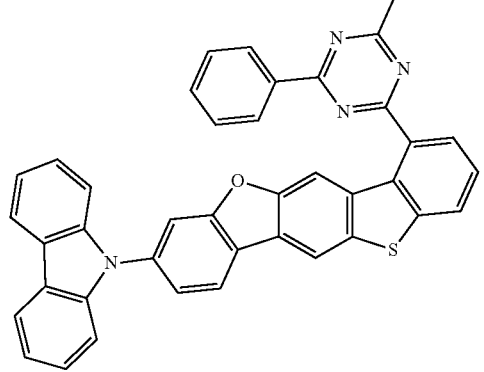
186
-continued
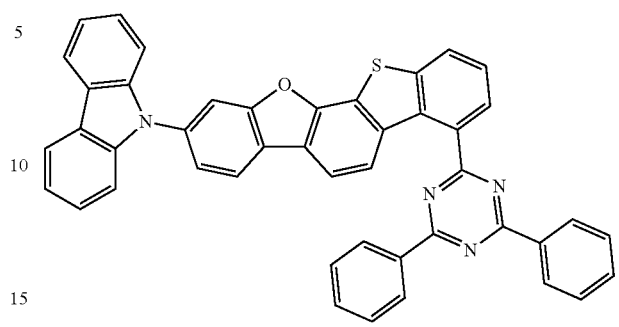
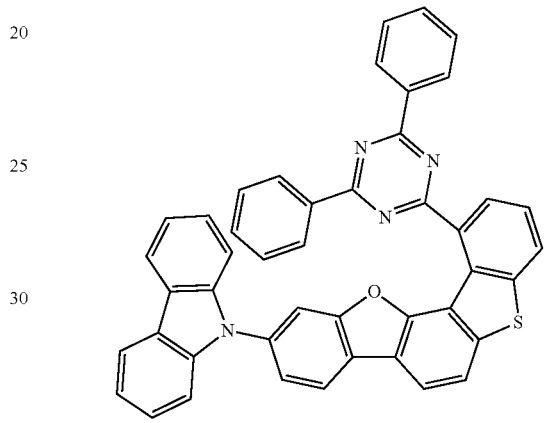
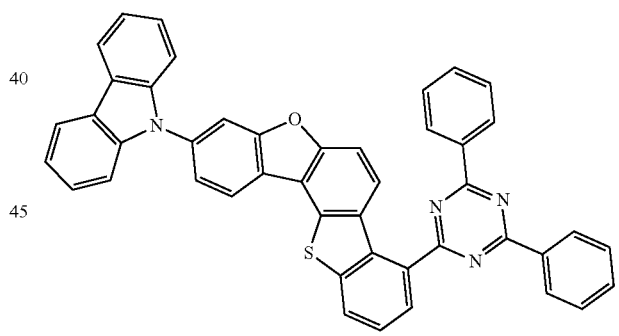
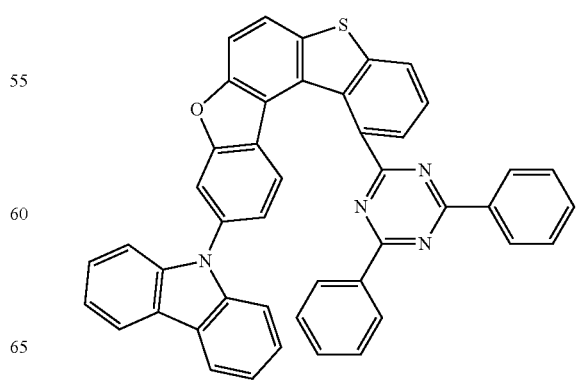

187
-continued
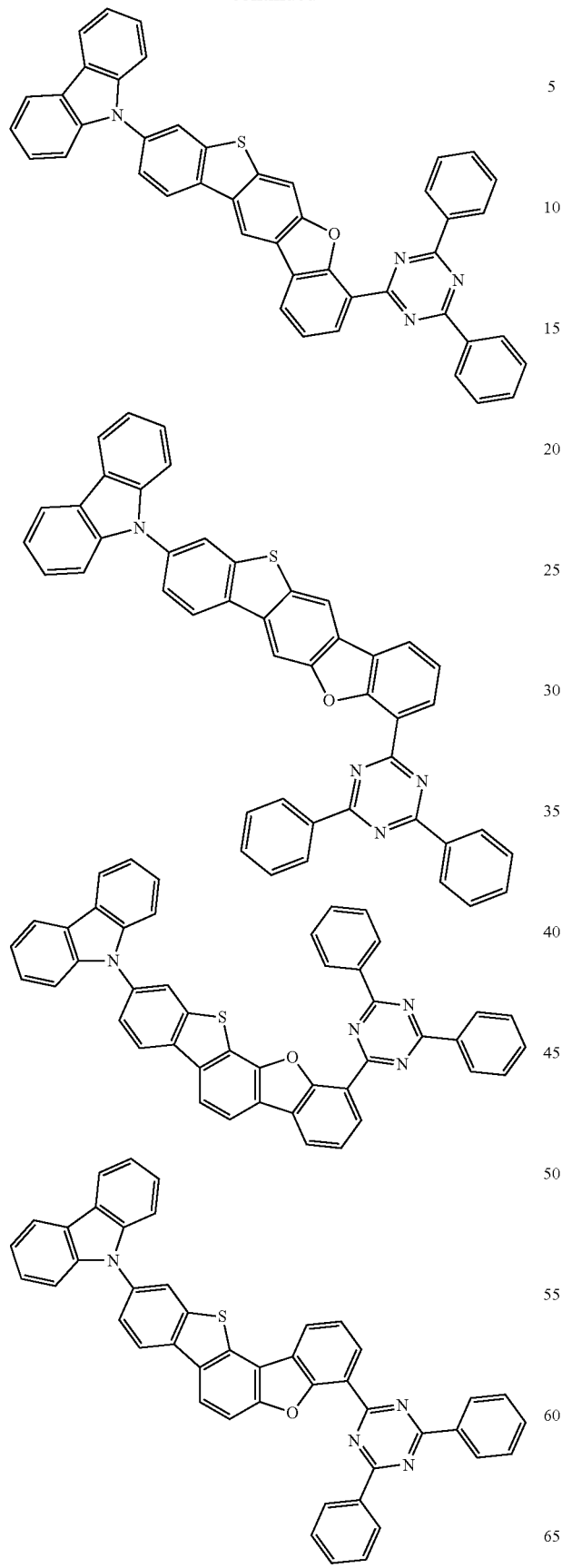
188
-continued
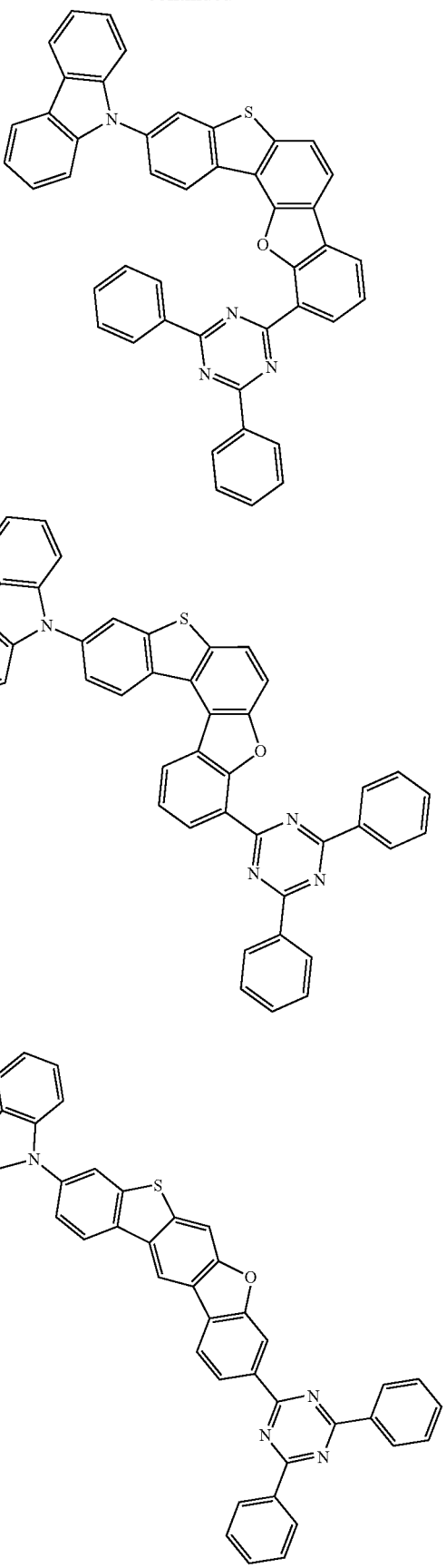

189
-continued
190
-continued
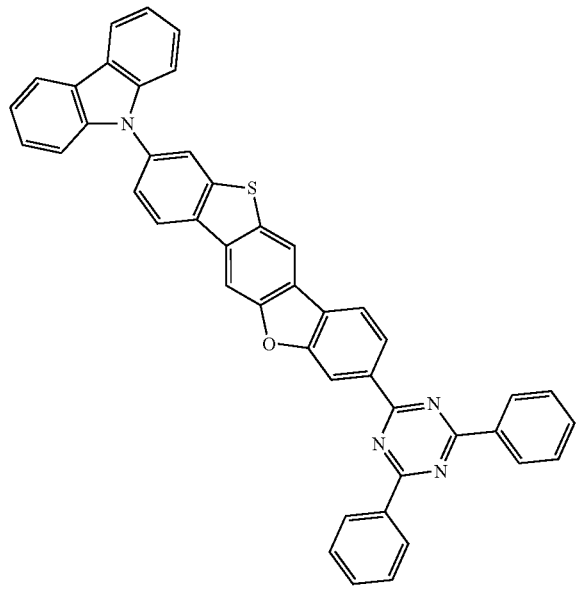
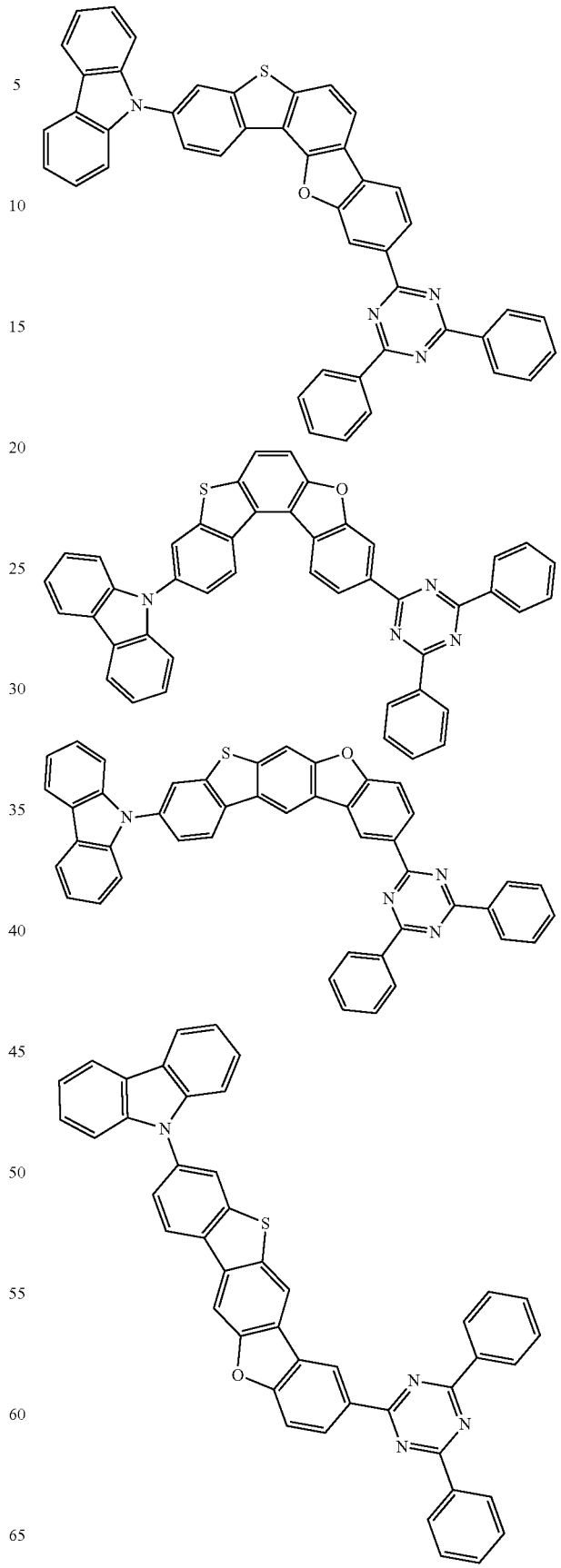

191
-continued
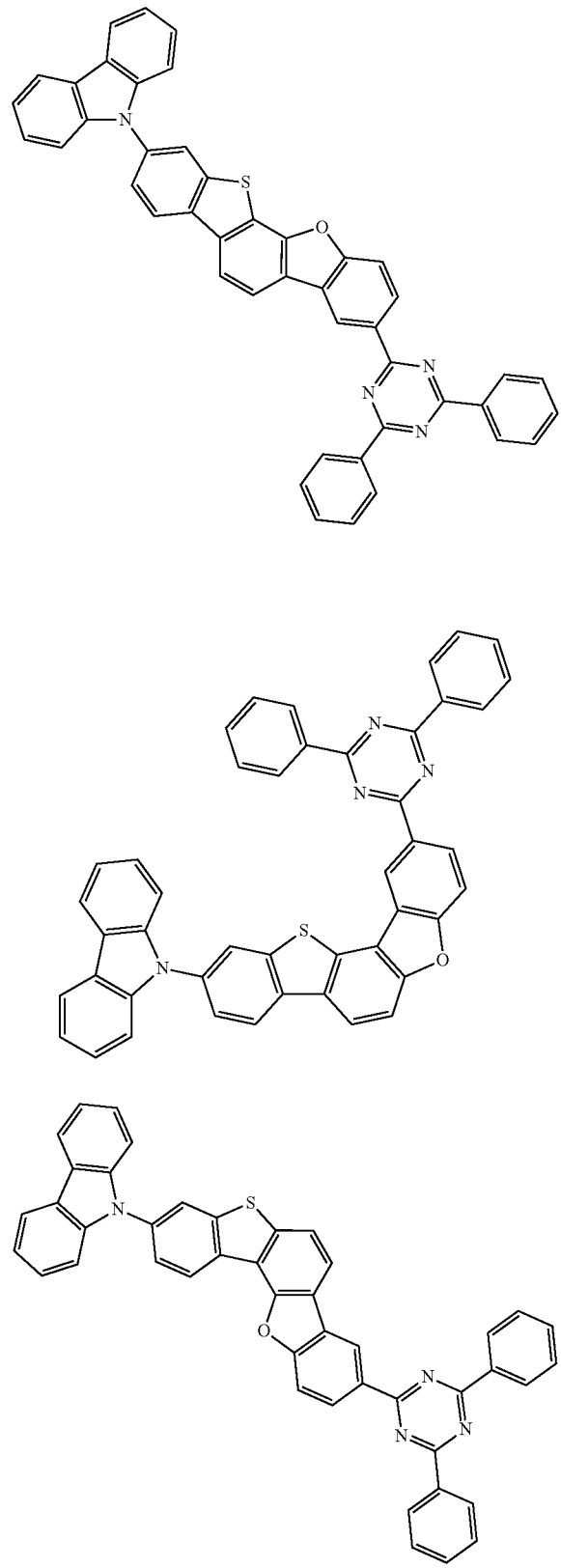
192
-continued
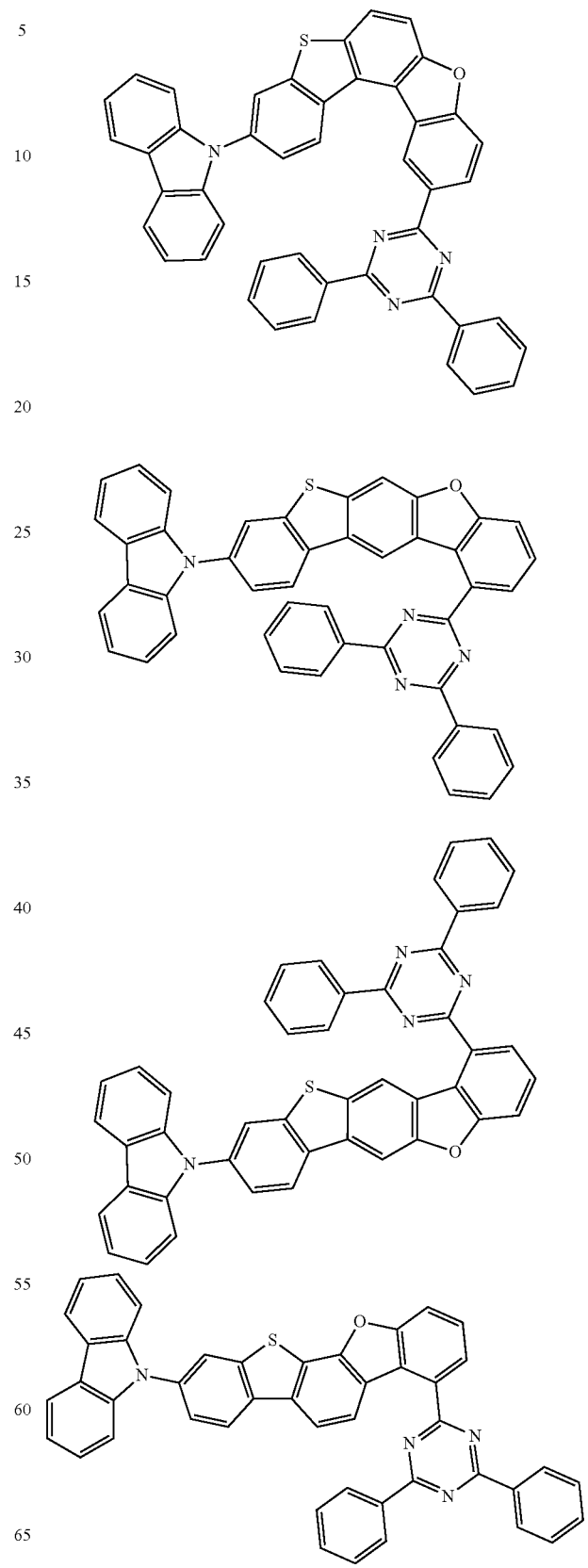

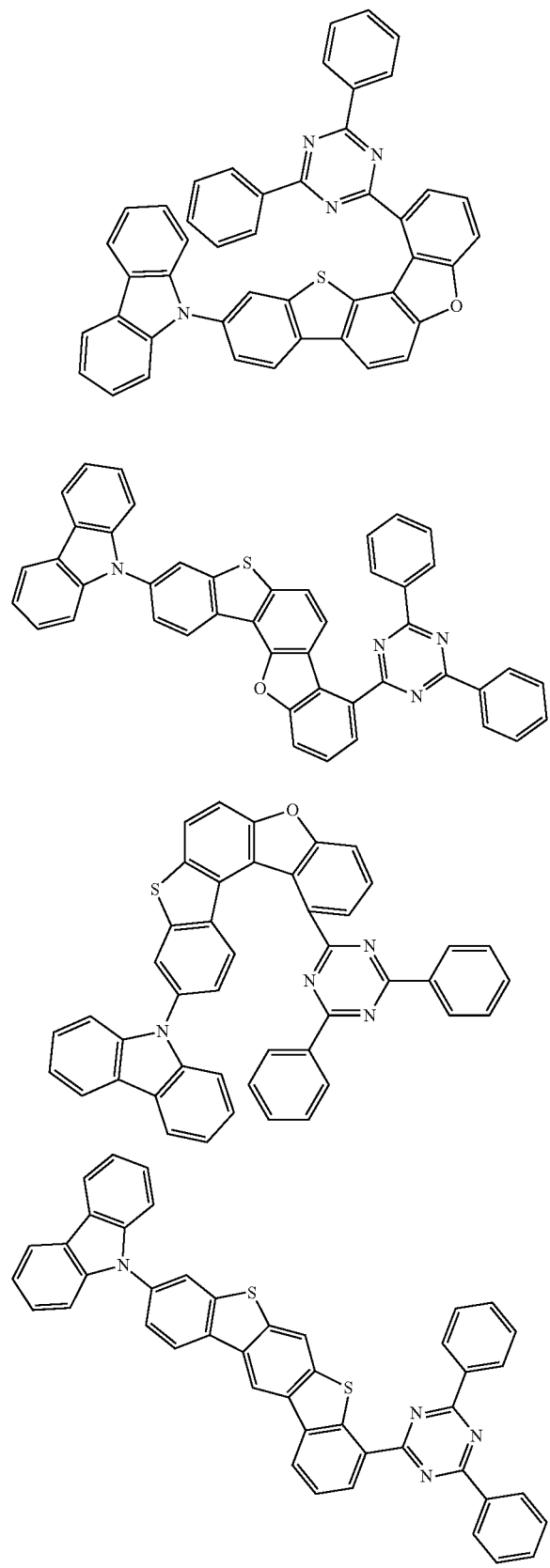
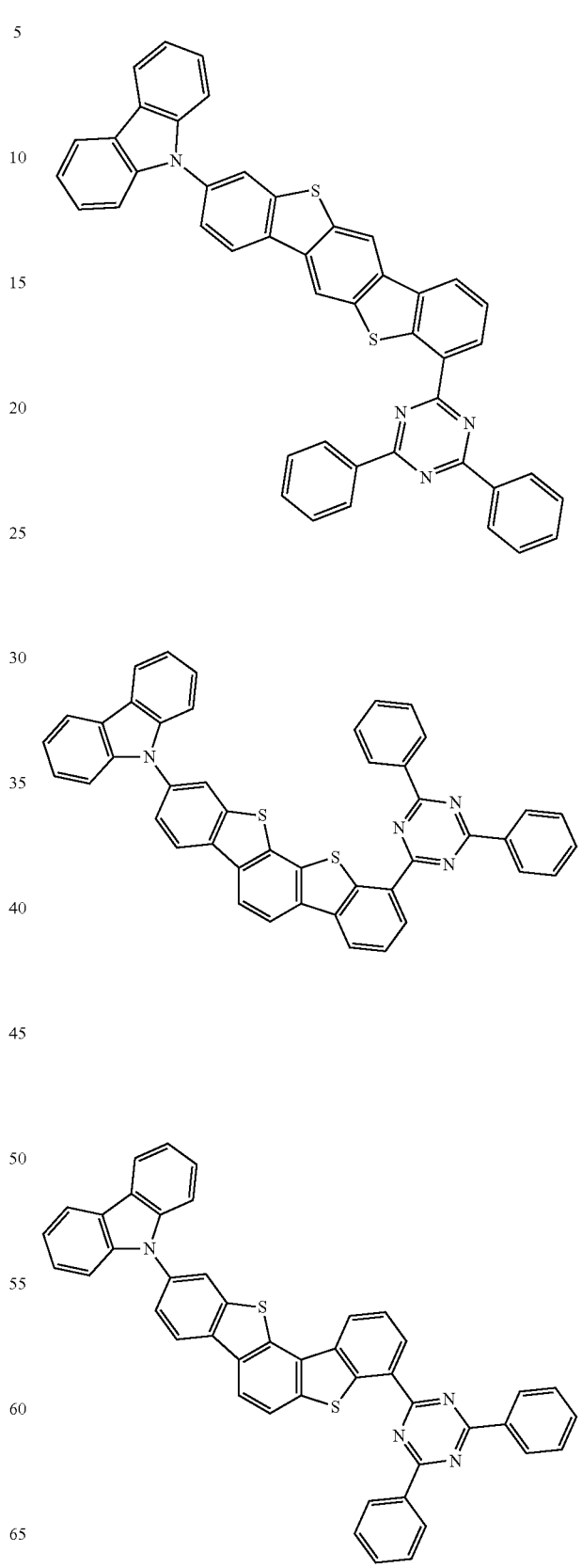

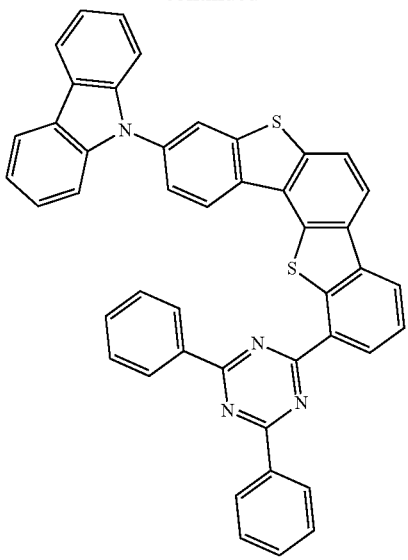
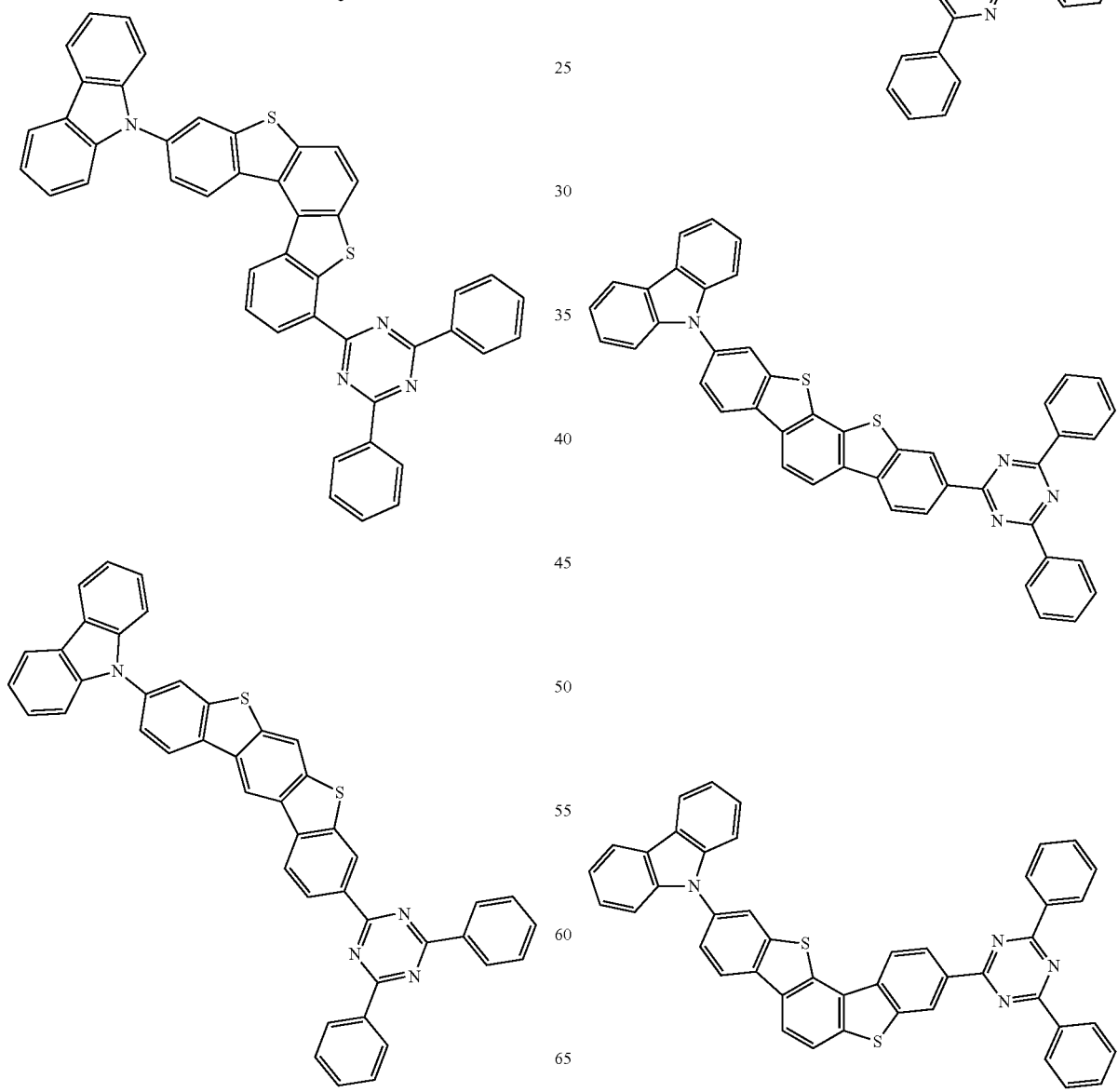

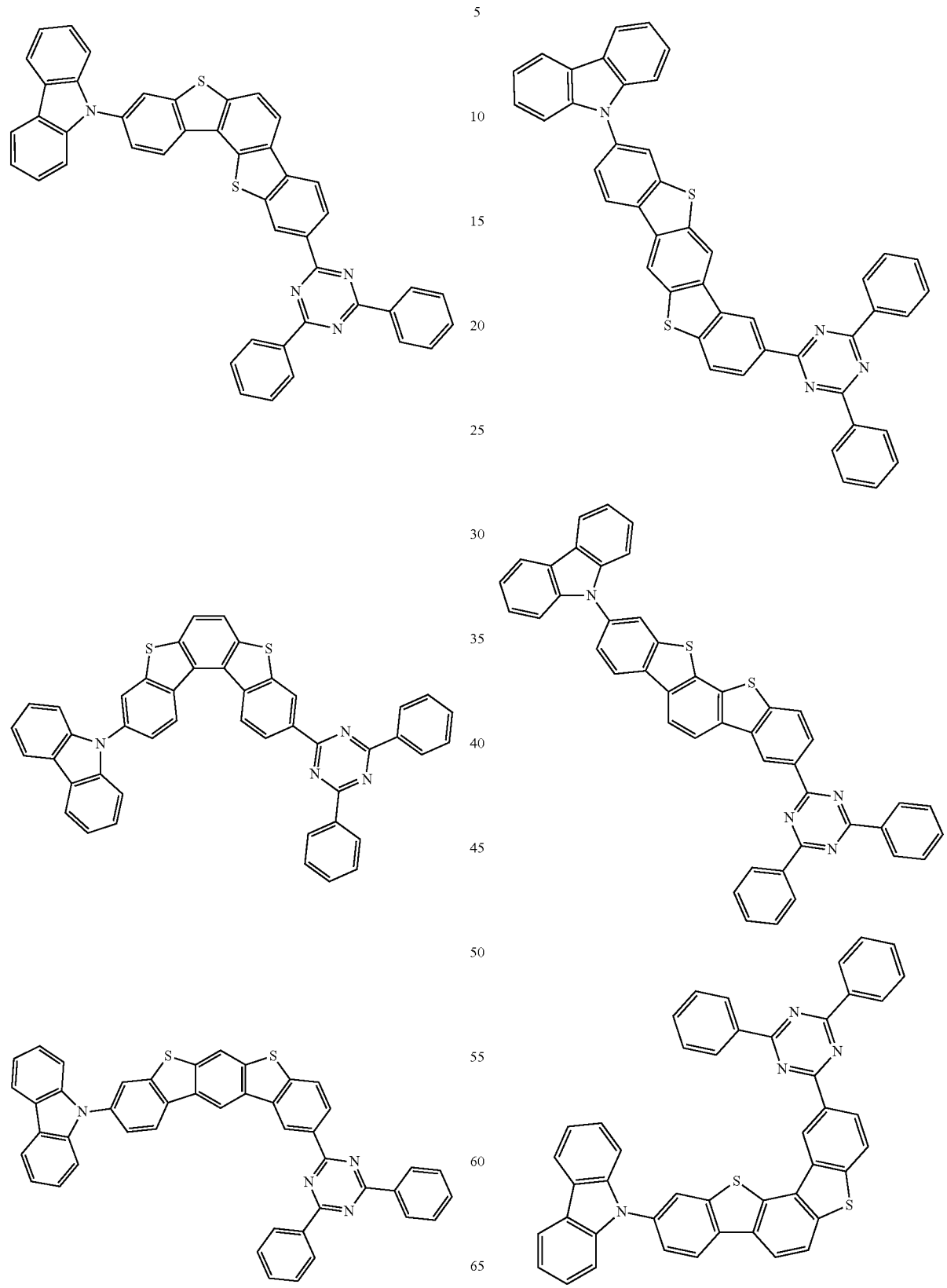

199
-continued
200
-continued
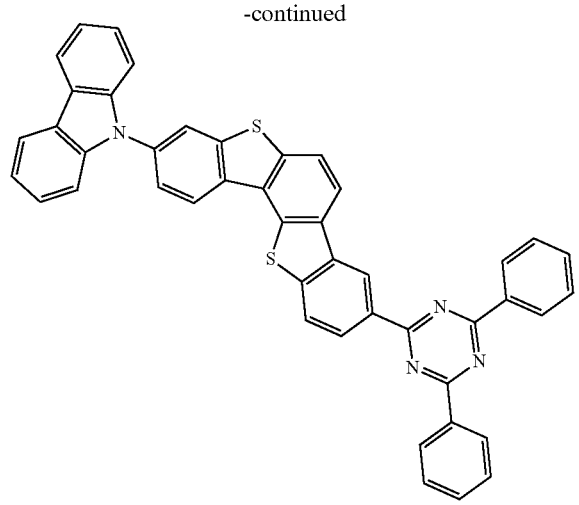
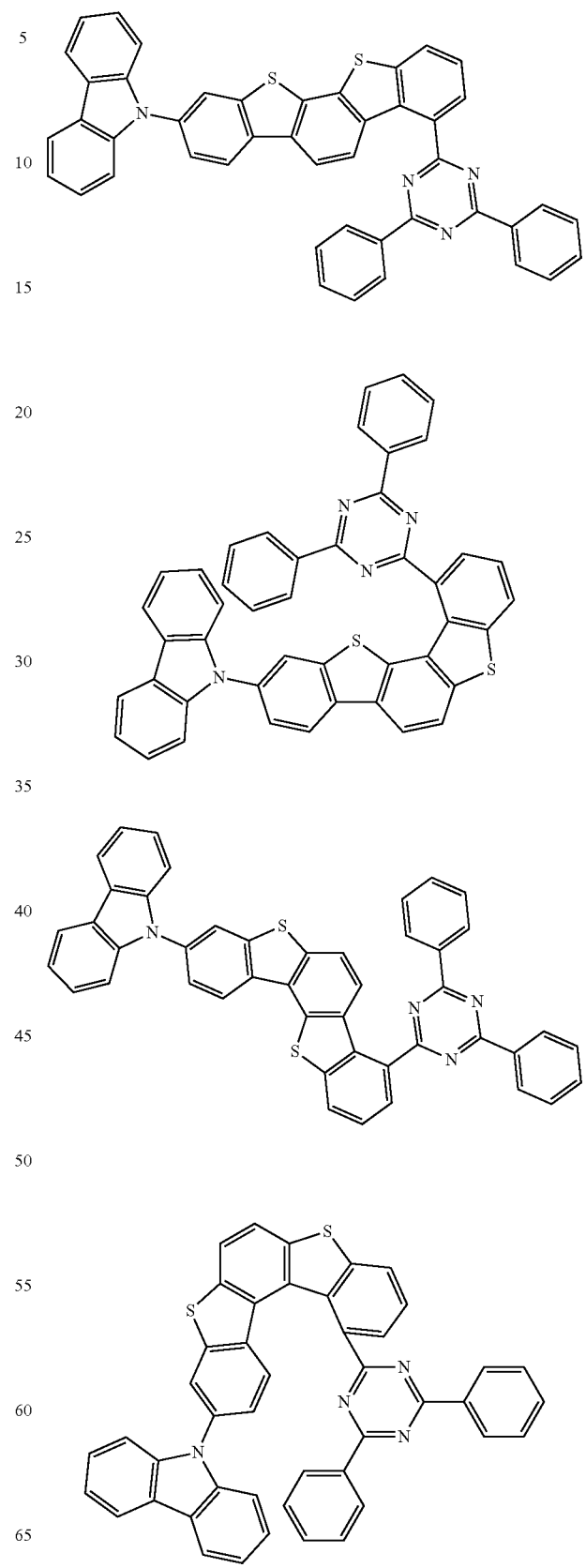

201
-continued
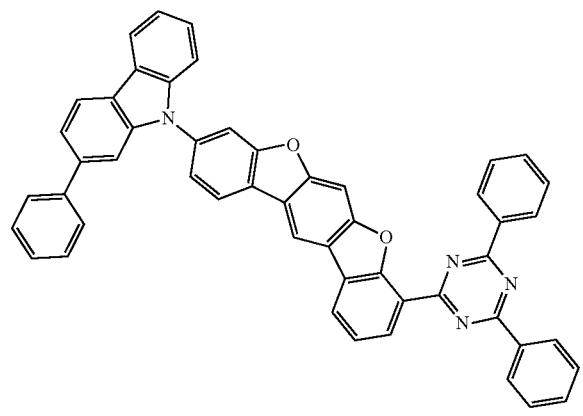
202
-continued
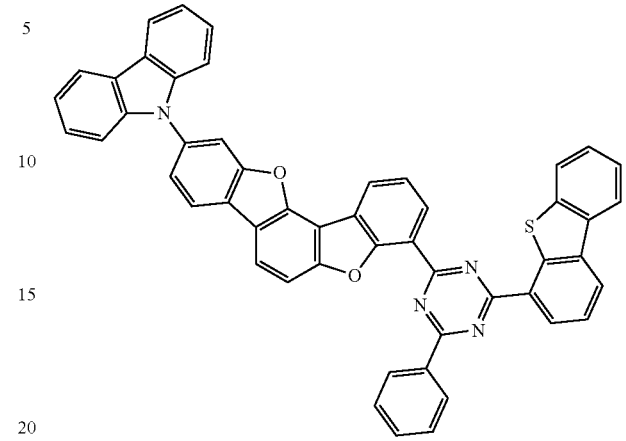
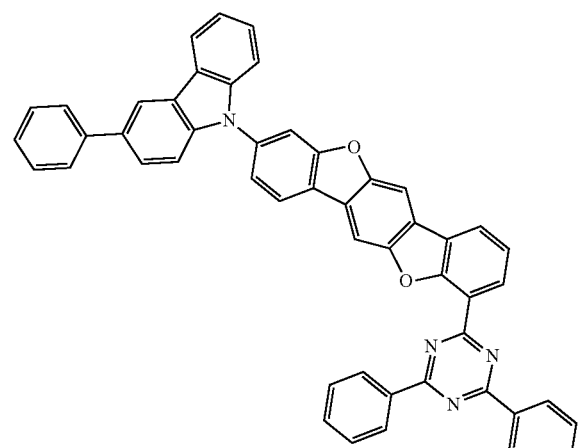
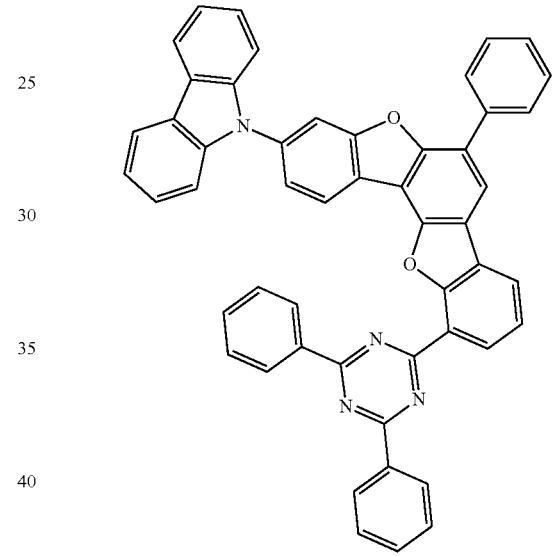
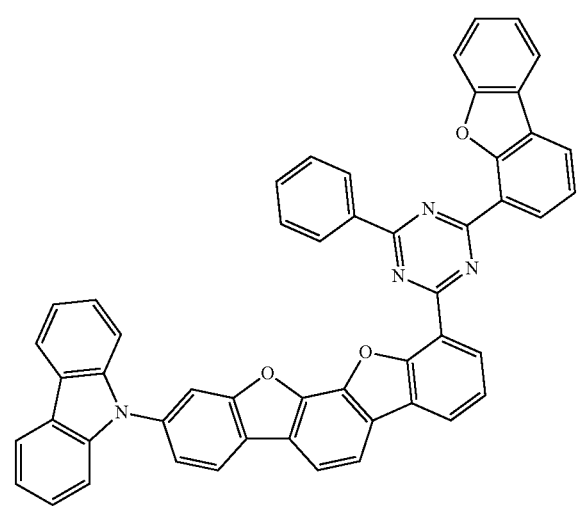
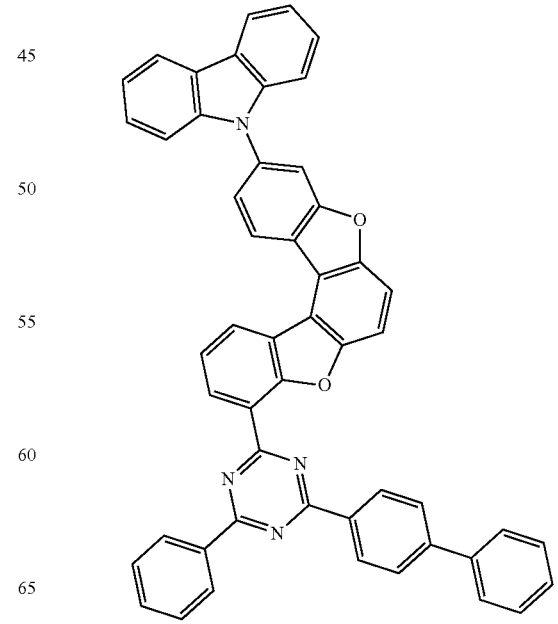

203
-continued
204
-continued
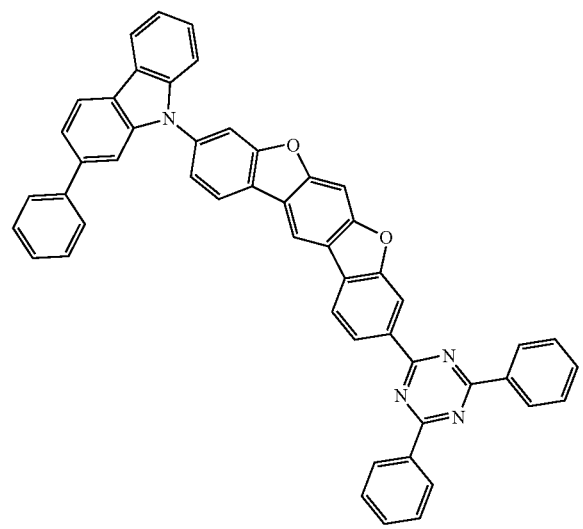
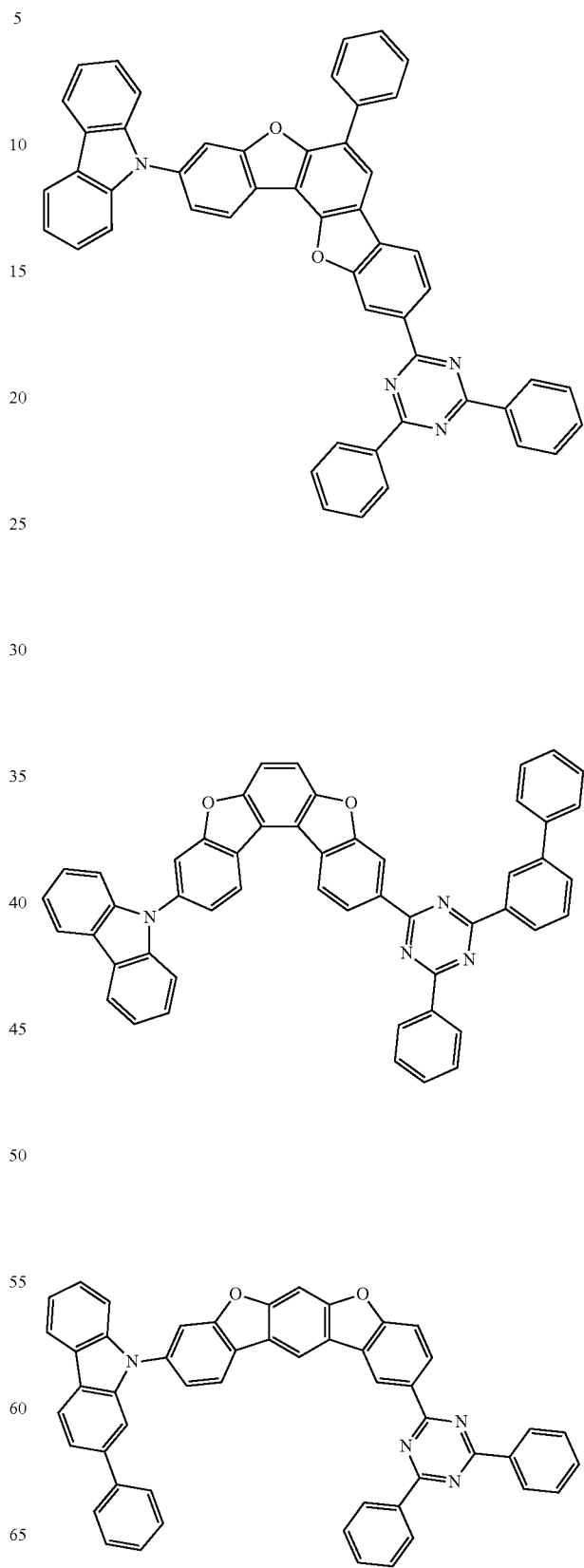

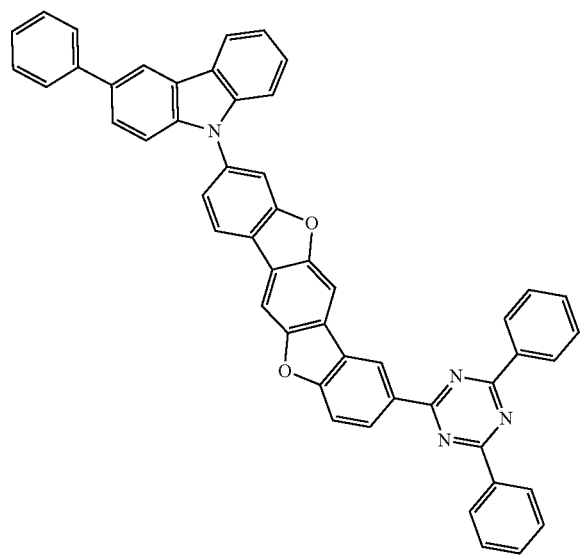
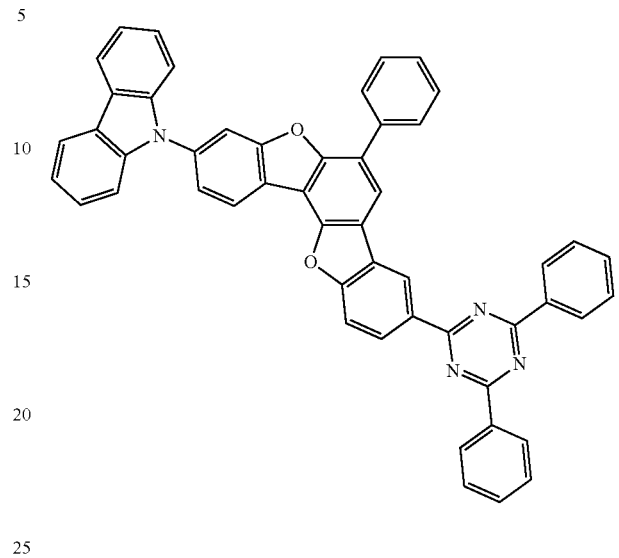
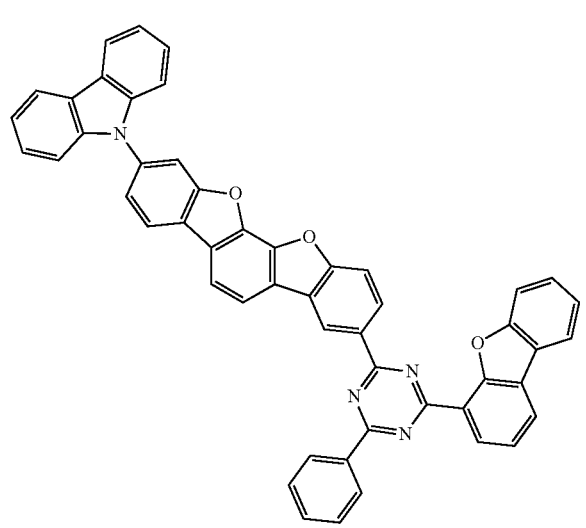
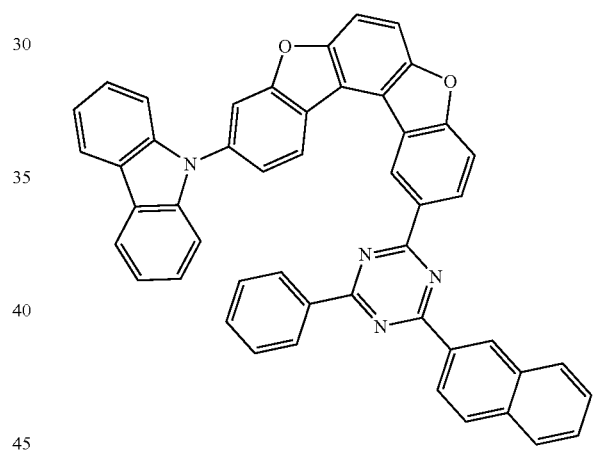
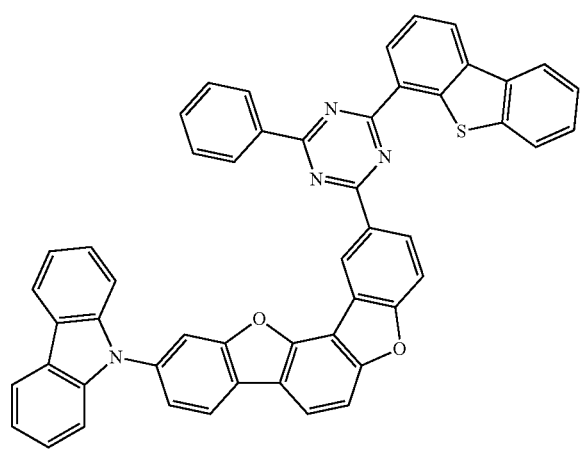
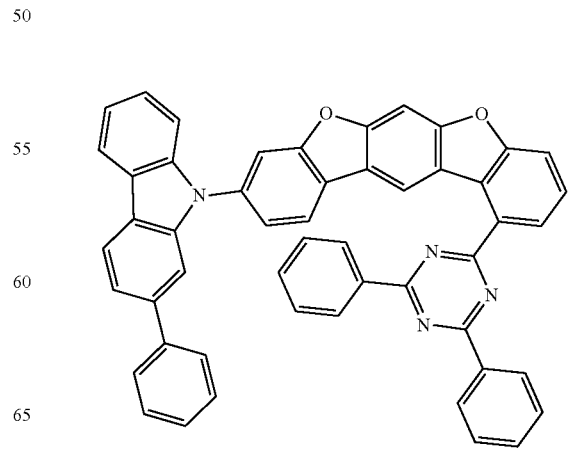

207
-continued
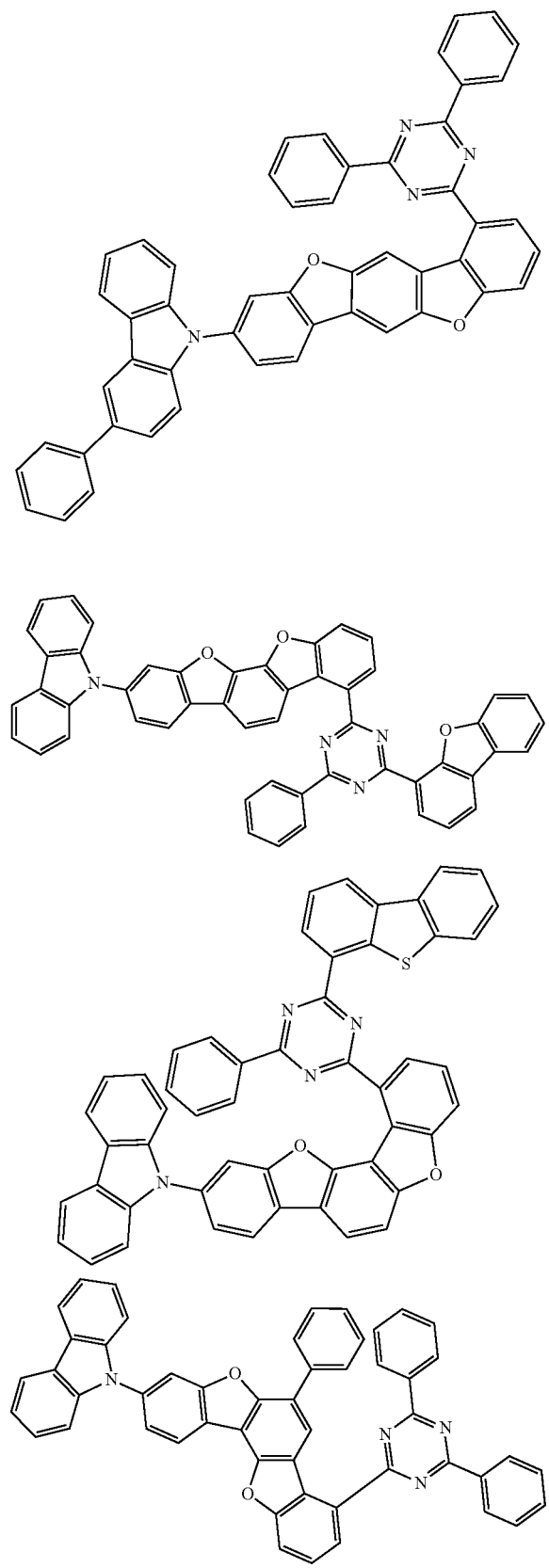
208
-continued
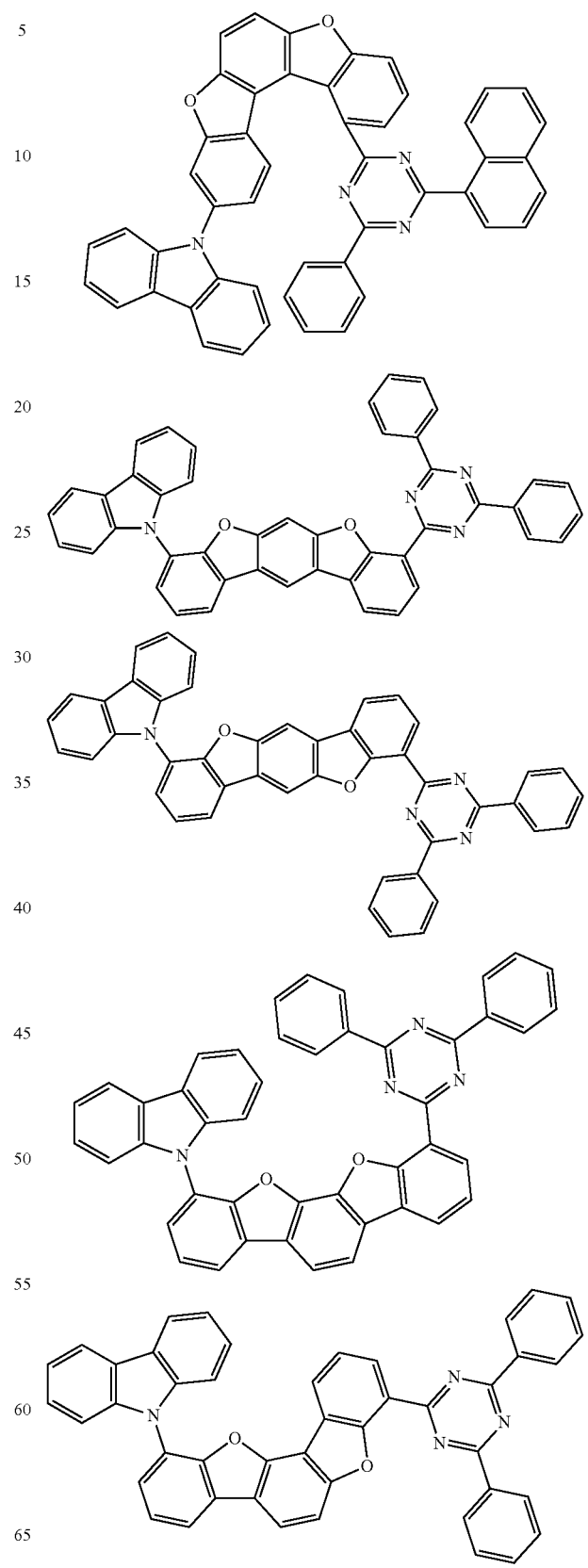

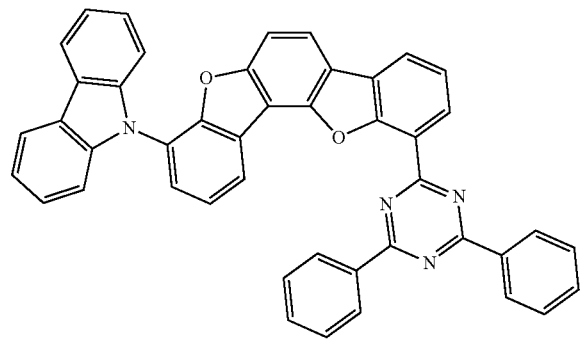
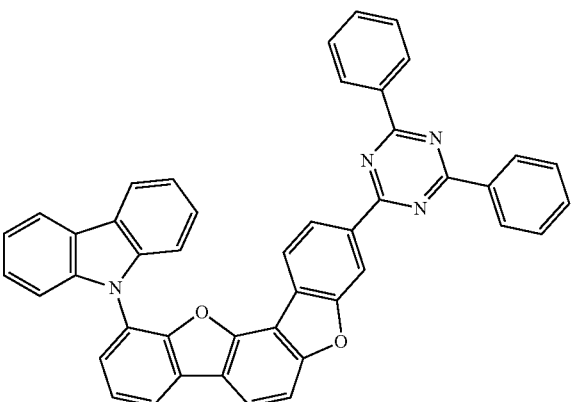
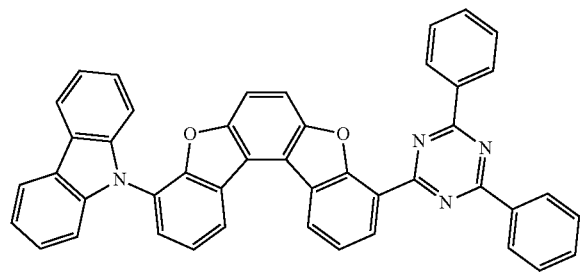
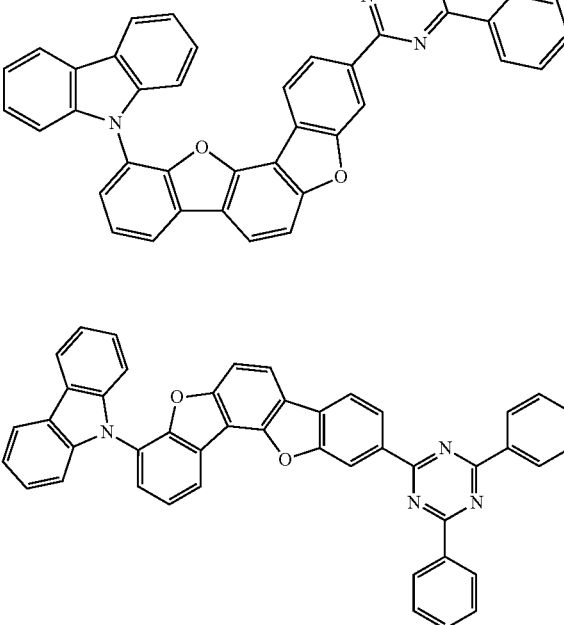
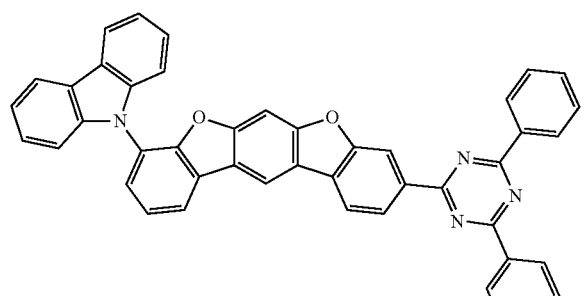
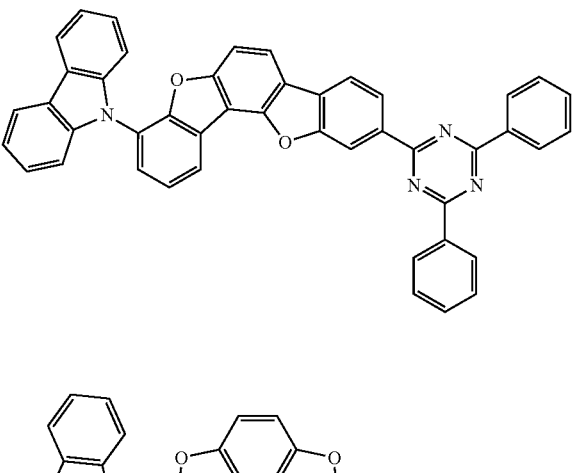
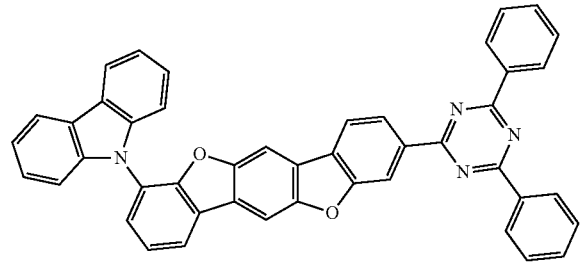
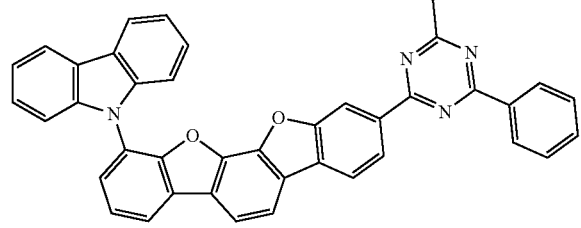
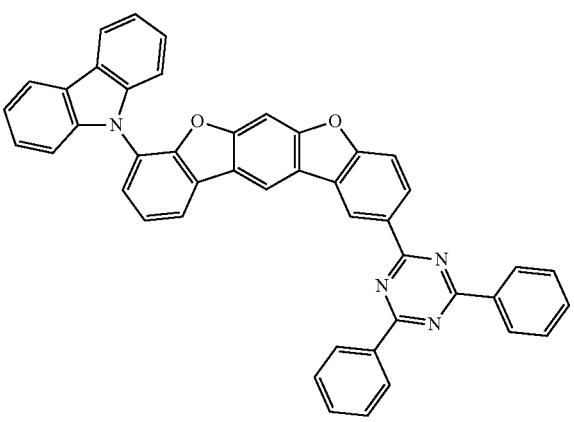

211
-continued
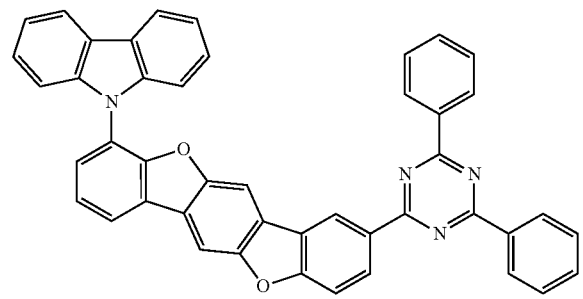
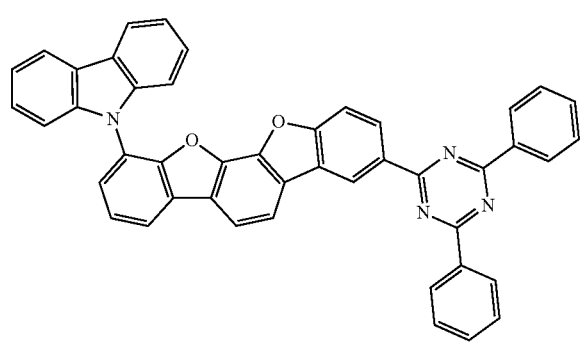
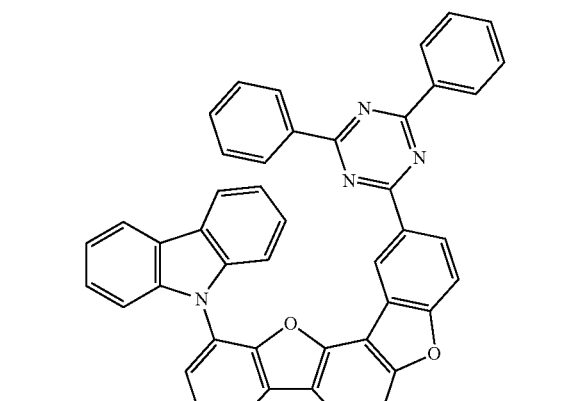
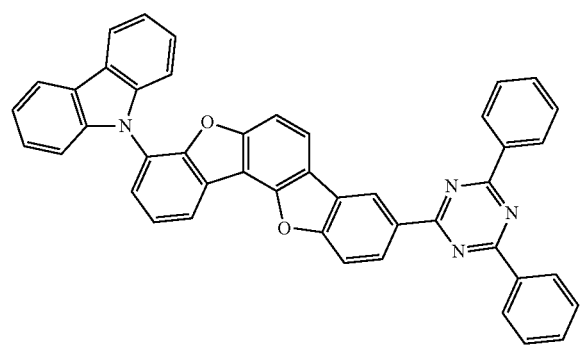
212
-continued
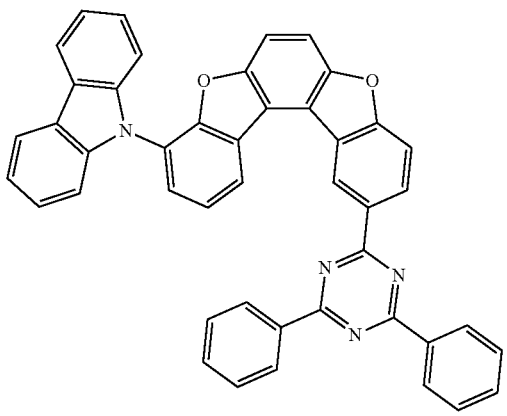
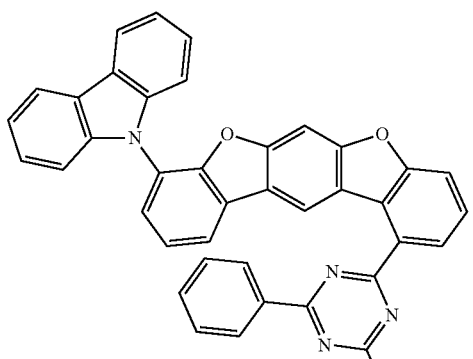
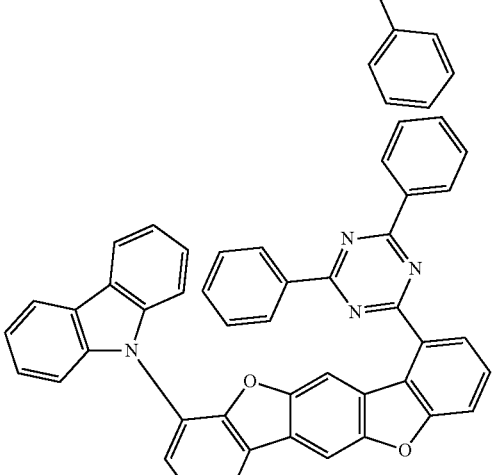
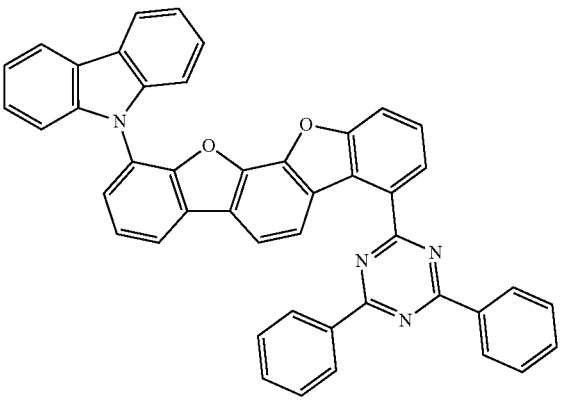

213
-continued
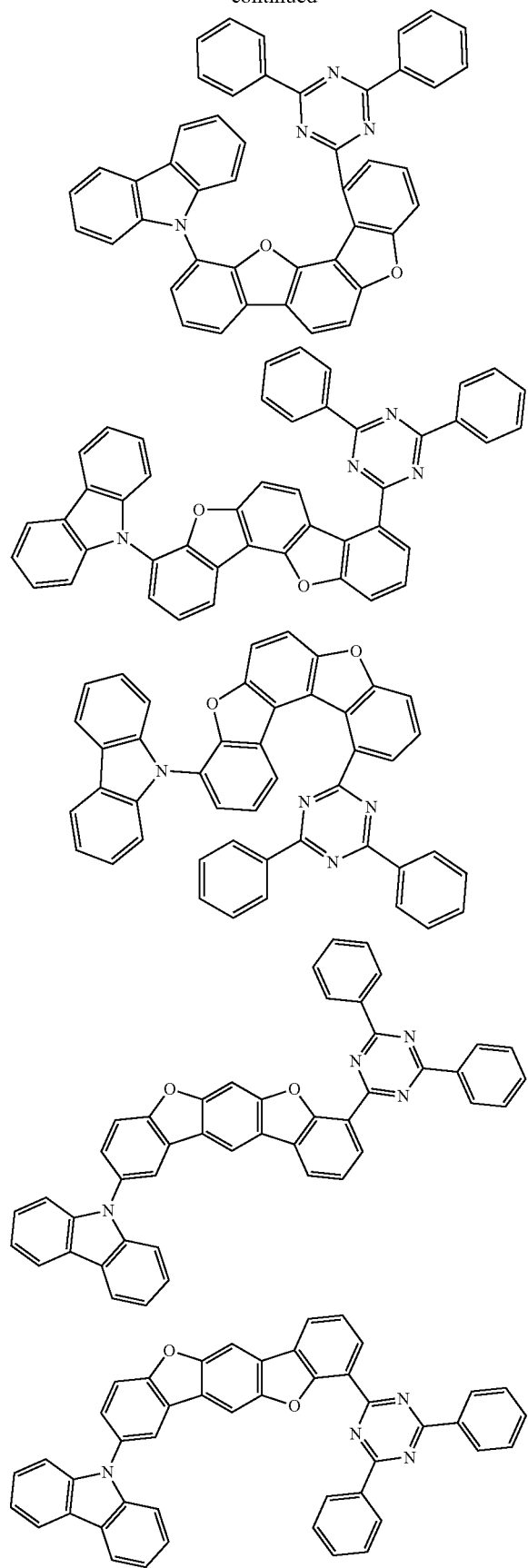
214
-continued
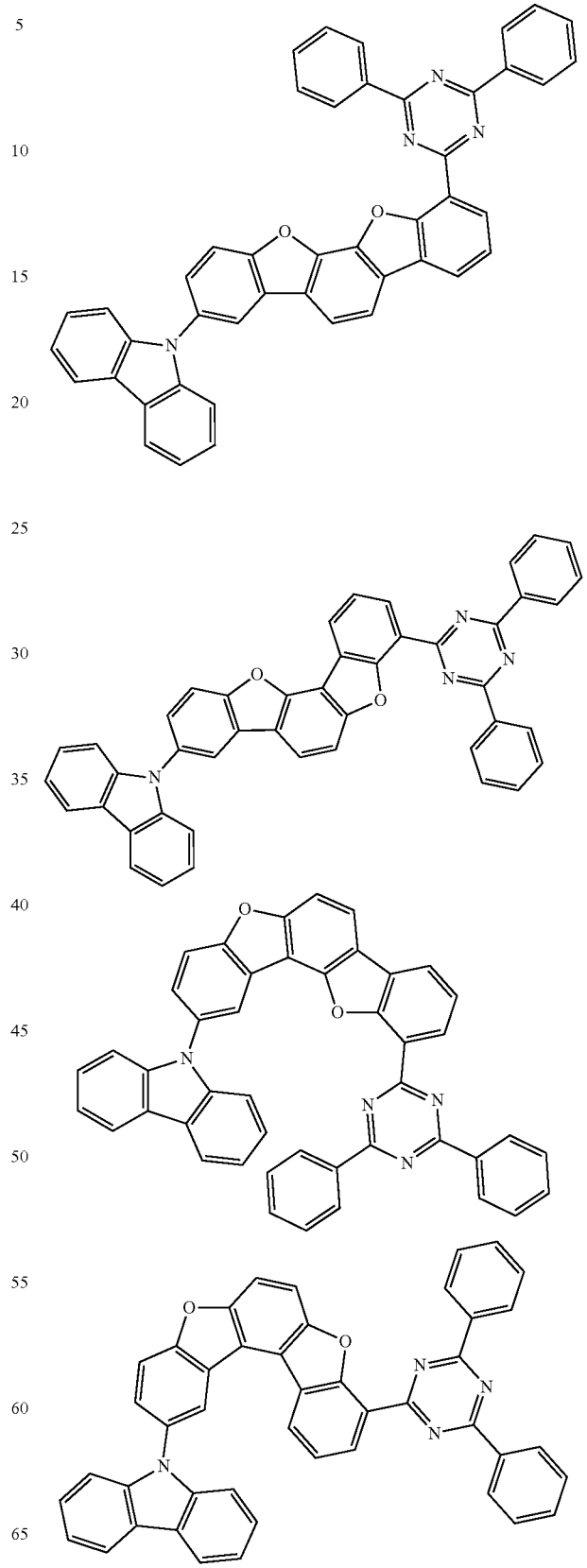

-continued
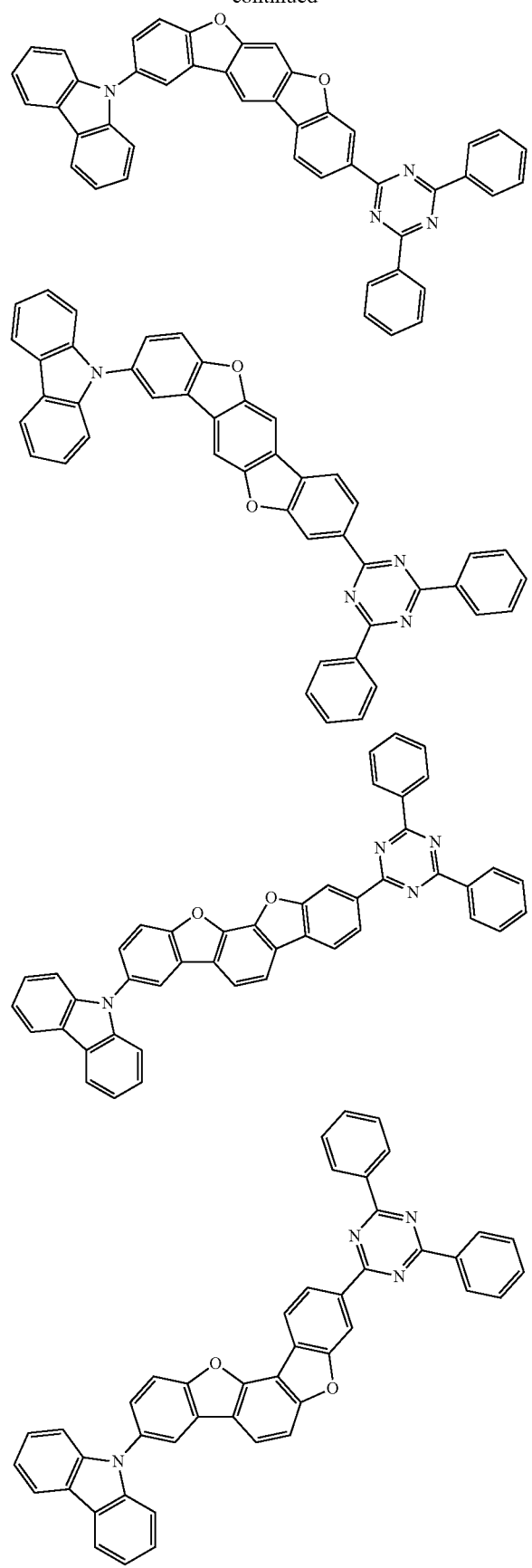
-continued
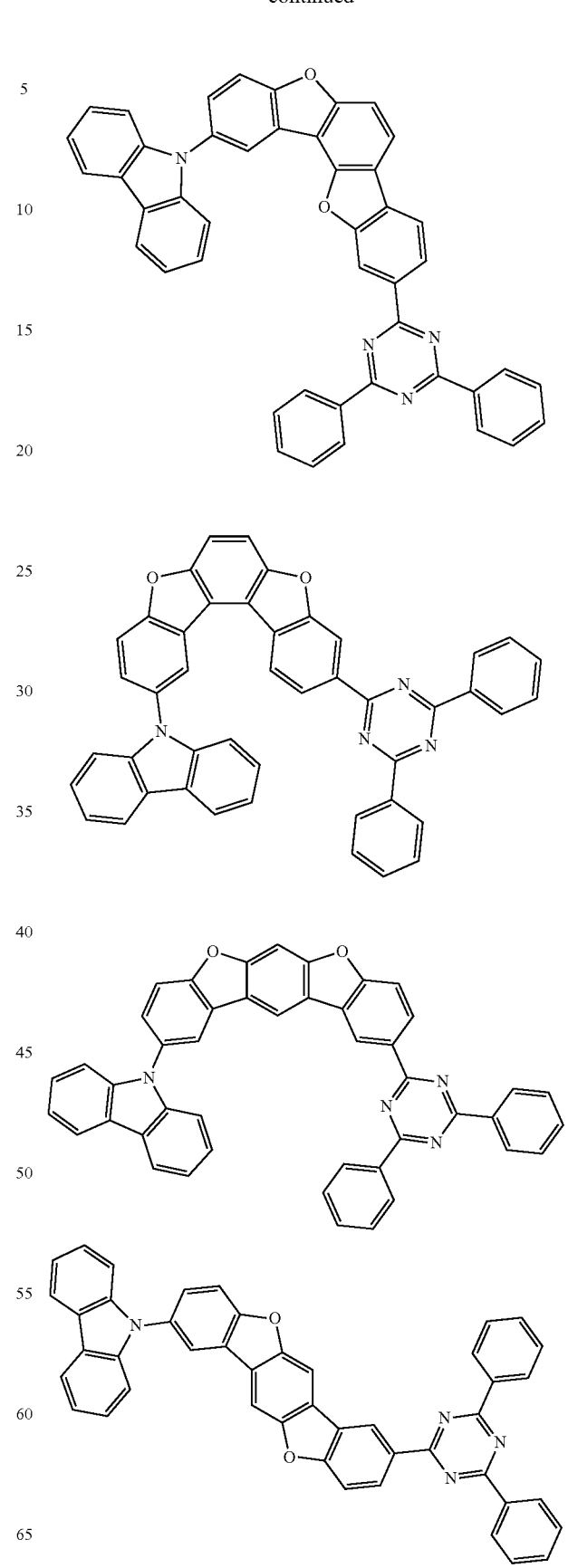

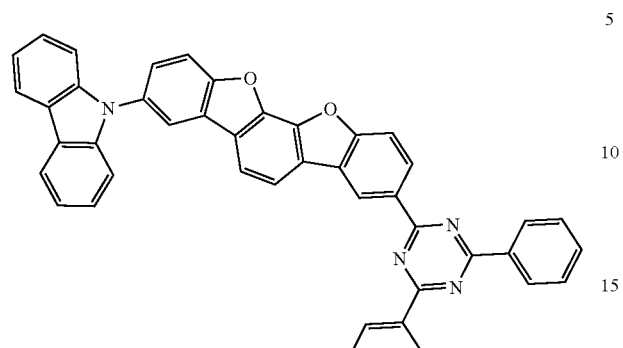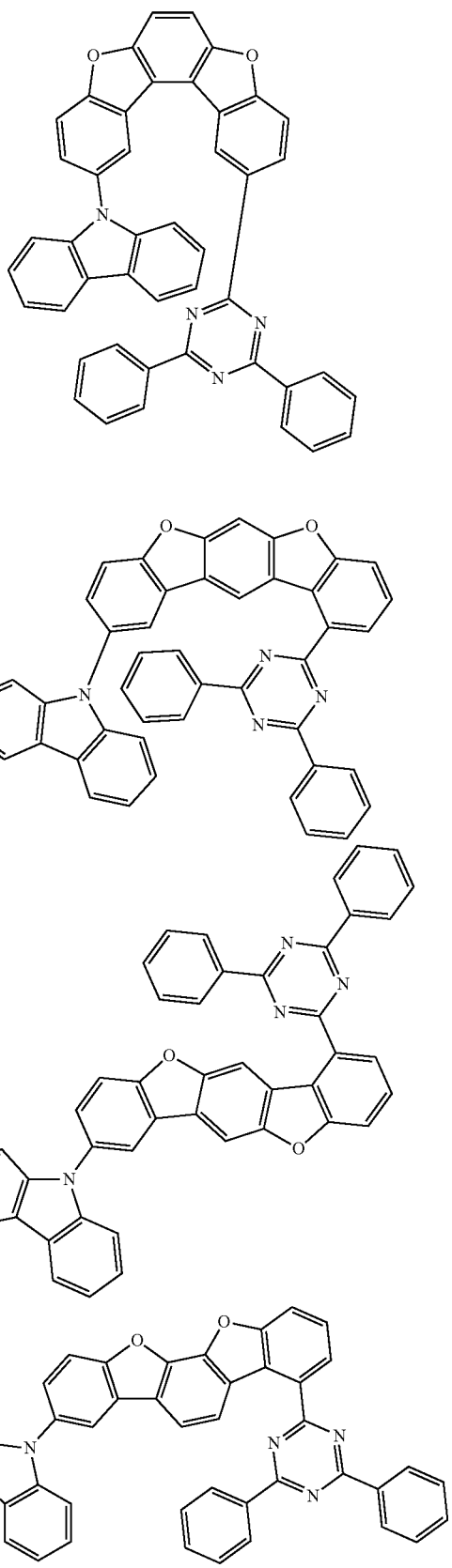

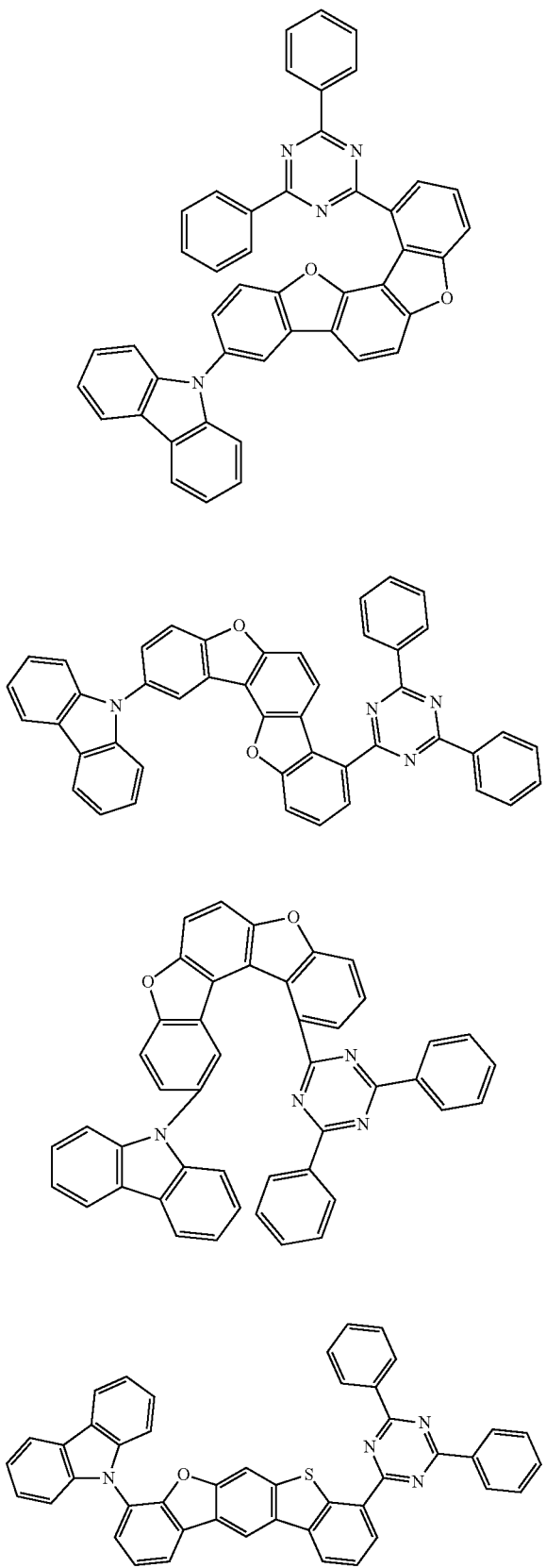
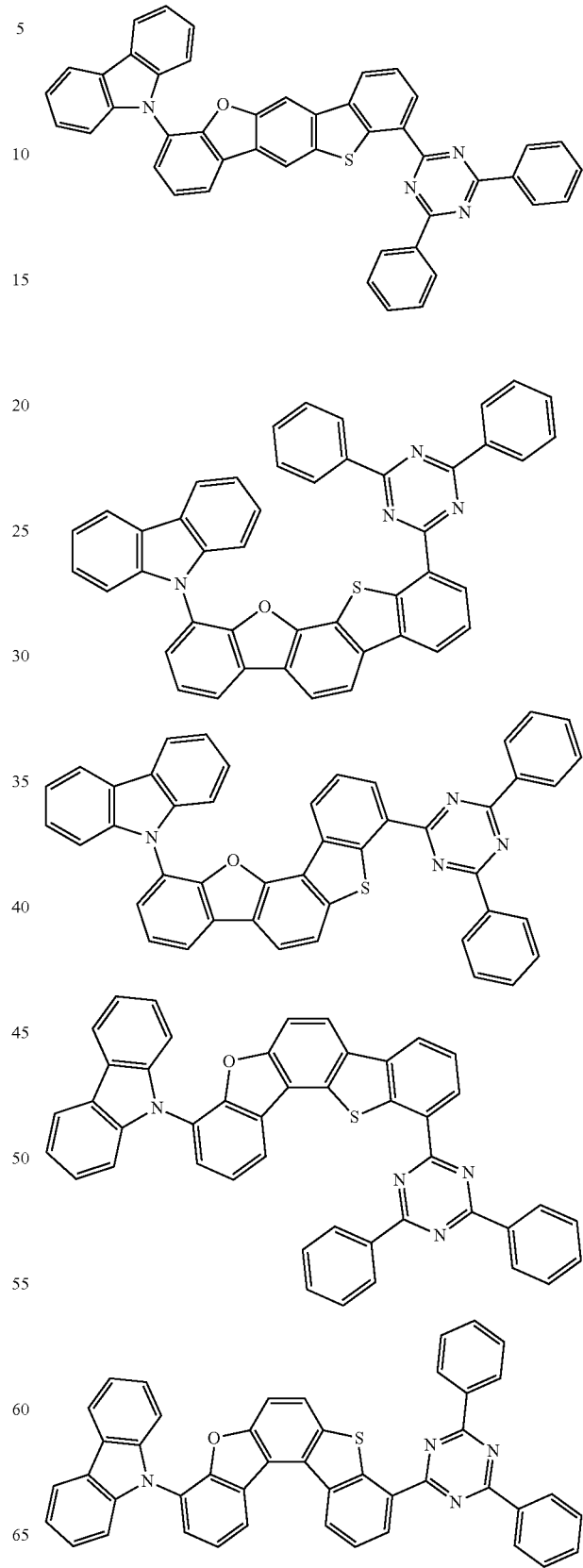

221
-continued
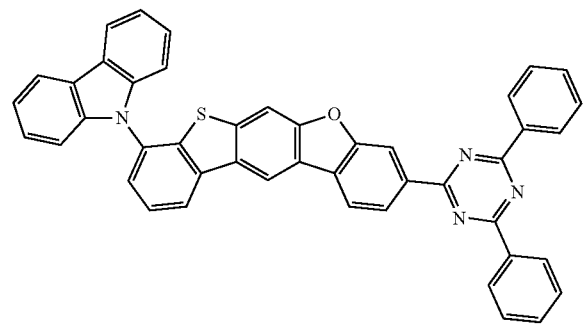
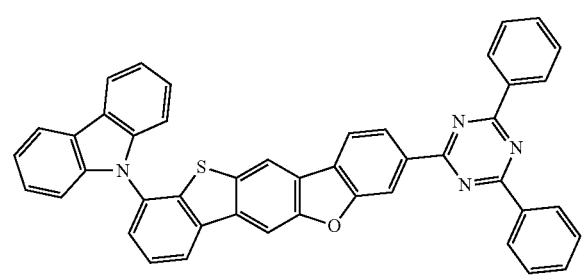
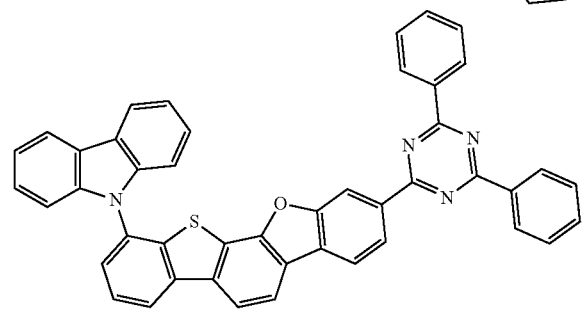
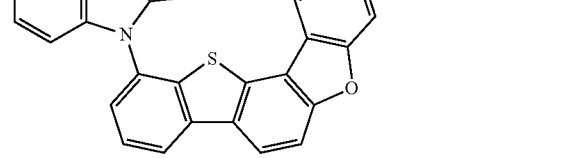
222
-continued
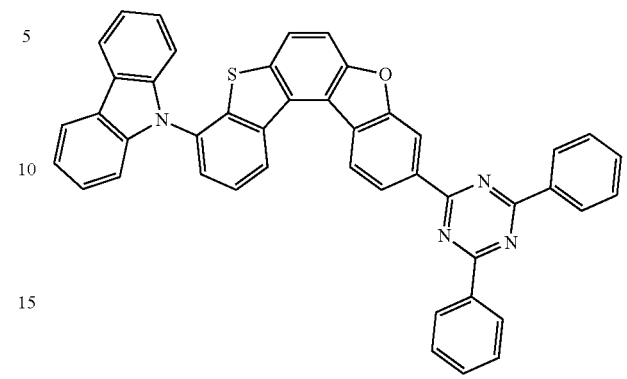
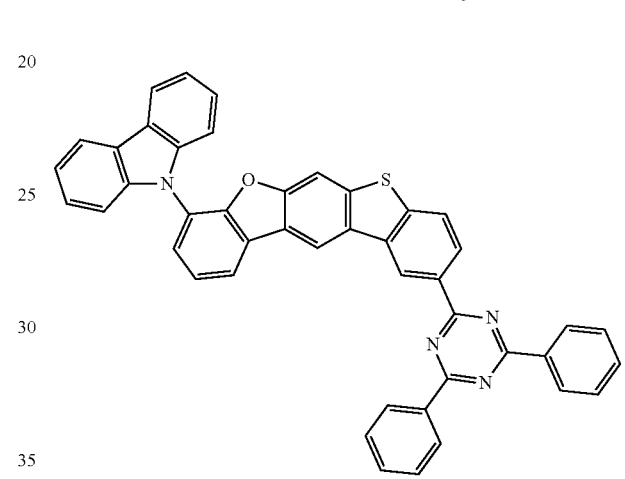
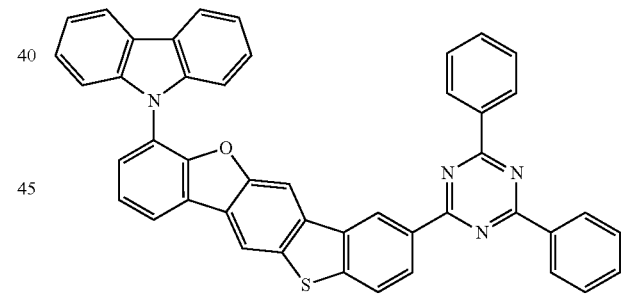
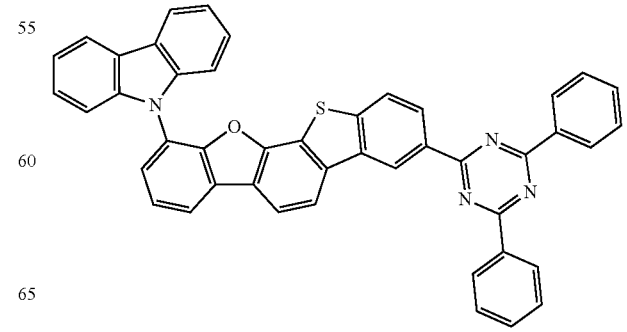

-continued
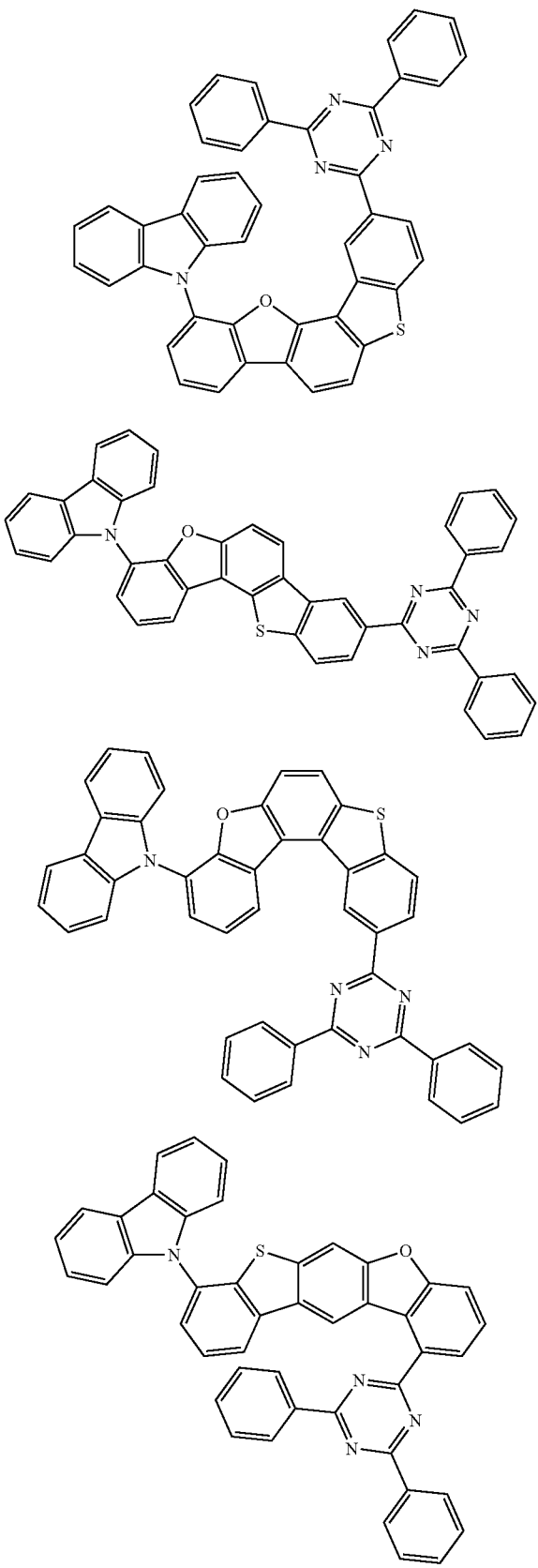
-continued
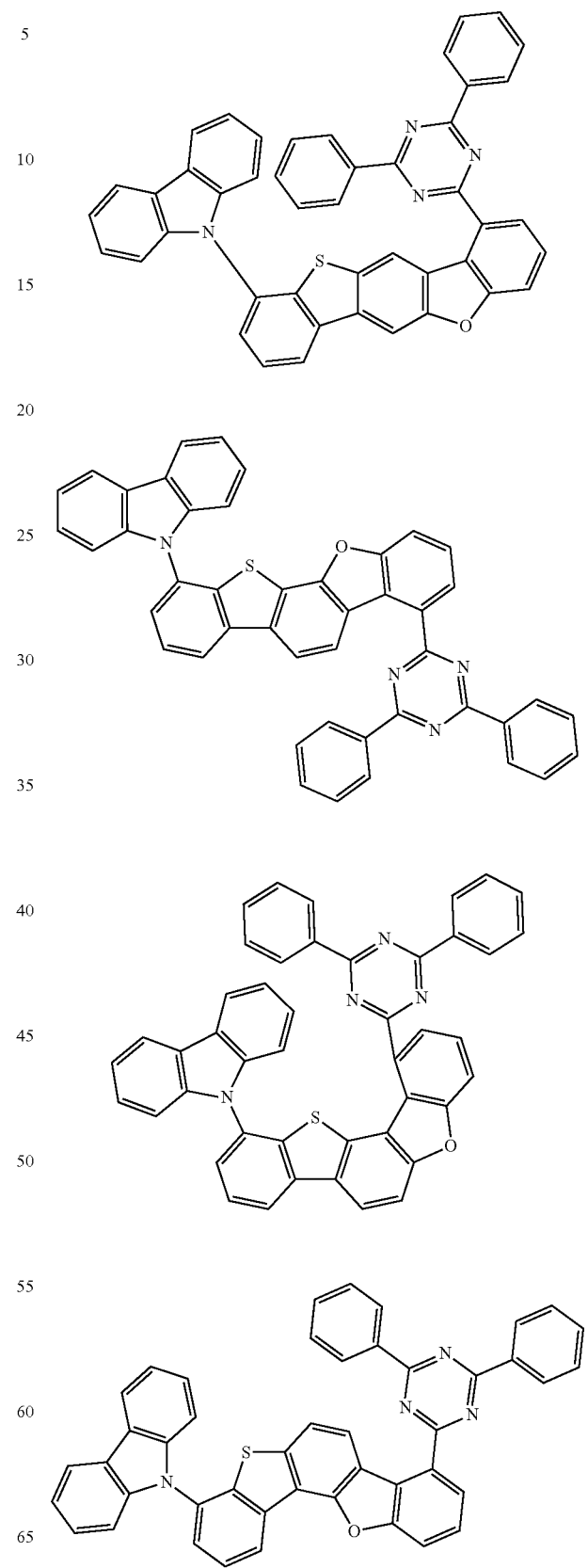

225
-continued
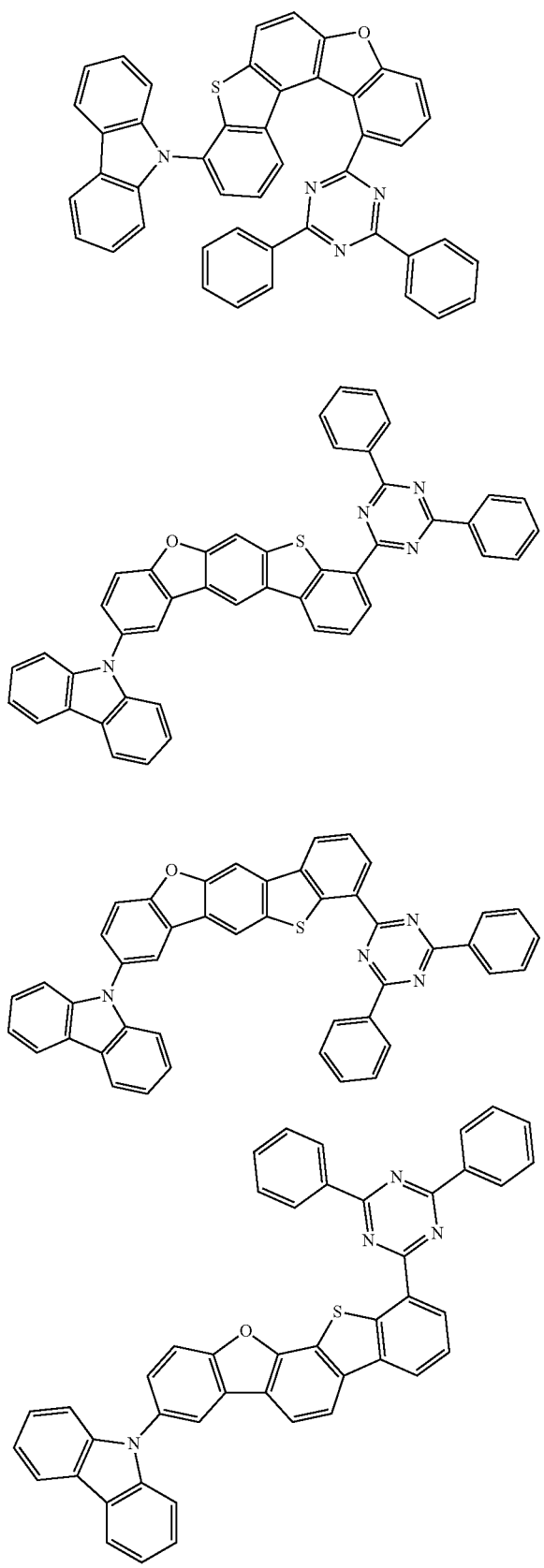
226
-continued
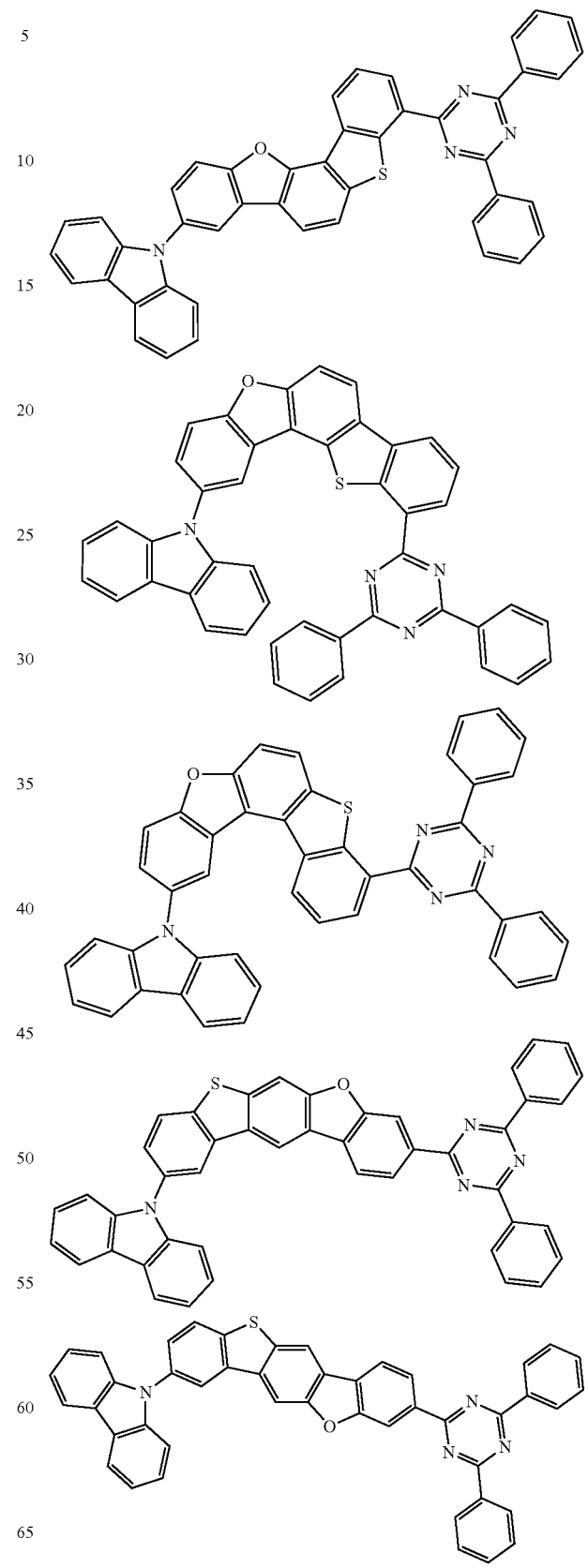

227
-continued
228
-continued
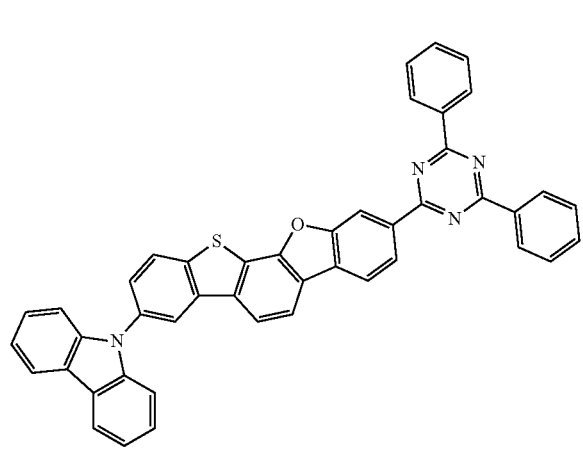
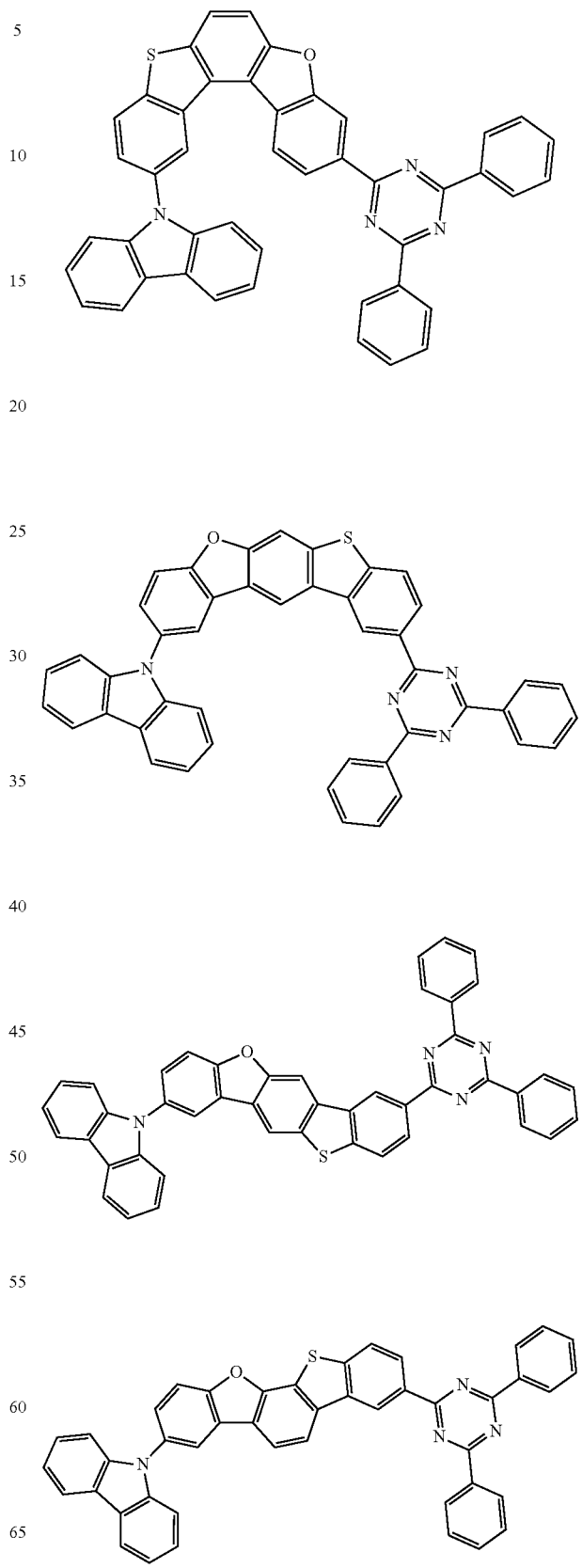

229
-continued
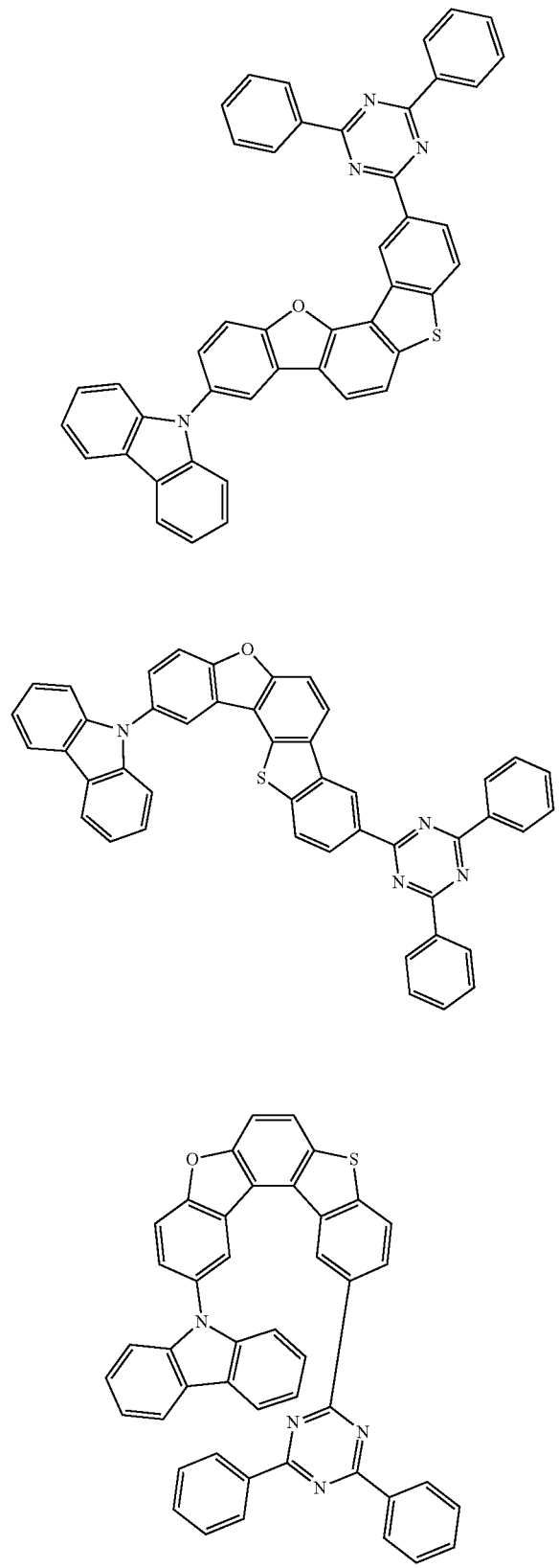
230
-continued
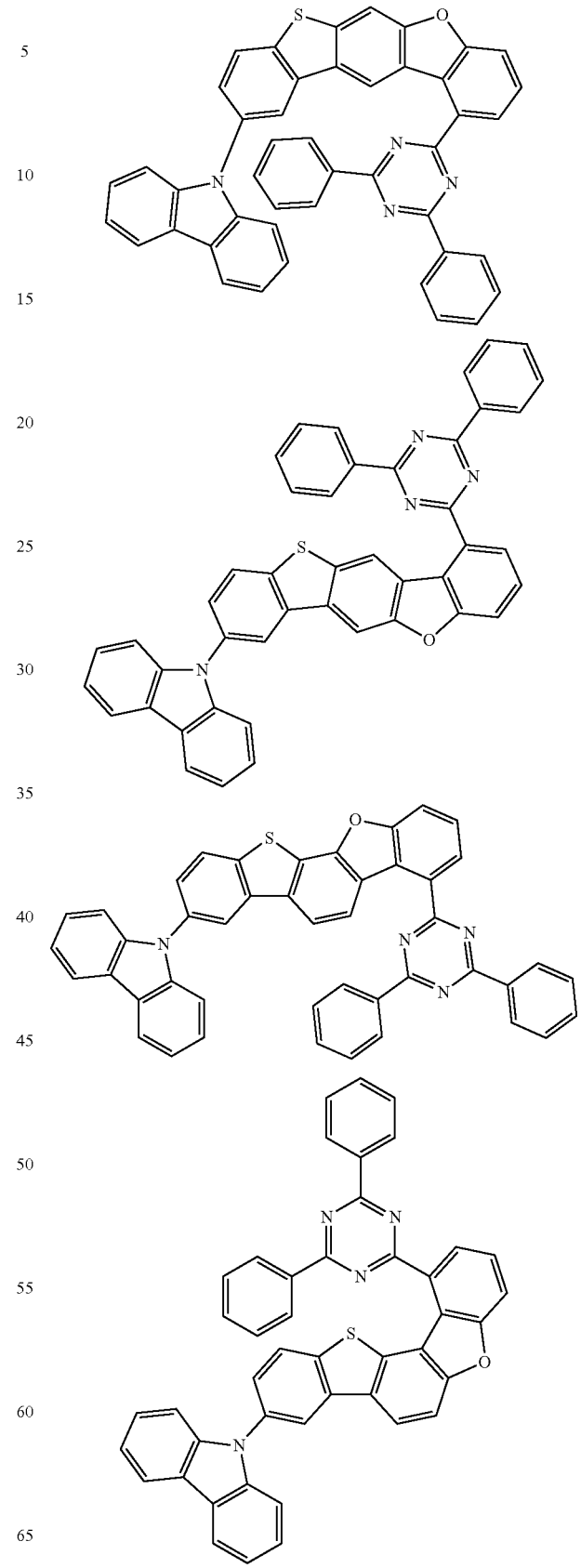

231
-continued
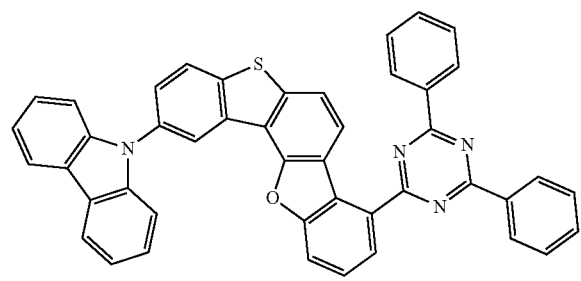
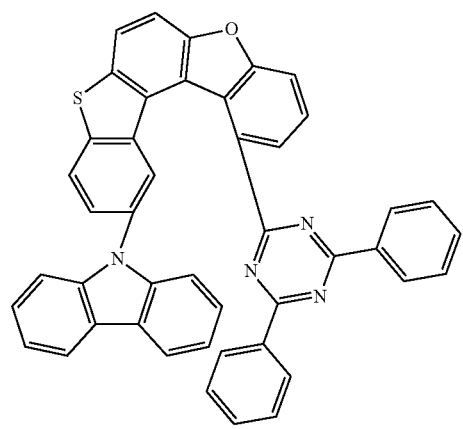
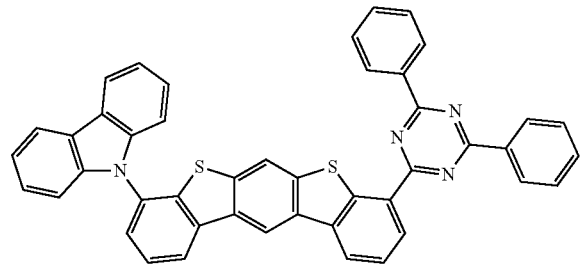
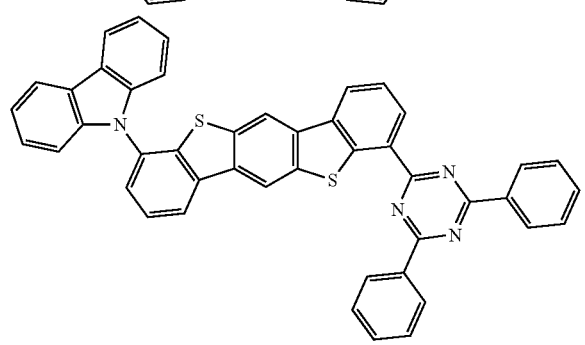
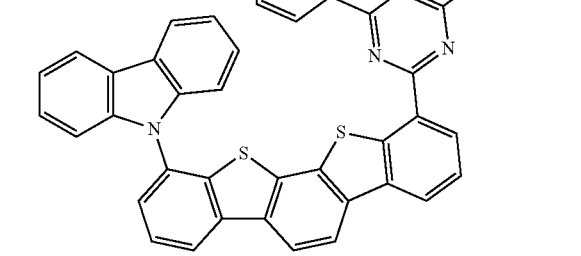
232
-continued
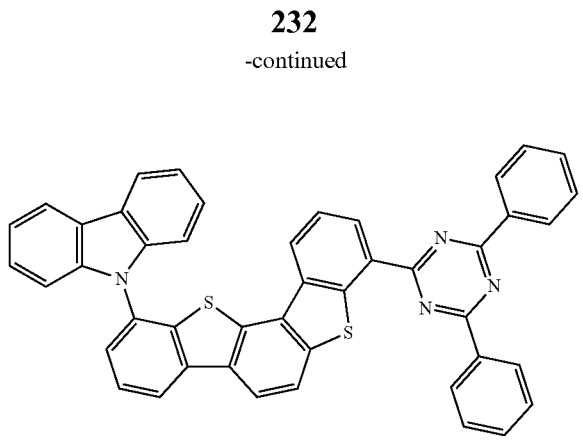
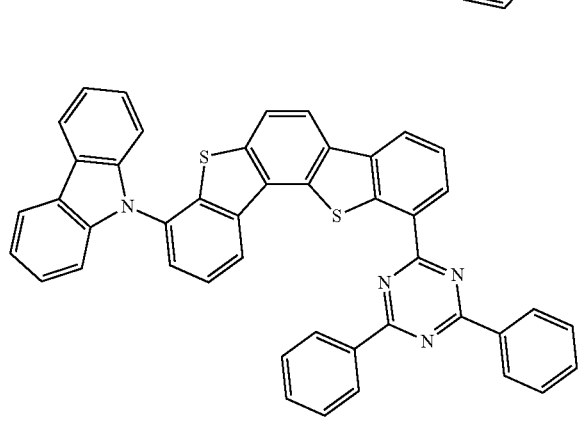
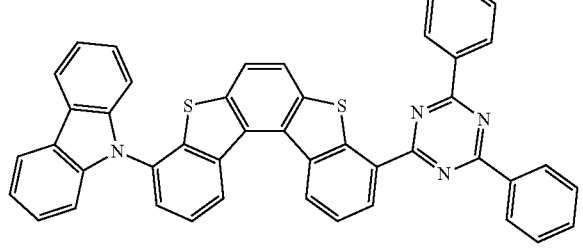
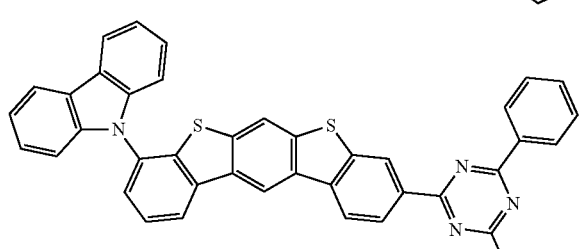
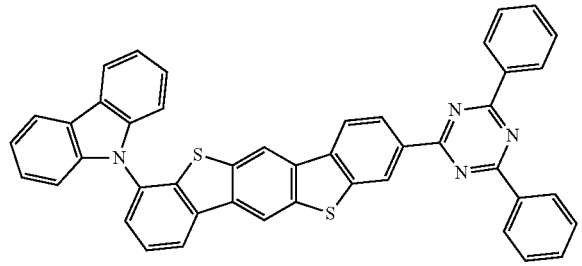

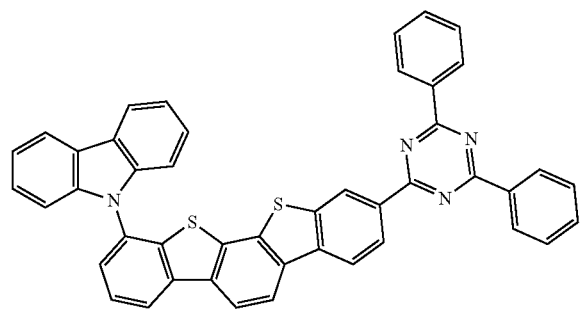
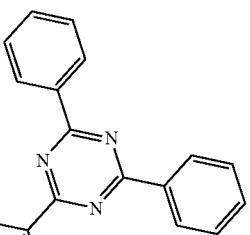
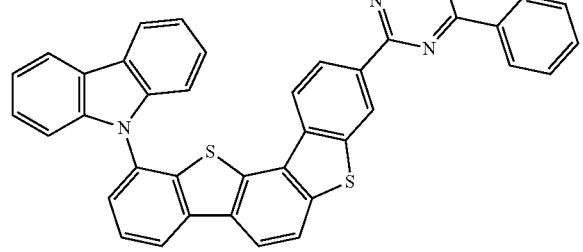
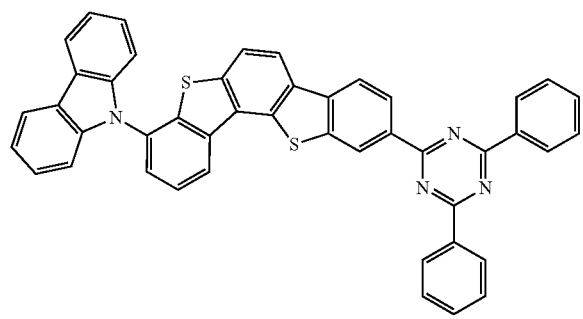
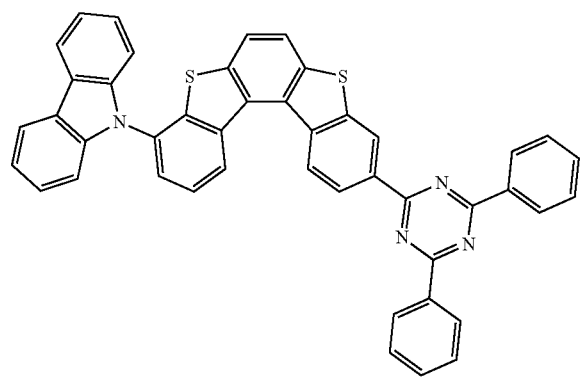
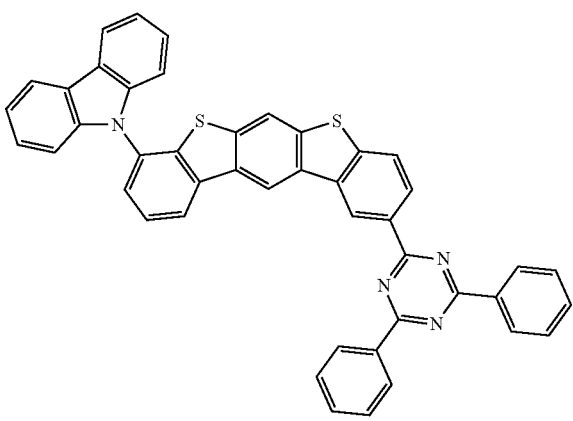
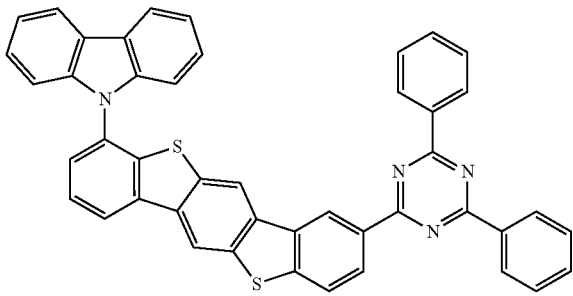
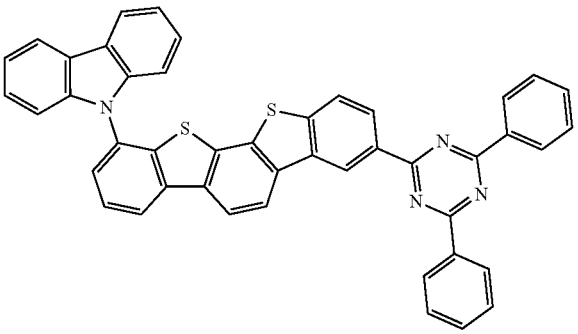
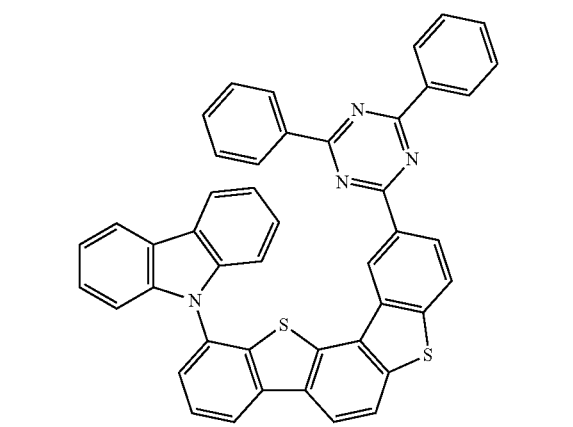

235
-continued
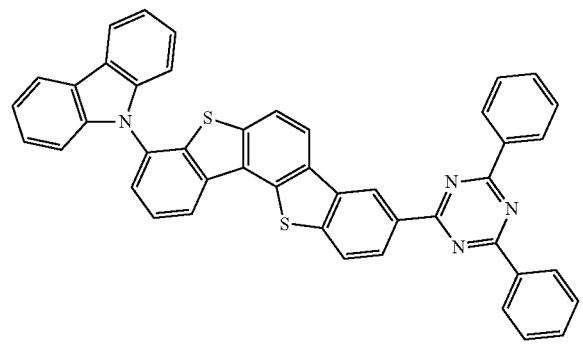
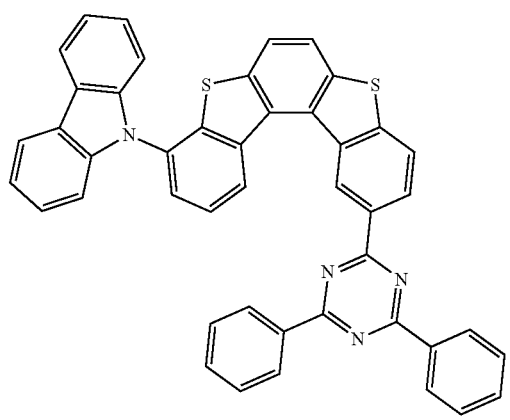
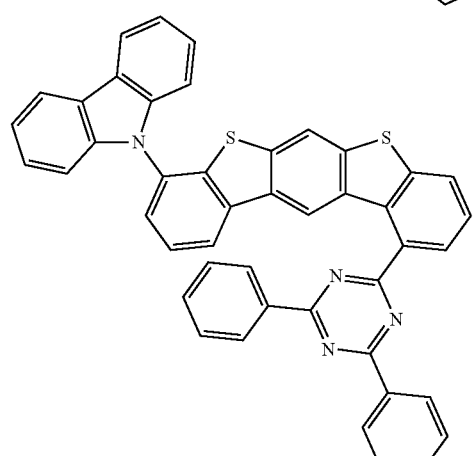
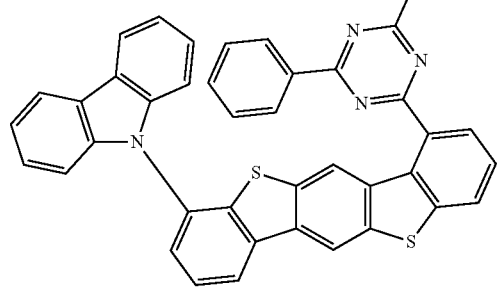
236
-continued
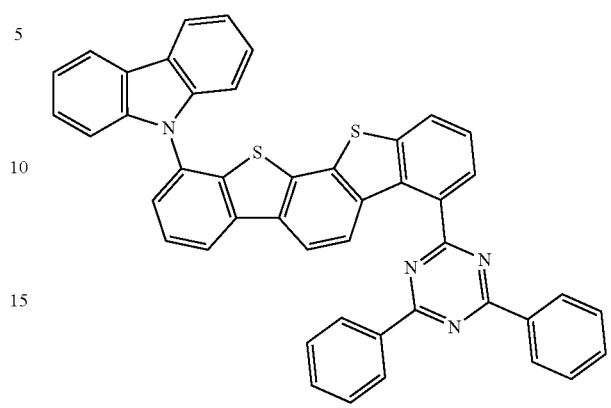
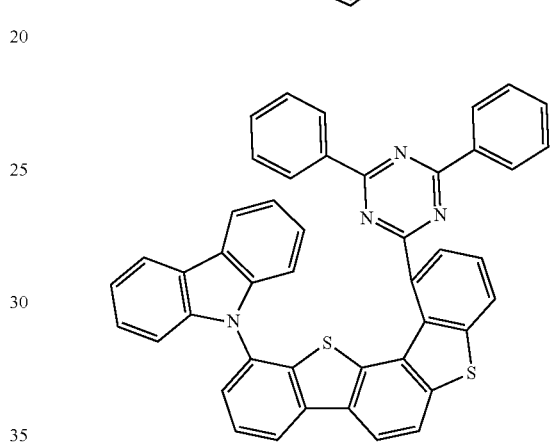
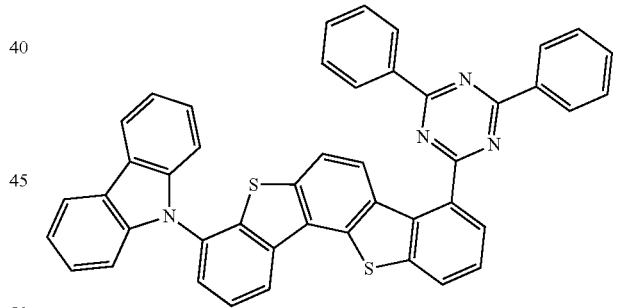
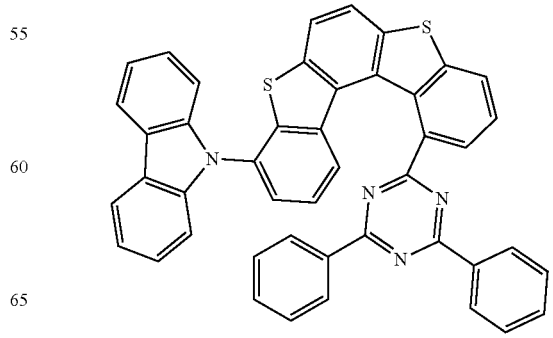

237
-continued
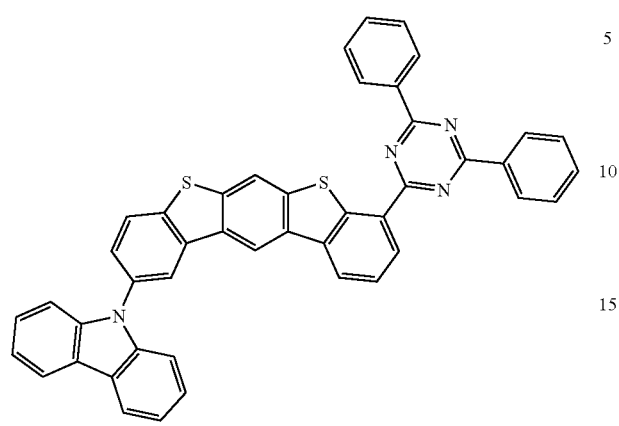
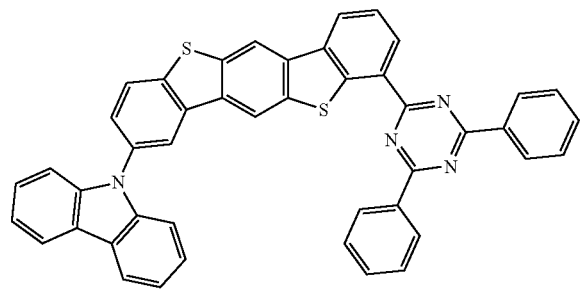
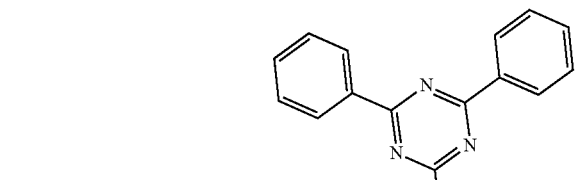
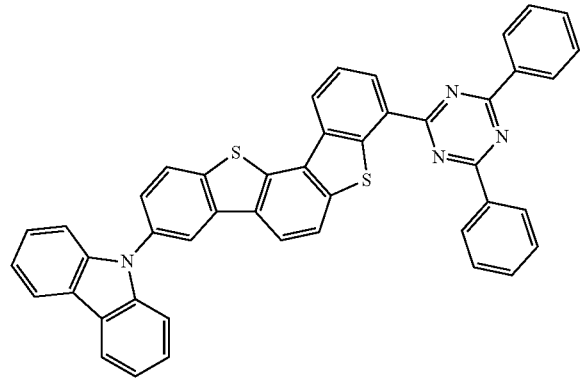
238
-continued
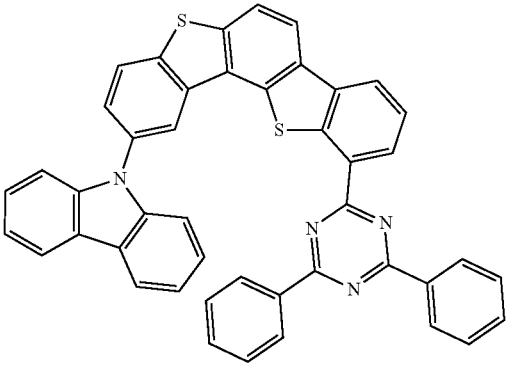
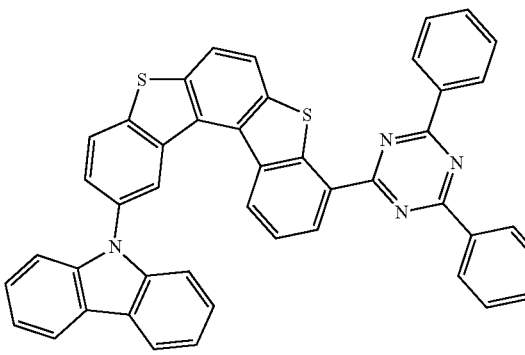
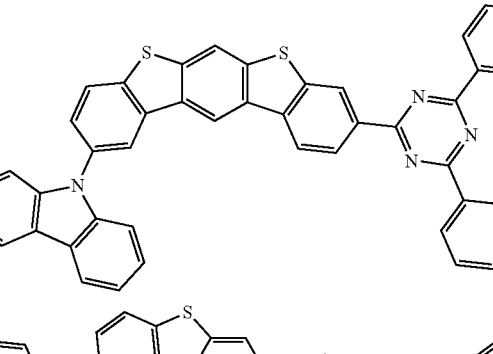
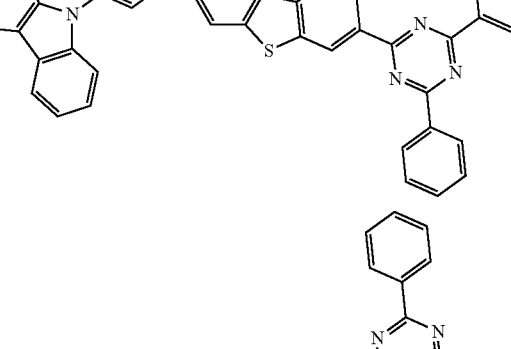
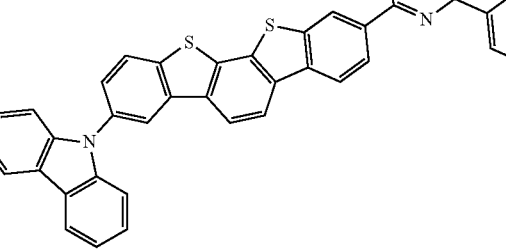

-continued
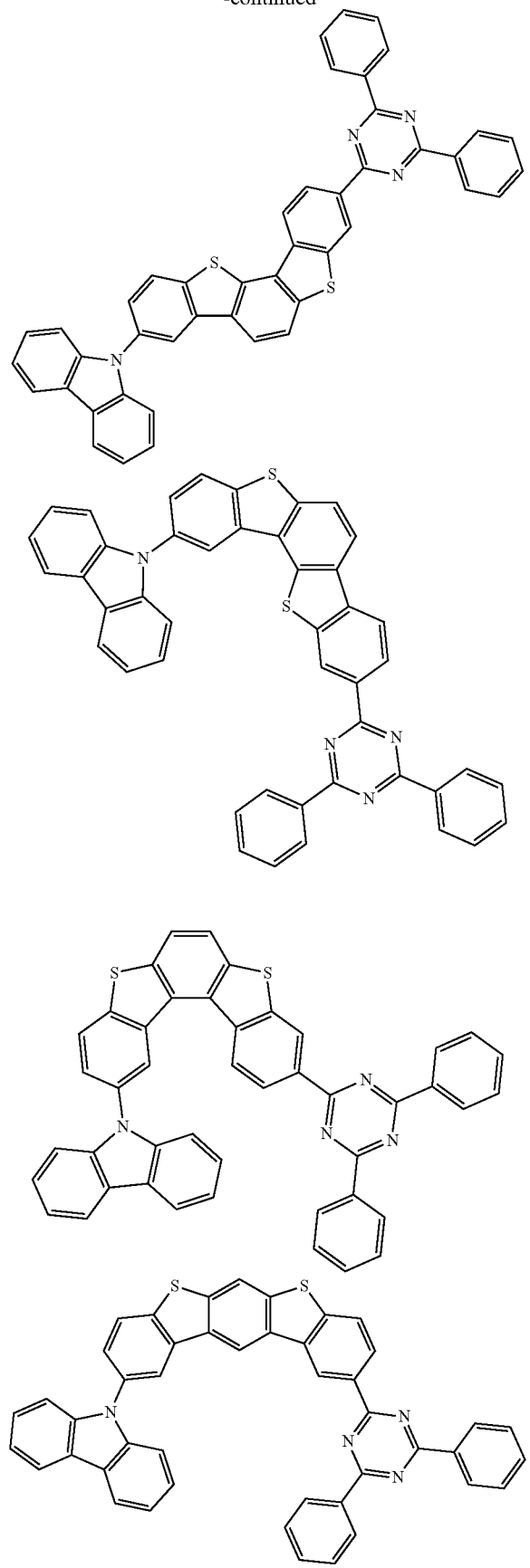
-continued
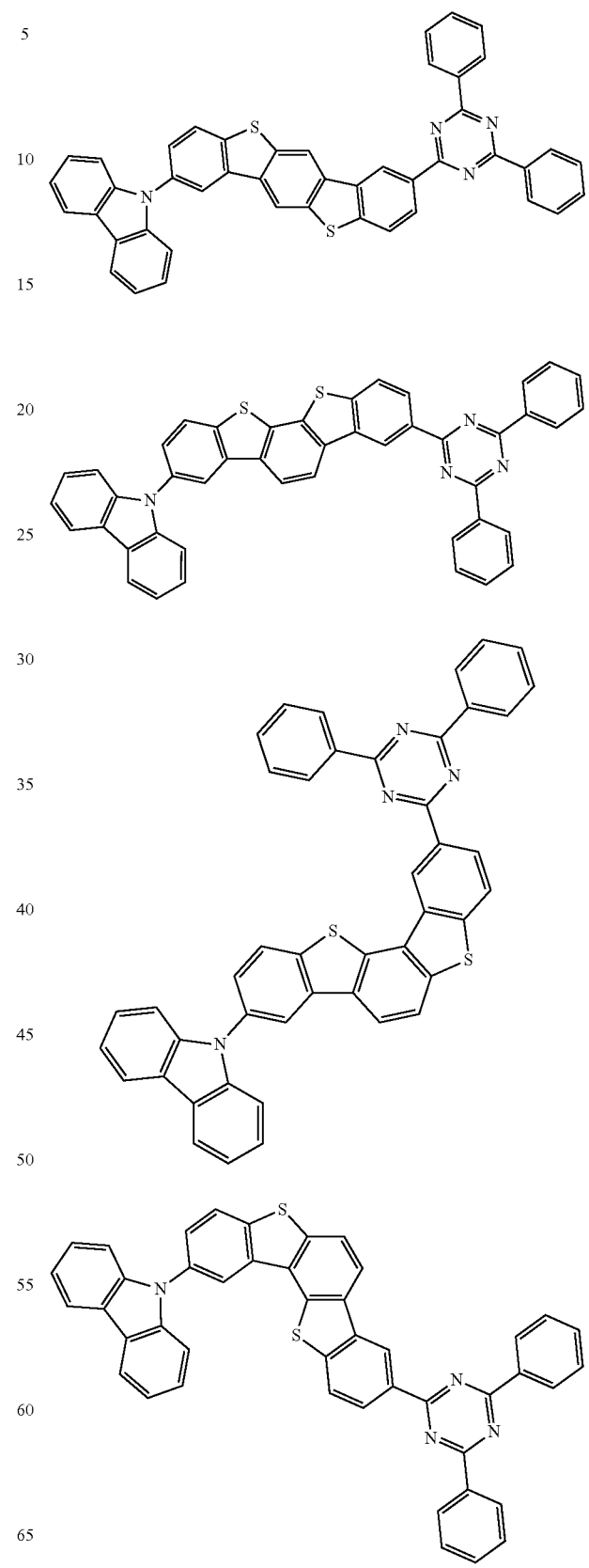

241
-continued
242
-continued
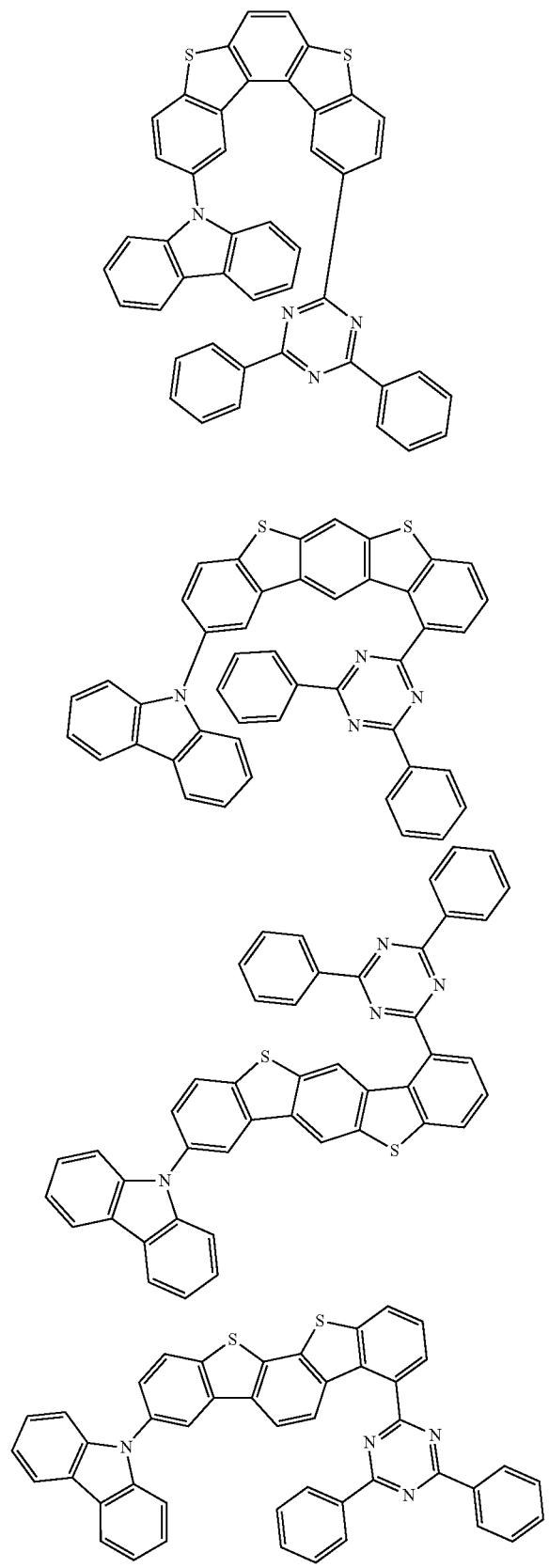
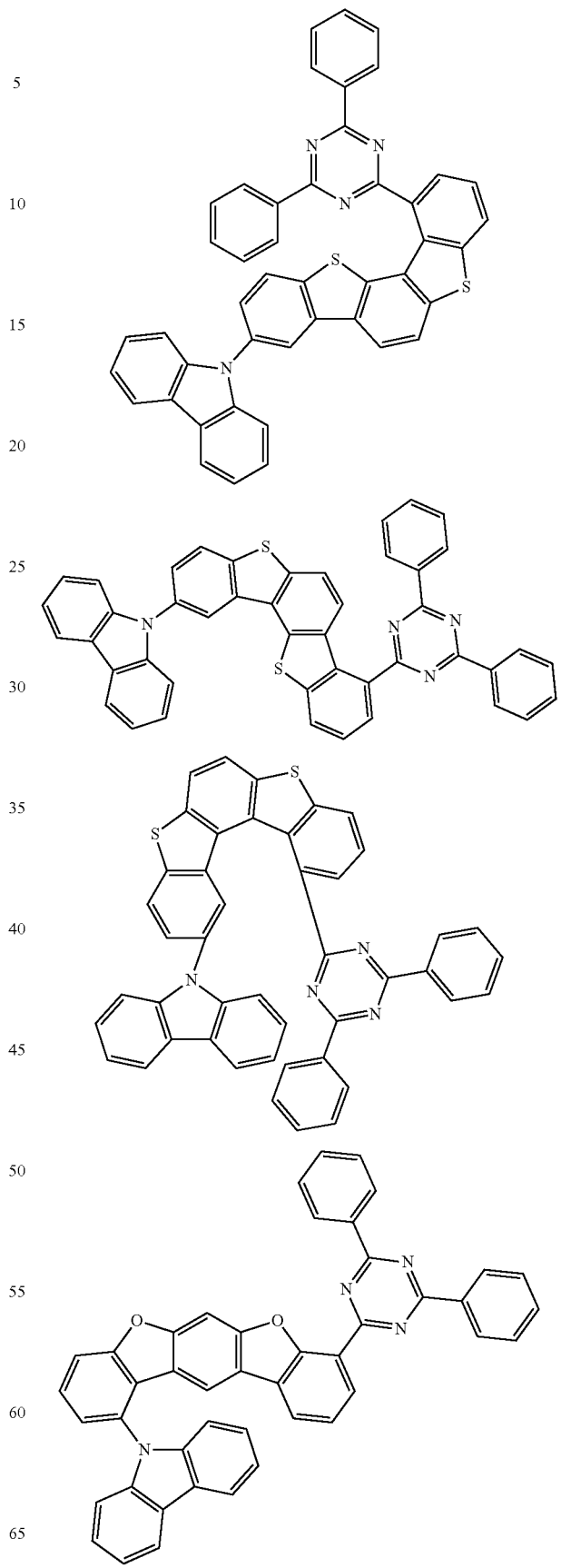

243
-continued
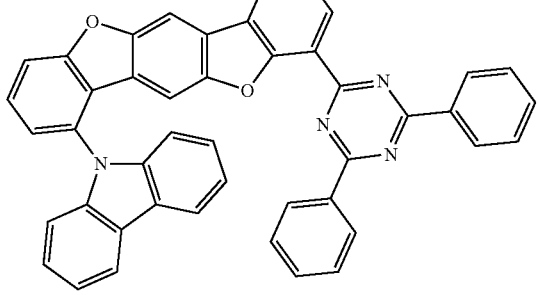
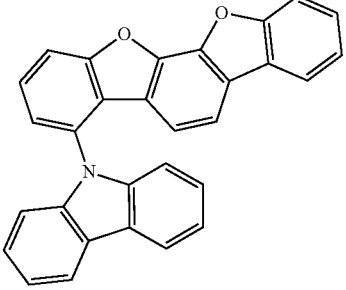
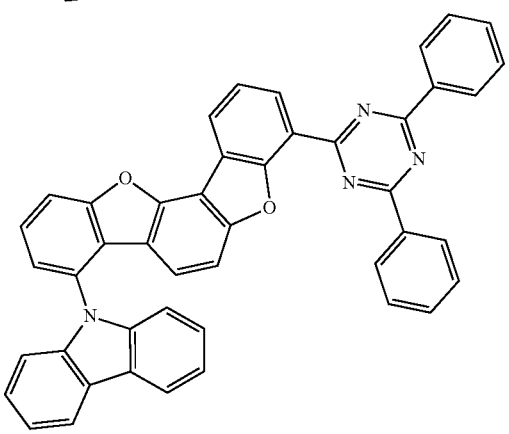
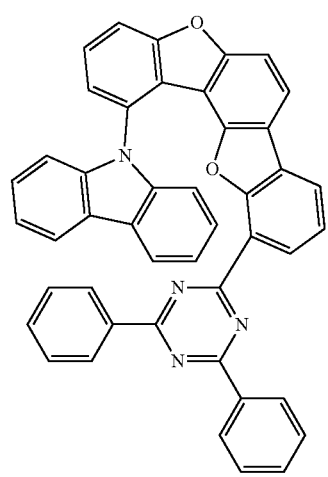
244
-continued
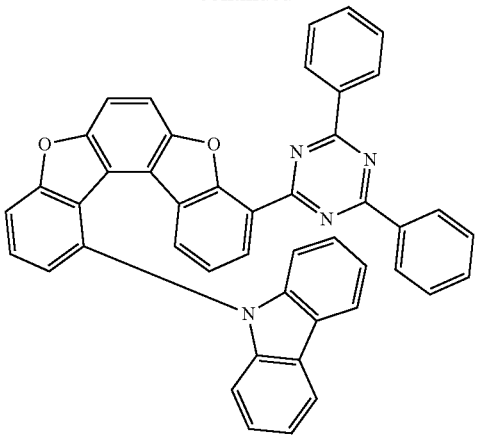
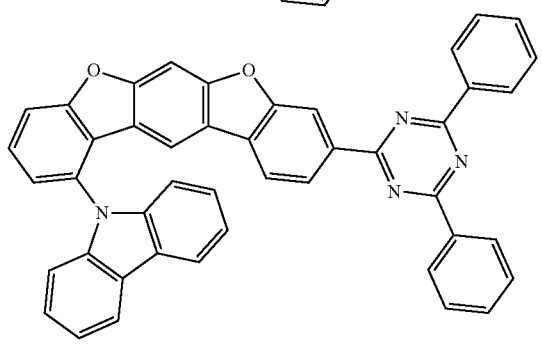
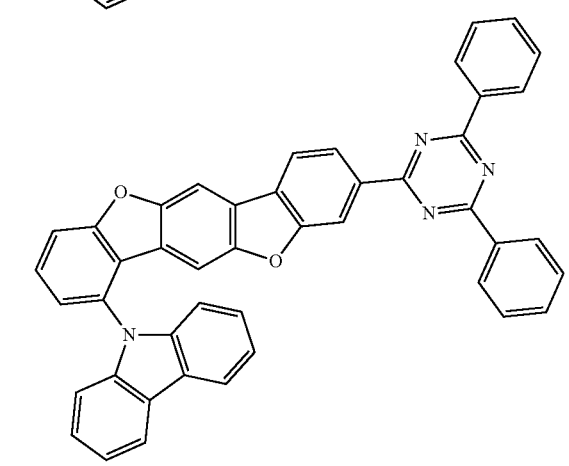
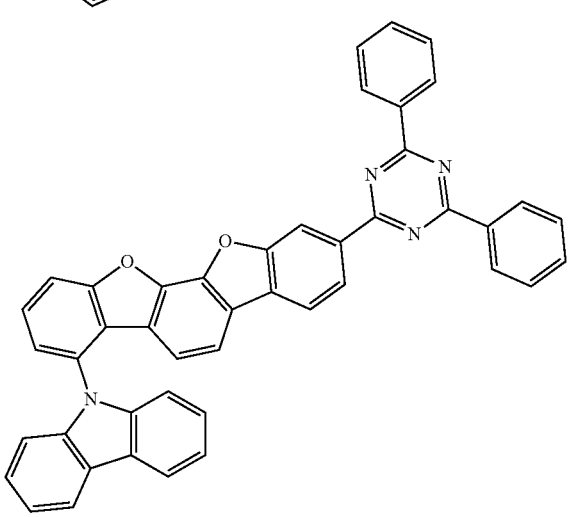

245
-continued
246
-continued
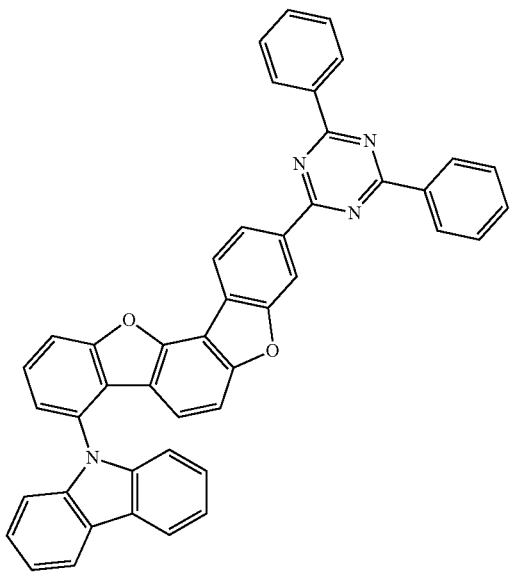
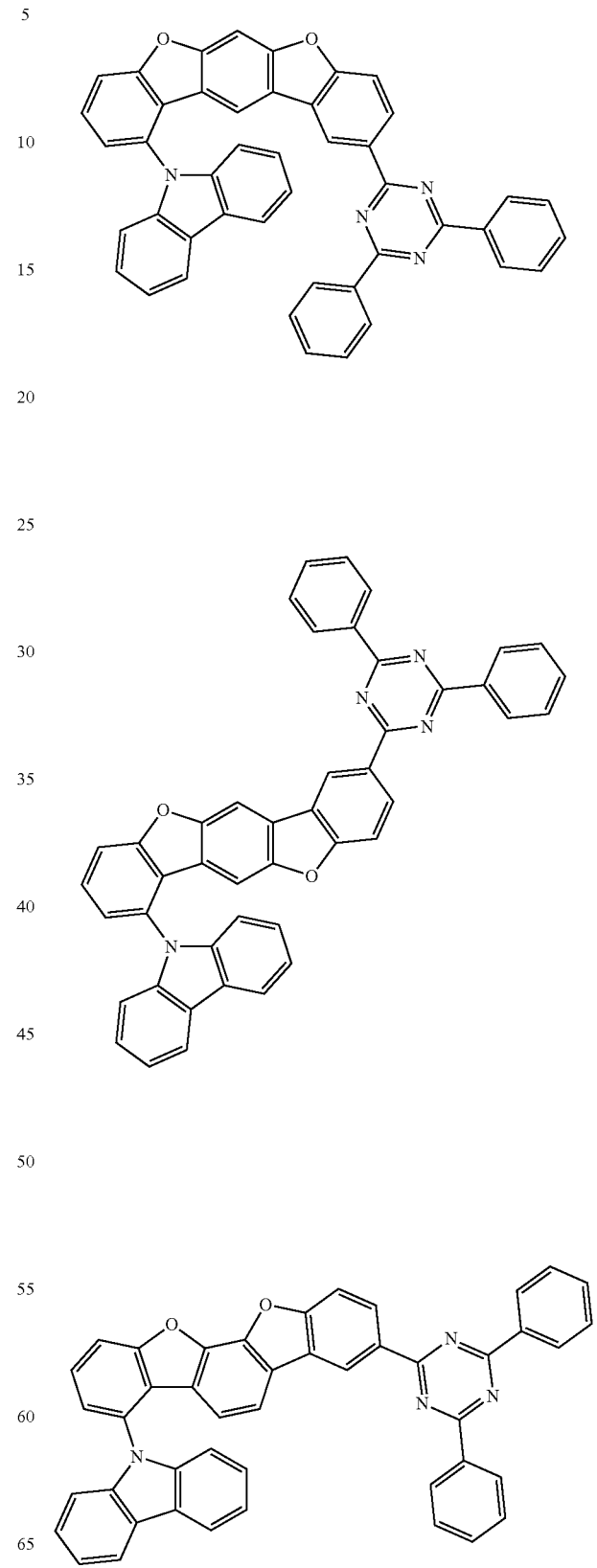

247
-continued
248
-continued
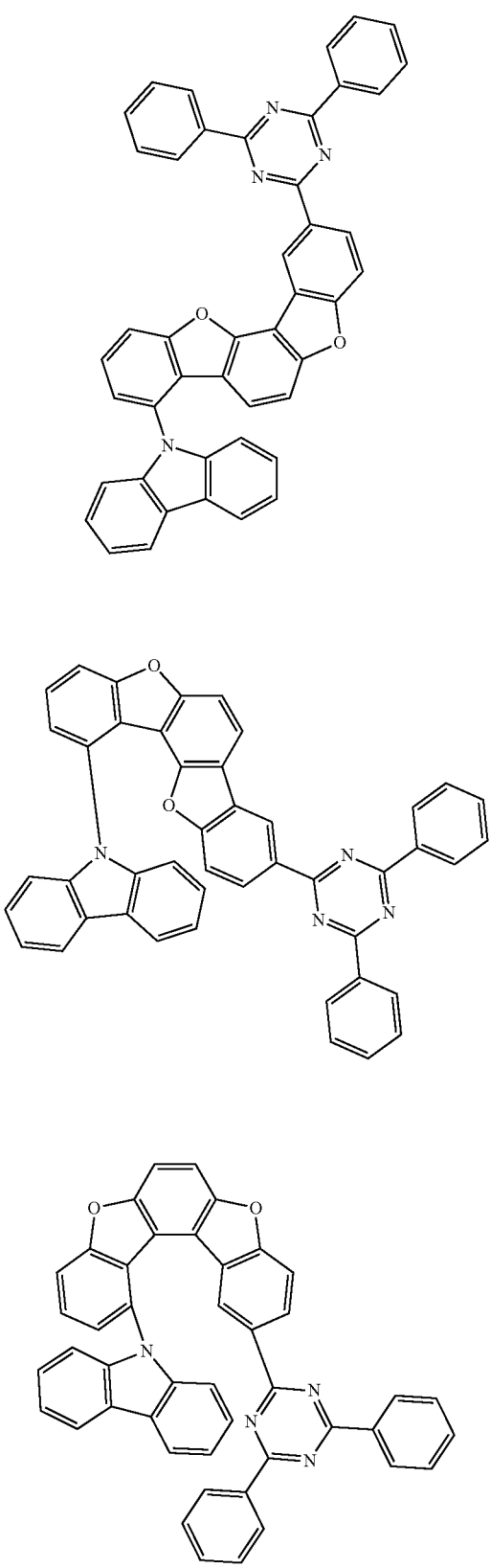
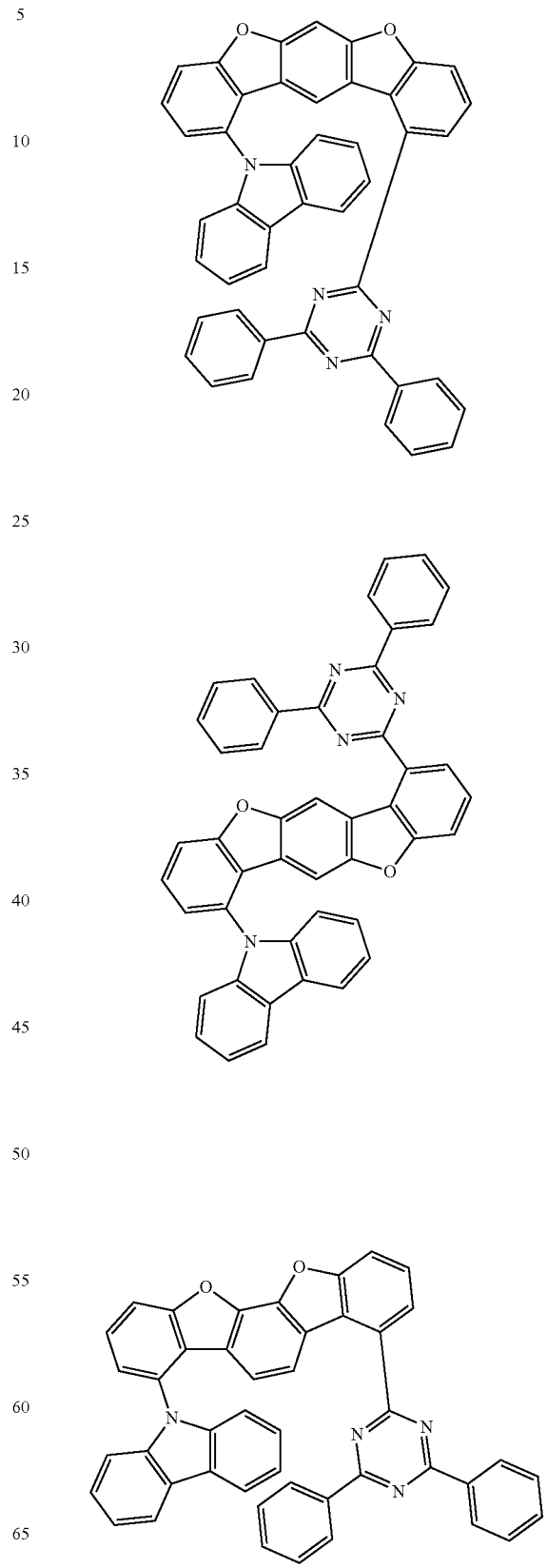

249
-continued
250
-continued
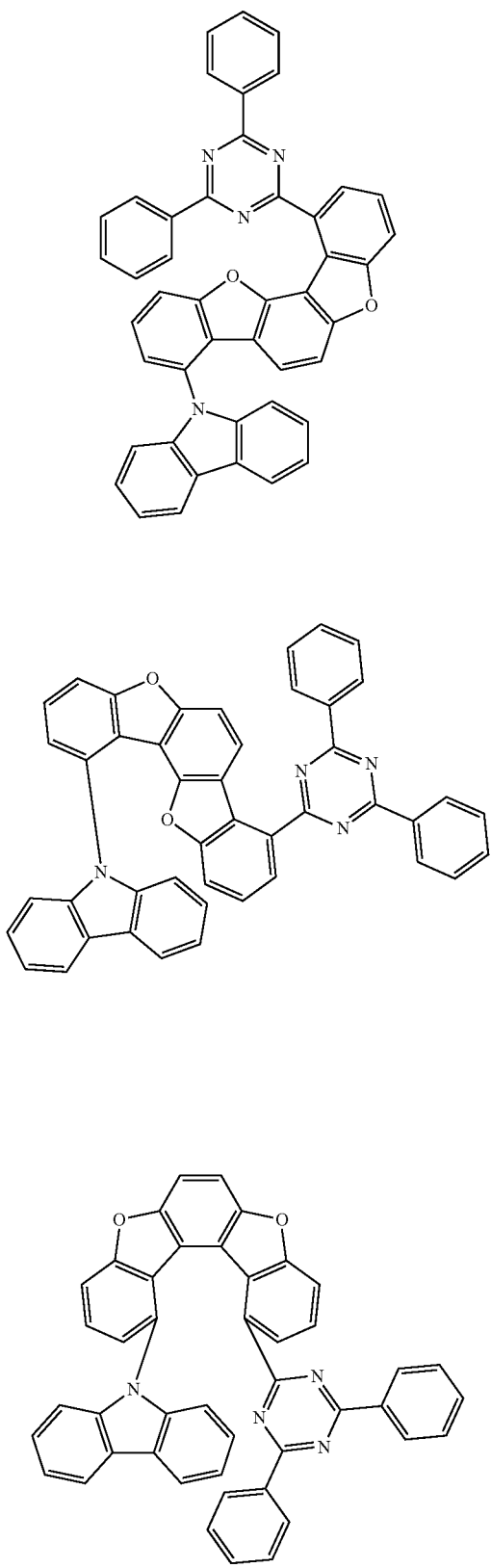
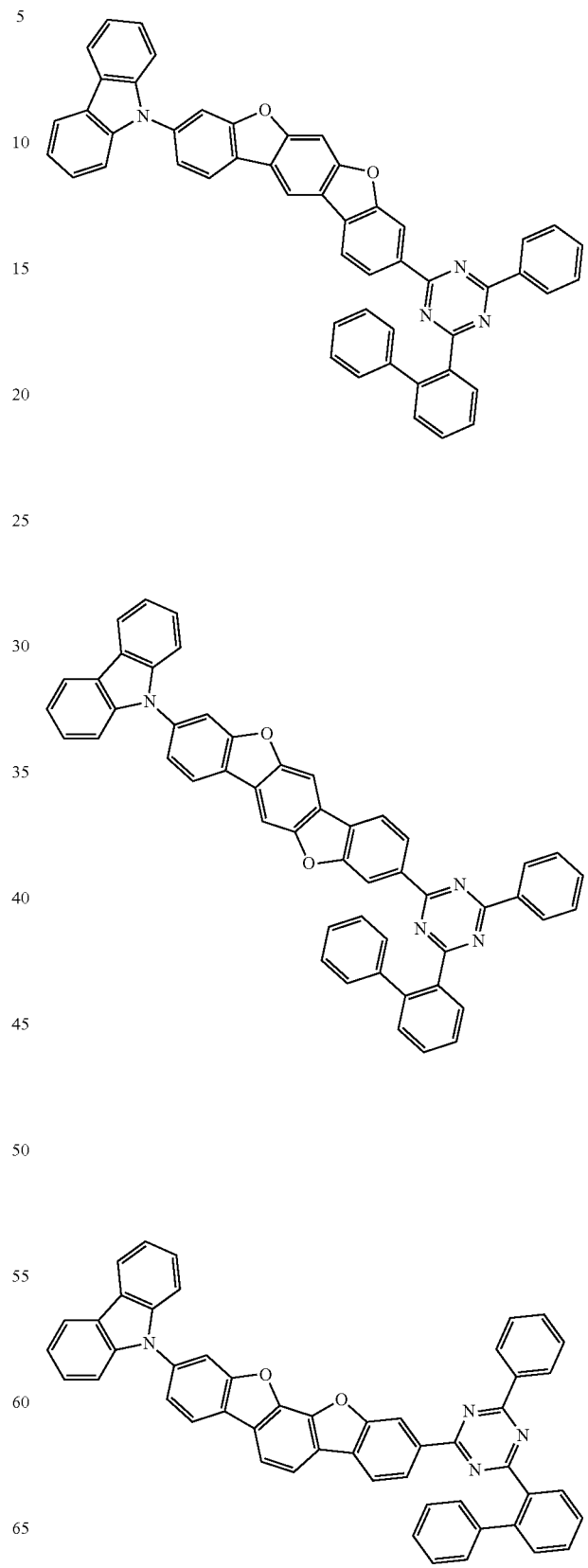

251
-continued
252
-continued
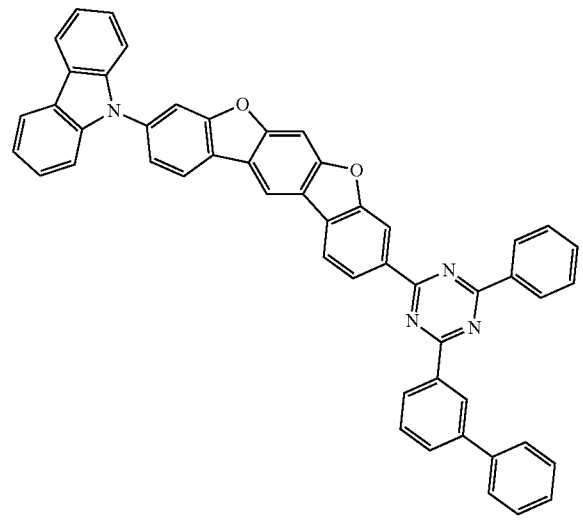
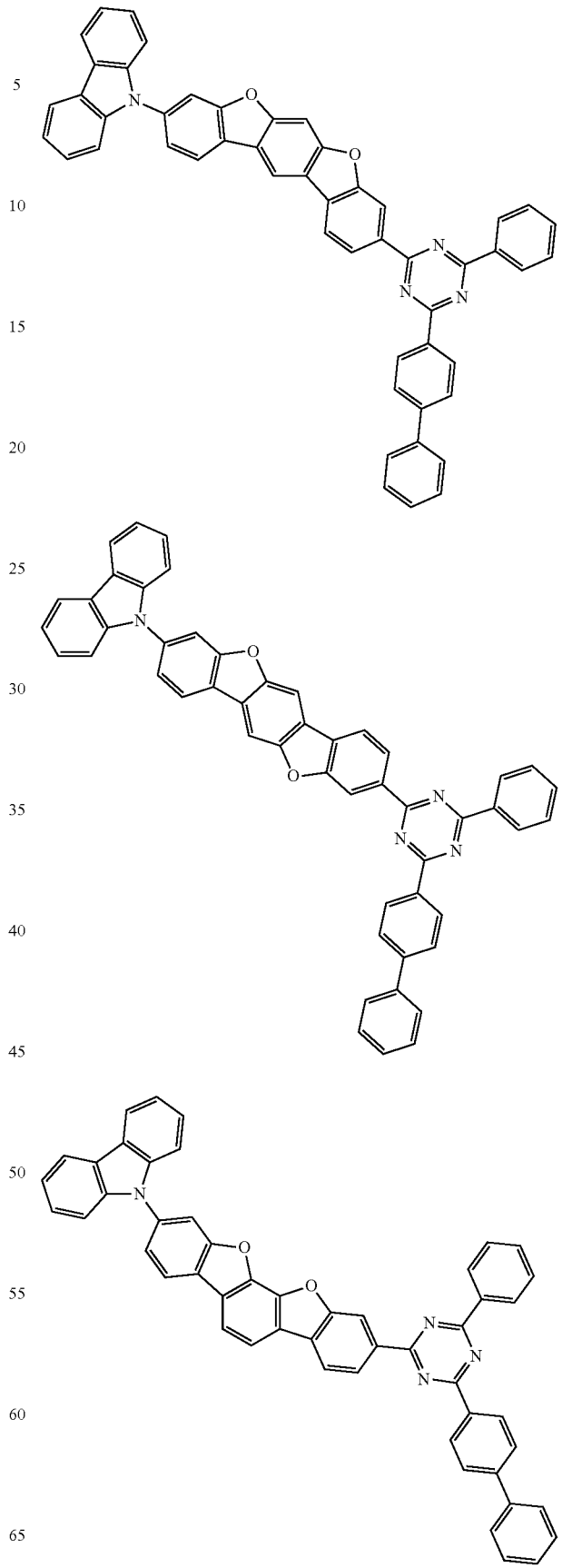

253
-continued
254
-continued
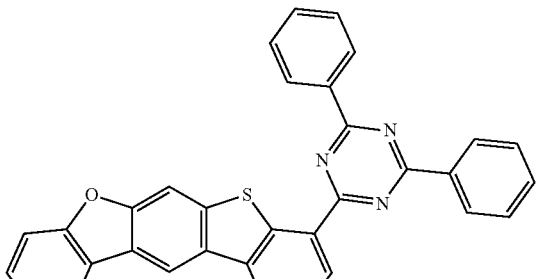
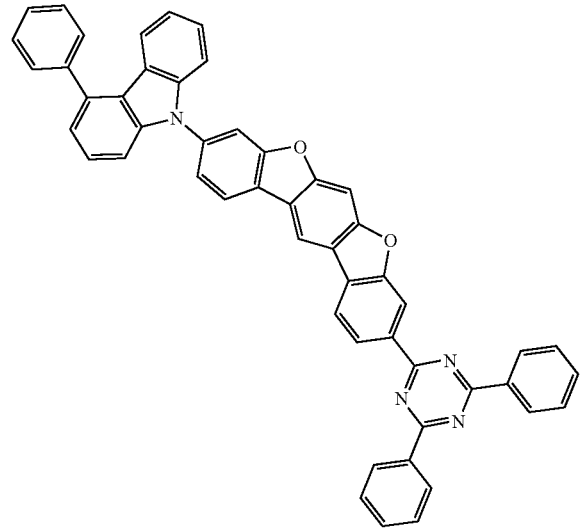
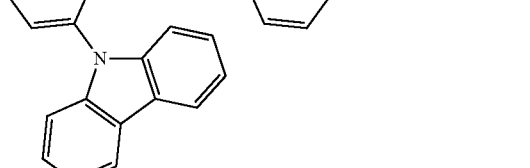
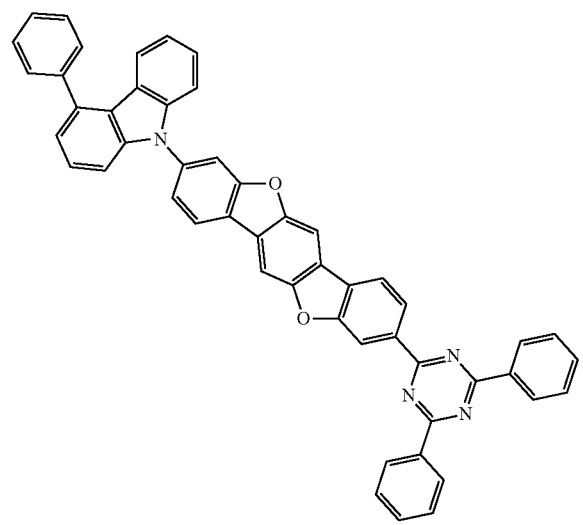
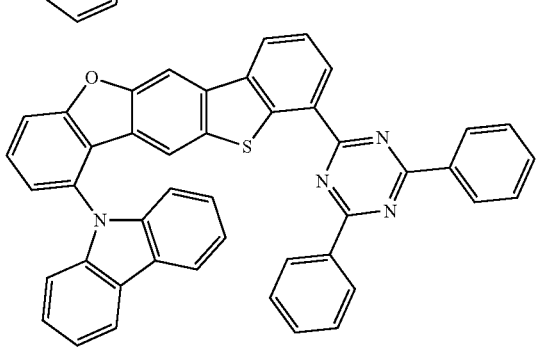
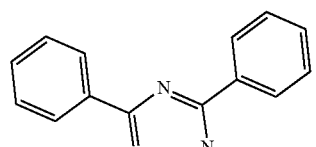
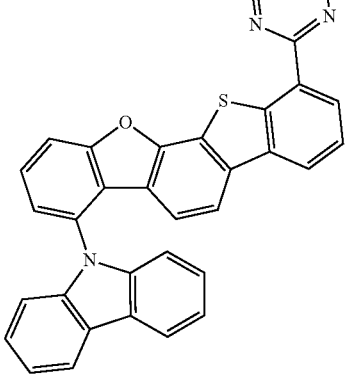
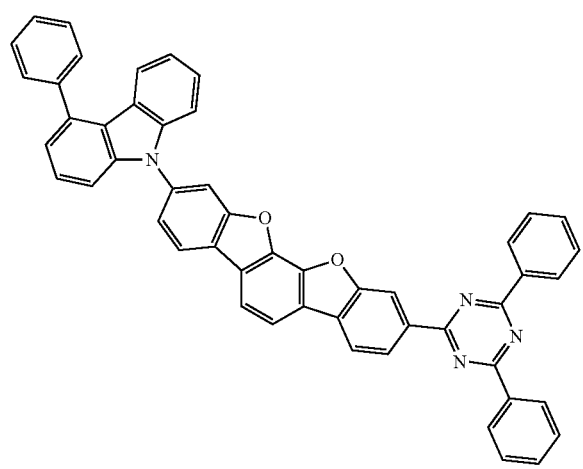 [SMILES: c1ccc(-c2nc(-c3ccccc3)nc(-c3ccc4c(c3)oc3c4ccc4c5ccc(-n6c7ccccc7c7c(-c8ccccc8)cccc76)cc5oc43)n2)cc1]
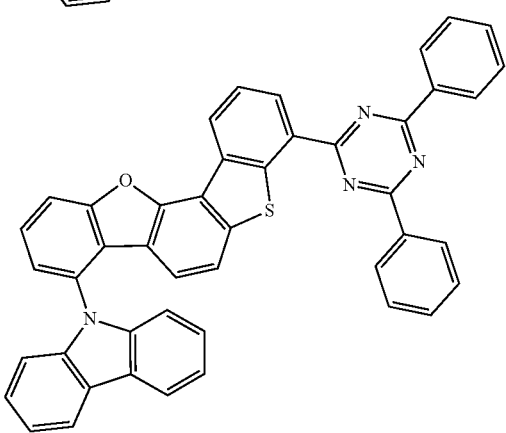

255
-continued
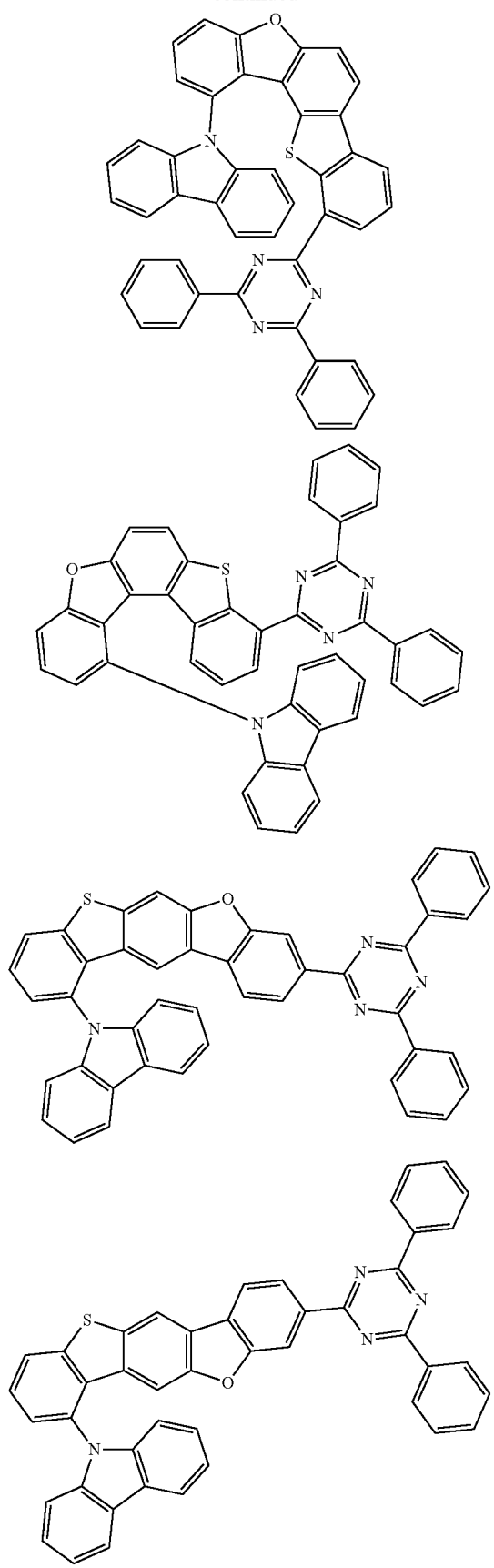
256
-continued
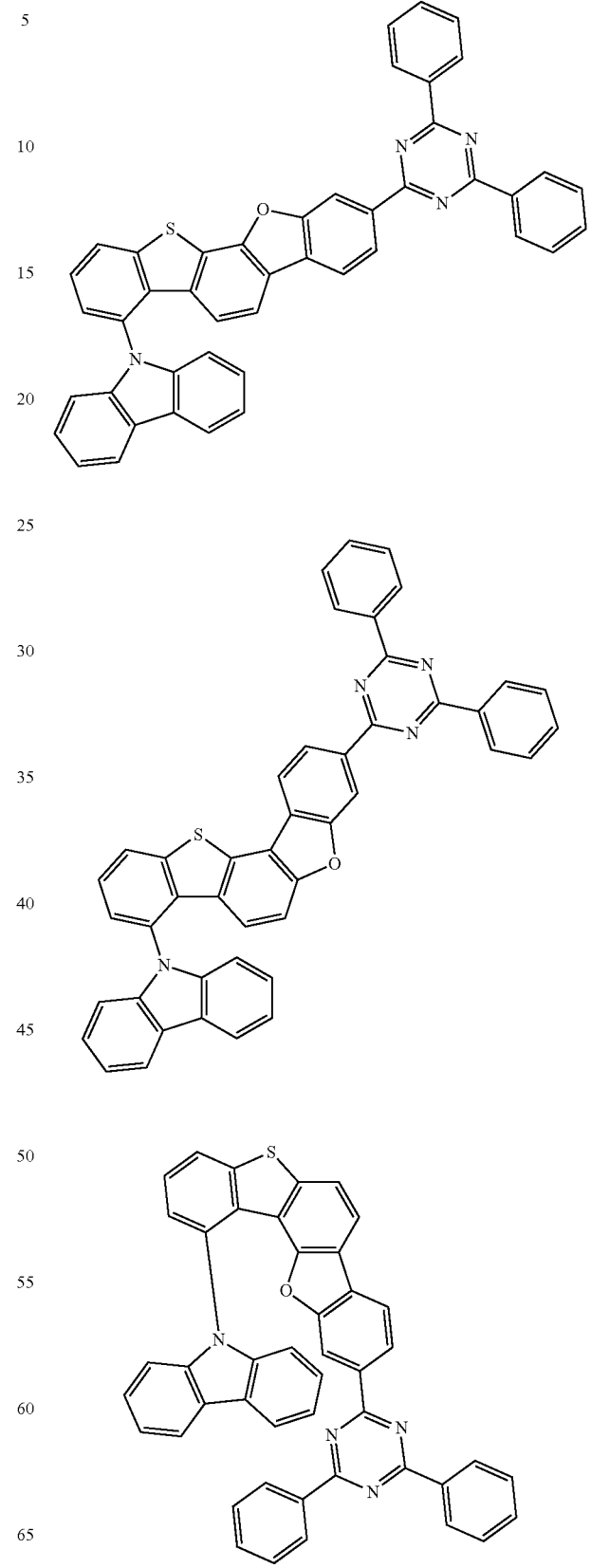

257
-continued
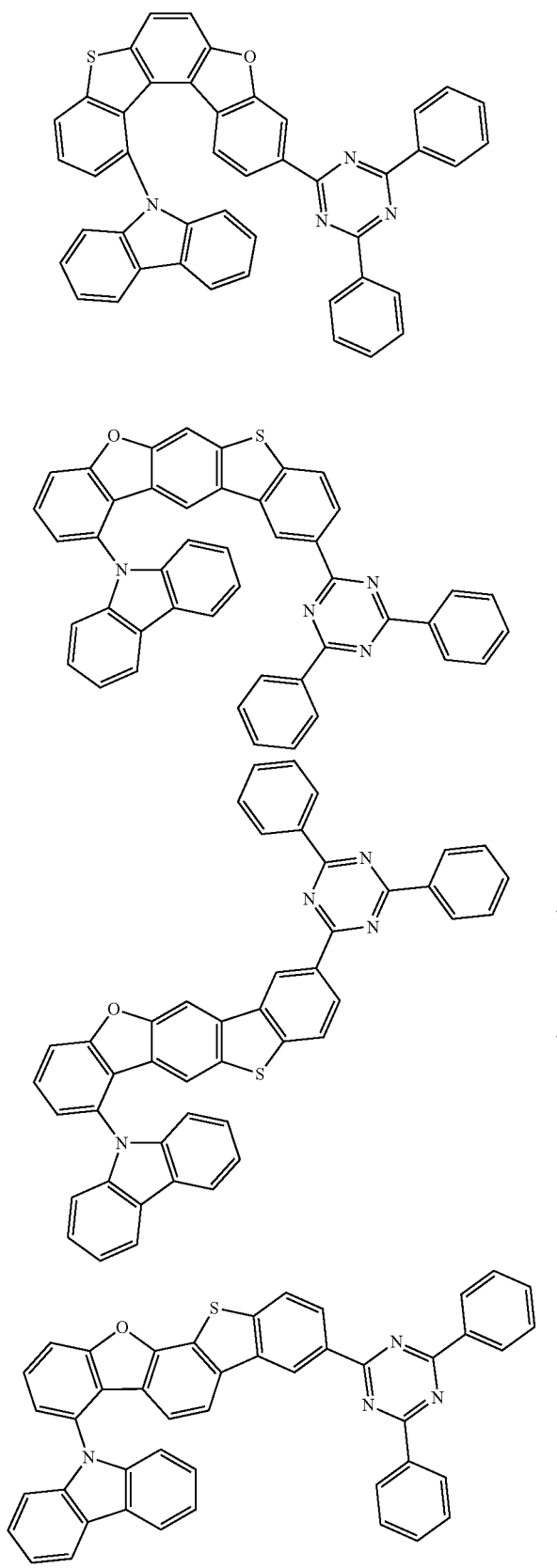
258
-continued
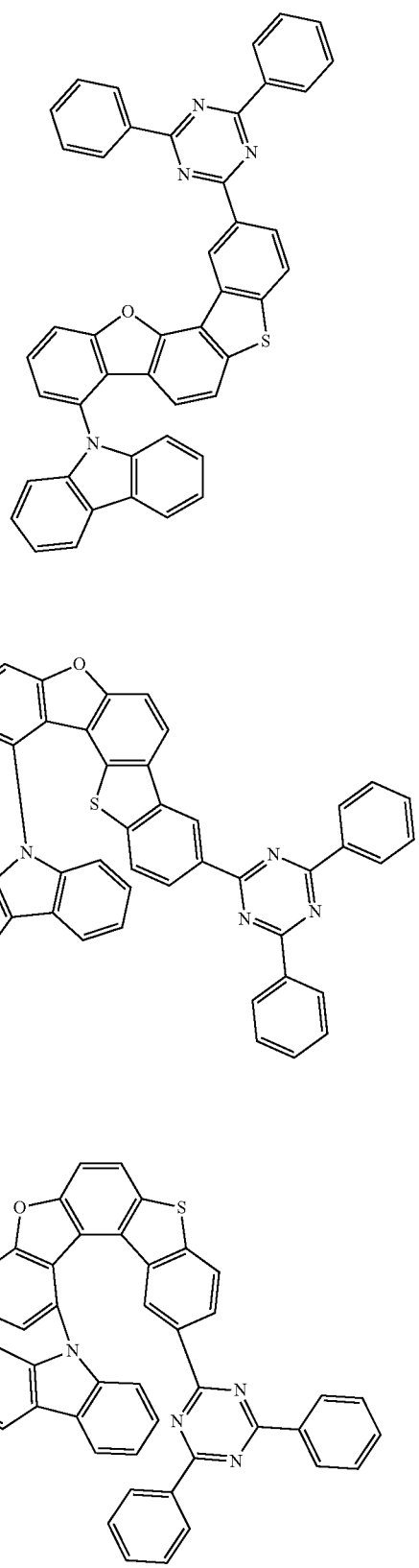

259
-continued
260
-continued
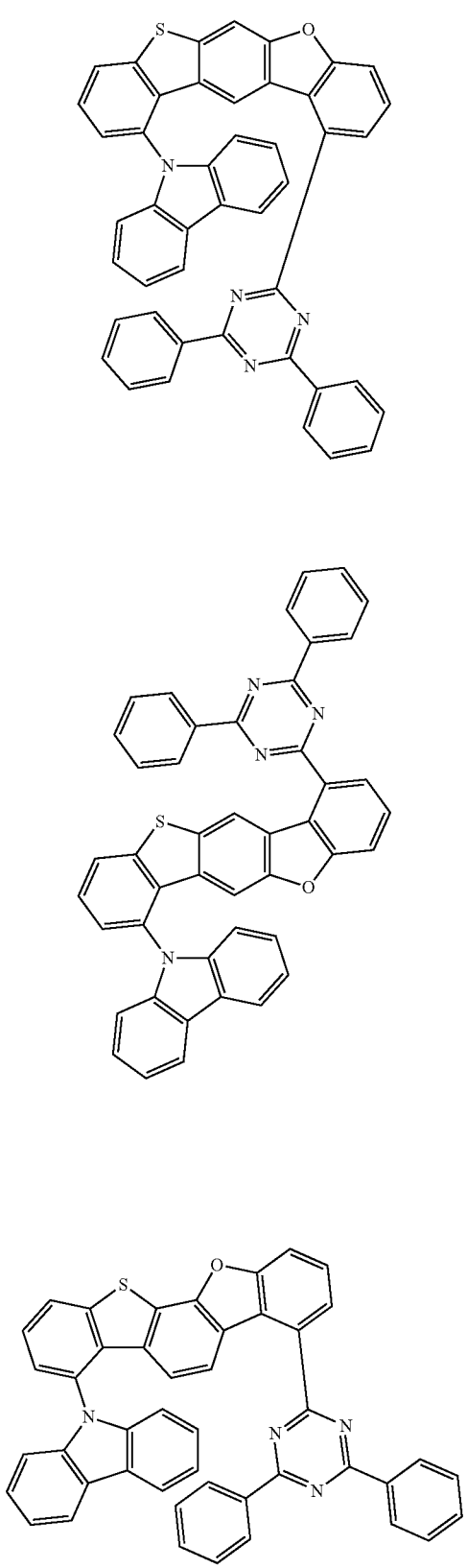
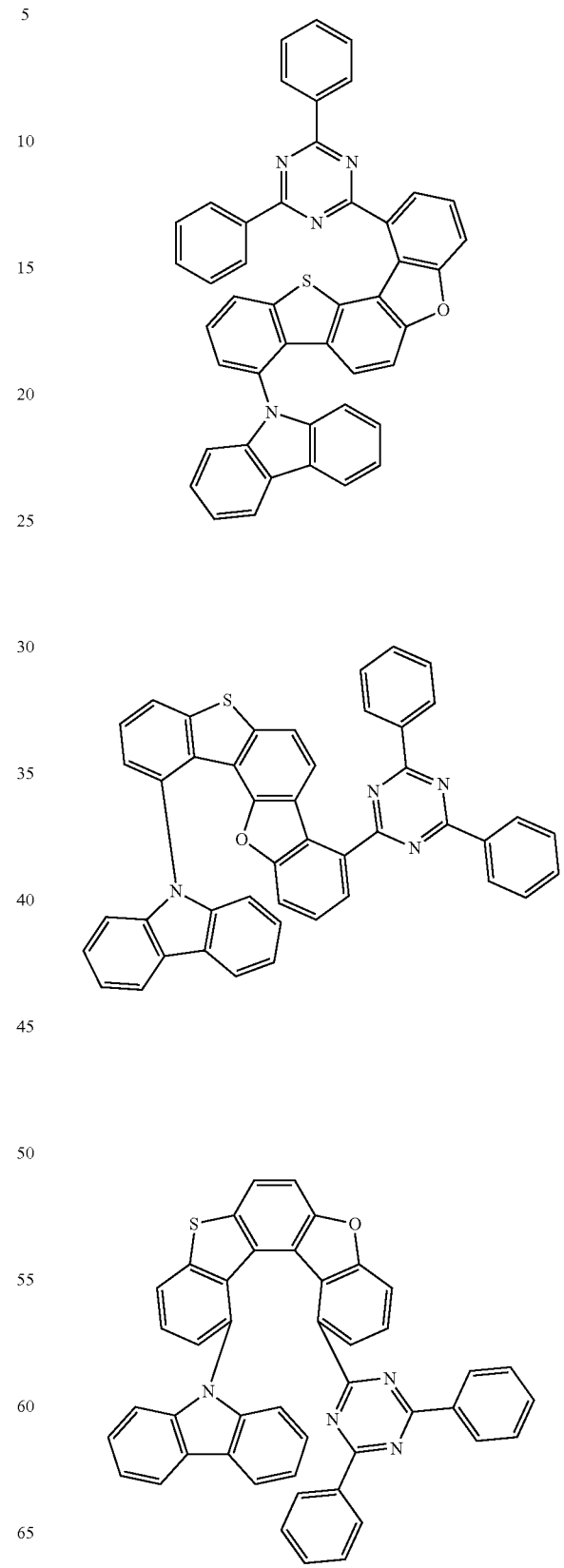

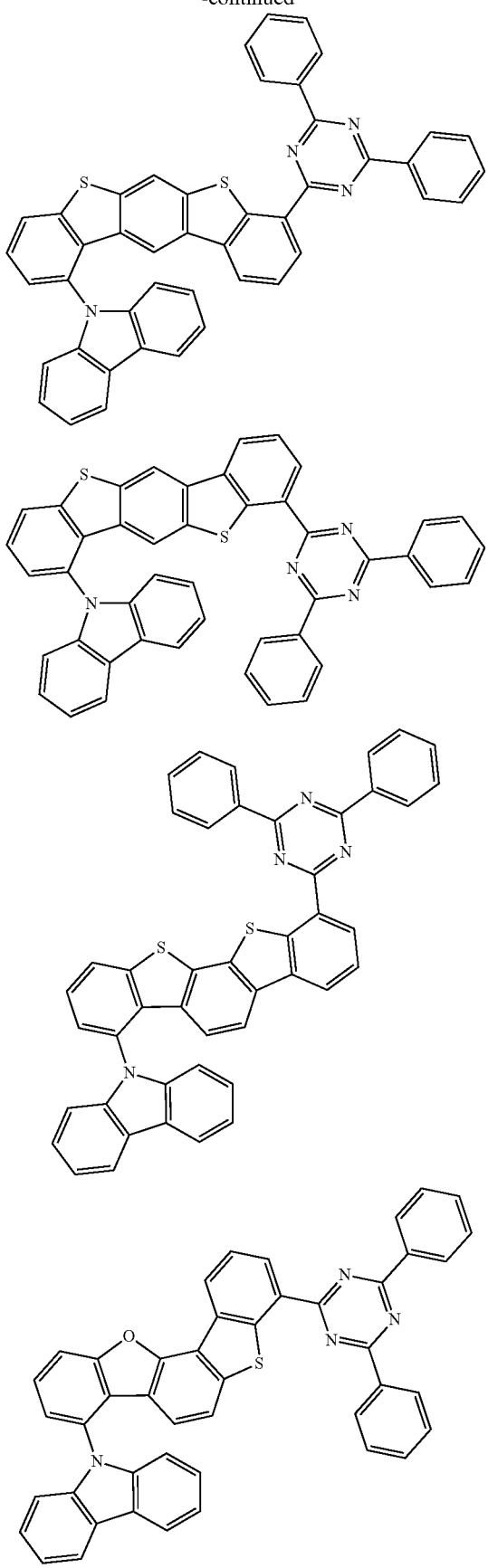
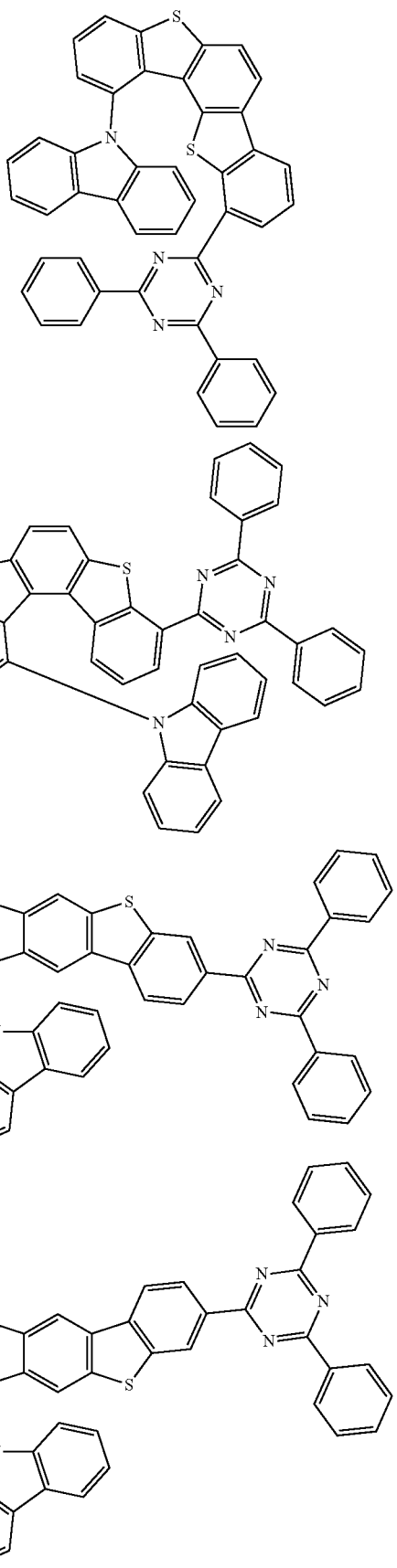

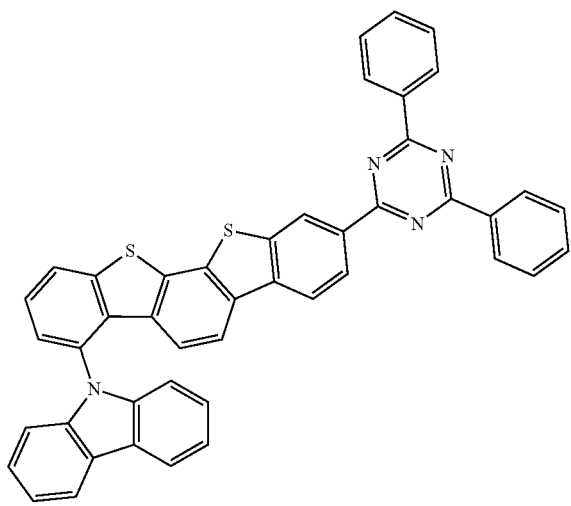
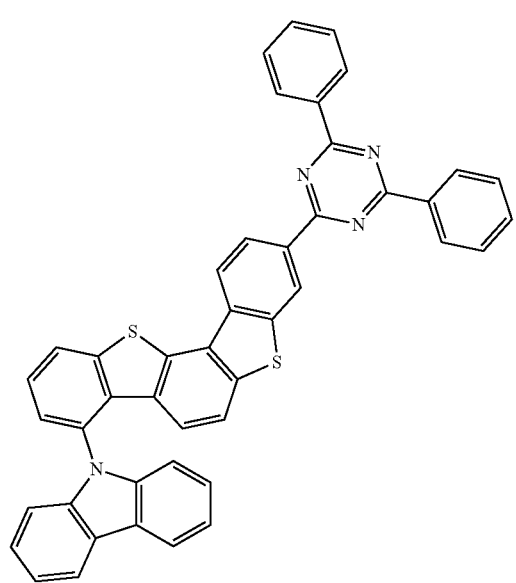
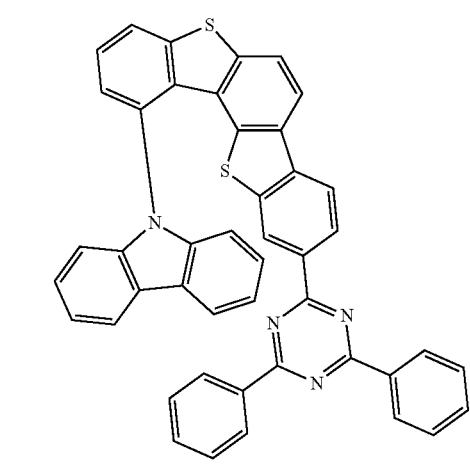
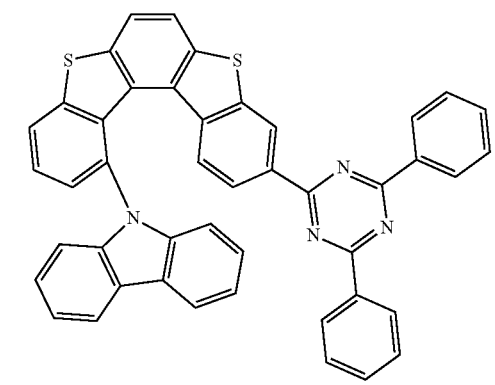
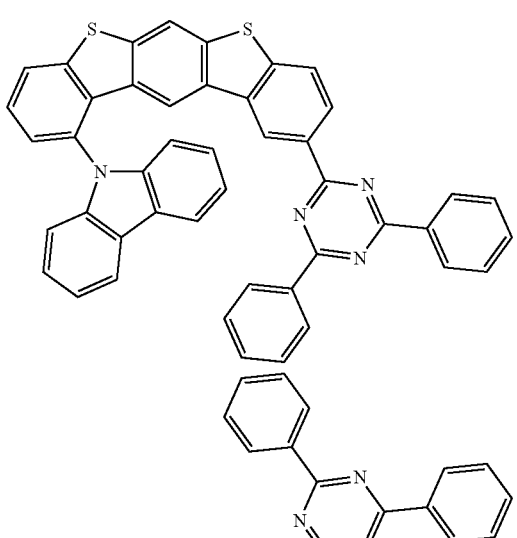
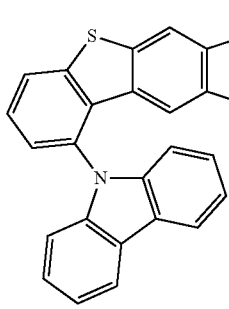
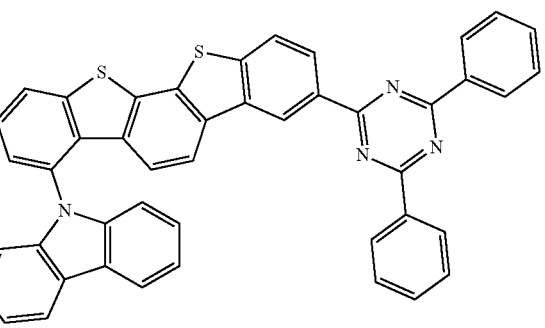

265
-continued
266
-continued
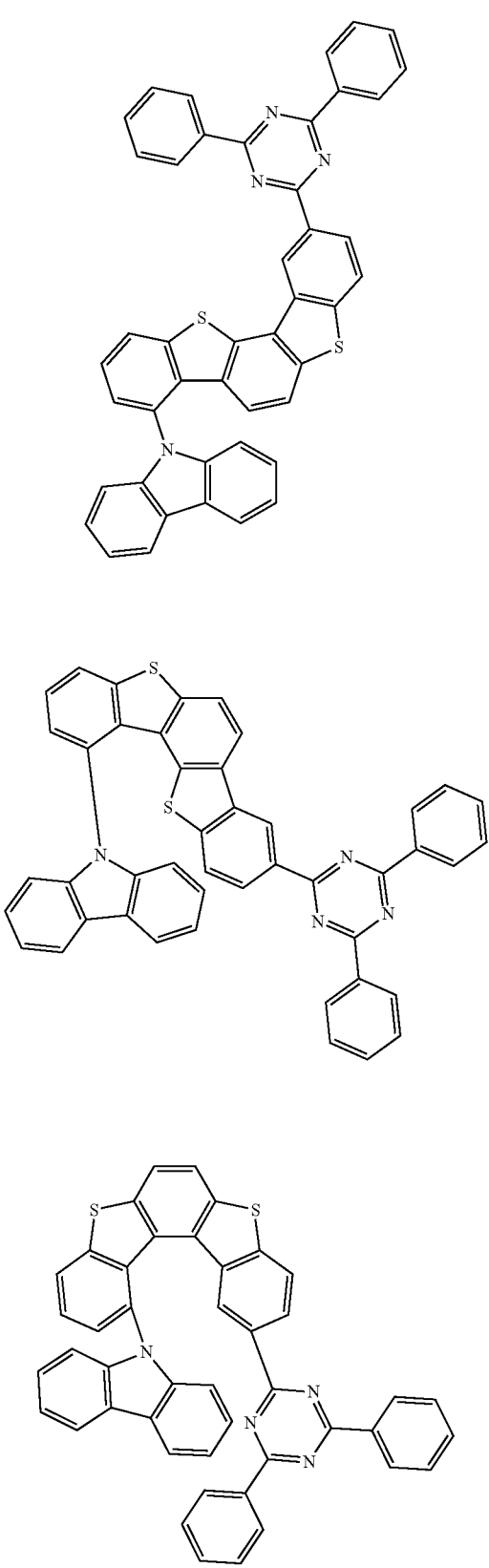 [SMILES: c1ccc(-c2nc(-c3ccccc3)nc(-c3ccc4sc5ccc6c(oc7cccc(-n8c9ccccc9c9ccccc98)c76)c5c4c3)n2)cc1 ; c1ccc(-c2nc(-c3ccccc3)nc(-c3ccc4sc5c(ccc6oc7cccc(-n8c9ccccc9c9ccccc98)c7c65)c4c3)n2)cc1 ; c1ccc(-c2nc(-c3ccccc3)nc(-c3ccc4sc5ccc6oc7cccc(-n8c9ccccc9c9ccccc98)c7c6c5c4c3)n2)cc1]
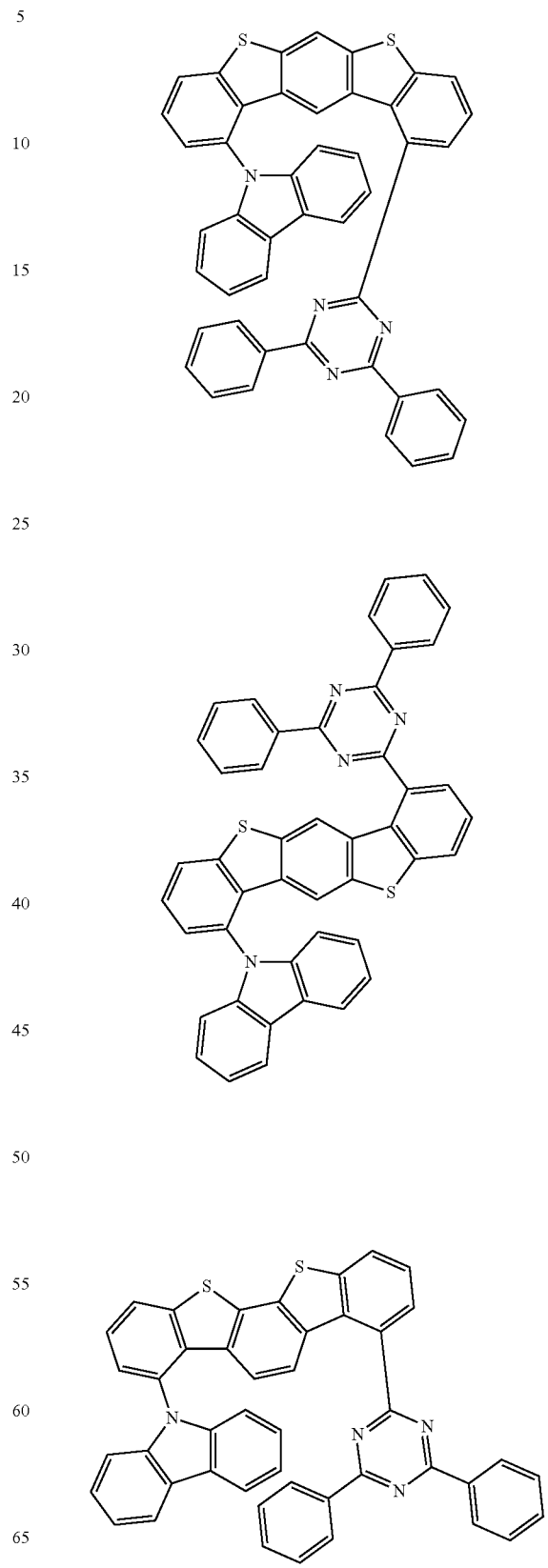

267 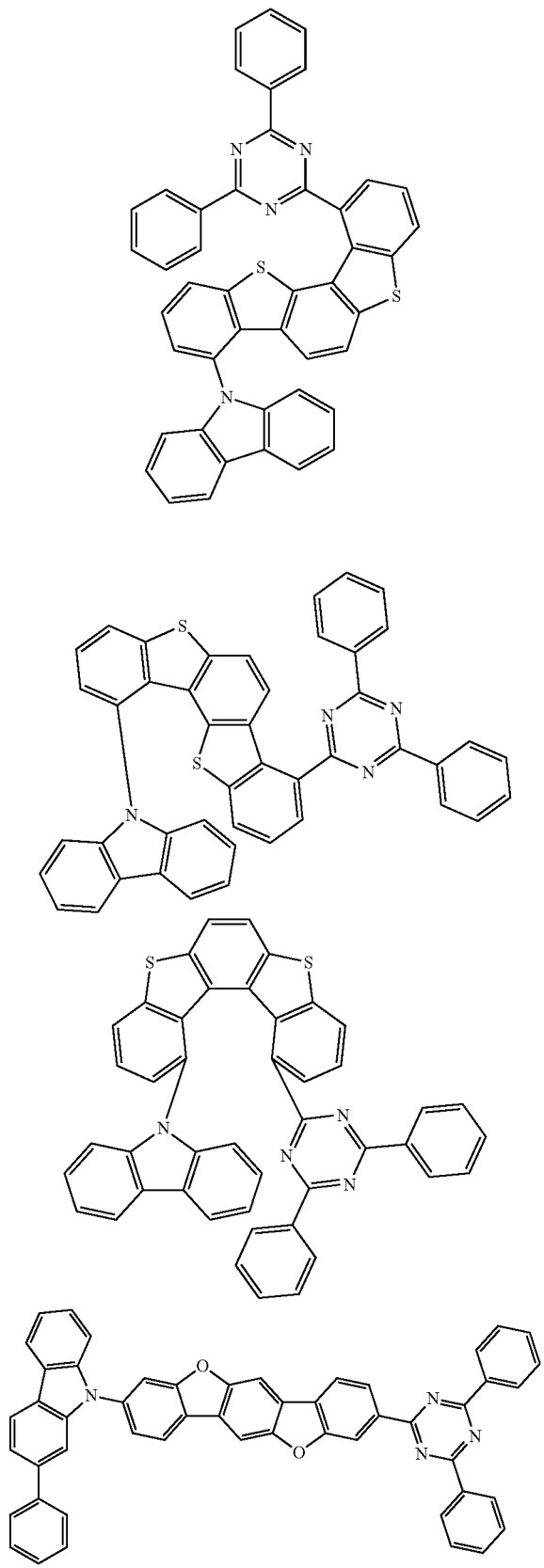
268 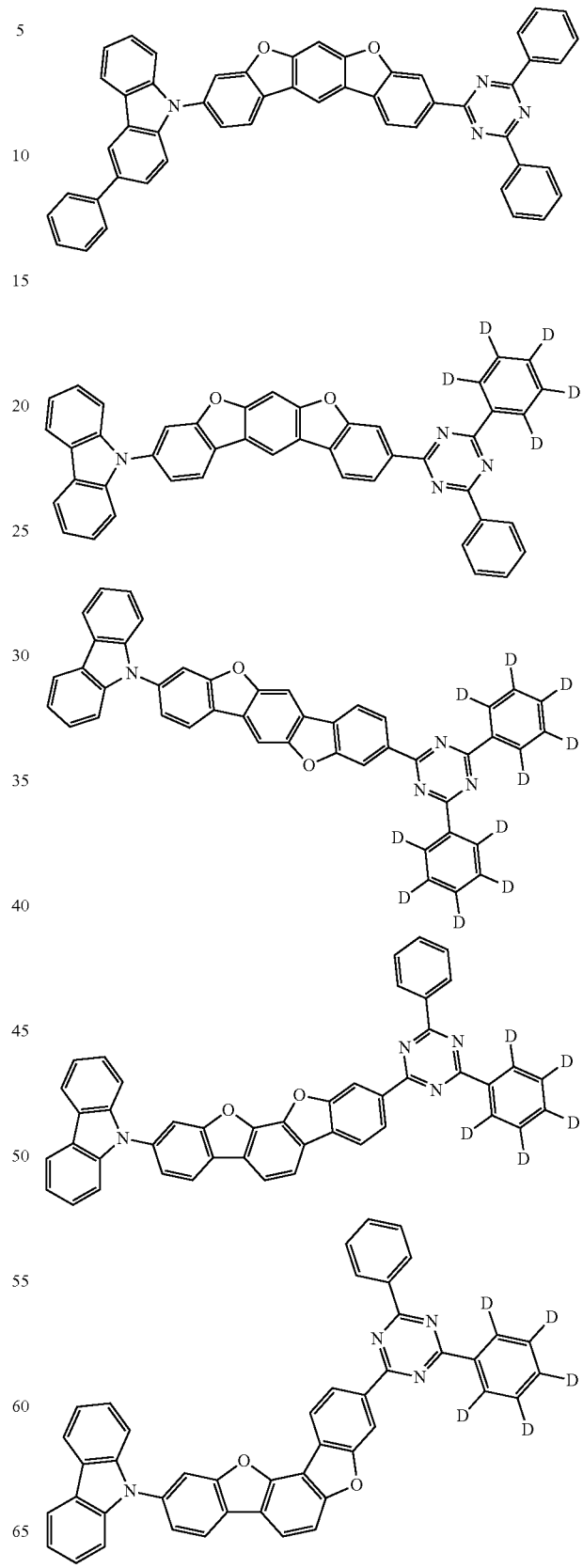

269
-continued
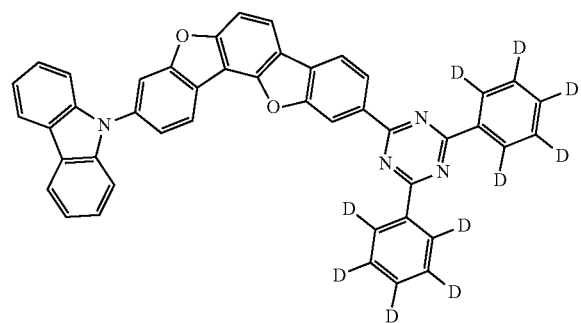
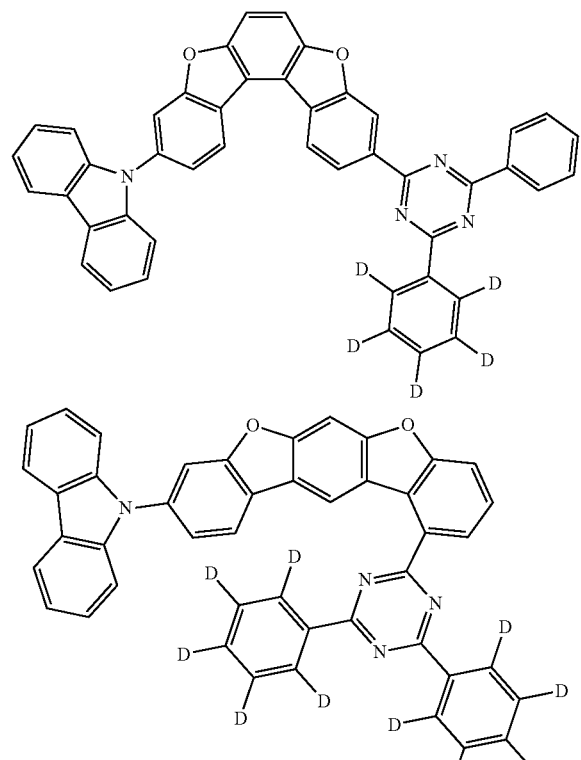
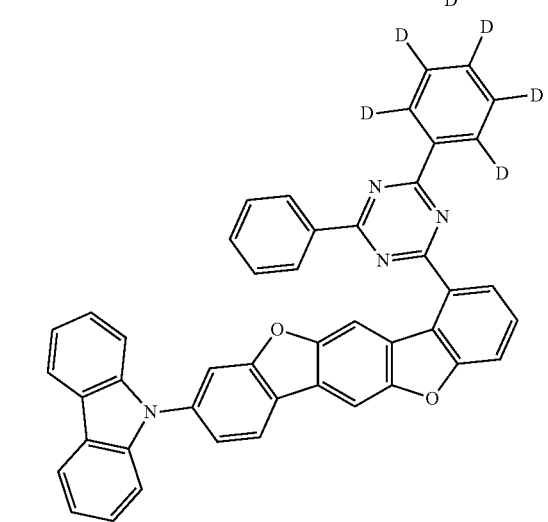
270
-continued
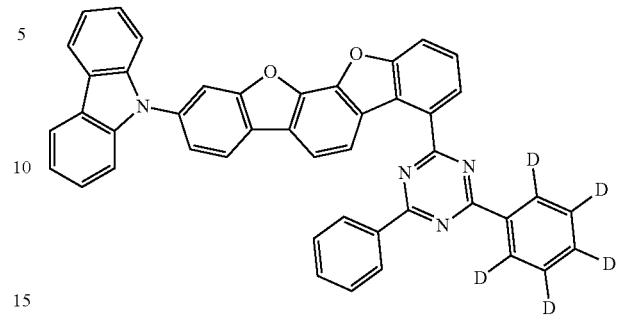
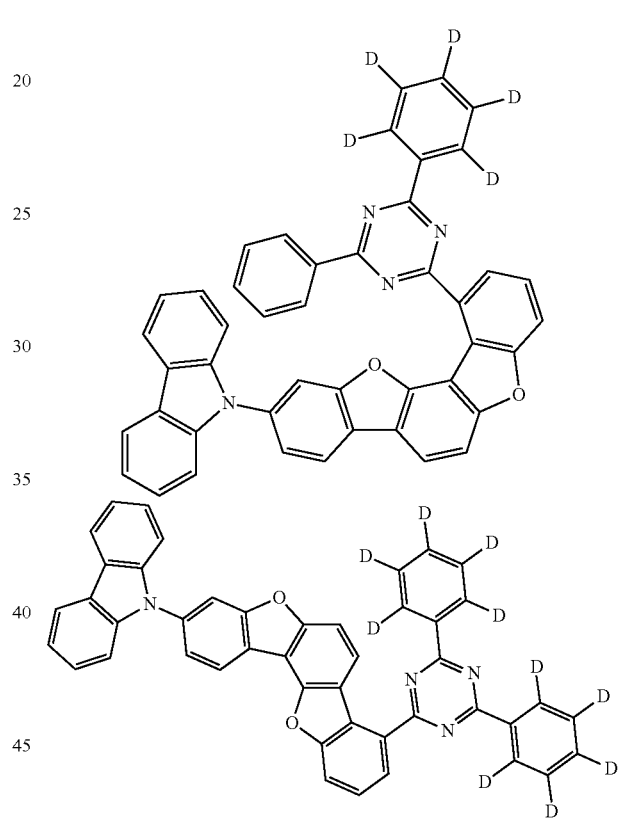
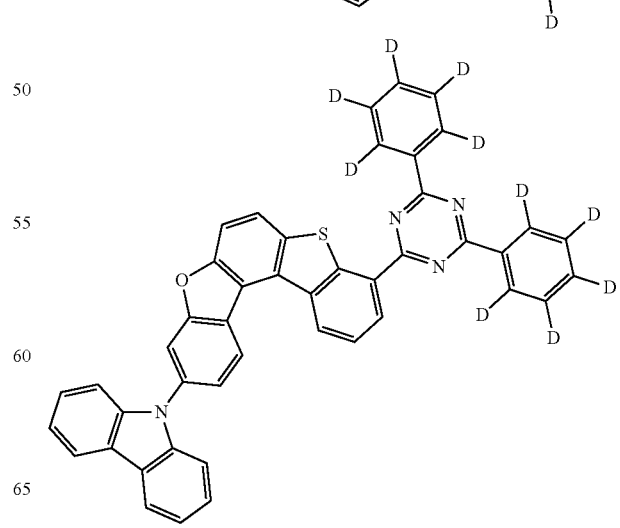

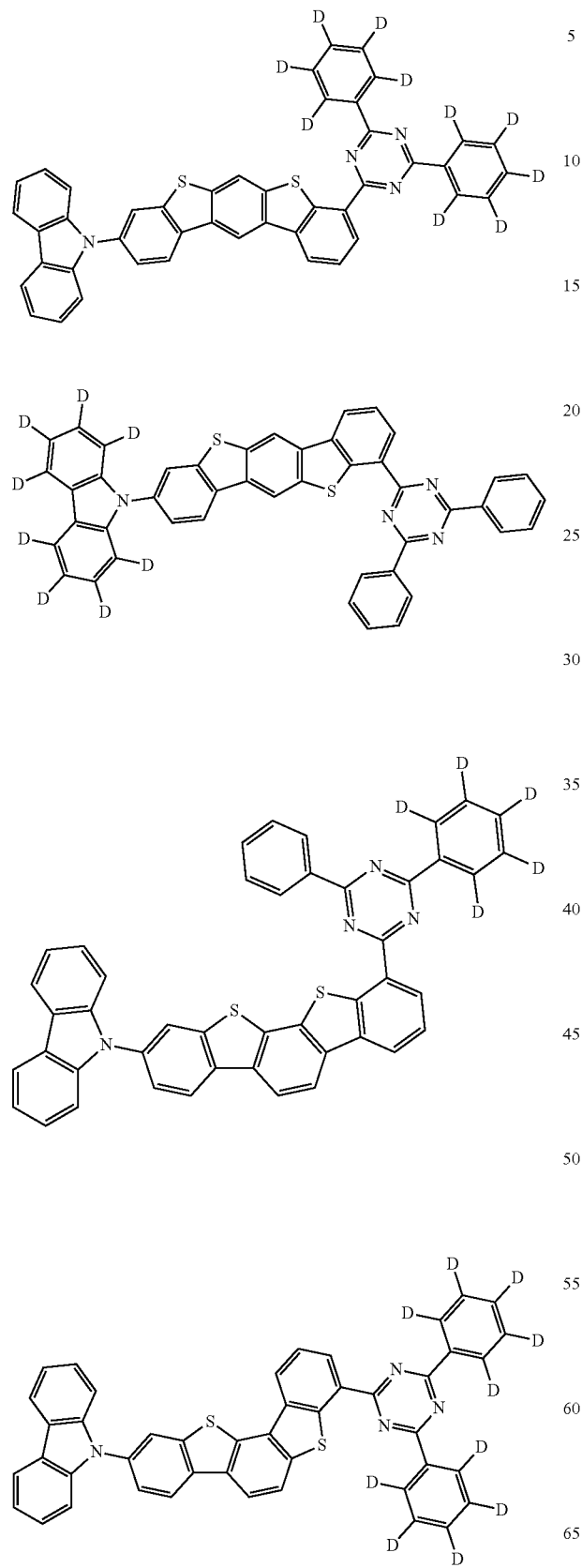
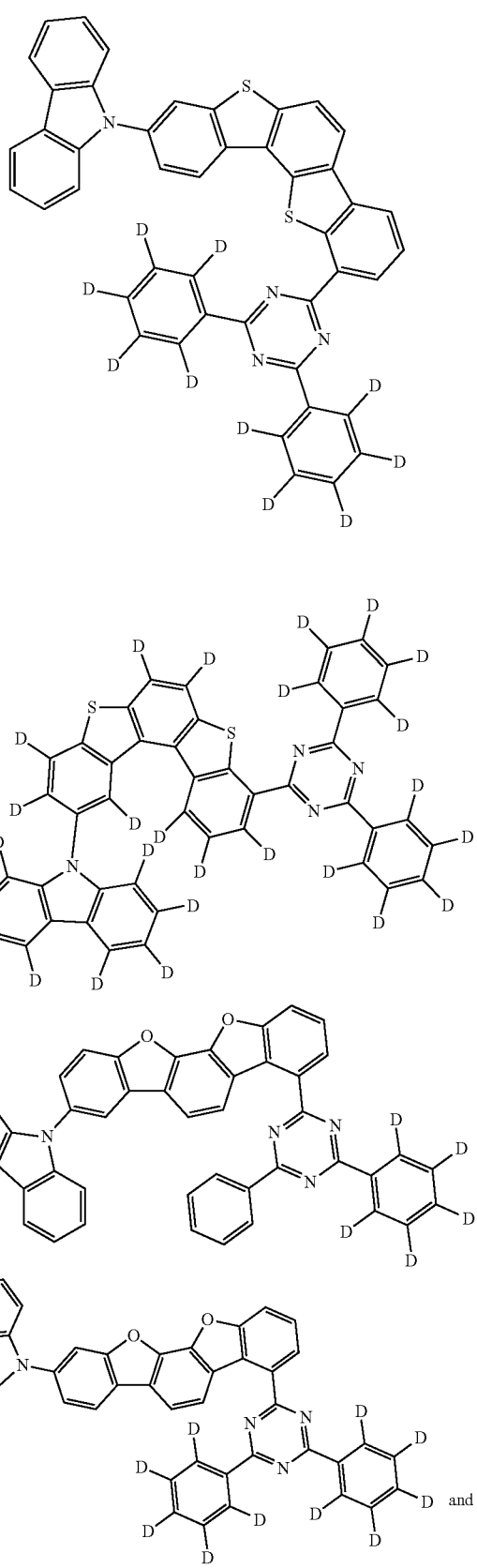

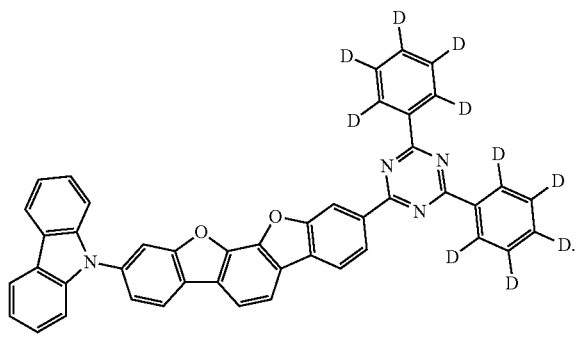

8. An organic light emitting device, comprising:
a first electrode;
a second electrode that is disposed opposite to the first electrode; and
one or more organic material layers that are disposed between the first electrode and the second electrode, wherein one or more layers of the organic material layers comprise the compound of Chemical Formula 1 of claim 1.

9. The organic light emitting device according to claim 8, wherein:
the organic material layer includes a light emitting layer, and the light emitting layer includes the compound.

10. The organic light emitting device according to claim 9, wherein:
the light emitting layer further comprises a compound of Chemical Formula 2:

Chemical Formula 2

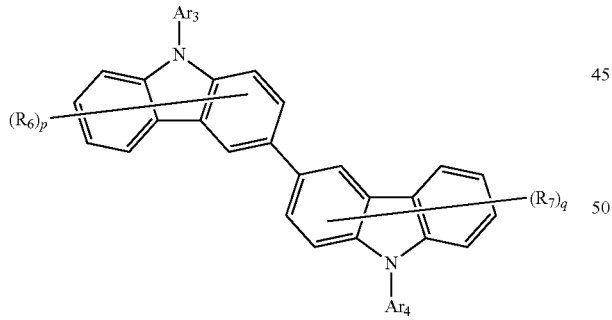

wherein in Chemical Formula 2:
Ar$_3$ and Ar$_4$ are each independently a substituted or unsubstituted C$_{6-60}$ aryl or a substituted or unsubstituted C$_{2-60}$ heteroaryl containing one or more heteroatoms selected from the group consisting of N, O, and S;
R$_6$ and R$_7$ are each independently hydrogen, deuterium, halogen, cyano, nitro, amino, a substituted or unsubstituted C$_{1-60}$ alkyl, a substituted or unsubstituted C$_{3-60}$ cycloalkyl, a substituted or unsubstituted C$_{2-60}$ alkenyl, a substituted or unsubstituted C$_{6-60}$ aryl, or a substituted or unsubstituted C$_{2-60}$ heteroaryl containing one or more heteroatoms selected from the group consisting of N, O, and S; and
p and q are each independently an integer of 0 to 7.

11. The organic light emitting device according to claim 10, wherein:
Ar$_3$ and Ar$_4$ are each independently a phenyl, biphenylyl, terphenylyl, naphthyl, dibenzofuranyl, dibenzothiophenyl, or dimethylfluorenyl.

12. The organic light emitting device according to claim 10, wherein:
R$_6$ and R$_7$ are each independently hydrogen.

13. The organic light emitting device according to claim 10, wherein:
the compound of Chemical Formula 2 is any one compound selected from the group consisting of the following compounds:

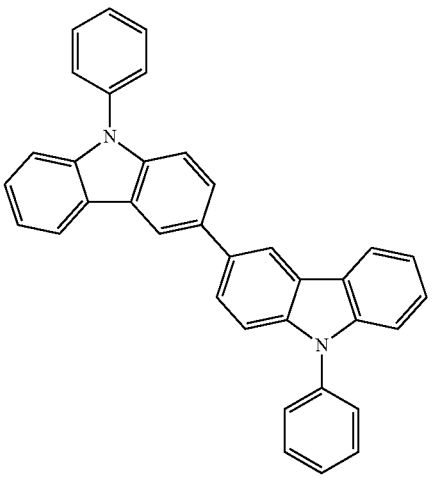

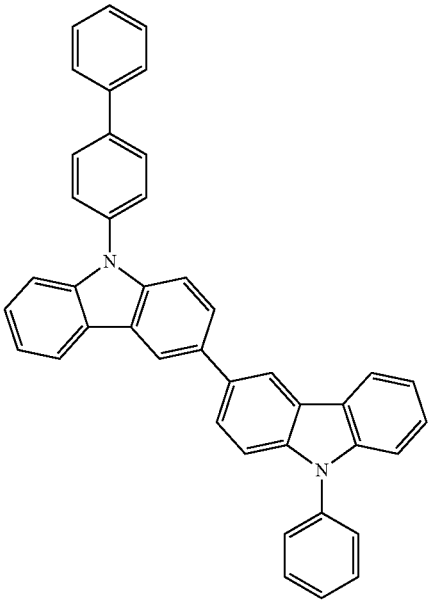

-continued
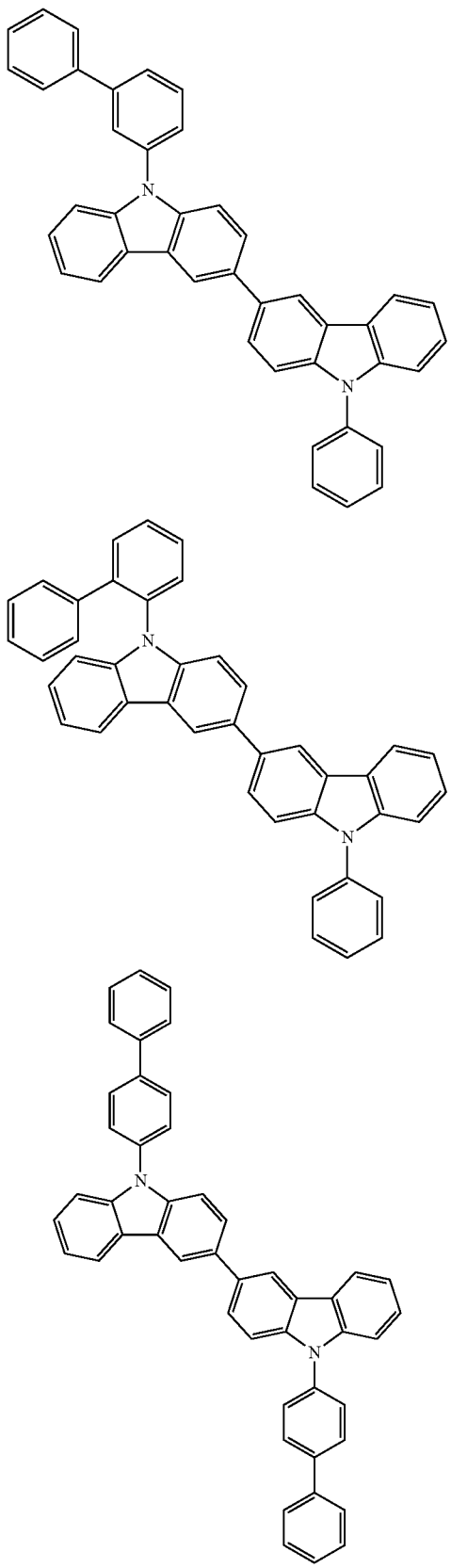
-continued
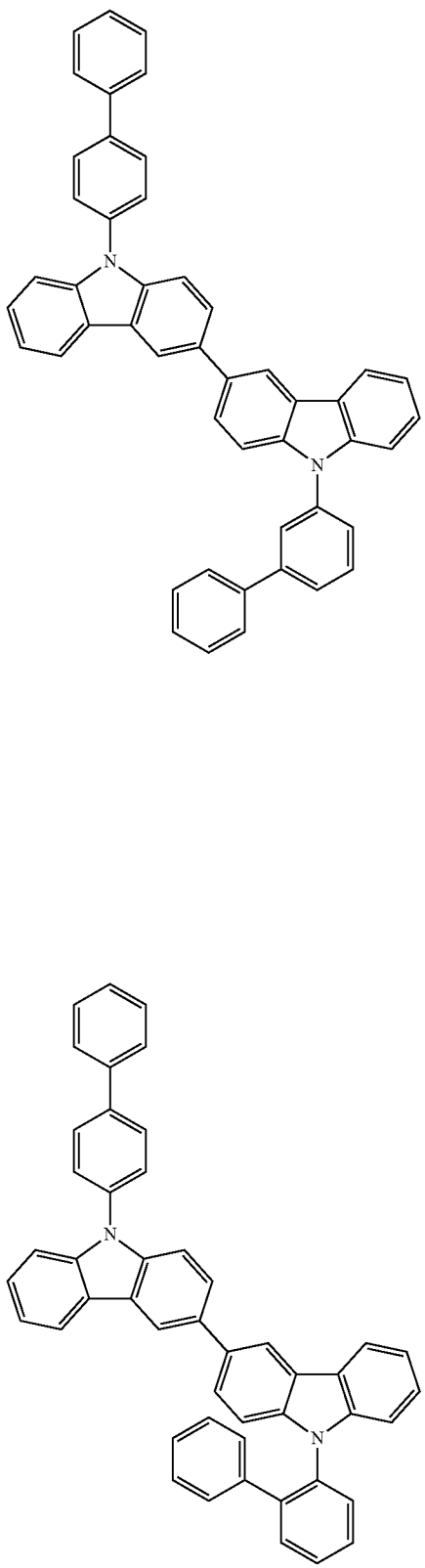

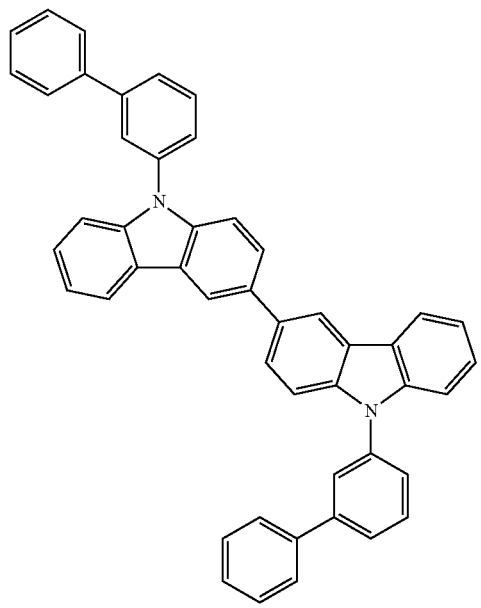
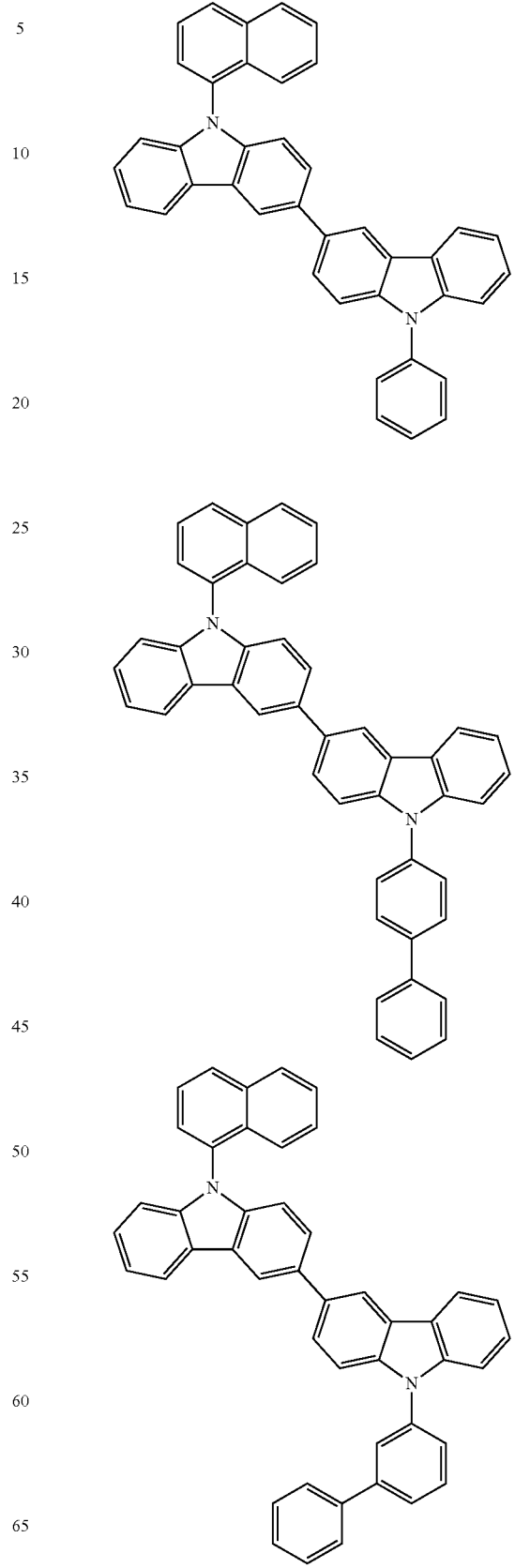

279
-continued
280
-continued
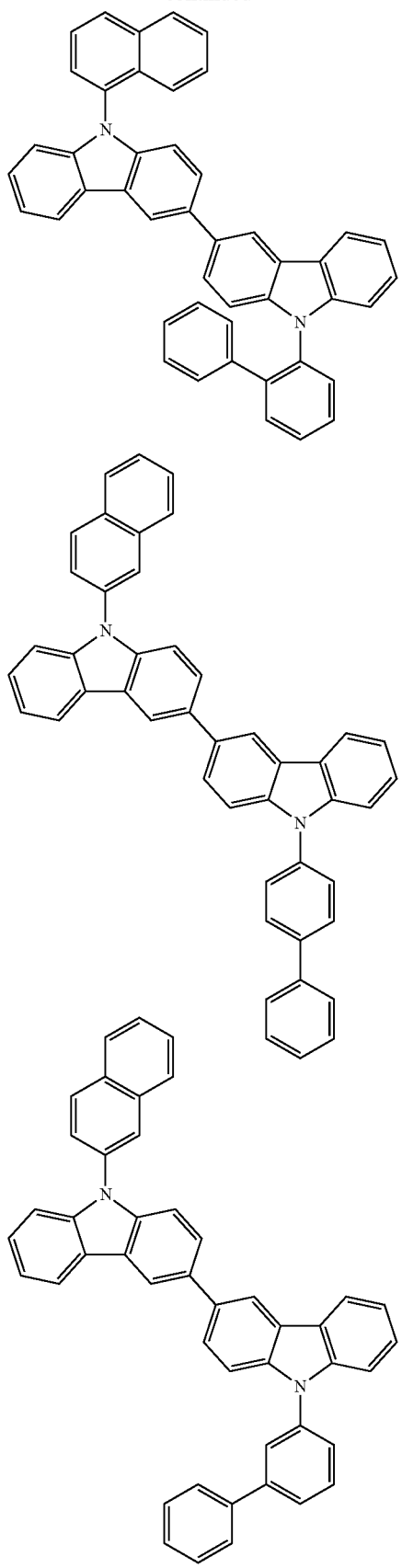
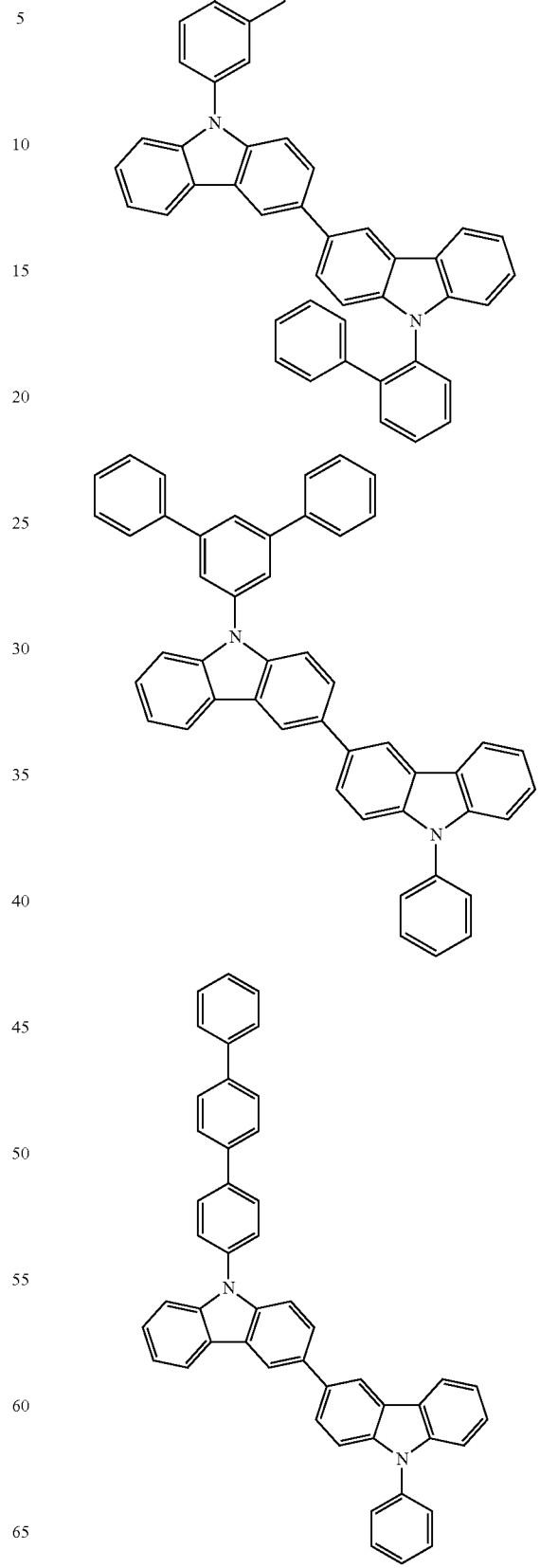

281
-continued
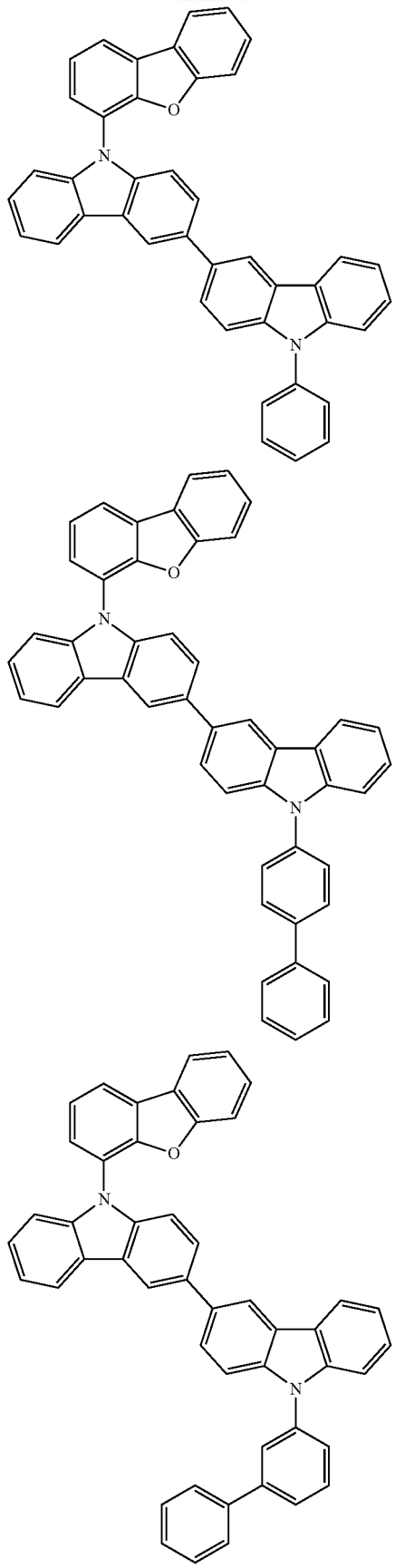
282
-continued
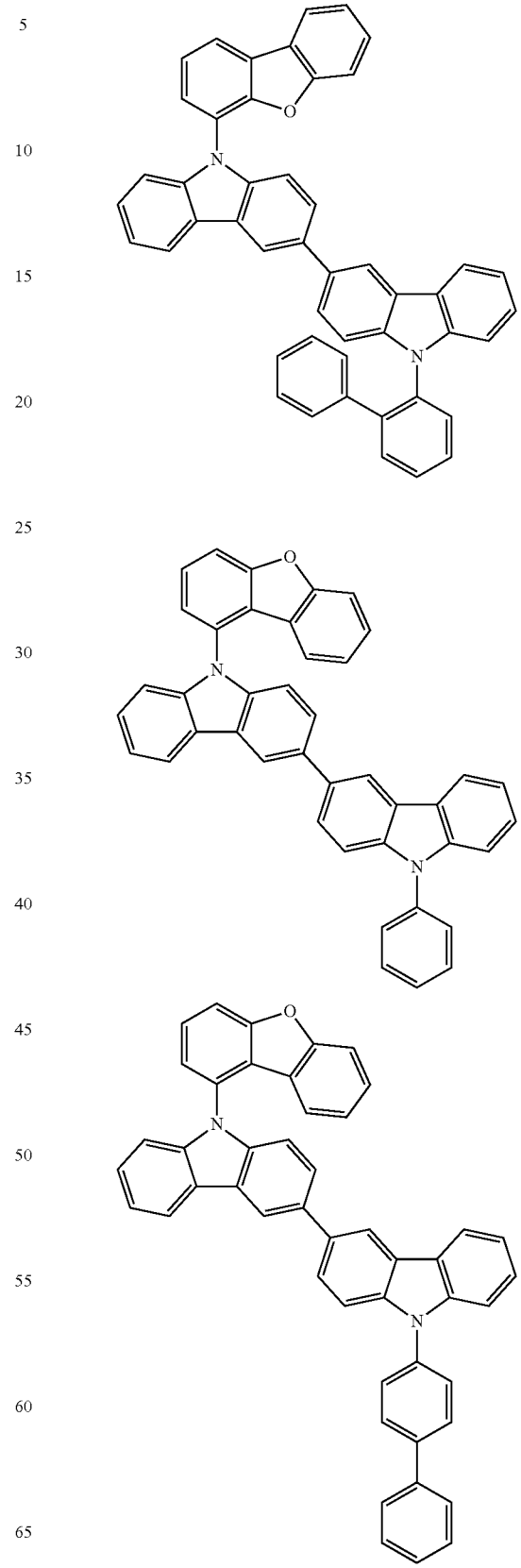

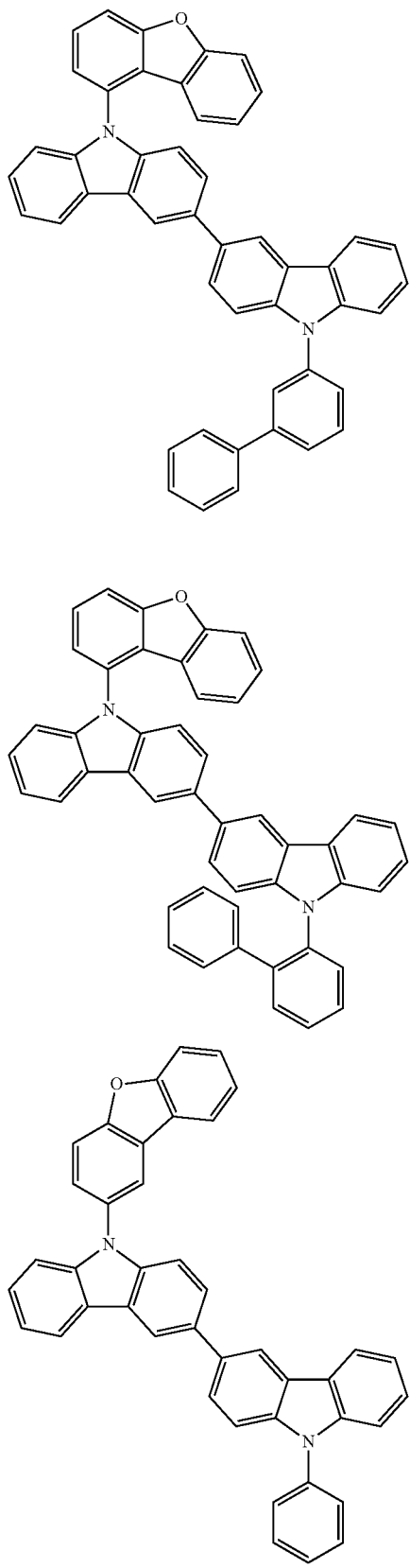
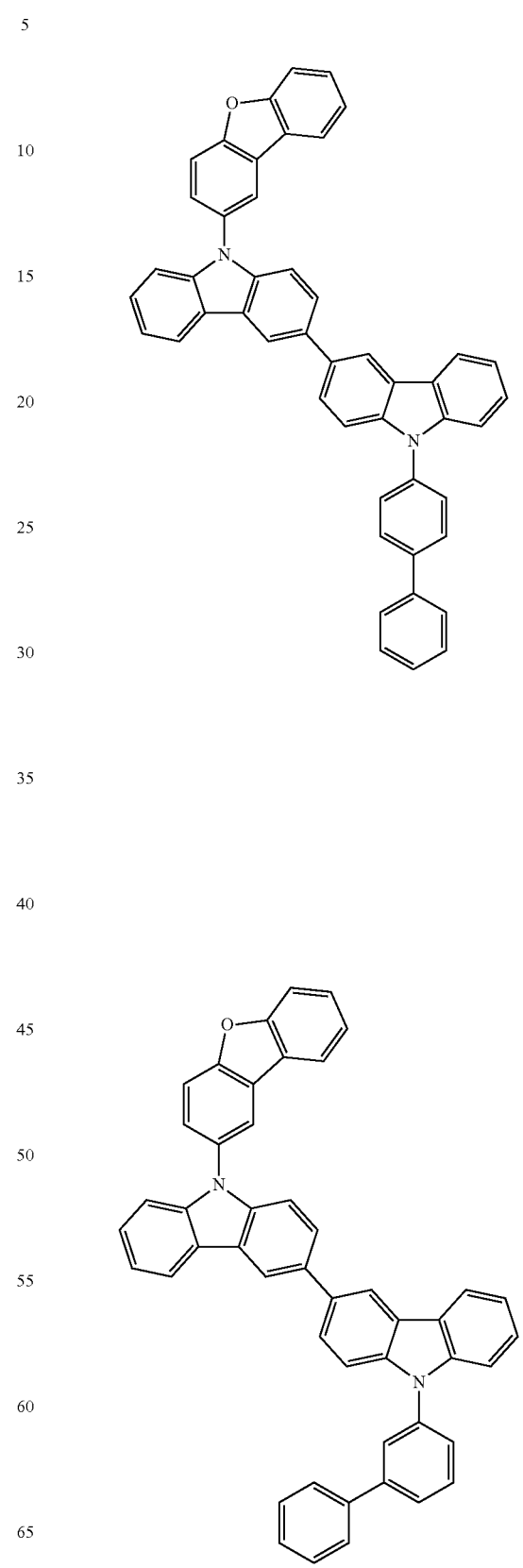

-continued
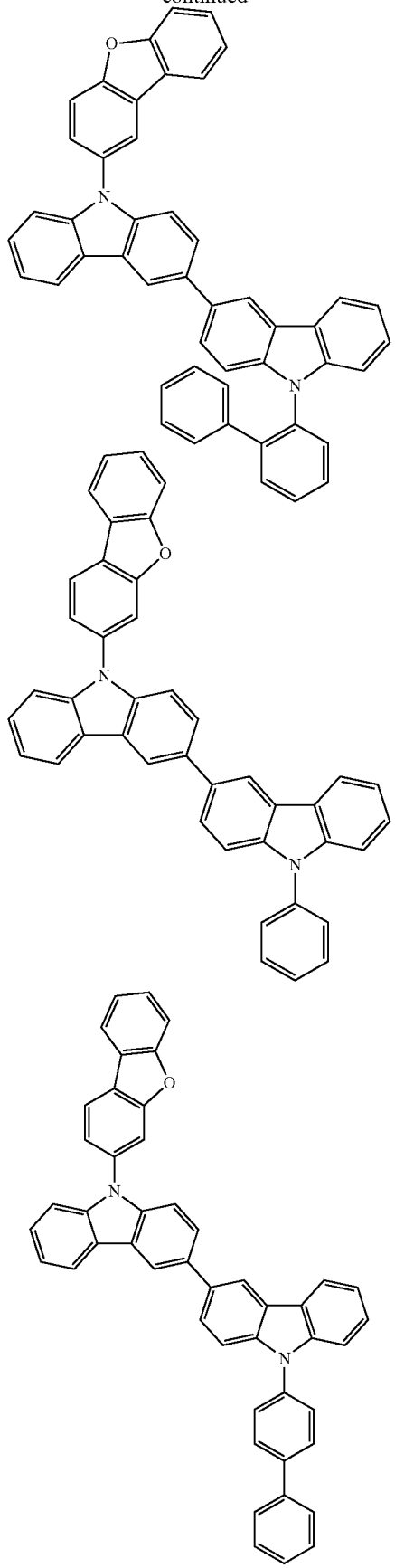
-continued
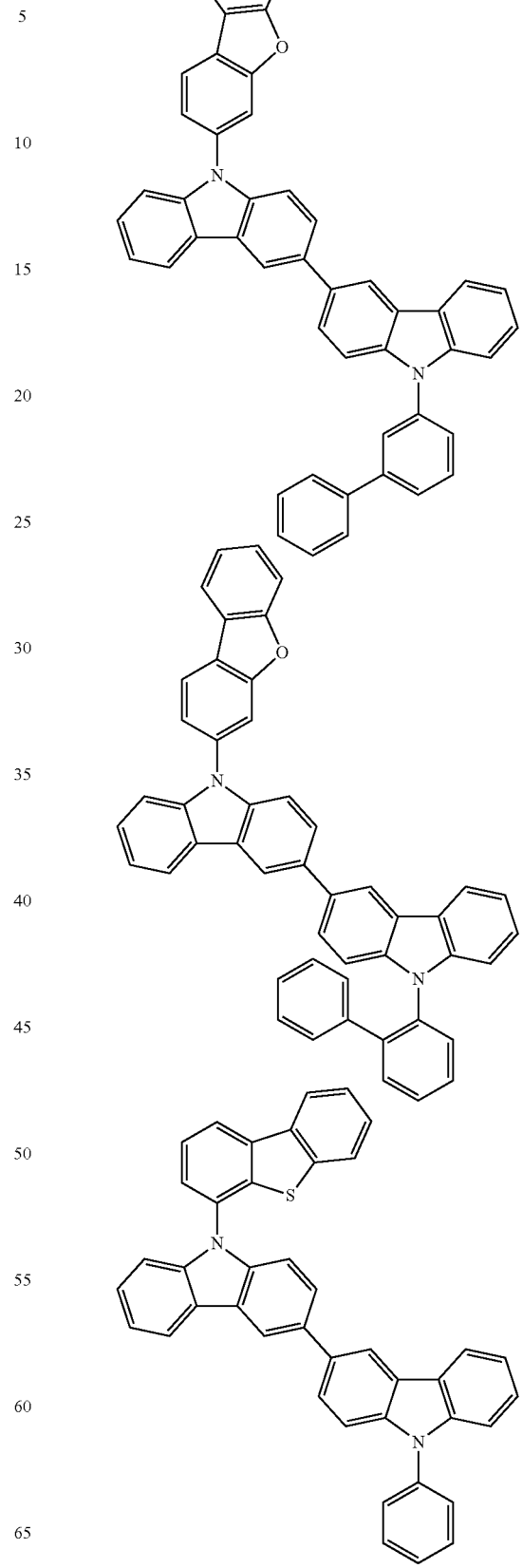

287
-continued
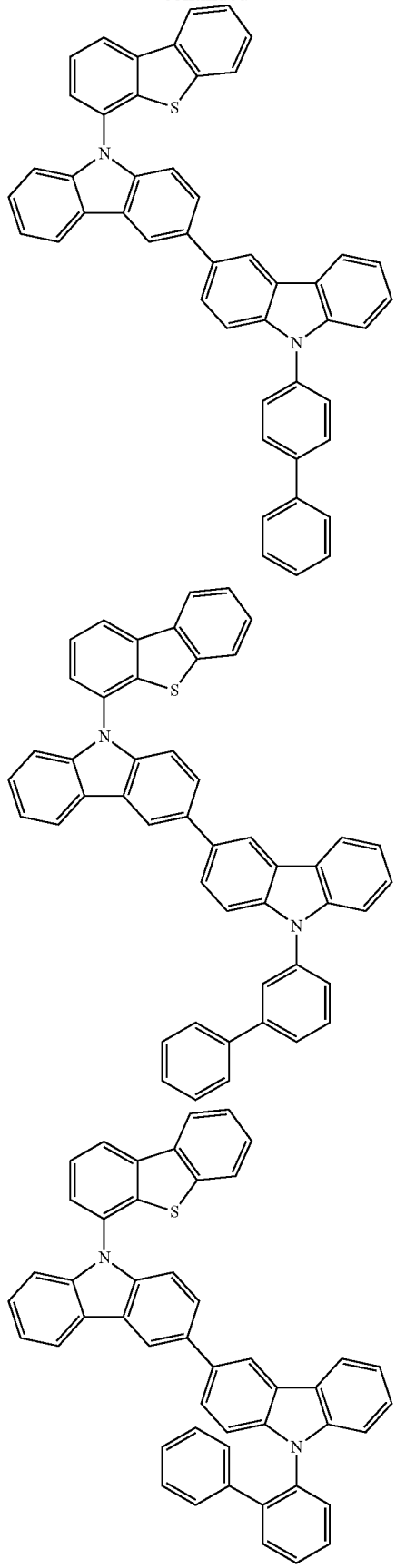
288
-continued
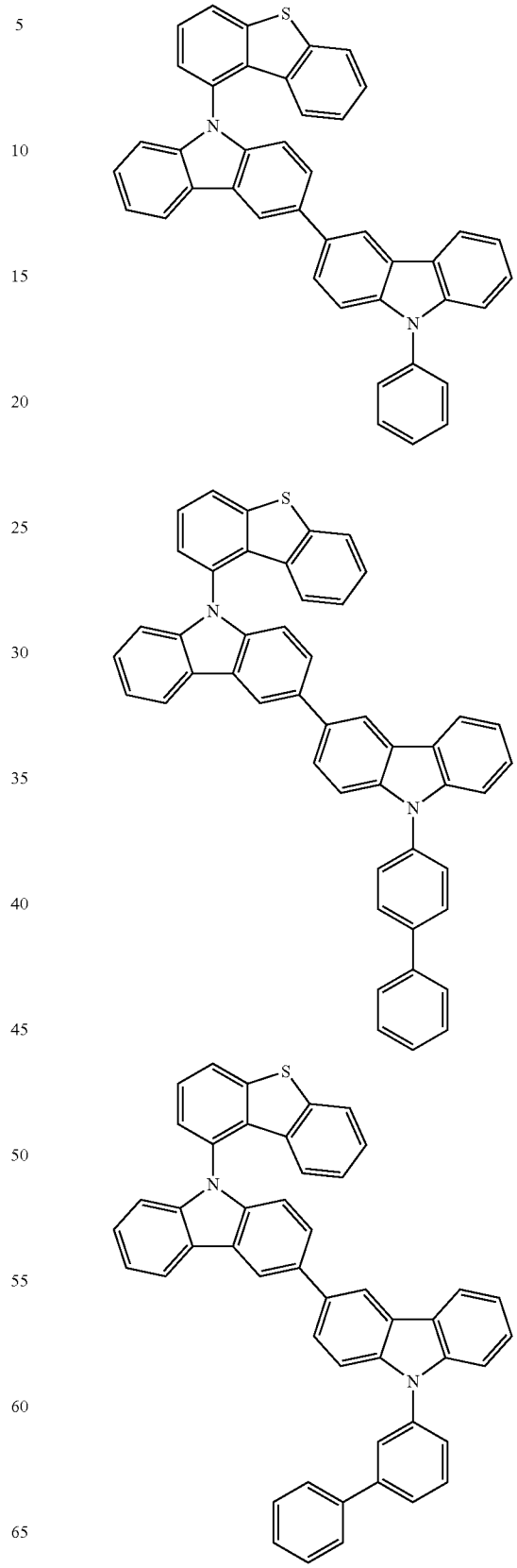

289
-continued
290
-continued
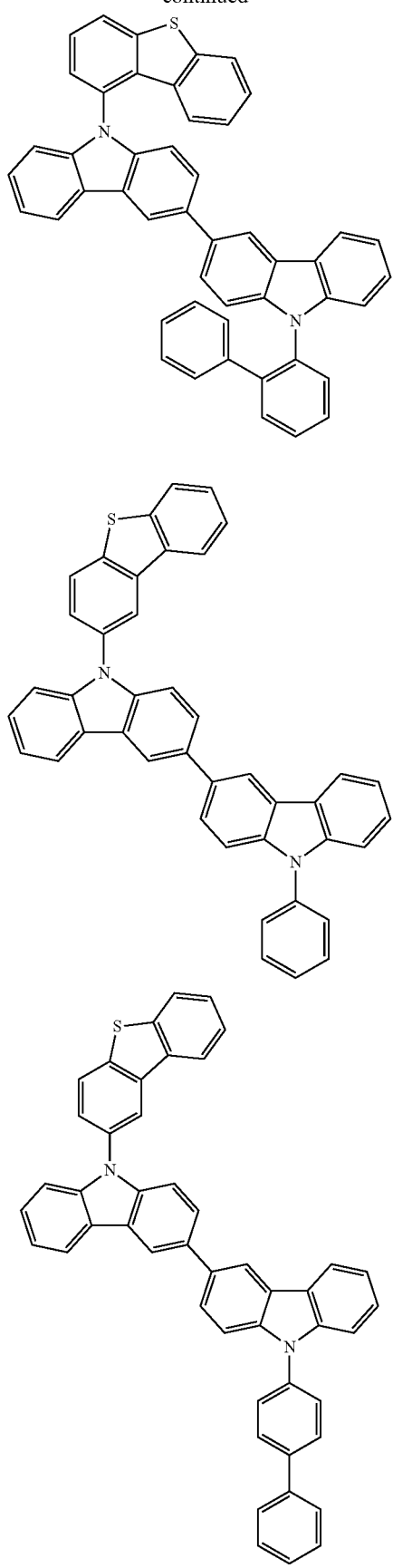
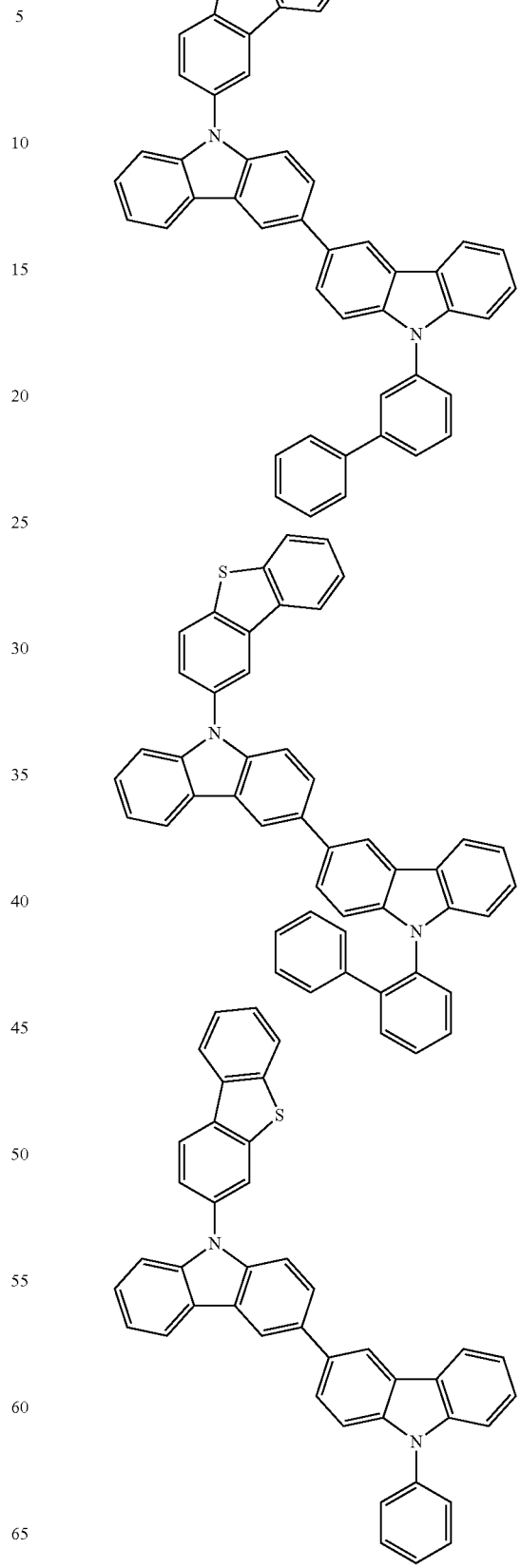

291
-continued
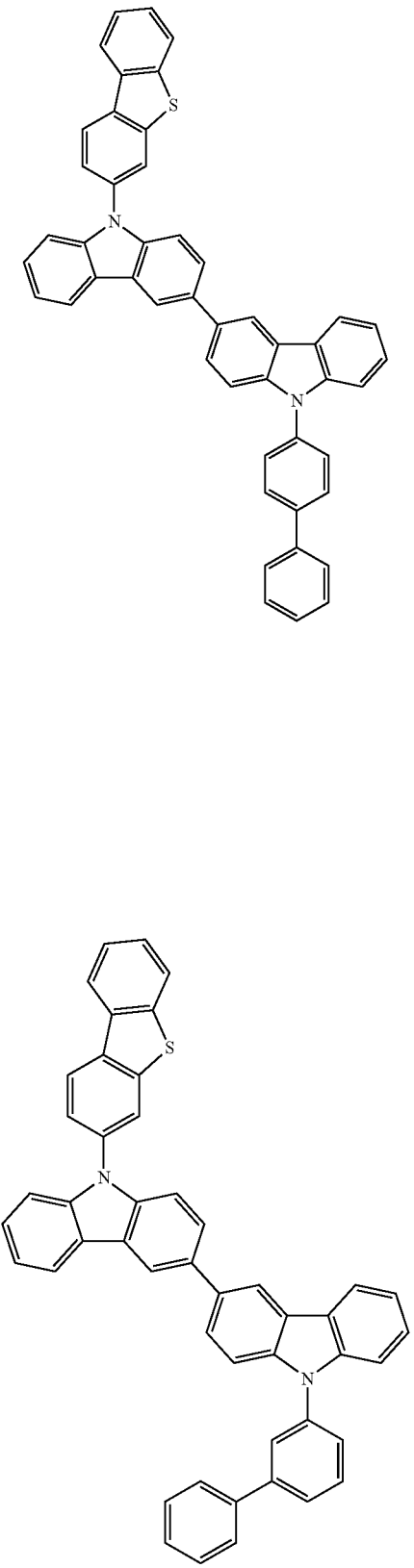
292
-continued
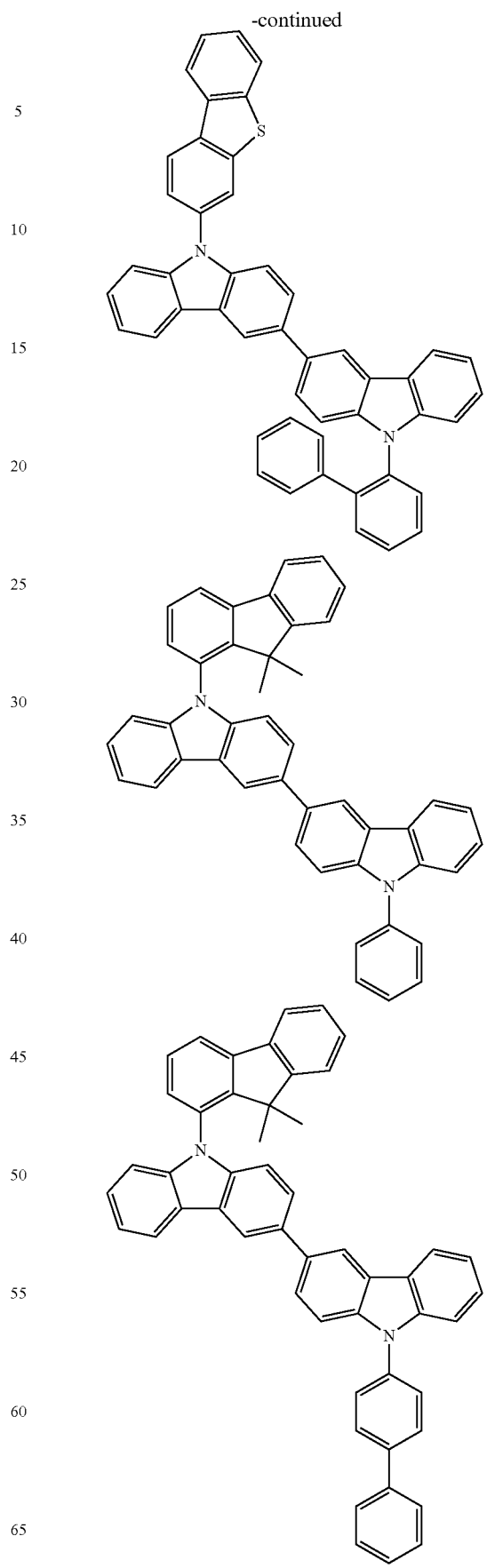

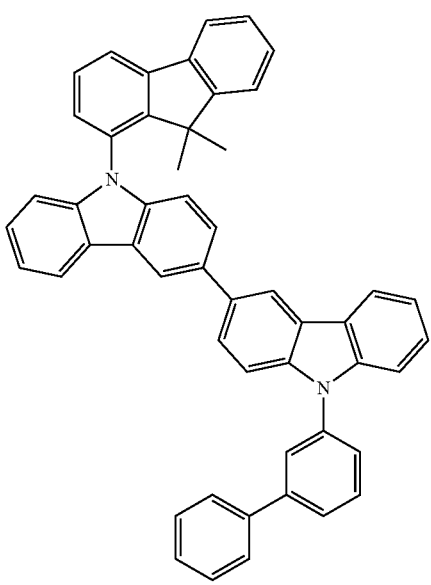
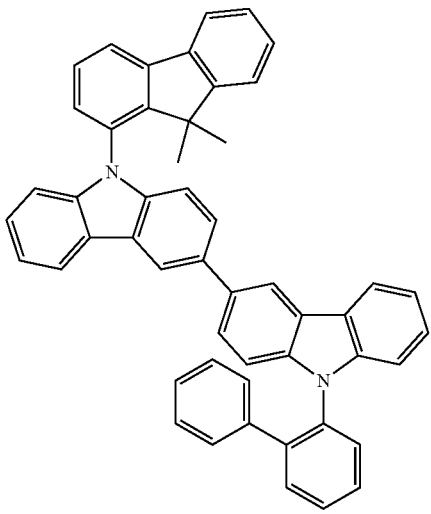
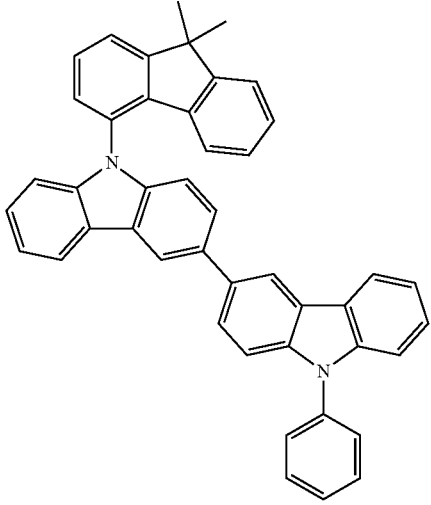
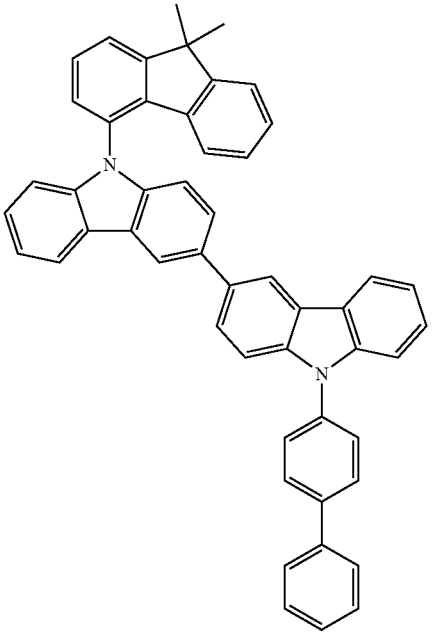
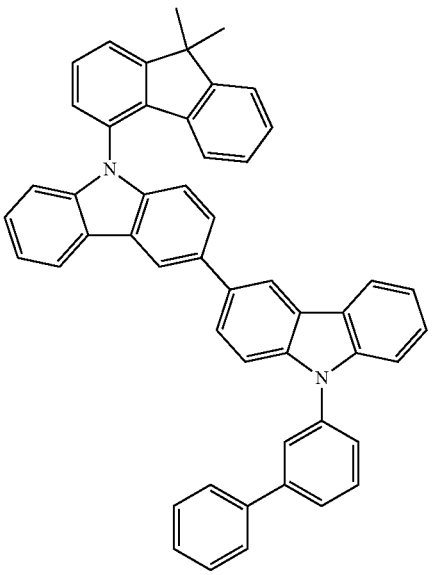
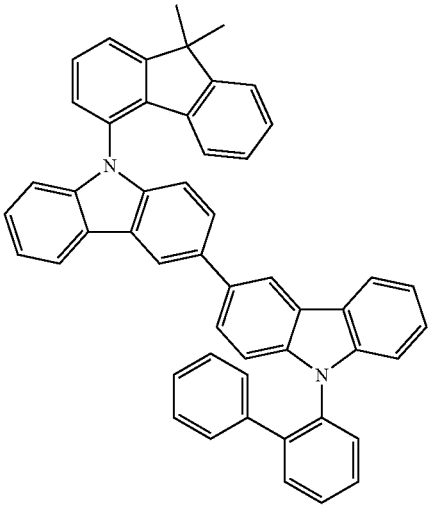

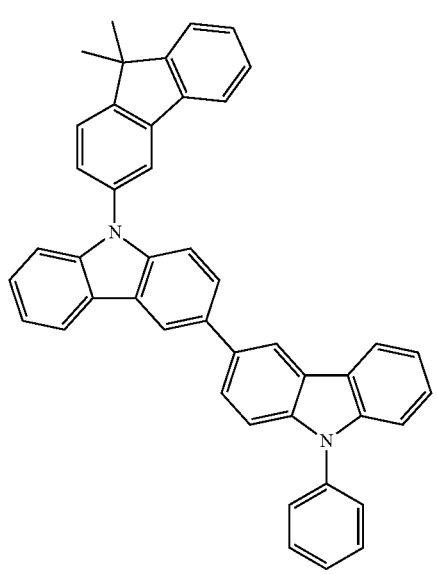
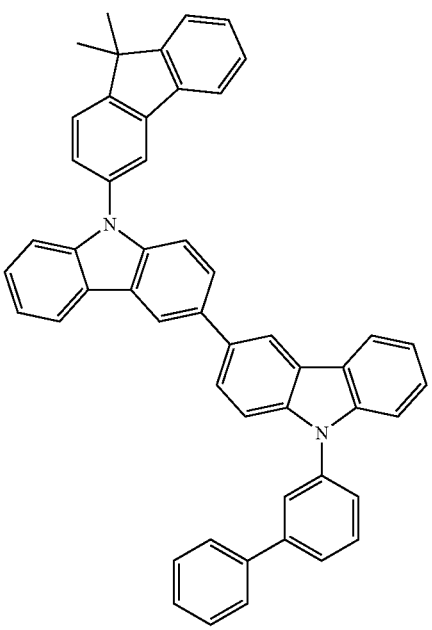
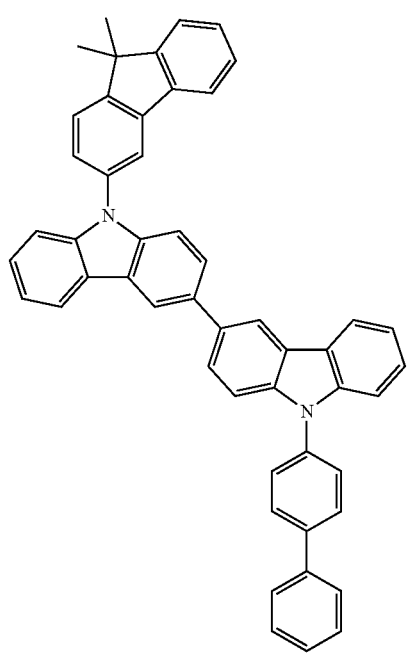
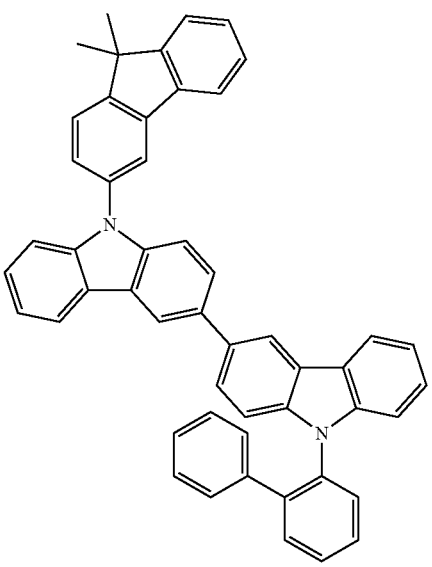

297
-continued
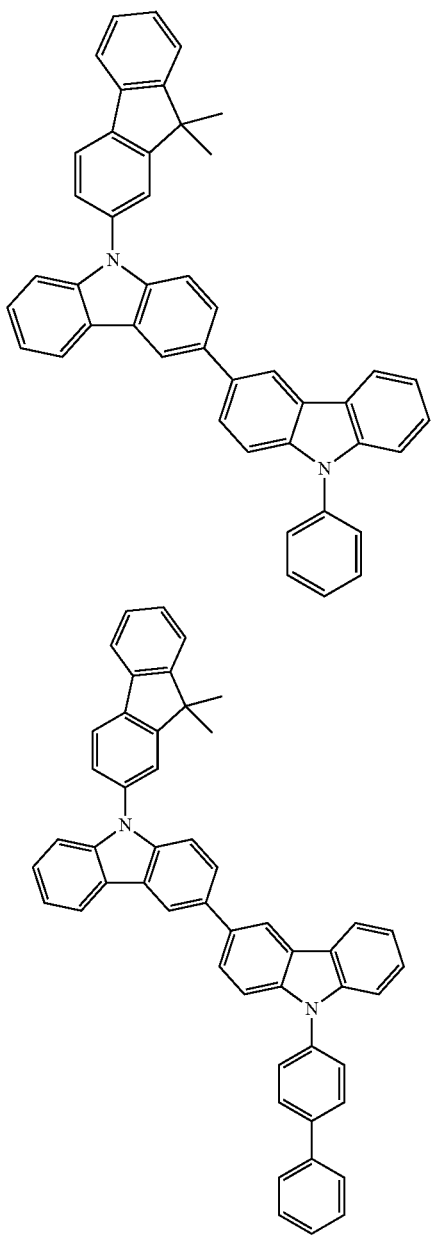
298
-continued
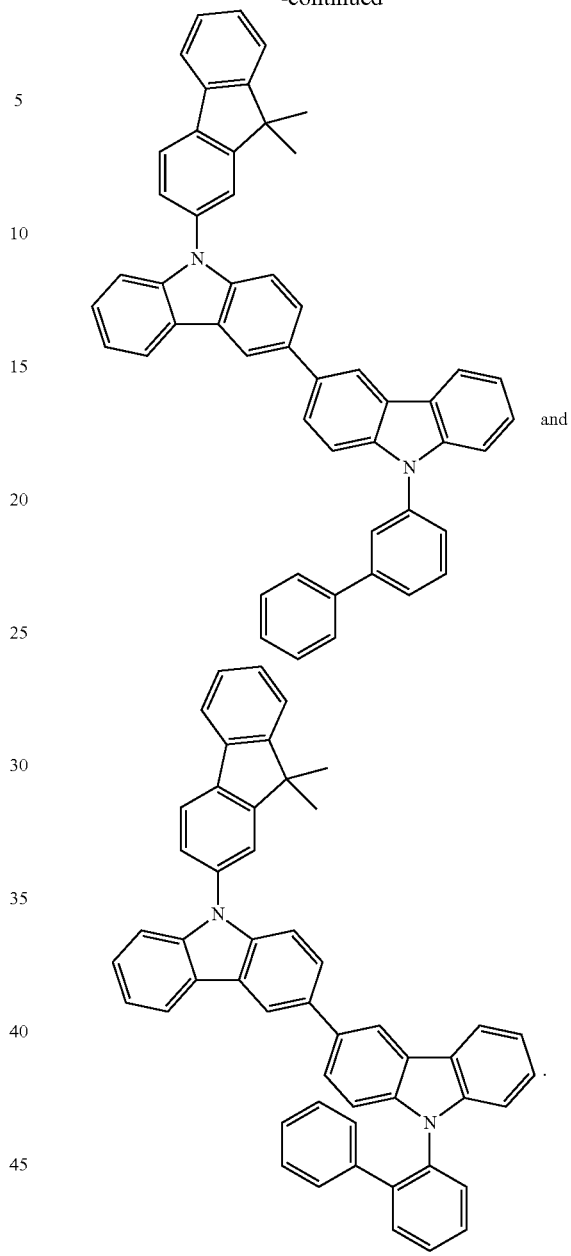
and
* * * * *